US009249191B2

(12) United States Patent
Ueno et al.

(10) Patent No.: US 9,249,191 B2
(45) Date of Patent: Feb. 2, 2016

(54) VIRUS LIKE PARTICLE COMPOSITION

(71) Applicant: VLP THERAPEUTICS, LLC, Wilmington, DE (US)

(72) Inventors: Ryuji Ueno, Potomac, MD (US); Wataru Akahata, Kensington, MD (US)

(73) Assignee: VLP Therapeutics, LLC, Wilmington, DE (US)

(*) Notice: Subject to any disclaimer, the term of this patent is extended or adjusted under 35 U.S.C. 154(b) by 0 days.

(21) Appl. No.: 13/768,801

(22) Filed: Feb. 15, 2013

(65) Prior Publication Data

US 2013/0251744 A1 Sep. 26, 2013

Related U.S. Application Data

(60) Provisional application No. 61/599,746, filed on Feb. 16, 2012.

(51) Int. Cl.

| | |
|---|---|
| ***A61K 39/12*** | (2006.01) |
| ***C07K 14/005*** | (2006.01) |
| ***C07K 14/525*** | (2006.01) |
| ***C07K 14/705*** | (2006.01) |
| ***C12N 7/00*** | (2006.01) |
| ***A61K 39/00*** | (2006.01) |

(52) U.S. Cl.

CPC .......... *C07K 14/005* (2013.01); *A61K 39/0008* (2013.01); *A61K 39/0011* (2013.01); *C07K 14/525* (2013.01); *C07K 14/70521* (2013.01); *C07K 14/70596* (2013.01); *C12N 7/00* (2013.01); *A61K 2039/5256* (2013.01); *A61K 2039/53* (2013.01); *C07K 2319/00* (2013.01); *C07K 2319/735* (2013.01); *C12N 2770/24122* (2013.01); *C12N 2770/36122* (2013.01); *C12N 2770/36123* (2013.01); *C12N 2770/36134* (2013.01); *C12N 2770/36143* (2013.01)

(58) Field of Classification Search

CPC .......... C07K 14/005; C07K 14/70521; C07K 14/525; C07K 2319/735; A61K 39/0008; A61K 39/0011; A61K 2039/5256; C12N 7/00; C12N 2770/36143; C12N 2770/36134; C12N 2770/36123; C12N 2770/36122

See application file for complete search history.

(56) References Cited

U.S. PATENT DOCUMENTS

| | | | | |
|---|---|---|---|---|
| 5,580,773 | A * | 12/1996 | Kang et al. .................... | 435/236 |
| 2012/0003266 | A1 | 1/2012 | Nable et al. | |

FOREIGN PATENT DOCUMENTS

| | | | |
|---|---|---|---|
| CN | 102321639 | A | 1/2012 |
| WO | 97/12048 | A1 | 4/1997 |
| WO | 2010/062396 | A2 | 6/2010 |
| WO | 2012/006180 | A1 | 1/2012 |
| WO | 2012/106356 | A2 | 8/2012 |

OTHER PUBLICATIONS

Akahata, W., and G. J. Nabel, 2012, A specific domain of the Chikungunya virus E2 protein regulates particle formation in human cells: implications for alphavirus vaccine design, J. Virol. 86(16):8879-8883.*

Kuo, S.-C., et al., 2012, Cell-based analysis of Chikungunya virus E1 protein in membrane fusion, J. Biomed. Sci. 19(44):1-12.*

Wataru Akahata et al., "A VLP vaccine for epidemic Chikungunya virus protects non-human primates against infection", Nat. Med., 2010, 16(3): 334-338.

Ira Mellman et al., "Cancer immunotherapy comes of age", Nature, 2011, 480: 480-489.

António Roldão et al., "Virus-like particles in vaccine development", Expert Rev. Vaccines, 2010, 9(10): 1149-1176.

Search Report issued in corresponding International Application No. PCT/JP2013/054422 on May 28, 2013.

Gunther Spohn et al., "A Virus-Like Particle-Based Vaccine Selectively Targeting Soluble TNF-α Protects from Arthritis without Inducing Reactivation of Latent Tuberculosis", *The Journal of Immunology,* 2007, 178: 7450-7457.

Elizabeth V.L. Grgacic et al., "Virus-like particles: Passport to immune recognition", *Methods,* 2006, 40: 60-65.

Gary T. Jennings et al., "Immunodrugs: Therapeutic VLP-Based Vaccines for Chronic Diseases", *Annu. Rev. Pharmacol. Toxicol.,* 2009, 49: 303-326.

Heinz Leibl et al., "Adjuvant/carrier activity of inactivated tick-borne encephalitis virus", *Vaccine,* 1998, 16(4): 340-345.

Bryce Chackerian et al., "Determinants of Autoantibody Induction by Conjugated Papillomavirus Virus-Like Particles", *The Journal of Immunology,* 2002, 169: 6120-6126.

Maria Lia Palomba et al., "CD8$^+$T-Cell-Dependent Immunity Following Xenogeneic DNA Immunization against CD20 in a Tumor Challenge Model of B-Cell Lymphoma", *Clinical Cancer Research,* 2005, 370(11): 370-379.

Wendy K. Roberts et al., "Vaccination with CD20 peptides induces a biologically active, specific immune response in mice", *Blood,* 2002, 99: 3748-3755.

Kathy D. McCoy et al., "Cytotoxic T Lymphocyte-associated Antigen 4 (CTLA-4) Can Regulate Dendritic Cell-induced Activation and Cytotoxicity of CD8$^+$T Cells Independently of CD4+ T Cell Help", *J. Exp. Med.,* 1999, 189(7): 1157-1162.

Gregory J. Atkins et al., "Therapeutic and prophylactic applications of alphavirus vectors", Expert Reviews in Molecular Medicine, 2008, 10(e33): 1-17.

Communication, dated Sep. 16, 2015, issued by the European Patent Office in counterpart European Patent Application No. 13749307.8.

Communication, dated Oct. 2, 2015, issued by the European Patent Office in counterpart European Patent Application No. 13749307.8.

Siyang Sun et al: "Structural analyses at pseudo atomic resolution of Chikungunya virus and antibodies show mechanisms of neutralization", eLIFE, Apr. 2, 2013, vol. 2, pp. 1-27.

* cited by examiner

*Primary Examiner* — Jeffrey Parkin
(74) *Attorney, Agent, or Firm* — Sughrue Mion, PLLC

(57) ABSTRACT

The present invention provides a particle comprising a polypeptide and at least one antigen, and a composition comprising thereof.

14 Claims, 11 Drawing Sheets

FIG. 1

Original TNF-alpha sequence

RTPSDKPVAHVVANPQAEGQLQWLNRRANALLANGVELRDNQLVVPSEGL
YLIYSQVLFKGQGCPSTHVLLTHTISRIAVSYQTKVNLLSAIKSPCQRET
PEGAEAKPWYEPIYLGGVFQLEKGDRLSAEINRPDYLDFAESGQVYFGII
AL (SEQ ID NO: 18)

Modified TNF-alpha sequence inserted into CHIKV

SGGKPVAHVVANPQAEGQLQWLNRRANALLANGVELRDNQLVVPSEGLYL
IYSQVLFKGQGCPSTHVLLTHTISRIAVSYQTKVNLLSAIKSPCQRETPE
GAEAKPWYEPIYLGGVFQLEKGDRLSAEINRPDYLDFAESGQVYFGIIAL
TRGGS (SEQ ID NO: 19)

Nucleotide sequence encoding the modified TNF-alpha tccggaggtaagcctgtagcccatgttgtagcaaaccctcaagctgaggg
gcagctccagtggctgaaccgccgggccaatgccctcctggccaatggcg
tggagctgagagataaccagctggtggtgccatcagagggcctgtacctc
atctactcccaggtcctcttcaagggccaaggctgcccctccacccatgt
gctcctcacccacaccatcagccgcatcgccgtctcctaccagaccaagg
tcaacctcctctctgccatcaagagcccctgccagagggagaccccagag
gggctgaggccaagccctggtatgagcccatctatctgggaggggtctt
ccagctggagaagggtgaccgactcagcgctgagatcaatcggcccgact
atctcgactttgccgagtctgggcaggtctactttgggatcattgccctg
acgcgtggaggatcc (SEQ ID NO: 20)

Fig.2

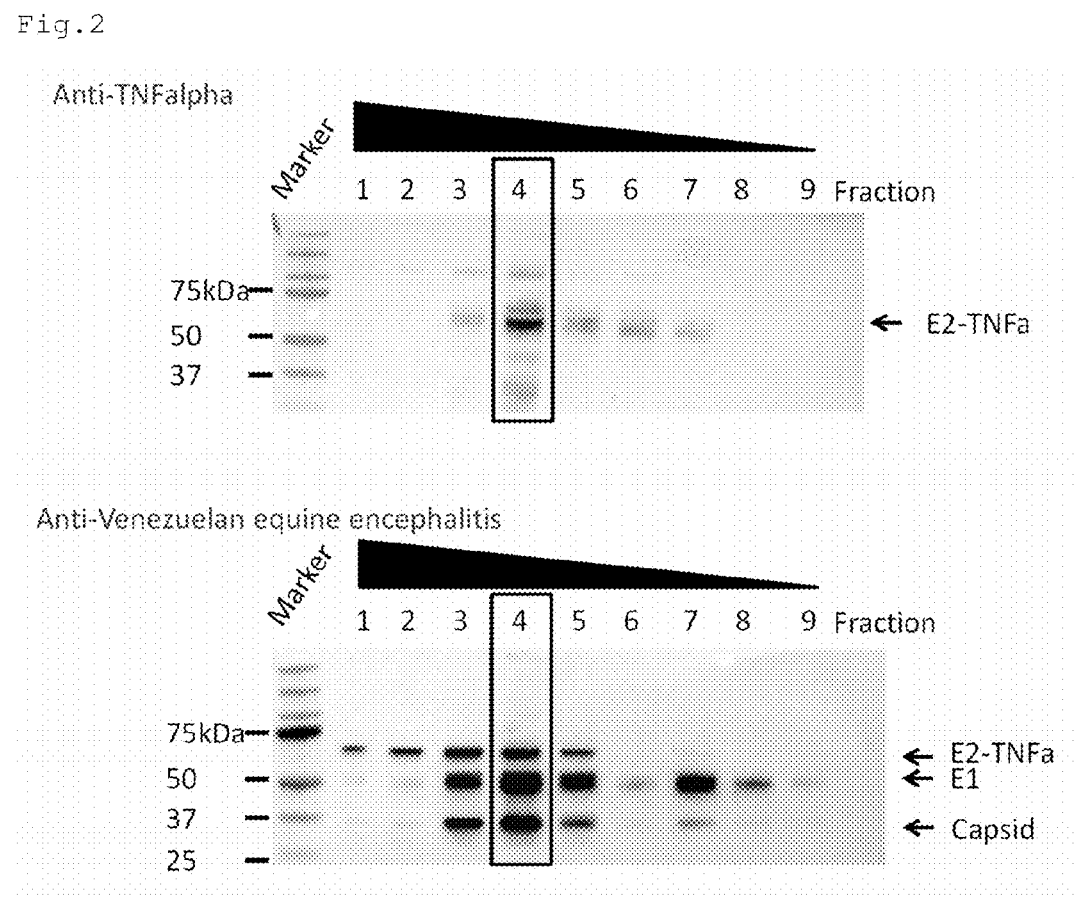

Anti-TNFalpha

Marker 1 2 3 4 5 6 7 8 9 Fraction

75kDa

50

37

E2-TNFa

Anti-Venezuelan equine encephalitis

Marker 1 2 3 4 5 6 7 8 9 Fraction

75kDa

50

37

25

E2-TNFa

E1

Capsid

Figure 6:
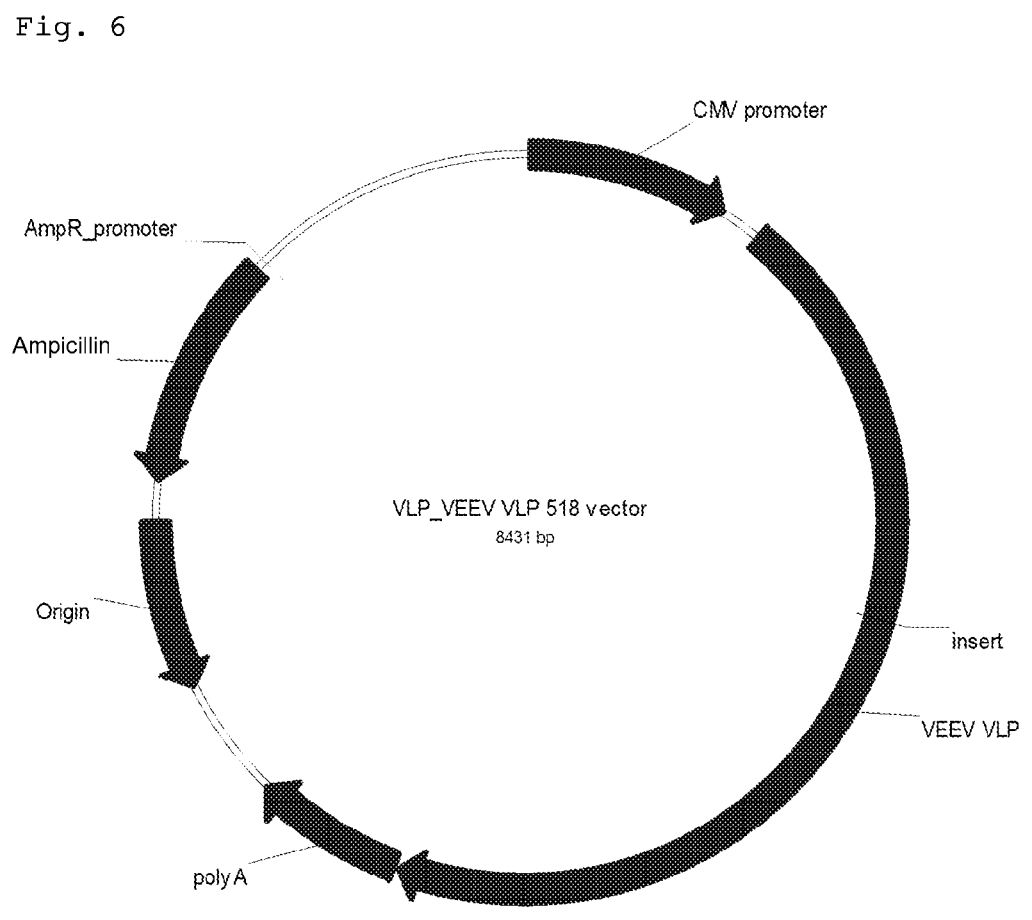

Figure 7:
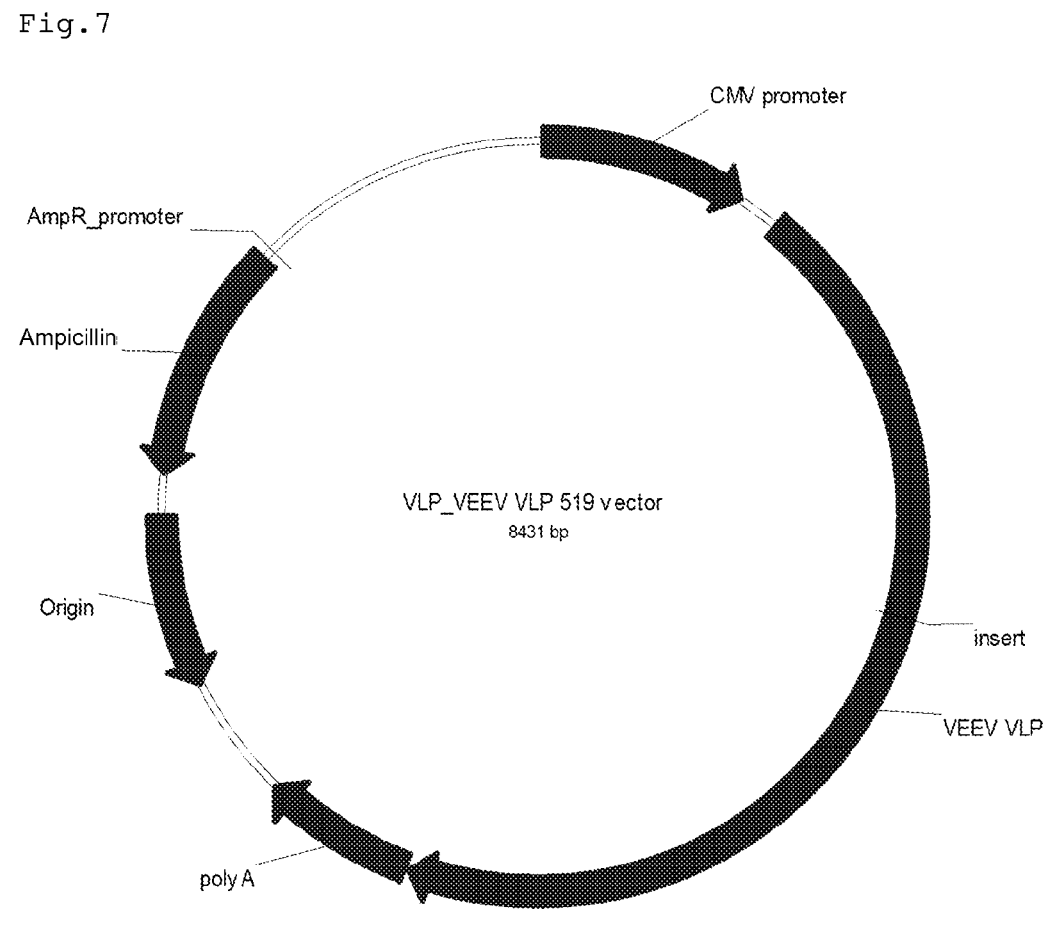

VLP-CD20 Induced anti-CD20 (Human) antibodies

SEQUENCE LISTING

```
<160> NUMBER OF SEQ ID NOS: 52

<210> SEQ ID NO 1
<211> LENGTH: 1248
<212> TYPE: PRT
<213> ORGANISM: Artificial Sequence
<220> FEATURE:
<223> OTHER INFORMATION: Synthetic peptide

<400> SEQUENCE: 1

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80
```

-continued

```
Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495
```

```
Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
```

```
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                 1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Val  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Met  Pro Ile Ser Ile Asp  Ile Pro Glu Ala Ala  Phe Thr Arg
    1085                 1090                 1095

Val Val  Asp Ala Pro Ser Leu  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125

Tyr Ala  Ala Ser Lys Lys Gly  Lys Cys Ala Val His  Ser Met Thr
    1130                 1135                 1140

Asn Ala  Val Thr Ile Arg Glu  Ala Glu Ile Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Glu
    1175                 1180                 1185

Cys His  Pro Pro Lys Asp His  Ile Val Asn Tyr Pro  Ala Ser His
    1190                 1195                 1200

Thr Thr  Leu Gly Val Gln Asp  Ile Ser Ala Thr Ala  Met Ser Trp
    1205                 1210                 1215

Val Gln  Lys Ile Thr Gly Gly  Val Gly Leu Val Val  Ala Val Ala
    1220                 1225                 1230

Ala Leu  Ile Leu Ile Val Val  Leu Cys Val Ser Phe  Ser Arg His
    1235                 1240                 1245


<210> SEQ ID NO 2
<211> LENGTH: 1248
<212> TYPE: PRT
<213> ORGANISM: Artificial Sequence
<220> FEATURE:
<223> OTHER INFORMATION: Synthetic peptide

<400> SEQUENCE: 2

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
```

-continued

```
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445
```

```
Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
    610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Ile Val Ser Val Ala Ser Phe Val Leu Leu
    690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
    850                 855                 860
```

-continued

```
Pro Ser Pro Tyr Val Lys Cys Cys Gly Thr Ala Glu Cys Lys Asp Lys
865                 870                 875                 880

Ser Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                1015                1020

Ala Asn  Thr Gln Leu Val Leu  Gln Arg Pro Ala Ala  Gly Thr Val
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Val Asn Cys  Ala Val Gly
    1070                1075                1080

Asn Ile  Pro Ile Ser Ile Asp  Ile Pro Asp Ala Ala  Phe Thr Arg
    1085                1090                1095

Val Val  Asp Ala Pro Ser Val  Thr Asp Met Ser Cys  Glu Val Pro
    1100                1105                1110

Ala Cys  Thr His Ser Ser Asp  Phe Gly Gly Val Ala  Ile Ile Lys
    1115                1120                1125

Tyr Thr  Ala Ser Lys Lys Gly  Lys Cys Ala Val His  Ser Met Thr
    1130                1135                1140

Asn Ala  Val Thr Ile Arg Glu  Ala Asp Val Glu Val  Glu Gly Asn
    1145                1150                1155

Ser Gln  Leu Gln Ile Ser Phe  Ser Thr Ala Leu Ala  Ser Ala Glu
    1160                1165                1170

Phe Arg  Val Gln Val Cys Ser  Thr Gln Val His Cys  Ala Ala Ala
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Thr Thr Ala  Met Ser Trp
    1205                1210                1215

Val Gln  Lys Ile Thr Gly Gly  Val Gly Leu Ile Val  Ala Val Ala
    1220                1225                1230

Ala Leu  Ile Leu Ile Val Val  Leu Cys Val Ser Phe  Ser Arg His
    1235                1240                1245
```

<210> SEQ ID NO 3
<211> LENGTH: 1255
<212> TYPE: PRT

```
<213> ORGANISM: Artificial Sequence
<220> FEATURE:
<223> OTHER INFORMATION: Synthetic peptide

<400> SEQUENCE: 3

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Ala
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
```

-continued

```
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
        515                 520                 525

Ser Ala Leu Val Glu Cys Glu Cys Gly Gly Thr Lys Ile Ser Glu Thr
    530                 535                 540

Ile Asn Lys Thr Lys Gln Phe Ser Gln Cys Thr Lys Lys Glu Gln Cys
545                 550                 555                 560

Arg Ala Tyr Arg Leu Gln Asn Asp Lys Trp Val Tyr Asn Ser Asp Lys
                565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
        595                 600                 605

Met Ile Thr Phe Gly Phe Arg Ser Val Ser Leu Lys Leu His Pro Lys
    610                 615                 620

Asn Pro Thr Tyr Leu Ile Thr Arg Gln Leu Ala Asp Glu Pro His Tyr
625                 630                 635                 640

Thr His Glu Leu Ile Ser Glu Pro Ala Val Arg Asn Phe Thr Val Thr
                645                 650                 655

Glu Lys Gly Trp Glu Phe Val Trp Gly Asn His Pro Pro Lys Arg Phe
            660                 665                 670

Trp Ala Gln Glu Thr Ala Pro Gly Asn Pro His Gly Leu Pro His Glu
        675                 680                 685

Val Ile Thr His Tyr Tyr His Arg Tyr Pro Met Ser Thr Ile Leu Gly
    690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
                725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
        755                 760                 765

Asn Asn Asn Gln Gln Met Phe Trp Ile Gln Leu Leu Ile Pro Leu Ala
    770                 775                 780

Ala Leu Ile Val Val Thr Arg Leu Leu Arg Cys Val Cys Cys Val Val
785                 790                 795                 800

Pro Phe Leu Val Met Ala Gly Ala Ala Gly Ala Gly Ala Tyr Glu His
                805                 810                 815
```

```
Ala Thr Thr Met Pro Ser Gln Ala Gly Ile Ser Tyr Asn Thr Ile Val
            820                 825                 830

Asn Arg Ala Gly Tyr Ala Pro Leu Pro Ile Ser Ile Thr Pro Thr Lys
        835                 840                 845

Ile Lys Leu Ile Pro Thr Val Asn Leu Glu Tyr Val Thr Cys His Tyr
    850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
                885                 890                 895

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
        915                 920                 925

Ala Asp His Ala Glu Ala Tyr Lys Ala His Thr Ala Ser Val Gln Ala
    930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
            980                 985                 990

Tyr Ala Gly Glu Ile Tyr Asn Tyr  Asp Phe Pro Glu Tyr  Gly Ala Gly
        995                 1000                1005

Gln Pro  Gly Ala Phe Gly Asp  Ile Gln Ser Arg Thr  Val Ser Ser
    1010                1015                1020

Ser Asp  Leu Tyr Ala Asn Thr  Asn Leu Val Leu Gln  Arg Pro Lys
    1025                1030                1035

Ala Gly  Ala Ile His Val Pro  Tyr Thr Gln Ala Pro  Ser Gly Phe
    1040                1045                1050

Glu Gln  Trp Lys Lys Asp Lys  Ala Pro Ser Leu Lys  Phe Thr Ala
    1055                1060                1065

Pro Phe  Gly Cys Glu Ile Tyr  Thr Asn Pro Ile Arg  Ala Glu Asn
    1070                1075                1080

Cys Ala  Val Gly Ser Ile Pro  Leu Ala Phe Asp Ile  Pro Asp Ala
    1085                1090                1095

Leu Phe  Thr Arg Val Ser Glu  Thr Pro Thr Leu Ser  Ala Ala Glu
    1100                1105                1110

Cys Thr  Leu Asn Glu Cys Val  Tyr Ser Ser Asp Phe  Gly Gly Ile
    1115                1120                1125

Ala Thr  Val Lys Tyr Ser Ala  Ser Lys Ser Gly Lys  Cys Ala Val
    1130                1135                1140

His Val  Pro Ser Gly Thr Ala  Thr Leu Lys Glu Ala  Ala Val Glu
    1145                1150                1155

Leu Thr  Glu Gln Gly Ser Ala  Thr Ile His Phe Ser  Thr Ala Asn
    1160                1165                1170

Ile His  Pro Glu Phe Arg Leu  Gln Ile Cys Thr Ser  Tyr Val Thr
    1175                1180                1185

Cys Lys  Gly Asp Cys His Pro  Pro Lys Asp His Ile  Val Thr His
    1190                1195                1200

Pro Gln  Tyr His Ala Gln Thr  Phe Thr Ala Ala Val  Ser Lys Thr
    1205                1210                1215
```

```
Ala Trp  Thr Trp Leu Thr Ser  Leu Leu Gly Gly Ser  Ala Val Ile
    1220                1225                1230

Ile Ile  Ile Gly Leu Val Leu  Ala Thr Ile Val Ala  Met Tyr Val
    1235                1240                1245

Leu Thr  Asn Gln Lys His Asn
    1250                1255


<210> SEQ ID NO 4
<211> LENGTH: 1405
<212> TYPE: PRT
<213> ORGANISM: Artificial Sequence
<220> FEATURE:
<223> OTHER INFORMATION: Synthetic CHIKV+TNFalpha peptide

<400> SEQUENCE: 4

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320
```

```
His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Ser Gly Gly Lys Pro Val Ala His Val
        515                 520                 525

Val Ala Asn Pro Gln Ala Glu Gly Gln Leu Gln Trp Leu Asn Arg Arg
    530                 535                 540

Ala Asn Ala Leu Leu Ala Asn Gly Val Glu Leu Arg Asp Asn Gln Leu
545                 550                 555                 560

Val Val Pro Ser Glu Gly Leu Tyr Leu Ile Tyr Ser Gln Val Leu Phe
                565                 570                 575

Lys Gly Gln Gly Cys Pro Ser Thr His Val Leu Leu Thr His Thr Ile
            580                 585                 590

Ser Arg Ile Ala Val Ser Tyr Gln Thr Lys Val Asn Leu Leu Ser Ala
        595                 600                 605

Ile Lys Ser Pro Cys Gln Arg Glu Thr Pro Glu Gly Ala Glu Ala Lys
    610                 615                 620

Pro Trp Tyr Glu Pro Ile Tyr Leu Gly Gly Val Phe Gln Leu Glu Lys
625                 630                 635                 640

Gly Asp Arg Leu Ser Ala Glu Ile Asn Arg Pro Asp Tyr Leu Asp Phe
                645                 650                 655

Ala Glu Ser Gly Gln Val Tyr Phe Gly Ile Ile Ala Leu Thr Arg Gly
            660                 665                 670

Gly Ser Gly Gly Gln Thr Val Arg Tyr Lys Cys Asn Cys Gly Gly Ser
        675                 680                 685

Asn Glu Gly Leu Thr Thr Thr Asp Lys Val Ile Asn Asn Cys Lys Ile
    690                 695                 700

Asp Gln Cys His Ala Ala Val Thr Asn His Lys Asn Trp Gln Tyr Asn
705                 710                 715                 720

Ser Pro Leu Val Pro Arg Asn Ala Glu Leu Gly Asp Arg Lys Gly Lys
                725                 730                 735

Ile His Ile Pro Phe Pro Leu Ala Asn Val Thr Cys Arg Val Pro Lys
```

```
            740                 745                 750

Ala Arg Asn Pro Thr Val Thr Tyr Gly Lys Asn Gln Val Thr Met Leu
        755                 760                 765

Leu Tyr Pro Asp His Pro Thr Leu Leu Ser Tyr Arg Asn Met Gly Gln
    770                 775                 780

Glu Pro Asn Tyr His Glu Glu Trp Val Thr His Lys Lys Glu Val Thr
785                 790                 795                 800

Leu Thr Val Pro Thr Glu Gly Leu Glu Val Thr Trp Gly Asn Asn Glu
                805                 810                 815

Pro Tyr Lys Tyr Trp Pro Gln Met Ser Thr Asn Gly Thr Ala His Gly
            820                 825                 830

His Pro His Glu Ile Ile Leu Tyr Tyr Tyr Glu Leu Tyr Pro Thr Met
        835                 840                 845

Thr Val Val Ile Val Ser Val Ala Ser Phe Val Leu Leu Ser Met Val
    850                 855                 860

Gly Thr Ala Val Gly Met Cys Val Cys Ala Arg Arg Arg Cys Ile Thr
865                 870                 875                 880

Pro Tyr Glu Leu Thr Pro Gly Ala Thr Val Pro Phe Leu Leu Ser Leu
                885                 890                 895

Leu Cys Cys Val Arg Thr Thr Lys Ala Ala Thr Tyr Tyr Glu Ala Ala
            900                 905                 910

Ala Tyr Leu Trp Asn Glu Gln Gln Pro Leu Phe Trp Leu Gln Ala Leu
        915                 920                 925

Ile Pro Leu Ala Ala Leu Ile Val Leu Cys Asn Cys Leu Lys Leu Leu
    930                 935                 940

Pro Cys Cys Cys Lys Thr Leu Ala Phe Leu Ala Val Met Ser Ile Gly
945                 950                 955                 960

Ala His Thr Val Ser Ala Tyr Glu His Val Thr Val Ile Pro Asn Thr
                965                 970                 975

Val Gly Val Pro Tyr Lys Thr Leu Val Asn Arg Pro Gly Tyr Ser Pro
            980                 985                 990

Met Val Leu Glu Met Glu Leu Gln  Ser Val Thr Leu Glu  Pro Thr Leu
        995                 1000                1005

Ser Leu  Asp Tyr Ile Thr Cys  Glu Tyr Lys Thr Val  Ile Pro Ser
    1010                 1015                 1020

Pro Tyr  Val Lys Cys Cys Gly  Thr Ala Glu Cys Lys  Asp Lys Ser
    1025                 1030                 1035

Leu Pro  Asp Tyr Ser Cys Lys  Val Phe Thr Gly Val  Tyr Pro Phe
    1040                 1045                 1050

Met Trp  Gly Gly Ala Tyr Cys  Phe Cys Asp Ala Glu  Asn Thr Gln
    1055                 1060                 1065

Leu Ser  Glu Ala His Val Glu  Lys Ser Glu Ser Cys  Lys Thr Glu
    1070                 1075                 1080

Phe Ala  Ser Ala Tyr Arg Ala  His Thr Ala Ser Ala  Ser Ala Lys
    1085                 1090                 1095

Leu Arg  Val Leu Tyr Gln Gly  Asn Asn Ile Thr Val  Ala Ala Tyr
    1100                 1105                 1110

Ala Asn  Gly Asp His Ala Val  Thr Val Lys Asp Ala  Lys Phe Val
    1115                 1120                 1125

Val Gly  Pro Met Ser Ser Ala  Trp Thr Pro Phe Asp  Asn Lys Ile
    1130                 1135                 1140

Val Val  Tyr Lys Gly Asp Val  Tyr Asn Met Asp Tyr  Pro Pro Phe
    1145                 1150                 1155
```

```
Gly Ala  Gly Arg Pro Gly Gln  Phe Gly Asp Ile Gln  Ser Arg Thr
    1160                 1165                 1170

Pro Glu  Ser Lys Asp Val Tyr  Ala Asn Thr Gln Leu  Val Leu Gln
    1175                 1180                 1185

Arg Pro  Ala Ala Gly Thr Val  His Val Pro Tyr Ser  Gln Ala Pro
    1190                 1195                 1200

Ser Gly  Phe Lys Tyr Trp Leu  Lys Glu Arg Gly Ala  Ser Leu Gln
    1205                 1210                 1215

His Thr  Ala Pro Phe Gly Cys  Gln Ile Ala Thr Asn  Pro Val Arg
    1220                 1225                 1230

Ala Val  Asn Cys Ala Val Gly  Asn Ile Pro Ile Ser  Ile Asp Ile
    1235                 1240                 1245

Pro Asp  Ala Ala Phe Thr Arg  Val Val Asp Ala Pro  Ser Val Thr
    1250                 1255                 1260

Asp Met  Ser Cys Glu Val Pro  Ala Cys Thr His Ser  Ser Asp Phe
    1265                 1270                 1275

Gly Gly  Val Ala Ile Ile Lys  Tyr Thr Ala Ser Lys  Lys Gly Lys
    1280                 1285                 1290

Cys Ala  Val His Ser Met Thr  Asn Ala Val Thr Ile  Arg Glu Ala
    1295                 1300                 1305

Asp Val  Glu Val Glu Gly Asn  Ser Gln Leu Gln Ile  Ser Phe Ser
    1310                 1315                 1320

Thr Ala  Leu Ala Ser Ala Glu  Phe Arg Val Gln Val  Cys Ser Thr
    1325                 1330                 1335

Gln Val  His Cys Ala Ala Ala  Cys His Pro Pro Lys  Asp His Ile
    1340                 1345                 1350

Val Asn  Tyr Pro Ala Ser His  Thr Thr Leu Gly Val  Gln Asp Ile
    1355                 1360                 1365

Ser Thr  Thr Ala Met Ser Trp  Val Gln Lys Ile Thr  Gly Gly Val
    1370                 1375                 1380

Gly Leu  Ile Val Ala Val Ala  Ala Leu Ile Leu Ile  Val Val Leu
    1385                 1390                 1395

Cys Val  Ser Phe Ser Arg His
    1400                 1405


<210> SEQ ID NO 5
<211> LENGTH: 1276
<212> TYPE: PRT
<213> ORGANISM: Artificial Sequence
<220> FEATURE:
<223> OTHER INFORMATION: Synthetic CHIKV+CD20 peptide

<400> SEQUENCE: 5

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95
```

```
Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510
```

```
Val Lys Ile Thr Val Asn Gly Gln Thr Val Arg Tyr Lys Cys Asn Cys
        515                 520                 525

Gly Gly Ser Gly Gly Ile Tyr Asn Cys Glu Pro Ala Asn Pro Ser Glu
    530                 535                 540

Lys Asn Ser Pro Ser Thr Gln Tyr Cys Tyr Ser Ile Gln Gly Ser Asn
545                 550                 555                 560

Glu Gly Leu Thr Thr Thr Asp Lys Val Ile Asn Asn Cys Lys Ile Asp
                565                 570                 575

Gln Cys His Ala Ala Val Thr Asn His Lys Asn Trp Gln Tyr Asn Ser
            580                 585                 590

Pro Leu Val Pro Arg Asn Ala Glu Leu Gly Asp Arg Lys Gly Lys Ile
        595                 600                 605

His Ile Pro Phe Pro Leu Ala Asn Val Thr Cys Arg Val Pro Lys Ala
    610                 615                 620

Arg Asn Pro Thr Val Thr Tyr Gly Lys Asn Gln Val Thr Met Leu Leu
625                 630                 635                 640

Tyr Pro Asp His Pro Thr Leu Leu Ser Tyr Arg Asn Met Gly Gln Glu
                645                 650                 655

Pro Asn Tyr His Glu Glu Trp Val Thr His Lys Lys Glu Val Thr Leu
            660                 665                 670

Thr Val Pro Thr Glu Gly Leu Glu Val Thr Trp Gly Asn Asn Glu Pro
        675                 680                 685

Tyr Lys Tyr Trp Pro Gln Met Ser Thr Asn Gly Thr Ala His Gly His
    690                 695                 700

Pro His Glu Ile Ile Leu Tyr Tyr Tyr Glu Leu Tyr Pro Thr Met Thr
705                 710                 715                 720

Val Val Ile Val Ser Val Ala Ser Phe Val Leu Leu Ser Met Val Gly
                725                 730                 735

Thr Ala Val Gly Met Cys Val Cys Ala Arg Arg Arg Cys Ile Thr Pro
            740                 745                 750

Tyr Glu Leu Thr Pro Gly Ala Thr Val Pro Phe Leu Leu Ser Leu Leu
        755                 760                 765

Cys Cys Val Arg Thr Thr Lys Ala Ala Thr Tyr Tyr Glu Ala Ala Ala
    770                 775                 780

Tyr Leu Trp Asn Glu Gln Gln Pro Leu Phe Trp Leu Gln Ala Leu Ile
785                 790                 795                 800

Pro Leu Ala Ala Leu Ile Val Leu Cys Asn Cys Leu Lys Leu Leu Pro
                805                 810                 815

Cys Cys Cys Lys Thr Leu Ala Phe Leu Ala Val Met Ser Ile Gly Ala
            820                 825                 830

His Thr Val Ser Ala Tyr Glu His Val Thr Val Ile Pro Asn Thr Val
        835                 840                 845

Gly Val Pro Tyr Lys Thr Leu Val Asn Arg Pro Gly Tyr Ser Pro Met
    850                 855                 860

Val Leu Glu Met Glu Leu Gln Ser Val Thr Leu Glu Pro Thr Leu Ser
865                 870                 875                 880

Leu Asp Tyr Ile Thr Cys Glu Tyr Lys Thr Val Ile Pro Ser Pro Tyr
                885                 890                 895

Val Lys Cys Cys Gly Thr Ala Glu Cys Lys Asp Lys Ser Leu Pro Asp
            900                 905                 910

Tyr Ser Cys Lys Val Phe Thr Gly Val Tyr Pro Phe Met Trp Gly Gly
        915                 920                 925

Ala Tyr Cys Phe Cys Asp Ala Glu Asn Thr Gln Leu Ser Glu Ala His
```

```
930                 935                 940

Val Glu Lys Ser Glu Ser Cys Lys Thr Glu Phe Ala Ser Ala Tyr Arg
945                 950                 955                 960

Ala His Thr Ala Ser Ala Ser Ala Lys Leu Arg Val Leu Tyr Gln Gly
                965                 970                 975

Asn Asn Ile Thr Val Ala Ala Tyr Ala Asn Gly Asp His Ala Val Thr
            980                 985                 990

Val Lys Asp Ala Lys Phe Val Val  Gly Pro Met Ser Ser  Ala Trp Thr
        995                 1000                1005

Pro Phe  Asp Asn Lys Ile Val  Val Tyr Lys Gly Asp  Val Tyr Asn
    1010                 1015                1020

Met Asp  Tyr Pro Pro Phe Gly  Ala Gly Arg Pro Gly  Gln Phe Gly
    1025                 1030                1035

Asp Ile  Gln Ser Arg Thr Pro  Glu Ser Lys Asp Val  Tyr Ala Asn
    1040                 1045                1050

Thr Gln  Leu Val Leu Gln Arg  Pro Ala Ala Gly Thr  Val His Val
    1055                 1060                1065

Pro Tyr  Ser Gln Ala Pro Ser  Gly Phe Lys Tyr Trp  Leu Lys Glu
    1070                 1075                1080

Arg Gly  Ala Ser Leu Gln His  Thr Ala Pro Phe Gly  Cys Gln Ile
    1085                 1090                1095

Ala Thr  Asn Pro Val Arg Ala  Val Asn Cys Ala Val  Gly Asn Ile
    1100                 1105                1110

Pro Ile  Ser Ile Asp Ile Pro  Asp Ala Ala Phe Thr  Arg Val Val
    1115                 1120                1125

Asp Ala  Pro Ser Val Thr Asp  Met Ser Cys Glu Val  Pro Ala Cys
    1130                 1135                1140

Thr His  Ser Ser Asp Phe Gly  Gly Val Ala Ile Ile  Lys Tyr Thr
    1145                 1150                1155

Ala Ser  Lys Lys Gly Lys Cys  Ala Val His Ser Met  Thr Asn Ala
    1160                 1165                1170

Val Thr  Ile Arg Glu Ala Asp  Val Glu Val Glu Gly  Asn Ser Gln
    1175                 1180                1185

Leu Gln  Ile Ser Phe Ser Thr  Ala Leu Ala Ser Ala  Glu Phe Arg
    1190                 1195                1200

Val Gln  Val Cys Ser Thr Gln  Val His Cys Ala Ala  Ala Cys His
    1205                 1210                1215

Pro Pro  Lys Asp His Ile Val  Asn Tyr Pro Ala Ser  His Thr Thr
    1220                 1225                1230

Leu Gly  Val Gln Asp Ile Ser  Thr Thr Ala Met Ser  Trp Val Gln
    1235                 1240                1245

Lys Ile  Thr Gly Gly Val Gly  Leu Ile Val Ala Val  Ala Ala Leu
    1250                 1255                1260

Ile Leu  Ile Val Val Leu Cys  Val Ser Phe Ser Arg  His
    1265                 1270                1275


<210> SEQ ID NO 6
<211> LENGTH: 1410
<212> TYPE: PRT
<213> ORGANISM: Artificial Sequence
<220> FEATURE:
<223> OTHER INFORMATION: Synthetic VEEV+TNFalpha peptide

<400> SEQUENCE: 6

Met Phe Pro Phe Gln Pro Met Tyr Pro Met Gln Pro Met Pro Tyr Arg
```

-continued

```
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430
```

```
Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Lys Pro Val Ala His Val Val
        515                 520                 525

Ala Asn Pro Gln Ala Glu Gly Gln Leu Gln Trp Leu Asn Arg Arg Ala
    530                 535                 540

Asn Ala Leu Leu Ala Asn Gly Val Glu Leu Arg Asp Asn Gln Leu Val
545                 550                 555                 560

Val Pro Ser Glu Gly Leu Tyr Leu Ile Tyr Ser Gln Val Leu Phe Lys
                565                 570                 575

Gly Gln Gly Cys Pro Ser Thr His Val Leu Leu Thr His Thr Ile Ser
            580                 585                 590

Arg Ile Ala Val Ser Tyr Gln Thr Lys Val Asn Leu Leu Ser Ala Ile
        595                 600                 605

Lys Ser Pro Cys Gln Arg Glu Thr Pro Glu Gly Ala Glu Ala Lys Pro
    610                 615                 620

Trp Tyr Glu Pro Ile Tyr Leu Gly Gly Val Phe Gln Leu Glu Lys Gly
625                 630                 635                 640

Asp Arg Leu Ser Ala Glu Ile Asn Arg Pro Asp Tyr Leu Asp Phe Ala
                645                 650                 655

Glu Ser Gly Gln Val Tyr Phe Gly Ile Ile Ala Leu Thr Arg Gly Gly
            660                 665                 670

Ser Ser Val Thr Val Thr Pro Pro Asp Gly Thr Ser Ala Leu Val Glu
        675                 680                 685

Cys Glu Cys Gly Gly Thr Lys Ile Ser Glu Thr Ile Asn Lys Thr Lys
    690                 695                 700

Gln Phe Ser Gln Cys Thr Lys Lys Glu Gln Cys Arg Ala Tyr Arg Leu
705                 710                 715                 720

Gln Asn Asp Lys Trp Val Tyr Asn Ser Asp Lys Leu Pro Lys Ala Ala
                725                 730                 735

Gly Ala Thr Leu Lys Gly Lys Leu His Val Pro Phe Leu Leu Ala Asp
            740                 745                 750

Gly Lys Cys Thr Val Pro Leu Ala Pro Glu Pro Met Ile Thr Phe Gly
        755                 760                 765

Phe Arg Ser Val Ser Leu Lys Leu His Pro Lys Asn Pro Thr Tyr Leu
    770                 775                 780

Ile Thr Arg Gln Leu Ala Asp Glu Pro His Tyr Thr His Glu Leu Ile
785                 790                 795                 800

Ser Glu Pro Ala Val Arg Asn Phe Thr Val Thr Glu Lys Gly Trp Glu
                805                 810                 815

Phe Val Trp Gly Asn His Pro Pro Lys Arg Phe Trp Ala Gln Glu Thr
            820                 825                 830

Ala Pro Gly Asn Pro His Gly Leu Pro His Glu Val Ile Thr His Tyr
        835                 840                 845
```

```
Tyr His Arg Tyr Pro Met Ser Thr Ile Leu Gly Leu Ser Ile Cys Ala
    850                 855                 860

Ala Ile Ala Thr Val Ser Val Ala Ala Ser Thr Trp Leu Phe Cys Arg
865                 870                 875                 880

Ser Arg Val Ala Cys Leu Thr Pro Tyr Arg Leu Thr Pro Asn Ala Arg
                885                 890                 895

Ile Pro Phe Cys Leu Ala Val Leu Cys Cys Ala Arg Thr Ala Arg Ala
            900                 905                 910

Glu Thr Thr Trp Glu Ser Leu Asp His Leu Trp Asn Asn Asn Gln Gln
        915                 920                 925

Met Phe Trp Ile Gln Leu Leu Ile Pro Leu Ala Ala Leu Ile Val Val
    930                 935                 940

Thr Arg Leu Leu Arg Cys Val Cys Cys Val Val Pro Phe Leu Val Met
945                 950                 955                 960

Ala Gly Ala Ala Gly Ala Gly Ala Tyr Glu His Ala Thr Thr Met Pro
                965                 970                 975

Ser Gln Ala Gly Ile Ser Tyr Asn Thr Ile Val Asn Arg Ala Gly Tyr
            980                 985                 990

Ala Pro Leu Pro Ile Ser Ile Thr  Pro Thr Lys Ile Lys  Leu Ile Pro
        995                 1000                1005

Thr Val  Asn Leu Glu Tyr Val  Thr Cys His Tyr Lys  Thr Gly Met
    1010                1015                1020

Asp Ser  Pro Ala Ile Lys Cys  Cys Gly Ser Gln Glu  Cys Thr Pro
    1025                1030                1035

Thr Tyr  Arg Pro Asp Glu Gln  Cys Lys Val Phe Thr  Gly Val Tyr
    1040                1045                1050

Pro Phe  Met Trp Gly Gly Ala  Tyr Cys Phe Cys Asp  Thr Glu Asn
    1055                1060                1065

Thr Gln  Val Ser Lys Ala Tyr  Val Met Lys Ser Asp  Asp Cys Leu
    1070                1075                1080

Ala Asp  His Ala Glu Ala Tyr  Lys Ala His Thr Ala  Ser Val Gln
    1085                1090                1095

Ala Phe  Leu Asn Ile Thr Val  Gly Glu His Ser Ile  Val Thr Thr
    1100                1105                1110

Val Tyr  Val Asn Gly Glu Thr  Pro Val Asn Phe Asn  Gly Val Lys
    1115                1120                1125

Ile Thr  Ala Gly Pro Leu Ser  Thr Ala Trp Thr Pro  Phe Asp Arg
    1130                1135                1140

Lys Ile  Val Gln Tyr Ala Gly  Glu Ile Tyr Asn Tyr  Asp Phe Pro
    1145                1150                1155

Glu Tyr  Gly Ala Gly Gln Pro  Gly Ala Phe Gly Asp  Ile Gln Ser
    1160                1165                1170

Arg Thr  Val Ser Ser Ser Asp  Leu Tyr Ala Asn Thr  Asn Leu Val
    1175                1180                1185

Leu Gln  Arg Pro Lys Ala Gly  Ala Ile His Val Pro  Tyr Thr Gln
    1190                1195                1200

Ala Pro  Ser Gly Phe Glu Gln  Trp Lys Lys Asp Lys  Ala Pro Ser
    1205                1210                1215

Leu Lys  Phe Thr Ala Pro Phe  Gly Cys Glu Ile Tyr  Thr Asn Pro
    1220                1225                1230

Ile Arg  Ala Glu Asn Cys Ala  Val Gly Ser Ile Pro  Leu Ala Phe
    1235                1240                1245

Asp Ile  Pro Asp Ala Leu Phe  Thr Arg Val Ser Glu  Thr Pro Thr
```

```
    1250                1255                1260

Leu Ser  Ala Ala Glu Cys Thr  Leu Asn Glu Cys Val  Tyr Ser Ser
    1265                1270                1275

Asp Phe  Gly Gly Ile Ala Thr  Val Lys Tyr Ser Ala  Ser Lys Ser
    1280                1285                1290

Gly Lys  Cys Ala Val His Val  Pro Ser Gly Thr Ala  Thr Leu Lys
    1295                1300                1305

Glu Ala  Ala Val Glu Leu Thr  Glu Gln Gly Ser Ala  Thr Ile His
    1310                1315                1320

Phe Ser  Thr Ala Asn Ile His  Pro Glu Phe Arg Leu  Gln Ile Cys
    1325                1330                1335

Thr Ser  Tyr Val Thr Cys Lys  Gly Asp Cys His Pro  Pro Lys Asp
    1340                1345                1350

His Ile  Val Thr His Pro Gln  Tyr His Ala Gln Thr  Phe Thr Ala
    1355                1360                1365

Ala Val  Ser Lys Thr Ala Trp  Thr Trp Leu Thr Ser  Leu Leu Gly
    1370                1375                1380

Gly Ser  Ala Val Ile Ile Ile  Ile Gly Leu Val Leu  Ala Thr Ile
    1385                1390                1395

Val Ala  Met Tyr Val Leu Thr  Asn Gln Lys His Asn
    1400                1405                1410


<210> SEQ ID NO 7
<211> LENGTH: 1284
<212> TYPE: PRT
<213> ORGANISM: Artificial Sequence
<220> FEATURE:
<223> OTHER INFORMATION: Synthetic VEEV+CD20 peptide

<400> SEQUENCE: 7

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
```

```
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Ile Tyr Asn Cys Glu Pro Ala
        515                 520                 525

Asn Pro Ser Glu Lys Asn Ser Pro Ser Thr Gln Tyr Cys Tyr Ser Ile
    530                 535                 540

Gln Gly Ser Ser Val Thr Val Thr Pro Pro Asp Gly Thr Ser Ala Leu
545                 550                 555                 560

Val Glu Cys Glu Cys Gly Gly Thr Lys Ile Ser Glu Thr Ile Asn Lys
                565                 570                 575

Thr Lys Gln Phe Ser Gln Cys Thr Lys Lys Glu Gln Cys Arg Ala Tyr
            580                 585                 590

Arg Leu Gln Asn Asp Lys Trp Val Tyr Asn Ser Asp Lys Leu Pro Lys
        595                 600                 605

Ala Ala Gly Ala Thr Leu Lys Gly Lys Leu His Val Pro Phe Leu Leu
    610                 615                 620
```

```
Ala Asp Gly Lys Cys Thr Val Pro Leu Ala Pro Glu Pro Met Ile Thr
625                 630                 635                 640

Phe Gly Phe Arg Ser Val Ser Leu Lys Leu His Pro Lys Asn Pro Thr
                645                 650                 655

Tyr Leu Ile Thr Arg Gln Leu Ala Asp Glu Pro His Tyr Thr His Glu
            660                 665                 670

Leu Ile Ser Glu Pro Ala Val Arg Asn Phe Thr Val Thr Glu Lys Gly
        675                 680                 685

Trp Glu Phe Val Trp Gly Asn His Pro Pro Lys Arg Phe Trp Ala Gln
    690                 695                 700

Glu Thr Ala Pro Gly Asn Pro His Gly Leu Pro His Glu Val Ile Thr
705                 710                 715                 720

His Tyr Tyr His Arg Tyr Pro Met Ser Thr Ile Leu Gly Leu Ser Ile
                725                 730                 735

Cys Ala Ala Ile Ala Thr Val Ser Val Ala Ala Ser Thr Trp Leu Phe
            740                 745                 750

Cys Arg Ser Arg Val Ala Cys Leu Thr Pro Tyr Arg Leu Thr Pro Asn
        755                 760                 765

Ala Arg Ile Pro Phe Cys Leu Ala Val Leu Cys Cys Ala Arg Thr Ala
    770                 775                 780

Arg Ala Glu Thr Thr Trp Glu Ser Leu Asp His Leu Trp Asn Asn Asn
785                 790                 795                 800

Gln Gln Met Phe Trp Ile Gln Leu Leu Ile Pro Leu Ala Ala Leu Ile
                805                 810                 815

Val Val Thr Arg Leu Leu Arg Cys Val Cys Cys Val Val Pro Phe Leu
            820                 825                 830

Val Met Ala Gly Ala Ala Gly Ala Gly Ala Tyr Glu His Ala Thr Thr
        835                 840                 845

Met Pro Ser Gln Ala Gly Ile Ser Tyr Asn Thr Ile Val Asn Arg Ala
    850                 855                 860

Gly Tyr Ala Pro Leu Pro Ile Ser Ile Thr Pro Thr Lys Ile Lys Leu
865                 870                 875                 880

Ile Pro Thr Val Asn Leu Glu Tyr Val Thr Cys His Tyr Lys Thr Gly
                885                 890                 895

Met Asp Ser Pro Ala Ile Lys Cys Cys Gly Ser Gln Glu Cys Thr Pro
            900                 905                 910

Thr Tyr Arg Pro Asp Glu Gln Cys Lys Val Phe Thr Gly Val Tyr Pro
        915                 920                 925

Phe Met Trp Gly Gly Ala Tyr Cys Phe Cys Asp Thr Glu Asn Thr Gln
    930                 935                 940

Val Ser Lys Ala Tyr Val Met Lys Ser Asp Asp Cys Leu Ala Asp His
945                 950                 955                 960

Ala Glu Ala Tyr Lys Ala His Thr Ala Ser Val Gln Ala Phe Leu Asn
                965                 970                 975

Ile Thr Val Gly Glu His Ser Ile Val Thr Thr Val Tyr Val Asn Gly
            980                 985                 990

Glu Thr Pro Val Asn Phe Asn Gly  Val Lys Ile Thr Ala  Gly Pro Leu
        995                 1000                1005

Ser Thr  Ala Trp Thr Pro Phe  Asp Arg Lys Ile Val  Gln Tyr Ala
    1010                1015                1020

Gly Glu  Ile Tyr Asn Tyr Asp  Phe Pro Glu Tyr Gly  Ala Gly Gln
    1025                1030                1035
```

```
Pro Gly  Ala Phe Gly Asp Ile  Gln Ser Arg Thr Val  Ser Ser Ser
    1040                 1045                 1050

Asp Leu  Tyr Ala Asn Thr Asn  Leu Val Leu Gln Arg  Pro Lys Ala
    1055                 1060                 1065

Gly Ala  Ile His Val Pro Tyr  Thr Gln Ala Pro Ser  Gly Phe Glu
    1070                 1075                 1080

Gln Trp  Lys Lys Asp Lys Ala  Pro Ser Leu Lys Phe  Thr Ala Pro
    1085                 1090                 1095

Phe Gly  Cys Glu Ile Tyr Thr  Asn Pro Ile Arg Ala  Glu Asn Cys
    1100                 1105                 1110

Ala Val  Gly Ser Ile Pro Leu  Ala Phe Asp Ile Pro  Asp Ala Leu
    1115                 1120                 1125

Phe Thr  Arg Val Ser Glu Thr  Pro Thr Leu Ser Ala  Ala Glu Cys
    1130                 1135                 1140

Thr Leu  Asn Glu Cys Val Tyr  Ser Ser Asp Phe Gly  Gly Ile Ala
    1145                 1150                 1155

Thr Val  Lys Tyr Ser Ala Ser  Lys Ser Gly Lys Cys  Ala Val His
    1160                 1165                 1170

Val Pro  Ser Gly Thr Ala Thr  Leu Lys Glu Ala Ala  Val Glu Leu
    1175                 1180                 1185

Thr Glu  Gln Gly Ser Ala Thr  Ile His Phe Ser Thr  Ala Asn Ile
    1190                 1195                 1200

His Pro  Glu Phe Arg Leu Gln  Ile Cys Thr Ser Tyr  Val Thr Cys
    1205                 1210                 1215

Lys Gly  Asp Cys His Pro Pro  Lys Asp His Ile Val  Thr His Pro
    1220                 1225                 1230

Gln Tyr  His Ala Gln Thr Phe  Thr Ala Ala Val Ser  Lys Thr Ala
    1235                 1240                 1245

Trp Thr  Trp Leu Thr Ser Leu  Leu Gly Gly Ser Ala  Val Ile Ile
    1250                 1255                 1260

Ile Ile  Gly Leu Val Leu Ala  Thr Ile Val Ala Met  Tyr Val Leu
    1265                 1270                 1275

Thr Asn  Gln Lys His Asn
    1280


<210> SEQ ID NO 8
<211> LENGTH: 1279
<212> TYPE: PRT
<213> ORGANISM: Artificial Sequence
<220> FEATURE:
<223> OTHER INFORMATION: Synthetic VEEV+CTLA4 peptide

<400> SEQUENCE: 8

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95
```

```
Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Gly Cys Lys Val Glu Leu Met
```

-continued

```
        515                 520                 525

Tyr Pro Pro Pro Tyr Tyr Leu Gly Ile Gly Gly Gly Gly Ser Ser Val
    530                 535                 540

Thr Val Thr Pro Pro Asp Gly Thr Ser Ala Leu Val Glu Cys Glu Cys
545                 550                 555                 560

Gly Gly Thr Lys Ile Ser Glu Thr Ile Asn Lys Thr Lys Gln Phe Ser
                565                 570                 575

Gln Cys Thr Lys Lys Glu Gln Cys Arg Ala Tyr Arg Leu Gln Asn Asp
            580                 585                 590

Lys Trp Val Tyr Asn Ser Asp Lys Leu Pro Lys Ala Ala Gly Ala Thr
        595                 600                 605

Leu Lys Gly Lys Leu His Val Pro Phe Leu Leu Ala Asp Gly Lys Cys
    610                 615                 620

Thr Val Pro Leu Ala Pro Glu Pro Met Ile Thr Phe Gly Phe Arg Ser
625                 630                 635                 640

Val Ser Leu Lys Leu His Pro Lys Asn Pro Thr Tyr Leu Ile Thr Arg
                645                 650                 655

Gln Leu Ala Asp Glu Pro His Tyr Thr His Glu Leu Ile Ser Glu Pro
            660                 665                 670

Ala Val Arg Asn Phe Thr Val Thr Glu Lys Gly Trp Glu Phe Val Trp
        675                 680                 685

Gly Asn His Pro Pro Lys Arg Phe Trp Ala Gln Glu Thr Ala Pro Gly
    690                 695                 700

Asn Pro His Gly Leu Pro His Glu Val Ile Thr His Tyr Tyr His Arg
705                 710                 715                 720

Tyr Pro Met Ser Thr Ile Leu Gly Leu Ser Ile Cys Ala Ala Ile Ala
                725                 730                 735

Thr Val Ser Val Ala Ala Ser Thr Trp Leu Phe Cys Arg Ser Arg Val
            740                 745                 750

Ala Cys Leu Thr Pro Tyr Arg Leu Thr Pro Asn Ala Arg Ile Pro Phe
        755                 760                 765

Cys Leu Ala Val Leu Cys Cys Ala Arg Thr Ala Arg Ala Glu Thr Thr
    770                 775                 780

Trp Glu Ser Leu Asp His Leu Trp Asn Asn Asn Gln Gln Met Phe Trp
785                 790                 795                 800

Ile Gln Leu Leu Ile Pro Leu Ala Ala Leu Ile Val Val Thr Arg Leu
                805                 810                 815

Leu Arg Cys Val Cys Cys Val Val Pro Phe Leu Val Met Ala Gly Ala
            820                 825                 830

Ala Gly Ala Gly Ala Tyr Glu His Ala Thr Thr Met Pro Ser Gln Ala
        835                 840                 845

Gly Ile Ser Tyr Asn Thr Ile Val Asn Arg Ala Gly Tyr Ala Pro Leu
    850                 855                 860

Pro Ile Ser Ile Thr Pro Thr Lys Ile Lys Leu Ile Pro Thr Val Asn
865                 870                 875                 880

Leu Glu Tyr Val Thr Cys His Tyr Lys Thr Gly Met Asp Ser Pro Ala
                885                 890                 895

Ile Lys Cys Cys Gly Ser Gln Glu Cys Thr Pro Thr Tyr Arg Pro Asp
            900                 905                 910

Glu Gln Cys Lys Val Phe Thr Gly Val Tyr Pro Phe Met Trp Gly Gly
        915                 920                 925

Ala Tyr Cys Phe Cys Asp Thr Glu Asn Thr Gln Val Ser Lys Ala Tyr
    930                 935                 940
```

```
Val Met Lys Ser Asp Asp Cys Leu Ala Asp His Ala Glu Ala Tyr Lys
945                 950                 955                 960

Ala His Thr Ala Ser Val Gln Ala Phe Leu Asn Ile Thr Val Gly Glu
                965                 970                 975

His Ser Ile Val Thr Thr Val Tyr Val Asn Gly Glu Thr Pro Val Asn
            980                 985                 990

Phe Asn Gly Val Lys Ile Thr Ala  Gly Pro Leu Ser Thr  Ala Trp Thr
        995                 1000                 1005

Pro Phe  Asp Arg Lys Ile Val  Gln Tyr Ala Gly Glu  Ile Tyr Asn
    1010                 1015                 1020

Tyr Asp  Phe Pro Glu Tyr Gly  Ala Gly Gln Pro Gly  Ala Phe Gly
    1025                 1030                 1035

Asp Ile  Gln Ser Arg Thr Val  Ser Ser Ser Asp Leu  Tyr Ala Asn
    1040                 1045                 1050

Thr Asn  Leu Val Leu Gln Arg  Pro Lys Ala Gly Ala  Ile His Val
    1055                 1060                 1065

Pro Tyr  Thr Gln Ala Pro Ser  Gly Phe Glu Gln Trp  Lys Lys Asp
    1070                 1075                 1080

Lys Ala  Pro Ser Leu Lys Phe  Thr Ala Pro Phe Gly  Cys Glu Ile
    1085                 1090                 1095

Tyr Thr  Asn Pro Ile Arg Ala  Glu Asn Cys Ala Val  Gly Ser Ile
    1100                 1105                 1110

Pro Leu  Ala Phe Asp Ile Pro  Asp Ala Leu Phe Thr  Arg Val Ser
    1115                 1120                 1125

Glu Thr  Pro Thr Leu Ser Ala  Ala Glu Cys Thr Leu  Asn Glu Cys
    1130                 1135                 1140

Val Tyr  Ser Ser Asp Phe Gly  Gly Ile Ala Thr Val  Lys Tyr Ser
    1145                 1150                 1155

Ala Ser  Lys Ser Gly Lys Cys  Ala Val His Val Pro  Ser Gly Thr
    1160                 1165                 1170

Ala Thr  Leu Lys Glu Ala Ala  Val Glu Leu Thr Glu  Gln Gly Ser
    1175                 1180                 1185

Ala Thr  Ile His Phe Ser Thr  Ala Asn Ile His Pro  Glu Phe Arg
    1190                 1195                 1200

Leu Gln  Ile Cys Thr Ser Tyr  Val Thr Cys Lys Gly  Asp Cys His
    1205                 1210                 1215

Pro Pro  Lys Asp His Ile Val  Thr His Pro Gln Tyr  His Ala Gln
    1220                 1225                 1230

Thr Phe  Thr Ala Ala Val Ser  Lys Thr Ala Trp Thr  Trp Leu Thr
    1235                 1240                 1245

Ser Leu  Leu Gly Gly Ser Ala  Val Ile Ile Ile Ile  Gly Leu Val
    1250                 1255                 1260

Leu Ala  Thr Ile Val Ala Met  Tyr Val Leu Thr Asn  Gln Lys His
    1265                 1270                 1275

Asn
```

<210> SEQ ID NO 9
<211> LENGTH: 2964
<212> TYPE: DNA
<213> ORGANISM: Artificial Sequence
<220> FEATURE:
<223> OTHER INFORMATION: Synthetic polynucleotide

<400> SEQUENCE: 9

-continued

```
atgagcctcg ccctcccggt cttgtgcctg ttggcaaaca ctacattccc ctgctctcag     60
ccgccttgca caccctgctg ctacgaaaag gaaccggaaa gcaccttgcg catgcttgag    120
gacaacgtga tgagacccgg atactaccag ctactaaaag catcgctgac ttgctctccc    180
caccgccaaa gacgcagtac taaggacaat tttaatgtct ataaagccac aagaccatat    240
ctagctcatt gtcctgactg cggagaaggg cattcgtgcc acagccctat cgcattggag    300
cgcatcagaa atgaagcaac ggacggaacg ctgaaaatcc aggtctcttt gcagatcggg    360
ataaagacag atgacagcca cgattggacc aagctgcgct atatggatag ccatacgcca    420
gcggacgcgg agcgagccgg attgcttgta aggacttcag caccgtgcac gatcaccggg    480
accatgggac actttattct cgcccgatgc ccgaaaggag agacgctgac agtgggattt    540
acggacagca gaaagatcag ccacacatgc acacacccgt tccatcatga accacctgtg    600
ataggtaggg agaggttcca ctctcgacca caacatggta aagagttacc ttgcagcacg    660
tacgtgcaga gcaccgctgc cactgctgag gagatagagg tgcatatgcc cccagatact    720
cctgaccgca cgctgatgac gcagcagtct ggcaacgtga agatcacagt taatgggcag    780
acggtgcggt acaagtgcaa ctgcggtggc tcaaacgagg gactgacaac cacagacaaa    840
gtgatcaata actgcaaaat tgatcagtgc catgctgcag tcactaatca caagaattgg    900
caatacaact cccctttagt cccgcgcaac gctgaactcg gggaccgtaa aggaaagatc    960
cacatcccat tcccattggc aaacgtgact tgcagagtgc caaaagcaag aaaccctaca   1020
gtaacttacg gaaaaaacca agtcaccatg ctgctgtatc ctgaccatcc gacactcttg   1080
tcttaccgta acatgggaca ggaaccaaat taccacgagg agtgggtgac acacaagaag   1140
gaggttacct tgaccgtgcc tactgagggt ctggaggtca cttggggcaa caacgaacca   1200
tacaagtact ggccgcagat gtctacgaac ggtactgctc atggtcaccc acatgagata   1260
atcttgtact attatgagct gtaccccact atgactgtag tcattgtgtc ggtggcctcg   1320
ttcgtgcttc tgtcgatggt gggcacagca gtgggaatgt gtgtgtgcgc acggcgcaga   1380
tgcattacac catatgaatt aacaccagga gccactgttc ccttcctgct cagcctgcta   1440
tgctgcgtca gaacgaccaa ggcggccaca tattacgagg ctgcggcata tctatggaac   1500
gaacagcagc ccctgttctg gttgcaggct cttatcccgc tggccgcctt gatcgtcctg   1560
tgcaactgtc tgaaactctt gccatgctgc tgtaagaccc tggctttttt agccgtaatg   1620
agcatcggtg cccacactgt gagcgcgtac gaacacgtaa cagtgatccc gaacacggtg   1680
ggagtaccgt ataagactct tgtcaacaga ccgggttaca gccccatggt gttggagatg   1740
gagctacaat cagtcacctt ggaaccaaca ctgtcacttg actacatcac gtgcgagtac   1800
aaaactgtca tcccctcccc gtacgtgaag tgctgtggta cagcagagtg caaggacaag   1860
agcctaccag actacagctg caaggtcttt actggagtct acccatttat gtggggcggc   1920
gcctactgct tttgcgacgc cgaaaatacg caattgagcg aggcacatgt agagaaatct   1980
gaatcttgca aaacagagtt tgcatcggcc tacagagccc acaccgcatc ggcgtcggcg   2040
aagctccgcg tcctttacca aggaaacaac attaccgtag ctgcctacgc taacggtgac   2100
catgccgtca cagtaaagga cgccaagttt gtcgtgggcc caatgtcctc cgcctggaca   2160
ccttttgaca acaaaatcgt ggtgtacaaa ggcgacgtct acaacatgga ctacccacct   2220
tttggcgcag gaagaccagg acaatttggt gacattcaaa gtcgtacacc ggaaagtaaa   2280
gacgtttatg ccaacactca gttggtacta cagaggccag cagcaggcac ggtacatgta   2340
ccatactctc aggcaccatc tggcttcaag tattggctga aggaacgagg agcatcgcta   2400
```

```
cagcacacgg caccgttcgg ttgccagatt gcgacaaacc cggtaagagc tgtaaattgc   2460

gctgtgggga acataccaat ttccatcgac ataccggatg cggcctttac tagggttgtc   2520

gatgcaccct ctgtaacgga catgtcatgc gaagtaccag cctgcactca ctcctccgac   2580

tttgggggcg tcgccatcat caaatacaca gctagcaaga aaggtaaatg tgcagtacat   2640

tcgatgacca acgccgttac cattcgagaa gccgacgtag aagtagaggg gaactcccag   2700

ctgcaaatat ccttctcaac agccctggca agcgccgagt ttcgcgtgca agtgtgctcc   2760

acacaagtac actgcgcagc cgcatgccac cctccaaagg accacatagt caattaccca   2820

gcatcacaca ccacccttgg ggtccaggat atatccacaa cggcaatgtc ttgggtgcag   2880

aagattacgg gaggagtagg attaattgtt gctgttgctg ccttaatttt aattgtggtg   2940

ctatgcgtgt cgtttagcag gcac                                          2964
```

<210> SEQ ID NO 10
<211> LENGTH: 2964
<212> TYPE: DNA
<213> ORGANISM: Artificial Sequence
<220> FEATURE:
<223> OTHER INFORMATION: Synthetic polynucleotide

<400> SEQUENCE: 10

```
atgagtcttg ccatcccagt tatgtgcctg ttggcaaaca ccacgttccc ctgctcccag     60

ccccttgca cgccctgctg ctacgaaaag gaaccggagg aaaccctacg catgcttgag    120

gacaacgtca tgagacctgg gtactatcag ctgctacaag catccttaac atgttctccc    180

caccgccagc gacgcagcac caaggacaac ttcaatgtct ataaagccac aagaccatac    240

ttagctcact gtcccgactg tggagaaggg cactcgtgcc atagtcccgt agcactagaa    300

cgcatcagaa atgaagcgac agacgggacg ctgaaaatcc aggtctcctt gcaaatcgga    360

ataaagacgg atgacagcca cgattggacc aagctgcgtt atatggacaa ccacatgcca    420

gcagacgcag agagggcggg gctatttgta agaacatcag caccgtgtac gattactgga    480

acaatgggac acttcatcct ggcccgatgt ccaaaagggg aaactctgac ggtgggattc    540

actgacagta ggaagattag tcactcatgt acgcacccat ttcaccacga ccctcctgtg    600

ataggtcggg aaaaattcca ttcccgaccg cagcacggta aagagctacc ttgcagcacg    660

tacgtgcaga gcaccgccgc aactaccgag gagatagagg tacacatgcc cccagacacc    720

cctgatcgca cattaatgtc acaacagtcc ggcaacgtaa agatcacagt caatggccag    780

acggtgcggt acaagtgtaa ttgcggtggc tcaaatgaag gactaacaac tacagacaaa    840

gtgattaata actgcaaggt tgatcaatgt catgccgcgg tcaccaatca caaaaagtgg    900

cagtataact cccctctggt cccgcgtaat gctgaacttg gggaccgaaa aggaaaaatt    960

cacatcccgt ttccgctggc aaatgtaaca tgcagggtgc ctaaagcaag gaaccccacc   1020

gtgacgtacg ggaaaaacca agtcatcatg ctactgtatc ctgaccaccc aacactcctg   1080

tcctaccgga atatgggaga agaaccaaac tatcaagaag agtgggtgat gcataagaag   1140

gaagtcgtgc taaccgtgcc gactgaaggg ctcgaggtca cgtggggcaa caacgagccg   1200

tataagtatt ggccgcagtt atctacaaac ggtacagccc atggccaccc gcatgagata   1260

attctgtatt attatgagct gtaccccact atgactgtag tagttgtgtc agtggccacg   1320

ttcatactcc tgtcgatggt gggtatggca gcggggatgt gcatgtgtgc acgacgcaga   1380

tgcatcacac cgtatgaact gacaccagga gctaccgtcc ctttcctgct tagcctaata   1440
```

```
tgctgcatca gaacagctaa agcggccaca taccaagagg ctgcgatata cctgtggaac   1500
gagcagcaac ctttgttttg gctacaagcc cttattccgc tggcagccct gattgttcta   1560
tgcaactgtc tgagactctt accatgctgc tgtaaaacgt tggctttttt agccgtaatg   1620
agcgtcggtg cccacactgt gagcgcgtac gaacacgtaa cagtgatccc gaacacggtg   1680
ggagtaccgt ataagactct agtcaataga cctggctaca gccccatggt attggagatg   1740
gaactactgt cagtcacttt ggagccaaca ctatcgcttg attacatcac gtgcgagtac   1800
aaaaccgtca tcccgtctcc gtacgtgaag tgctgcggta cagcagagtg caaggacaaa   1860
aacctacctg actacagctg taaggtcttc accggcgtct acccatttat gtggggcggc   1920
gcctactgct tctgcgacgc tgaaaacacg cagttgagcg aagcacacgt ggagaagtcc   1980
gaatcatgca aaacagaatt tgcatcagca tacagggctc ataccgcatc tgcatcagct   2040
aagctccgcg tcctttacca aggaaataac atcactgtaa ctgcctatgc aaacggcgac   2100
catgccgtca cagttaagga cgccaaattc attgtggggc caatgtcttc agcctggaca   2160
cctttcgaca acaaaattgt ggtgtacaaa ggtgacgtct ataacatgga ctacccgccc   2220
tttggcgcag gaagaccagg acaatttggc gatatccaaa gtcgcacacc tgagagtaaa   2280
gacgtctatg ctaatacaca actggtactg cagagaccgg ctgtgggtac ggtacacgtg   2340
ccatactctc aggcaccatc tggctttaag tattggctaa aagaacgcgg ggcgtcgctg   2400
cagcacacag caccatttgg ctgccaaata gcaacaaacc cggtaagagc ggtgaactgc   2460
gccgtaggga acatgcccat ctccatcgac ataccggaag cggccttcac tagggtcgtc   2520
gacgcgccct ctttaacgga catgtcgtgc gaggtaccag cctgcaccca ttcctcagac   2580
tttgggggcg tcgccattat taaatatgca gccagcaaga aaggcaagtg tgcggtgcat   2640
tcgatgacta acgccgtcac tattcgggaa gctgagatag aagttgaagg gaattctcag   2700
ctgcaaatct ctttctcgac ggccttagcc agcgccgaat tccgcgtaca agtctgttct   2760
acacaagtac actgtgcagc cgagtgccac cccccgaagg accacatagt caactacccg   2820
gcgtcacata ccaccctcgg ggtccaggac atctccgcta cggcgatgtc atgggtgcag   2880
aagatcacgg gaggtgtggg actggttgtt gctgttgccg cactgattct aatcgtggtg   2940
ctatgcgtgt cgttcagcag gcac                                           2964
```

<210> SEQ ID NO 11
<211> LENGTH: 3747
<212> TYPE: DNA
<213> ORGANISM: Artificial Sequence
<220> FEATURE:
<223> OTHER INFORMATION: Synthetic polynucleotide

<400> SEQUENCE: 11

```
atggagttca tcccgacgca aactttctat aacagaaggt accaaccccg accctgggcc     60
ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
```

```
gagaaacccg aggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacacccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tcaaacgagg gactgacaac cacagacaaa   1620
gtgatcaata actgcaaaat tgatcagtgc catgctgcag tcactaatca caagaattgg   1680
caatacaact cccctttagt cccgcgcaac gctgaactcg gggaccgtaa aggaaagatc   1740
cacatcccat tcccattggc aaacgtgact tgcagagtgc caaaagcaag aaaccctaca   1800
gtaacttacg gaaaaaacca agtcaccatg ctgctgtatc ctgaccatcc gacactcttg   1860
tcttaccgta acatgggaca ggaaccaaat taccacgagg agtgggtgac acacaagaag   1920
gaggttacct tgaccgtgcc tactgagggt ctggaggtca cttggggcaa caacgaacca   1980
tacaagtact ggccgcagat gtctacgaac ggtactgctc atggtcaccc acatgagata   2040
atcttgtact attatgagct gtaccccact atgactgtag tcattgtgtc ggtggcctcg   2100
ttcgtgcttc tgtcgatggt gggcacagca gtgggaatgt gtgtgtgcgc acggcgcaga   2160
tgcattacac catatgaatt aacaccagga gccactgttc ccttcctgct cagcctgcta   2220
tgctgcgtca gaacgaccaa ggcggccaca tattacgagg ctgcggcata tctatggaac   2280
gaacagcagc ccctgttctg gttgcaggct cttatcccgc tggccgcctt gatcgtcctg   2340
tgcaactgtc tgaaactctt gccatgctgc tgtaagaccc tggctttttt agccgtaatg   2400
agcatcggtg cccacactgt gagcgcgtac gaacacgtaa cagtgatccc gaacacggtg   2460
ggagtaccgt ataagactct tgtcaacaga ccgggttaca gccccatggt gttggagatg   2520
gagctacaat cagtcacctt ggaaccaaca ctgtcacttg actacatcac gtgcgagtac   2580
aaaactgtca tcccctcccc gtacgtgaag tgctgtggta cagcagagtg caaggacaag   2640
agcctaccag actacagctg caaggtcttt actggagtct acccatttat gtggggcggc   2700
gcctactgct tttgcgacgc cgaaaatacg caattgagcg aggcacatgt agagaaatct   2760
gaatcttgca aaacagagtt tgcatcggcc tacagagccc acaccgcatc ggcgtcggcg   2820
aagctccgcg tcctttacca aggaaacaac attaccgtag ctgcctacgc taacggtgac   2880
```

```
catgccgtca cagtaaagga cgccaagttt gtcgtgggcc caatgtcctc cgcctggaca   2940

ccttttgaca acaaaatcgt ggtgtacaaa ggcgacgtct acaacatgga ctacccacct   3000

tttggcgcag gaagaccagg acaatttggt gacattcaaa gtcgtacacc ggaaagtaaa   3060

gacgtttatg ccaacactca gttggtacta cagaggccag cagcaggcac ggtacatgta   3120

ccatactctc aggcaccatc tggcttcaag tattggctga aggaacgagg agcatcgcta   3180

cagcacacgg caccgttcgg ttgccagatt gcgacaaacc cggtaagagc tgtaaattgc   3240

gctgtgggga acataccaat ttccatcgac ataccggatg cggcctttac tagggttgtc   3300

gatgcaccct ctgtaacgga catgtcatgc gaagtaccag cctgcactca ctcctccgac   3360

tttgggggcg tcgccatcat caaatacaca gctagcaaga aaggtaaatg tgcagtacat   3420

tcgatgacca acgccgttac cattcgagaa gccgacgtag aagtagaggg gaactcccag   3480

ctgcaaatat ccttctcaac agccctggca agcgccgagt ttcgcgtgca agtgtgctcc   3540

acacaagtac actgcgcagc cgcatgccac cctccaaagg accacatagt caattaccca   3600

gcatcacaca ccaccccttgg ggtccaggat atatccacaa cggcaatgtc ttgggtgcag   3660

aagattacgg gaggagtagg attaattgtt gctgttgctg ccttaatttt aattgtggtg   3720

ctatgcgtgt cgtttagcag gcactaa                                          3747
```

```
<210> SEQ ID NO 12
<211> LENGTH: 3747
<212> TYPE: DNA
<213> ORGANISM: Artificial Sequence
<220> FEATURE:
<223> OTHER INFORMATION: Synthetic polynucleotide

<400> SEQUENCE: 12
```

```
atggagttca tcccaaccca aactttttac aataggaggt accagcctcg accctggact     60

ccgcgcccta ctatccaagt catcaggccc agaccgcgcc ctcagaggca agctgggcaa    120

cttgcccagc tgatctcagc agttaataaa ctgacaatgc gcgcggtacc acaacagaag    180

ccacgcagga atcggaagaa taagaagcaa aagcaaaaac aacaggcgcc acaaaacaac    240

acaaatcaaa agaagcagcc acctaaaaag aaaccggctc aaaagaaaaa gaagccgggc    300

cgcagagaga ggatgtgcat gaaaatcgaa aatgattgta ttttcgaagt caagcacgaa    360

ggtaaggtaa caggttacgc gtgcctggtg ggggacaaag taatgaaacc agcacacgta    420

aaggggacca tcgataacgc ggacctggcc aaactggcct ttaagcggtc atctaagtat    480

gaccttgaat gcgcgcagat acccgtgcac atgaagtccg acgcttcgaa gttcacccat    540

gagaaaccgg aggggtacta caactggcac cacggagcag tacagtactc aggaggccgg    600

ttcaccatcc ctacaggtgc tggcaaacca ggggacagcg gcagaccgat cttcgacaac    660

aagggacgcg tggtggccat agtcttagga ggagctaatg aaggagcccg tacagccctc    720

tcggtggtga cctggaataa agacattgtc actaaaatca cccccgaggg ggccgaagag    780

tggagtcttg ccatcccagt tatgtgcctg ttggcaaaca ccacgttccc ctgctcccag    840

ccccccttgca cgccctgctg ctacgaaaag gaaccggagg aaaccctacg catgcttgag    900

gacaacgtca tgagacctgg gtactatcag ctgctacaag catccttaac atgttctccc    960

caccgccagc gacgcagcac caaggacaac ttcaatgtct ataaagccac aagaccatac   1020

ttagctcact gtcccgactg tggagaaggg cactcgtgcc atagtcccgt agcactagaa   1080

cgcatcagaa atgaagcgac agacgggacg ctgaaaatcc aggtctcctt gcaaatcgga   1140

ataaagacgg atgacagcca cgattggacc aagctgcgtt atatggacaa ccacatgcca   1200
```

```
gcagacgcag agagggcggg gctatttgta agaacatcag caccgtgtac gattactgga   1260
acaatgggac acttcatcct ggcccgatgt ccaaaagggg aaactctgac ggtgggattc   1320
actgacagta ggaagattag tcactcatgt acgcacccat ttcaccacga ccctcctgtg   1380
ataggtcggg aaaaattcca ttcccgaccg cagcacggta aagagctacc ttgcagcacg   1440
tacgtgcaga gcaccgccgc aactaccgag gagatagagg tacacatgcc cccagacacc   1500
cctgatcgca cattaatgtc acaacagtcc ggcaacgtaa agatcacagt caatggccag   1560
acggtgcggt acaagtgtaa ttgcggtggc tcaaatgaag gactaacaac tacagacaaa   1620
gtgattaata actgcaaggt tgatcaatgt catgccgcgg tcaccaatca caaaaagtgg   1680
cagtataact cccctctggt cccgcgtaat gctgaacttg ggaccgaaaa aggaaaaatt   1740
cacatcccgt ttccgctggc aaatgtaaca tgcagggtgc ctaaagcaag gaaccccacc   1800
gtgacgtacg ggaaaaacca agtcatcatg ctactgtatc ctgaccaccc aacactcctg   1860
tcctaccgga atatgggaga agaaccaaac tatcaagaag agtgggtgat gcataagaag   1920
gaagtcgtgc taaccgtgcc gactgaaggg ctcgaggtca cgtggggcaa caacgagccg   1980
tataagtatt ggccgcagtt atctacaaac ggtacagccc atggccaccc gcatgagata   2040
attctgtatt attatgagct gtaccccact atgactgtag tagttgtgtc agtggccacg   2100
ttcatactcc tgtcgatggt gggtatggca gcggggatgt gcatgtgtgc acgacgcaga   2160
tgcatcacac cgtatgaact gacaccagga gctaccgtcc ctttcctgct tagcctaata   2220
tgctgcatca gaacagctaa agcggccaca taccaagagg ctgcgatata cctgtggaac   2280
gagcagcaac ctttgttttg gctacaagcc cttattccgc tggcagccct gattgttcta   2340
tgcaactgtc tgagactctt accatgctgc tgtaaaacgt tggctttttt agccgtaatg   2400
agcgtcggtg cccacactgt gagcgcgtac gaacacgtaa cagtgatccc gaacacggtg   2460
ggagtaccgt ataagactct agtcaataga cctggctaca gccccatggt attggagatg   2520
gaactactgt cagtcacttt ggagccaaca ctatcgcttg attacatcac gtgcgagtac   2580
aaaaccgtca tcccgtctcc gtacgtgaag tgctgcggta cagcagagtg caaggacaaa   2640
aacctacctg actacagctg taaggtcttc accggcgtct acccatttat gtggggcggc   2700
gcctactgct tctgcgacgc tgaaaacacg cagttgagcg aagcacacgt ggagaagtcc   2760
gaatcatgca aaacagaatt tgcatcagca tacagggctc ataccgcatc tgcatcagct   2820
aagctccgcg tcctttacca aggaaataac atcactgtaa ctgcctatgc aaacggcgac   2880
catgccgtca cagttaagga cgccaaattc attgtggggc caatgtcttc agcctggaca   2940
cctttcgaca acaaaattgt ggtgtacaaa ggtgacgtct ataacatgga ctacccgccc   3000
tttggcgcag gaagaccagg acaatttggc gatatccaaa gtcgcacacc tgagagtaaa   3060
gacgtctatg ctaatacaca actggtactg cagagaccgg ctgtgggtac ggtacacgtg   3120
ccatactctc aggcaccatc tggctttaag tattggctaa aagaacgcgg ggcgtcgctg   3180
cagcacacag caccatttgg ctgccaaata gcaacaaacc cggtaagagc ggtgaactgc   3240
gccgtaggga acatgcccat ctccatcgac ataccggaag cggccttcac tagggtcgtc   3300
gacgcgccct ctttaacgga catgtcgtgc gaggtaccag cctgcaccca ttcctcagac   3360
tttgggggcg tcgccattat taaatatgca gccagcaaga aaggcaagtg tgcggtgcat   3420
tcgatgacta acgccgtcac tattcgggaa gctgagatag aagttgaagg gaattctcag   3480
ctgcaaatct ctttctcgac ggccttagcc agcgccgaat tccgcgtaca agtctgttct   3540
```

```
acacaagtac actgtgcagc cgagtgccac cccccgaagg accacatagt caactacccg   3600

gcgtcacata ccaccctcgg ggtccaggac atctccgcta cggcgatgtc atgggtgcag   3660

aagatcacgg gaggtgtggg actggttgtt gctgttgccg cactgattct aatcgtggtg   3720

ctatgcgtgt cgttcagcag gcactaa                                        3747
```

<210> SEQ ID NO 13
<211> LENGTH: 4215
<212> TYPE: DNA
<213> ORGANISM: Artificial Sequence
<220> FEATURE:
<223> OTHER INFORMATION: Synthetic polynucleotide encoding CHIKV+TNFalpha

<400> SEQUENCE: 13

```
atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

caccgccaaa gacgcagtac taaggacaat tttaatgtct ataaagccac aagaccatat   1020

ctagctcatt gtcctgactg cggagaaggg cattcgtgcc acagccctat cgcattggag   1080

cgcatcagaa atgaagcaac ggacggaacg ctgaaaatcc aggtctcttt gcagatcggg   1140

ataaagacag atgacagcca cgattggacc aagctgcgct atatggatag ccatacgcca   1200

gcggacgcgg agcgagccgg attgcttgta aggacttcag caccgtgcac gatcaccggg   1260

accatgggac actttattct cgcccgatgc ccgaaaggag agacgctgac agtgggattt   1320

acggacagca gaaagatcag ccacacatgc acacacccgt tccatcatga accacctgtg   1380

ataggtaggg agaggttcca ctctcgacca caacatggta aagagttacc ttgcagcacg   1440

tacgtgcaga gcaccgctgc cactgctgag gagatagagg tgcatatgcc cccagatact   1500

cctgaccgca cgctgatgac gcagcagtct ggcaacgtga agatcacagt taatggctcc   1560

ggaggtaagc ctgtagccca tgttgtagca aaccctcaag ctgaggggca gctccagtgg   1620

ctgaaccgcc gggccaatgc cctcctggcc aatggcgtgg agctgagaga taaccagctg   1680

gtggtgccat cagagggcct gtacctcatc tactcccagg tcctcttcaa gggccaaggc   1740

tgcccctcca cccatgtgct cctcacccac accatcagcc gcatcgccgt ctcctaccag   1800
```

```
accaaggtca acctcctctc tgccatcaag agcccctgcc agagggagac cccagagggg   1860
gctgaggcca agccctggta tgagcccatc tatctgggag ggtcttcca gctggagaag   1920
ggtgaccgac tcagcgctga gatcaatcgg cccgactatc tcgactttgc cgagtctggg   1980
caggtctact ttgggatcat tgccctgacg cgtggaggat ccggcgggca gacggtgcgg   2040
tacaagtgca actgcggtgg ctcaaacgag ggactgacaa ccacagacaa agtgatcaat   2100
aactgcaaaa ttgatcagtg ccatgctgca gtcactaatc acaagaattg gcaatacaac   2160
tcccctttag tcccgcgcaa cgctgaactc ggggaccgta aaggaaagat ccacatccca   2220
ttcccattgg caaacgtgac ttgcagagtg ccaaaagcaa gaaaccctac agtaacttac   2280
ggaaaaaacc aagtcaccat gctgctgtat cctgaccatc cgacactctt gtcttaccgt   2340
aacatgggac aggaaccaaa ttaccacgag gagtgggtga cacacaagaa ggaggttacc   2400
ttgaccgtgc ctactgaggg tctggaggtc acttggggca acaacgaacc atacaagtac   2460
tggccgcaga tgtctacgaa cggtactgct catggtcacc cacatgagat aatcttgtac   2520
tattatgagc tgtaccccac tatgactgta gtcattgtgt cggtggcctc gttcgtgctt   2580
ctgtcgatgg tgggcacagc agtgggaatg tgtgtgtgcg cacggcgcag atgcattaca   2640
ccatatgaat taacaccagg agccactgtt cccttcctgc tcagcctgct atgctgcgtc   2700
agaacgacca aggcggccac atattacgag gctgcggcat atctatggaa cgaacagcag   2760
cccctgttct ggttgcaggc tcttatcccg ctggccgcct tgatcgtcct gtgcaactgt   2820
ctgaaactct tgccatgctg ctgtaagacc ctggcttttt tagccgtaat gagcatcggt   2880
gcccacactg tgagcgcgta cgaacacgta acagtgatcc cgaacacggt gggagtaccg   2940
tataagactc ttgtcaacag accgggttac agccccatgg tgttggagat ggagctacaa   3000
tcagtcacct tggaaccaac actgtcactt gactacatca cgtgcgagta caaaactgtc   3060
atcccctccc cgtacgtgaa gtgctgtggt acagcagagt gcaaggacaa gagcctacca   3120
gactacagct gcaaggtctt tactggagtc tacccattta tgtggggcgg cgcctactgc   3180
ttttgcgacg ccgaaaatac gcaattgagc gaggcacatg tagagaaatc tgaatcttgc   3240
aaaacagagt ttgcatcggc ctacagagcc cacaccgcat cggcgtcggc gaagctccgc   3300
gtcctttacc aaggaaacaa cattaccgta gctgcctacg ctaacggtga ccatgccgtc   3360
acagtaaagg acgccaagtt tgtcgtgggc ccaatgtcct ccgcctggac accttttgac   3420
aacaaaatcg tggtgtacaa aggcgacgtc tacaacatgg actacccacc ttttggcgca   3480
ggaagaccag gacaatttgg tgacattcaa agtcgtacac cggaaagtaa agacgtttat   3540
gccaacactc agttggtact acagaggcca gcagcaggca cggtacatgt accatactct   3600
caggcaccat ctggcttcaa gtattggctg aaggaacgag gagcatcgct acagcacacg   3660
gcaccgttcg gttgccagat tgcgacaaac ccggtaagag ctgtaaattg cgctgtgggg   3720
aacataccaa tttccatcga cataccggat gcggccttta ctagggttgt cgatgcaccc   3780
tctgtaacgg acatgtcatg cgaagtacca gcctgcactc actcctccga ctttgggggc   3840
gtcgccatca tcaaatacac agctagcaag aaaggtaaat gtgcagtaca ttcgatgacc   3900
aacgccgtta ccattcgaga agccgacgta gaagtagagg ggaactccca gctgcaaata   3960
tccttctcaa cagccctggc aagcgccgag tttcgcgtgc aagtgtgctc cacacaagta   4020
cactgcgcag ccgcatgcca ccctccaaag gaccacatag tcaattaccc agcatcacac   4080
accacccttg ggtccagga tatatccaca acggcaatgt cttgggtgca gaagattacg   4140
ggaggagtag gattaattgt tgctgttgct gccttaattt taattgtggt gctatgcgtg   4200
```

tcgtttagca ggcac 4215

<210> SEQ ID NO 14
<211> LENGTH: 3825
<212> TYPE: DNA
<213> ORGANISM: Artificial Sequence
<220> FEATURE:
<223> OTHER INFORMATION: Synthetic polynucleotide encoding CHIKV+CD20

<400> SEQUENCE: 14
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
caccgccaaa gacgcagtac taaggacaat tttaatgtct ataaagccac aagaccatat 1020
ctagctcatt gtcctgactg cggagaaggg cattcgtgcc acagccctat cgcattggag 1080
cgcatcagaa atgaagcaac ggacggaacg ctgaaaatcc aggtctcttt gcagatcggg 1140
ataaagacag atgacagcca cgattggacc aagctgcgct atatggatag ccatacgcca 1200
gcggacgcgg agcgagccgg attgcttgta aggacttcag caccgtgcac gatcaccggg 1260
accatgggac actttattct cgcccgatgc ccgaaaggag agacgctgac agtgggattt 1320
acggacagca gaaagatcag ccacacatgc acacacccgt tccatcatga accacctgtg 1380
ataggtaggg agaggttcca ctctcgacca caacatggta aagagttacc ttgcagcacg 1440
tacgtgcaga gcaccgctgc cactgctgag gagatagagg tgcatatgcc cccagatact 1500
cctgaccgca cgctgatgac gcagcagtcc ggaggtatat acaactgtga accagctaat 1560
ccctctgaga aaactcccc atctacccaa tactgttaca gcatacaagg atccaacgtg 1620
aagatcacag ttaatgggca gacggtgcgg tacaagtgca actgcggtgg ctcaaacgag 1680
ggactgacaa ccacagacaa agtgatcaat aactgcaaaa ttgatcagtg ccatgctgca 1740
gtcactaatc acaagaattg gcaatacaac tccccttag tcccgcgcaa cgctgaactc 1800
ggggaccgta aaggaaagat ccacatccca ttcccattgg caaacgtgac ttgcagagtg 1860
ccaaaagcaa gaaaccctac agtaacttac ggaaaaaacc aagtcaccat gctgctgtat 1920
cctgaccatc cgacactctt gtcttaccgt aacatgggac aggaaccaaa ttaccacgag 1980

```
gagtgggtga cacacaagaa ggaggttacc ttgaccgtgc ctactgaggg tctggaggtc   2040

acttggggca acaacgaacc atacaagtac tggccgcaga tgtctacgaa cggtactgct   2100

catggtcacc cacatgagat aatcttgtac tattatgagc tgtaccccac tatgactgta   2160

gtcattgtgt cggtggcctc gttcgtgctt ctgtcgatgg tgggcacagc agtgggaatg   2220

tgtgtgtgcg cacggcgcag atgcattaca ccatatgaat taacaccagg agccactgtt   2280

cccttcctgc tcagcctgct atgctgcgtc agaacgacca aggcggccac atattacgag   2340

gctgcggcat atctatggaa cgaacagcag cccctgttct ggttgcaggc tcttatcccg   2400

ctggccgcct tgatcgtcct gtgcaactgt ctgaaactct tgccatgctg ctgtaagacc   2460

ctggcttttt tagccgtaat gagcatcggt gcccacactg tgagcgcgta cgaacacgta   2520

acagtgatcc cgaacacggt gggagtaccg tataagactc ttgtcaacag accgggttac   2580

agccccatgg tgttggagat ggagctacaa tcagtcacct tggaaccaac actgtcactt   2640

gactacatca cgtgcgagta caaaactgtc atcccctccc cgtacgtgaa gtgctgtggt   2700

acagcagagt gcaaggacaa gagcctacca gactacagct gcaaggtctt tactggagtc   2760

tacccattta tgtggggcgg cgcctactgc ttttgcgacg ccgaaaatac gcaattgagc   2820

gaggcacatg tagagaaatc tgaatcttgc aaaacagagt ttgcatcggc ctacagagcc   2880

cacaccgcat cggcgtcggc gaagctccgc gtcctttacc aaggaaacaa cattaccgta   2940

gctgcctacg ctaacggtga ccatgccgtc acagtaaagg acgccaagtt tgtcgtgggc   3000

ccaatgtcct ccgcctggac accttttgac aacaaaatcg tggtgtacaa aggcgacgtc   3060

tacaacatgg actacccacc ttttggcgca ggaagaccag gacaatttgg tgacattcaa   3120

agtcgtacac cggaaagtaa agacgtttat gccaacactc agttggtact acagaggcca   3180

gcagcaggca cggtacatgt accatactct caggcaccat ctggcttcaa gtattggctg   3240

aaggaacgag gagcatcgct acagcacacg gcaccgttcg gttgccagat tgcgacaaac   3300

ccggtaagag ctgtaaattg cgctgtgggg aacataccaa tttccatcga cataccggat   3360

gcggccttta ctagggttgt cgatgcaccc tctgtaacgg acatgtcatg cgaagtacca   3420

gcctgcactc actcctccga ctttgggggc gtcgccatca tcaaatacac agctagcaag   3480

aaaggtaaat gtgcagtaca ttcgatgacc aacgccgtta ccattcgaga agccgacgta   3540

gaagtagagg ggaactccca gctgcaaata tccttctcaa cagccctggc aagcgccgag   3600

tttcgcgtgc aagtgtgctc cacacaagta cactgcgcag ccgcatgcca ccctccaaag   3660

gaccacatag tcaattaccc agcatcacac accacccttg ggtccagga tatatccaca   3720

acggcaatgt cttgggtgca gaagattacg ggaggagtag gattaattgt tgctgttgct   3780

gccttaattt taattgtggt gctatgcgtg tcgtttagca ggcac                  3825
```

```
<210> SEQ ID NO 15
<211> LENGTH: 4230
<212> TYPE: DNA
<213> ORGANISM: Artificial Sequence
<220> FEATURE:
<223> OTHER INFORMATION: Synthetic polynucleotide encoding VEEV+TNFalpha

<400> SEQUENCE: 15

atgttcccgt tccagccaat gtatccgatg cagccaatgc cctatcgcaa cccgttcgcg     60

gccccgcgca ggccctggtt ccccagaacc gaccctttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240
```

```
aagaagaaga agaaccaagg gaagaagaag gctaagacag ggccgcctaa tccgaaggca    300
cagaatggaa acaagaagaa gaccaacaag aaaccaggca agagacagcg catggtcatg    360
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttccgga   1560
ggtaagcctg tagcccatgt tgtagcaaac cctcaagctg aggggcagct ccagtggctg   1620
aaccgccggg ccaatgccct cctggccaat ggcgtggagc tgagagataa ccagctggtg   1680
gtgccatcag agggcctgta cctcatctac tcccaggtcc tcttcaaggg ccaaggctgc   1740
ccctccaccc atgtgctcct cacccacacc atcagccgca tcgccgtctc ctaccagacc   1800
aaggtcaacc tcctctctgc catcaagagc ccctgccaga gggagacccc agagggggct   1860
gaggccaagc cctggtatga gcccatctat ctgggagggg tcttccagct ggagaagggt   1920
gaccgactca gcgctgagat caatcggccc gactatctcg actttgccga gtctgggcag   1980
gtctactttg ggatcattgc cctgacgcgt ggaggatcct cagtcaccgt gacacctcct   2040
gatgggacta gcgccctggt ggaatgcgag tgtggcggca caaagatctc cgagaccatc   2100
aacaagacaa aacagttcag ccagtgcaca aagaaggagc agtgcagagc atatcggctg   2160
cagaacgata agtgggtgta taattctgac aaactgccca aagcagcggg agccacctta   2220
aaaggaaaac tgcatgtccc attcttgctg gcagacggca aatgcaccgt gcctctagca   2280
ccagaaccta tgataacctt cggtttcaga tcagtgtcac tgaaactgca ccctaagaat   2340
cccacatatc taatcacccg ccaacttgct gatgagcctc actacacgca cgagctcata   2400
tctgaaccag ctgttaggaa ttttaccgtc accgaaaaag ggtgggagtt tgtatgggga   2460
aaccacccgc cgaaaaggtt ttgggcacag gaaacagcac ccggaaatcc acatgggcta   2520
ccgcacgagg tgataactca ttattaccac agatacccta tgtccaccat cctgggtttg   2580
```

tcaatttgtg ccgccattgc aaccgtttcc gttgcagcgt ctacctggct gttttgcaga 2640
tcaagagttg cgtgcctaac tccttaccgg ctaacaccta acgctaggat accattttgt 2700
ctggctgtgc tttgctgcgc ccgcactgcc cgggccgaga ccacctggga gtccttggat 2760
cacctatgga acaataacca acagatgttc tggattcaat tgctgatccc tctggccgcc 2820
ttgatcgtag tgactcgcct gctcaggtgc gtgtgctgtg tcgtgccttt tttagtcatg 2880
gccggcgccg caggcgccgg cgcctacgag cacgcgacca cgatgccgag ccaagcggga 2940
atctcgtata acactatagt caacagagca ggctacgcac cactccctat cagcataaca 3000
ccaacaaaga tcaagctgat acctacagtg aacttggagt acgtcacctg ccactacaaa 3060
acaggaatgg attcaccagc catcaaatgc tgcggatctc aggaatgcac tccaacttac 3120
aggcctgatg aacagtgcaa agtcttcaca ggggtttacc cgttcatgtg ggtggtgca 3180 tattgctttt gcgacactga gaacacccaa gtcagcaagg cctacgtaat gaaatctgac 3240
gactgccttg cggatcatgc tgaagcatat aaagcgcaca cagcctcagt gcaggcgttc 3300
ctcaacatca cagtgggaga acactctatt gtgactaccg tgtatgtgaa tggagaaact 3360
cctgtgaatt tcaatggggt caaaataact gcaggtccgc tttccacagc ttggacaccc 3420
tttgatcgca aaatcgtgca gtatgccggg gagatctata attatgattt tcctgagtat 3480
ggggcaggac aaccaggagc atttggagat atacaatcca gaacagtctc aagctctgat 3540
ctgtatgcca ataccaacct agtgctgcag agacccaaag caggagcgat ccacgtgcca 3600
tacactcagg caccttcggg ttttgagcaa tggaagaaag ataaagctcc atcattgaaa 3660
tttaccgccc ctttcggatg cgaaatatat acaaacccca ttcgcgccga aaactgtgct 3720
gtagggtcaa ttccattagc ctttgacatt cccgacgcct tgttcaccag ggtgtcagaa 3780
acaccgacac tttcagcggc cgaatgcact cttaacgagt gcgtgtattc ttccgacttt 3840
ggtgggatcg ccacggtcaa gtactcggcc agcaagtcag gcaagtgcgc agtccatgtg 3900
ccatcaggga ctgctaccct aaaagaagca gcagtcgagc taaccgagca agggtcggcg 3960
actatccatt tctcgaccgc aaatatccac ccggagttca ggctccaaat atgcacatca 4020
tatgttacgt gcaaaggtga ttgtcacccc ccgaaagacc atattgtgac acaccctcag 4080
tatcacgccc aaacatttac agccgcggtg tcaaaaaccg cgtggacgtg gttaacatcc 4140
ctgctgggag gatcagccgt aattattata attggcttgg tgctggctac tattgtggcc 4200
atgtacgtgc tgaccaacca gaaacataat 4230

<210> SEQ ID NO 16
<211> LENGTH: 3852
<212> TYPE: DNA
<213> ORGANISM: Artificial Sequence
<220> FEATURE:
<223> OTHER INFORMATION: Synthetic polynucleotide encoding VEEV+CD20

<400> SEQUENCE: 16
atgttcccgt tccagccaat gtatccgatg cagccaatgc cctatcgcaa cccgttcgcg 60
gccccgcgca ggccctggtt ccccagaacc gaccctttttc tggcgatgca ggtgcaggaa 120
ttaacccgct cgatggctaa cctgacgttc aagcaacgcc gggacgcgcc acctgagggg 180
ccatccgcta ataaaccgaa gaaggaggcc tcgcaaaaac agaaaggggg aggccaaggg 240
aagaagaaga agaaccaagg gaagaagaag gctaagacag ggccgcctaa tccgaaggca 300
cagaatggaa acaagaagaa gaccaacaag aaaccaggca agagacagcg catggtcatg 360
aaattggaat ctgacaagac gttcccaatc atgttggaag ggaagataaa cggctacgct 420

-continued

```
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttccgga   1560
ggtatataca actgtgaacc agctaatccc tctgagaaaa actccccatc tacccaatac   1620
tgttacagca tacaaggatc ctcagtcacc gtgacacctc ctgatgggac tagcgccctg   1680
gtggaatgcg agtgtggcgg cacaaagatc tccgagacca tcaacaagac aaaacagttc   1740
agccagtgca caaagaagga gcagtgcaga gcatatcggc tgcagaacga taagtgggtg   1800
tataattctg acaaactgcc caaagcagcg ggagccacct taaaaggaaa actgcatgtc   1860
ccattcttgc tggcagacgg caaatgcacc gtgcctctag caccagaacc tatgataacc   1920
ttcggtttca gatcagtgtc actgaaactg caccctaaga atcccacata tctaatcacc   1980
cgccaacttg ctgatgagcc tcactacacg cacgagctca tatctgaacc agctgttagg   2040
aattttaccg tcaccgaaaa agggtgggag tttgtatggg gaaaccaccc gccgaaaagg   2100
ttttgggcac aggaaacagc acccggaaat ccacatgggc taccgcacga ggtgataact   2160
cattattacc acagataccc tatgtccacc atcctgggtt tgtcaatttg tgccgccatt   2220
gcaaccgttt ccgttgcagc gtctacctgg ctgttttgca gatcaagagt tgcgtgccta   2280
actccttacc ggctaacacc taacgctagg ataccatttt gtctggctgt gctttgctgc   2340
gcccgcactg cccgggccga gaccacctgg gagtccttgg atcacctatg gaacaataac   2400
caacagatgt tctggattca attgctgatc cctctggccg ccttgatcgt agtgactcgc   2460
ctgctcaggt gcgtgtgctg tgtcgtgcct tttttagtca tggccggcgc cgcaggcgcc   2520
ggcgcctacg agcacgcgac cacgatgccg agccaagcgg gaatctcgta taacactata   2580
gtcaacagag caggctacgc accactccct atcagcataa caccaacaaa gatcaagctg   2640
atacctacag tgaacttgga gtacgtcacc tgccactaca aaacaggaat ggattcacca   2700
gccatcaaat gctgcggatc tcaggaatgc actccaactt acaggcctga tgaacagtgc   2760
```

```
aaagtcttca caggggttta cccgttcatg tggggtggtg catattgctt ttgcgacact   2820

gagaacaccc aagtcagcaa ggcctacgta atgaaatctg acgactgcct tgcggatcat   2880

gctgaagcat ataaagcgca cacagcctca gtgcaggcgt tcctcaacat cacagtggga   2940

gaacactcta ttgtgactac cgtgtatgtg aatggagaaa ctcctgtgaa tttcaatggg   3000

gtcaaaataa ctgcaggtcc gctttccaca gcttggacac cctttgatcg caaaatcgtg   3060

cagtatgccg gggagatcta taattatgat tttcctgagt atggggcagg acaaccagga   3120

gcatttggag atatacaatc cagaacagtc tcaagctctg atctgtatgc caataccaac   3180

ctagtgctgc agagacccaa agcaggagcg atccacgtgc catacactca ggcaccttcg   3240

ggttttgagc aatggaagaa agataaagct ccatcattga aatttaccgc ccctttcgga   3300

tgcgaaatat atacaaaccc cattcgcgcc gaaaactgtg ctgtagggtc aattccatta   3360

gcctttgaca ttcccgacgc cttgttcacc agggtgtcag aaacaccgac actttcagcg   3420

gccgaatgca ctcttaacga gtgcgtgtat tcttccgact ttggtgggat cgccacggtc   3480

aagtactcgg ccagcaagtc aggcaagtgc gcagtccatg tgccatcagg gactgctacc   3540

ctaaaagaag cagcagtcga gctaaccgag caagggtcgg cgactatcca tttctcgacc   3600

gcaaatatcc acccggagtt caggctccaa atatgcacat catatgttac gtgcaaaggt   3660

gattgtcacc ccccgaaaga ccatattgtg acacaccctc agtatcacgc ccaaacattt   3720

acagccgcgg tgtcaaaaac cgcgtggacg tggttaacat ccctgctggg aggatcagcc   3780

gtaattatta taattggctt ggtgctggct actattgtgg ccatgtacgt gctgaccaac   3840

cagaaacata at                                                       3852
```

<210> SEQ ID NO 17
<211> LENGTH: 3837
<212> TYPE: DNA
<213> ORGANISM: Artificial Sequence
<220> FEATURE:
<223> OTHER INFORMATION: Synthetic polynucleotide encoding VEEV+CTLA4

<400> SEQUENCE: 17

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaaccccca aggctattac    600

agctggcatc atggagcagt ccaatatgaa aatgggcgtt tcacggtgcc gaaaggagtt    660

ggggccaagg gagacagcgg acgacccatt ctggataacc agggacgggt ggtcgctatt    720

gtgctgggag gtgtgaatga aggatctagg acagcccttt cagtcgtcat gtggaacgag    780

aagggagtta ccgtgaagta tactccagag aactgcgagc aatggtcact agtgaccacc    840

atgtgtctgc tcgccaatgt gacgttccca tgtgctcaac caccaatttg ctacgacaga    900

aaaccagcag agactttggc catgctcagc gttaacgttg acaacccggg ctacgatgag    960
```

-continued

```
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg ggcacgacgg ttatgttaga   1140
cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttgccag gtgcccggca   1320
ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttccgga   1560
ggaggctgca aggtggagct catgtaccca ccgccatact acctgggcat aggcggcggt   1620
ggatcctcag tcaccgtgac acctcctgat gggactagcg ccctggtgga atgcgagtgt   1680
ggcggcacaa agatctccga gaccatcaac aagacaaaac agttcagcca gtgcacaaag   1740
aaggagcagt gcagagcata tcggctgcag aacgataagt gggtgtataa ttctgacaaa   1800
ctgcccaaag cagcgggagc caccttaaaa ggaaaactgc atgtcccatt cttgctggca   1860
gacggcaaat gcaccgtgcc tctagcacca gaacctatga taaccttcgg tttcagatca   1920
gtgtcactga aactgcaccc taagaatccc acatatctaa tcacccgcca acttgctgat   1980
gagcctcact acacgcacga gctcatatct gaaccagctg ttaggaattt taccgtcacc   2040
gaaaaagggt gggagtttgt atggggaaac cacccgccga aaaggttttg ggcacaggaa   2100
acagcacccg gaaatccaca tgggctaccg cacgaggtga taactcatta ttaccacaga   2160
taccctatgt ccaccatcct gggtttgtca atttgtgccg ccattgcaac cgtttccgtt   2220
gcagcgtcta cctggctgtt ttgcagatca agagttgcgt gcctaactcc ttaccggcta   2280
acacctaacg ctaggatacc attttgtctg gctgtgcttt gctgcgcccg cactgcccgg   2340
gccgagacca cctgggagtc cttggatcac ctatggaaca ataaccaaca gatgttctgg   2400
attcaattgc tgatccctct ggccgccttg atcgtagtga ctcgcctgct caggtgcgtg   2460
tgctgtgtcg tgcctttttt agtcatggcc ggcgccgcag gcgccggcgc ctacgagcac   2520
gcgaccacga tgccgagcca agcgggaatc tcgtataaca ctatagtcaa cagagcaggc   2580
tacgcaccac tccctatcag cataacacca acaaagatca agctgatacc tacagtgaac   2640
ttggagtacg tcacctgcca ctacaaaaca ggaatggatt caccagccat caaatgctgc   2700
ggatctcagg aatgcactcc aacttacagg cctgatgaac agtgcaaagt cttcacaggg   2760
gtttacccgt tcatgtgggg tggtgcatat tgcttttgcg acactgagaa cacccaagtc   2820
agcaaggcct acgtaatgaa atctgacgac tgccttgcgg atcatgctga agcatataaa   2880
gcgcacacag cctcagtgca ggcgttcctc aacatcacag tgggagaaca ctctattgtg   2940
actaccgtgt atgtgaatgg agaaactcct gtgaatttca atggggtcaa aataactgca   3000
ggtccgcttt ccacagcttg gacacccttt gatcgcaaaa tcgtgcagta tgccggggag   3060
atctataatt atgattttcc tgagtatggg gcaggacaac caggagcatt tggagatata   3120
caatccagaa cagtctcaag ctctgatctg tatgccaata ccaacctagt gctgcagaga   3180
cccaaagcag gagcgatcca cgtgccatac actcaggcac cttcgggttt tgagcaatgg   3240
aagaaagata aagctccatc attgaaattt accgcccctt tcggatgcga aatatataca   3300
```

```
aaccccattc gcgccgaaaa ctgtgctgta gggtcaattc cattagcctt tgacattccc   3360

gacgccttgt tcaccagggt gtcagaaaca ccgacacttt cagcggccga atgcactctt   3420

aacgagtgcg tgtattcttc cgactttggt gggatcgcca cggtcaagta ctcggccagc   3480

aagtcaggca agtgcgcagt ccatgtgcca tcagggactg ctaccctaaa agaagcagca   3540

gtcgagctaa ccgagcaagg gtcggcgact atccatttct cgaccgcaaa tatccacccg   3600

gagttcaggc tccaaatatg cacatcatat gttacgtgca aaggtgattg tcacccccccg  3660

aaagaccata ttgtgacaca ccctcagtat cacgcccaaa catttacagc cgcggtgtca   3720

aaaaccgcgt ggacgtggtt aacatccctg ctgggaggat cagccgtaat tattataatt   3780

ggcttggtgc tggctactat tgtggccatg tacgtgctga ccaaccagaa acataat      3837
```

<210> SEQ ID NO 18
<211> LENGTH: 152
<212> TYPE: PRT
<213> ORGANISM: Artificial Sequence
<220> FEATURE:
<223> OTHER INFORMATION: Synthetic TNFalpha peptide

<400> SEQUENCE: 18

```
Arg Thr Pro Ser Asp Lys Pro Val Ala His Val Val Ala Asn Pro Gln
1               5                   10                  15

Ala Glu Gly Gln Leu Gln Trp Leu Asn Arg Arg Ala Asn Ala Leu Leu
            20                  25                  30

Ala Asn Gly Val Glu Leu Arg Asp Asn Gln Leu Val Val Pro Ser Glu
        35                  40                  45

Gly Leu Tyr Leu Ile Tyr Ser Gln Val Leu Phe Lys Gly Gln Gly Cys
    50                  55                  60

Pro Ser Thr His Val Leu Leu Thr His Thr Ile Ser Arg Ile Ala Val
65                  70                  75                  80

Ser Tyr Gln Thr Lys Val Asn Leu Leu Ser Ala Ile Lys Ser Pro Cys
                85                  90                  95

Gln Arg Glu Thr Pro Glu Gly Ala Glu Ala Lys Pro Trp Tyr Glu Pro
            100                 105                 110

Ile Tyr Leu Gly Gly Val Phe Gln Leu Glu Lys Gly Asp Arg Leu Ser
        115                 120                 125

Ala Glu Ile Asn Arg Pro Asp Tyr Leu Asp Phe Ala Glu Ser Gly Gln
    130                 135                 140

Val Tyr Phe Gly Ile Ile Ala Leu
145                 150
```

<210> SEQ ID NO 19
<211> LENGTH: 155
<212> TYPE: PRT
<213> ORGANISM: Artificial Sequence
<220> FEATURE:
<223> OTHER INFORMATION: Synthetic TNFalpha peptide

<400> SEQUENCE: 19

```
Ser Gly Gly Lys Pro Val Ala His Val Val Ala Asn Pro Gln Ala Glu
1               5                   10                  15

Gly Gln Leu Gln Trp Leu Asn Arg Arg Ala Asn Ala Leu Leu Ala Asn
            20                  25                  30

Gly Val Glu Leu Arg Asp Asn Gln Leu Val Val Pro Ser Glu Gly Leu
        35                  40                  45

Tyr Leu Ile Tyr Ser Gln Val Leu Phe Lys Gly Gln Gly Cys Pro Ser
    50                  55                  60
```

```
Thr His Val Leu Leu Thr His Thr Ile Ser Arg Ile Ala Val Ser Tyr
65                  70                  75                  80

Gln Thr Lys Val Asn Leu Leu Ser Ala Ile Lys Ser Pro Cys Gln Arg
                85                  90                  95

Glu Thr Pro Glu Gly Ala Glu Ala Lys Pro Trp Tyr Glu Pro Ile Tyr
            100                 105                 110

Leu Gly Gly Val Phe Gln Leu Glu Lys Gly Asp Arg Leu Ser Ala Glu
        115                 120                 125

Ile Asn Arg Pro Asp Tyr Leu Asp Phe Ala Glu Ser Gly Gln Val Tyr
    130                 135                 140

Phe Gly Ile Ile Ala Leu Thr Arg Gly Gly Ser
145                 150                 155


<210> SEQ ID NO 20
<211> LENGTH: 465
<212> TYPE: DNA
<213> ORGANISM: Artificial Sequence
<220> FEATURE:
<223> OTHER INFORMATION: Synthetic polynucleotide encoding TNFalpha

<400> SEQUENCE: 20

tccggaggta agcctgtagc ccatgttgta gcaaaccctc aagctgaggg gcagctccag     60

tggctgaacc gccgggccaa tgccctcctg gccaatggcg tggagctgag agataaccag    120

ctggtggtgc catcagaggg cctgtacctc atctactccc aggtcctctt caagggccaa    180

ggctgcccct ccacccatgt gctcctcacc cacaccatca gccgcatcgc cgtctcctac    240

cagaccaagg tcaacctcct ctctgccatc aagagcccct gccagaggga gaccccagag    300

ggggctgagg ccaagccctg gtatgagccc atctatctgg gaggggtctt ccagctggag    360

aagggtgacc gactcagcgc tgagatcaat cggcccgact atctcgactt tgccgagtct    420

gggcaggtct actttgggat cattgccctg acgcgtggag gatcc                    465


<210> SEQ ID NO 21
<211> LENGTH: 24
<212> TYPE: PRT
<213> ORGANISM: Artificial Sequence
<220> FEATURE:
<223> OTHER INFORMATION: Synthetic CD20 peptide

<400> SEQUENCE: 21

Ile Tyr Asn Cys Glu Pro Ala Asn Pro Ser Glu Lys Asn Ser Pro Ser
1               5                   10                  15

Thr Gln Tyr Cys Tyr Ser Ile Gln
            20


<210> SEQ ID NO 22
<211> LENGTH: 16
<212> TYPE: PRT
<213> ORGANISM: Artificial Sequence
<220> FEATURE:
<223> OTHER INFORMATION: Synthetic CTLA4 peptide

<400> SEQUENCE: 22

Cys Lys Val Glu Leu Met Tyr Pro Pro Pro Tyr Tyr Leu Gly Ile Gly
1               5                   10                  15


<210> SEQ ID NO 23
<211> LENGTH: 8404
<212> TYPE: DNA
<213> ORGANISM: Artificial Sequence
```

<220> FEATURE:
<223> OTHER INFORMATION: Synthetic polynucleotide

<400> SEQUENCE: 23

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgga gttcatcccg acgcaaactt tctataacag aaggtaccaa ccccgaccct    960
gggccccacg ccctacaatt caagtaatta gacctagacc acgtccacag aggcaggctg   1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaaagaag caaccaccac aaaagaagcc ggctcaaaag aagaagaaac   1200
caggccgtag ggagagaatg tgcatgaaaa ttgaaaatga ttgcatcttc gaagtcaagc   1260
atgaaggcaa agtgatgggc tacgcatgcc tggtggggga taaagtaatg aaaccagcac   1320
atgtgaaggg aactatcgac aatgccgatc tggctaaact ggcctttaag cggtcgtcta   1380
aatacgatct tgaatgtgca cagataccgg tgcacatgaa gtctgatgcc tcgaagttta   1440
cccacgagaa acccgagggg tactataact ggcatcacgg agcagtgcag tattcaggag   1500
gccggttcac tatcccgacg ggtgcaggca agccgggaga cagcggcaga ccgatcttcg   1560
acaacaaagg acgggtggtg gccatcgtcc taggaggggc caacgaaggt gcccgcacgg   1620
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa aatccaggtc tctttgcaga   2040
tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
```

```
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtccggagg atccaacgtg aagatcacag   2460
ttaatgggca gacggtgcgg tacaagtgca actgcggtgg ctcaaacgag ggactgacaa   2520
ccacagacaa agtgatcaat aactgcaaaa ttgatcagtg ccatgctgca gtcactaatc   2580
acaagaattg gcaatacaac tcccctttag tcccgcgcaa cgctgaactc ggggaccgta   2640
aaggaaagat ccacatccca ttcccattgg caaacgtgac ttgcagagtg ccaaaagcaa   2700
gaaaccctac agtaacttac ggaaaaaacc aagtcaccat gctgctgtat cctgaccatc   2760
cgacactctt gtcttaccgt aacatgggac aggaaccaaa ttaccacgag gagtgggtga   2820
cacacaagaa ggaggttacc ttgaccgtgc ctactgaggg tctggaggtc acttggggca   2880
acaacgaacc atacaagtac tggccgcaga tgtctacgaa cggtactgct catggtcacc   2940
cacatgagat aatcttgtac tattatgagc tgtaccccac tatgactgta gtcattgtgt   3000
cggtggcctc gttcgtgctt ctgtcgatgg tgggcacagc agtgggaatg tgtgtgtgcg   3060
cacggcgcag atgcattaca ccatatgaat taacaccagg agccactgtt cccttcctgc   3120
tcagcctgct atgctgcgtc agaacgacca aggcggccac atattacgag gctgcggcat   3180
atctatggaa cgaacagcag cccctgttct ggttgcaggc tcttatcccg ctggccgcct   3240
tgatcgtcct gtgcaactgt ctgaaactct tgccatgctg ctgtaagacc ctggcttttt   3300
tagccgtaat gagcatcggt gcccacactg tgagcgcgta cgaacacgta acagtgatcc   3360
cgaacacggt gggagtaccg tataagactc ttgtcaacag accgggttac agccccatgg   3420
tgttggagat ggagctacaa tcagtcacct tggaaccaac actgtcactt gactacatca   3480
cgtgcgagta caaaactgtc atcccctccc cgtacgtgaa gtgctgtggt acagcagagt   3540
gcaaggacaa gagcctacca gactacagct gcaaggtctt tactggagtc tacccattta   3600
tgtggggcgg cgcctactgc ttttgcgacg ccgaaaatac gcaattgagc gaggcacatg   3660
tagagaaatc tgaatcttgc aaaacagagt ttgcatcggc ctacagagcc cacaccgcat   3720
cggcgtcggc gaagctccgc gtcctttacc aaggaaacaa cattaccgta gctgcctacg   3780
ctaacggtga ccatgccgtc acagtaaagg acgccaagtt tgtcgtgggc ccaatgtcct   3840
ccgcctggac accttttgac aacaaaatcg tggtgtacaa aggcgacgtc tacaacatgg   3900
actacccacc ttttggcgca ggaagaccag gacaatttgg tgacattcaa agtcgtacac   3960
cggaaagtaa agacgtttat gccaacactc agttggtact acagaggcca gcagcaggca   4020
cggtacatgt accatactct caggcaccat ctggcttcaa gtattggctg aaggaacgag   4080
gagcatcgct acagcacacg gcaccgttcg gttgccagat tgcgacaaac ccggtaagag   4140
ctgtaaattg cgctgtgggg aacataccaa tttccatcga cataccggat gcggccttta   4200
ctagggttgt cgatgcaccc tctgtaacgg acatgtcatg cgaagtacca gcctgcactc   4260
actcctccga ctttgggggc gtcgccatca tcaaatacac agctagcaag aaaggtaaat   4320
gtgcagtaca ttcgatgacc aacgccgtta ccattcgaga agccgacgta gaagtagagg   4380
ggaactccca gctgcaaata tccttctcaa cagccctggc aagcgccgag tttcgcgtgc   4440
aagtgtgctc cacacaagta cactgcgcag ccgcatgcca ccctccaaag gaccacatag   4500
tcaattaccc agcatcacac accacccttg ggtccagga tatatccaca acggcaatgt   4560
cttgggtgca gaagattacg ggaggagtag gattaattgt tgctgttgct gccttaattt   4620
```

```
taattgtggt gctatgcgtg tcgtttagca ggcactaagg atctagatct gctgtgcctt   4680
ctagttgcca gccatctgtt gtttgcccct cccccgtgcc ttccttgacc ctggaaggtg   4740
ccactcccac tgtcctttcc taataaaatg aggaaattgc atcgcattgt ctgagtaggt   4800
gtcattctat tctggggggt ggggtggggc aggacagcaa gggggaggat tgggaagaca   4860
atagcaggca tgctggggat gcggtgggct ctatgggtac ccaggtgctg aagaattgac   4920
ccggttcctc ctgggccaga aagaagcagg cacatcccct tctctgtgac acaccctgtc   4980
cacgcccctg gttcttagtt ccagccccac tcataggaca ctcatagctc aggagggctc   5040
cgccttcaat cccacccgct aaagtacttg gagcggtctc tccctccctc atcagcccac   5100
caaaccaaac ctagcctcca agagtgggaa gaaattaaag caagataggc tattaagtgc   5160
agagggagag aaaatgcctc caacatgtga ggaagtaatg agagaaatca tagaatttta   5220
aggccatgat ttaaggccat catggcctaa gcttgaaagg agataggatc aaagcttggc   5280
gtaatcatgg tcatagctgt ttcctgtgtg aaattgttat ccgctcacaa ttccacacaa   5340
catacgagcc ggaagcataa agtgtaaagc ctggggtgcc taatgagtga gctaactcac   5400
attaattgcg ttgcgctcac tgcccgcttt ccagtcggga aacctgtcgt gccagctgca   5460
ttaatgaatc ggccaacgcg cggggagagg cggtttgcgt attgggcgct cttccgcttc   5520
ctcgctcact gactcgctgc gctcggtcgt tcggctgcgg cgagcggtat cagctcactc   5580
aaaggcggta atacggttat ccacagaatc aggggataac gcaggaaaga acatgtgagc   5640
aaaaggccag caaaaggcca ggaaccgtaa aaaggccgcg ttgctggcgt ttttccatag   5700
gctccgcccc cctgacgagc atcacaaaaa tcgacgctca agtcagaggt ggcgaaaccc   5760
gacaggacta taaagatacc aggcgtttcc ccctggaagc tccctcgtgc gctctcctgt   5820
tccgaccctg ccgcttaccg gatacctgtc cgcctttctc ccttcgggaa gcgtggcgct   5880
ttctcatagc tcacgctgta ggtatctcag ttcggtgtag gtcgttcgct ccaagctggg   5940
ctgtgtgcac gaaccccccg ttcagcccga ccgctgcgcc ttatccggta actatcgtct   6000
tgagtccaac ccggtaagac acgacttatc gccactggca gcagccactg gtaacaggat   6060
tagcagagcg aggtatgtag gcggtgctac agagttcttg aagtggtggc ctaactacgg   6120
ctacactaga agaacagtat ttggtatctg cgctctgctg aagccagtta ccttcggaaa   6180
aagagttggt agctcttgat ccggcaaaca aaccaccgct ggtagcggtg gtttttttgt   6240
ttgcaagcag cagattacgc gcagaaaaaa aggatctcaa gaagatcctt tgatcttttc   6300
tacggggtct gacgctcagt ggaacgaaaa ctcacgttaa gggattttgg tcatgagatt   6360
atcaaaaagg atcttcacct agatcctttt aaattaaaaa tgaagtttta aatcaatcta   6420
aagtatatat gagtaaactt ggtctgacag ttaccaatgc ttaatcagtg aggcacctat   6480
ctcagcgatc tgtctatttc gttcatccat agttgcctga ctccccgtcg tgtagataac   6540
tacgatacgg gagggcttac catctggccc cagtgctgca atgataccgc gagaaccacg   6600
ctcaccggct ccagatttat cagcaataaa ccagccagcc ggaagggccg agcgcagaag   6660
tggtcctgca actttatccg cctccatcca gtctattaat tgttgccggg aagctagagt   6720
aagtagttcg ccagttaata gtttgcgcaa cgttgttgcc attgctacag gcatcgtggt   6780
gtcacgctcg tcgtttggta tggcttcatt cagctccggt tcccaacgat caaggcgagt   6840
tacatgatcc cccatgttgt gcaaaaaagc ggttagctcc ttcggtcctc cgatcgttgt   6900
cagaagtaag ttggccgcag tgttatcact catggttatg gcagcactgc ataattctct   6960
```

```
tactgtcatg ccatccgtaa gatgcttttc tgtgactggt gagtactcaa ccaagtcatt   7020

ctgagaatag tgtatgcggc gaccgagttg ctcttgcccg gcgtcaatac gggataatac   7080

cgcgccacat agcagaactt taaaagtgct catcattgga aaacgttctt cggggcgaaa   7140

actctcaagg atcttaccgc tgttgagatc cagttcgatg taacccactc gtgcacccaa   7200

ctgatcttca gcatctttta ctttcaccag cgtttctggg tgagcaaaaa caggaaggca   7260

aaatgccgca aaaaagggaa taagggcgac acggaaatgt tgaatactca tactcttcct   7320

ttttcaatat tattgaagca tttatcaggg ttattgtctc atgagcggat acatatttga   7380

atgtatttag aaaaataaac aaataggggt tccgcgcaca tttccccgaa aagtgccacc   7440

tgacgtctaa gaaaccatta ttatcatgac attaacctat aaaaataggc gtatcacgag   7500

gccctttcgg gtcgcgcgtt tcggtgatga cggtgaaaac ctctgacaca tgcagctccc   7560

gttgacggtc acagcttgtc tgtaagcgga tgccgggagc agacaagccc gtcagggcgc   7620

gtcagcgggt gttggcgggt gtcggggctg gcttaactat gcggcatcag agcagattgt   7680

actgagagtg caccataaaa ttgtaaacgt taatattttg ttaaaattcg cgttaaattt   7740

ttgttaaatc agctcatttt ttaaccaata ggccgaaatc ggcaaaatcc cttataaatc   7800

aaaagaatag cccgagatag ggttgagtgt tgttccagtt tggaacaaga gtccactatt   7860

aaagaacgtg gactccaacg tcaaagggcg aaaaaccgtc tatcagggcg atggcccact   7920

acgtgaacca tcacccaaat caagtttttt ggggtcgagg tgccgtaaag cactaaatcg   7980

gaaccctaaa gggagccccc gatttagagc ttgacgggga aagccggcga acgtggcgag   8040

aaaggaaggg aagaaagcga aaggagcggg cgctagggcg ctggcaagtg tagcggtcac   8100

gctgcgcgta accaccacac ccgccgcgct taatgcgccg ctacagggcg cgtactatgg   8160

ttgctttgac gtatgcggtg tgaaataccg cacagatgcg taaggagaaa ataccgcatc   8220

aggcgccatt cgccattcag gctgcgcaac tgttgggaag ggcgatcggt gcgggcctct   8280

tcgctattac gccagctggc gaaaggggga tgtgctgcaa ggcgattaag ttgggtaacg   8340

ccagggtttt cccagtcacg acgttgtaaa acgacggcca gtgaattcca tggtctcaac   8400

tttc                                                                8404
```

<210> SEQ ID NO 24
<211> LENGTH: 8410
<212> TYPE: DNA
<213> ORGANISM: Artificial Sequence
<220> FEATURE:
<223> OTHER INFORMATION: Synthetic polynucleotide

<400> SEQUENCE: 24

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600
```

```
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgga gttcatcccg acgcaaactt tctataacag aaggtaccaa ccccgaccct    960
gggccccacg ccctacaatt caagtaatta gacctagacc acgtccacag aggcaggctg   1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaaagaag caaccaccac aaaagaagcc ggctcaaaag aagaagaaac   1200
caggccgtag ggagagaatg tgcatgaaaa ttgaaaatga ttgcatcttc gaagtcaagc   1260
atgaaggcaa agtgatgggc tacgcatgcc tggtggggga taaagtaatg aaaccagcac   1320
atgtgaaggg aactatcgac aatgccgatc tggctaaact ggcctttaag cggtcgtcta   1380
aatacgatct tgaatgtgca cagataccgg tgcacatgaa gtctgatgcc tcgaagttta   1440
cccacgagaa acccgagggg tactataact ggcatcacgg agcagtgcag tattcaggag   1500
gccggttcac tatcccgacg ggtgcaggca agccgggaga cagcggcaga ccgatcttcg   1560
acaacaaagg acgggtggtg gccatcgtcc taggaggggc caacgaaggt gcccgcacgg   1620
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa aatccaggtc tctttgcaga   2040
tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtctggcaa cgtgaagatc acagttaatg   2460
ggcagacggt gcggtacaag tgcaactgcg gtggctccgg aagtggatcc aacgagggac   2520
tgacaaccac agacaaagtg atcaataact gcaaaattga tcagtgccat gctgcagtca   2580
ctaatcacaa gaattggcaa tacaactccc ctttagtccc gcgcaacgct gaactcgggg   2640
accgtaaagg aaagatccac atcccattcc cattggcaaa cgtgacttgc agagtgccaa   2700
aagcaagaaa ccctacagta acttacggaa aaaaccaagt caccatgctg ctgtatcctg   2760
accatccgac actcttgtct taccgtaaca tgggacagga accaaattac cacgaggagt   2820
gggtgacaca caagaaggag gttaccttga ccgtgcctac tgagggtctg gaggtcactt   2880
ggggcaacaa cgaaccatac aagtactggc cgcagatgtc tacgaacggt actgctcatg   2940
```

-continued

```
gtcacccaca tgagataatc ttgtactatt atgagctgta ccccactatg actgtagtca   3000
ttgtgtcggt ggcctcgttc gtgcttctgt cgatggtggg cacagcagtg ggaatgtgtg   3060
tgtgcgcacg gcgcagatgc attacaccat atgaattaac accaggagcc actgttccct   3120
tcctgctcag cctgctatgc tgcgtcagaa cgaccaaggc ggccacatat tacgaggctg   3180
cggcatatct atggaacgaa cagcagcccc tgttctggtt gcaggctctt atcccgctgg   3240
ccgccttgat cgtcctgtgc aactgtctga aactcttgcc atgctgctgt aagaccctgg   3300
ctttttagc cgtaatgagc atcggtgccc acactgtgag cgcgtacgaa cacgtaacag    3360
tgatcccgaa cacggtggga gtaccgtata agactcttgt caacagaccg ggttacagcc   3420
ccatggtgtt ggagatggag ctacaatcag tcaccttgga accaacactg tcacttgact   3480
acatcacgtg cgagtacaaa actgtcatcc cctccccgta cgtgaagtgc tgtggtacag   3540
cagagtgcaa ggacaagagc ctaccagact acagctgcaa ggtctttact ggagtctacc   3600
catttatgtg gggcggcgcc tactgctttt gcgacgccga aaatacgcaa ttgagcgagg   3660
cacatgtaga gaaatctgaa tcttgcaaaa cagagtttgc atcggcctac agagcccaca   3720
ccgcatcggc gtcggcgaag ctccgcgtcc tttaccaagg aaacaacatt accgtagctg   3780
cctacgctaa cggtgaccat gccgtcacag taaaggacgc caagtttgtc gtgggcccaa   3840
tgtcctccgc ctggacacct tttgacaaca aaatcgtggt gtacaaaggc gacgtctaca   3900
acatggacta cccacctttt ggcgcaggaa gaccaggaca atttggtgac attcaaagtc   3960
gtacaccgga aagtaaagac gtttatgcca acactcagtt ggtactacag aggccagcag   4020
caggcacggt acatgtacca tactctcagg caccatctgg cttcaagtat tggctgaagg   4080
aacgaggagc atcgctacag cacacggcac cgttcggttg ccagattgcg acaaacccgg   4140
taagagctgt aaattgcgct gtggggaaca taccaatttc catcgacata ccggatgcgg   4200
cctttactag ggttgtcgat gcaccctctg taacggacat gtcatgcgaa gtaccagcct   4260
gcactcactc ctccgacttt gggggcgtcg ccatcatcaa atacacagct agcaagaaag   4320
gtaaatgtgc agtacattcg atgaccaacg ccgttaccat tcgagaagcc gacgtagaag   4380
tagaggggaa ctcccagctg caaatatcct tctcaacagc cctggcaagc gccgagtttc   4440
gcgtgcaagt gtgctccaca caagtacact gcgcagccgc atgccaccct ccaaaggacc   4500
acatagtcaa ttacccagca tcacacacca cccttggggt ccaggatata tccacaacgg   4560
caatgtcttg ggtgcagaag attacgggag gagtaggatt aattgttgct gttgctgcct   4620
taattttaat tgtggtgcta tgcgtgtcgt ttagcaggca ctaaggatct agatctgctg   4680
tgccttctag ttgccagcca tctgttgttt gcccctcccc cgtgccttcc ttgaccctgg   4740
aaggtgccac tcccactgtc ctttcctaat aaaatgagga aattgcatcg cattgtctga   4800
gtaggtgtca ttctattctg gggggtgggg tggggcagga cagcaagggg gaggattggg   4860
aagacaatag caggcatgct ggggatgcgg tgggctctat gggtacccag gtgctgaaga   4920
attgacccgg ttcctcctgg gccagaaaga agcaggcaca tccccttctc tgtgacacac   4980
cctgtccacg cccctggttc ttagttccag ccccactcat aggacactca tagctcagga   5040
gggctccgcc ttcaatccca cccgctaaag tacttggagc ggtctctccc tccctcatca   5100
gcccaccaaa ccaaacctag cctccaagag tgggaagaaa ttaaagcaag ataggctatt   5160
aagtgcagag ggagagaaaa tgcctccaac atgtgaggaa gtaatgagag aaatcataga   5220
attttaaggc catgatttaa ggccatcatg gcctaagctt gaaaggagat aggatccaag   5280
cttggcgtaa tcatggtcat agctgtttcc tgtgtgaaat tgttatccgc tcacaattcc   5340
```

```
acacaacata cgagccggaa gcataaagtg taaagcctgg ggtgcctaat gagtgagcta   5400

actcacatta attgcgttgc gctcactgcc cgctttccag tcgggaaacc tgtcgtgcca   5460

gctgcattaa tgaatcggcc aacgcgcggg gagaggcggt ttgcgtattg ggcgctcttc   5520

cgcttcctcg ctcactgact cgctgcgctc ggtcgttcgg ctgcggcgag cggtatcagc   5580

tcactcaaag gcggtaatac ggttatccac agaatcaggg gataacgcag gaaagaacat   5640

gtgagcaaaa ggccagcaaa aggccaggaa ccgtaaaaag gccgcgttgc tggcgttttt   5700

ccataggctc cgcccccctg acgagcatca caaaaatcga cgctcaagtc agaggtggcg   5760

aaacccgaca ggactataaa gataccaggc gtttccccct ggaagctccc tcgtgcgctc   5820

tcctgttccg accctgccgc ttaccggata cctgtccgcc tttctccctt cgggaagcgt   5880

ggcgctttct catagctcac gctgtaggta tctcagttcg gtgtaggtcg ttcgctccaa   5940

gctgggctgt gtgcacgaac cccccgttca gcccgaccgc tgcgccttat ccggtaacta   6000

tcgtcttgag tccaacccgg taagacacga cttatcgcca ctggcagcag ccactggtaa   6060

caggattagc agagcgaggt atgtaggcgg tgctacagag ttcttgaagt ggtggcctaa   6120

ctacggctac actagaagaa cagtatttgg tatctgcgct ctgctgaagc cagttacctt   6180

cggaaaaaga gttggtagct cttgatccgg caaacaaacc accgctggta gcggtggttt   6240

ttttgtttgc aagcagcaga ttacgcgcag aaaaaaagga tctcaagaag atcctttgat   6300

cttttctacg gggtctgacg ctcagtggaa cgaaaactca cgttaaggga ttttggtcat   6360

gagattatca aaaaggatct tcacctagat ccttttaaat taaaaatgaa gttttaaatc   6420

aatctaaagt atatatgagt aaacttggtc tgacagttac caatgcttaa tcagtgaggc   6480

acctatctca gcgatctgtc tatttcgttc atccatagtt gcctgactcc ccgtcgtgta   6540

gataactacg atacgggagg gcttaccatc tggccccagt gctgcaatga taccgcgaga   6600

accacgctca ccggctccag atttatcagc aataaaccag ccagccggaa gggccgagcg   6660

cagaagtggt cctgcaactt tatccgcctc catccagtct attaattgtt gccgggaagc   6720

tagagtaagt agttcgccag ttaatagttt gcgcaacgtt gttgccattg ctacaggcat   6780

cgtggtgtca cgctcgtcgt ttggtatggc ttcattcagc tccggttccc aacgatcaag   6840

gcgagttaca tgatccccca tgttgtgcaa aaaagcggtt agctccttcg gtcctccgat   6900

cgttgtcaga agtaagttgg ccgcagtgtt atcactcatg gttatggcag cactgcataa   6960

ttctcttact gtcatgccat ccgtaagatg cttttctgtg actggtgagt actcaaccaa   7020

gtcattctga gaatagtgta tgcggcgacc gagttgctct tgcccggcgt caatacggga   7080

taataccgcg ccacatagca gaactttaaa agtgctcatc attggaaaac gttcttcggg   7140

gcgaaaactc tcaaggatct taccgctgtt gagatccagt tcgatgtaac ccactcgtgc   7200

acccaactga tcttcagcat cttttacttt caccagcgtt tctgggtgag caaaaacagg   7260

aaggcaaaat gccgcaaaaa agggaataag ggcgacacgg aaatgttgaa tactcatact   7320

cttccttttt caatattatt gaagcattta tcagggttat tgtctcatga gcggatacat   7380

atttgaatgt atttagaaaa ataaacaaat aggggttccg cgcacatttc cccgaaaagt   7440

gccacctgac gtctaagaaa ccattattat catgacatta acctataaaa ataggcgtat   7500

cacgaggccc tttcgggtcg cgcgtttcgg tgatgacggt gaaaacctct gacacatgca   7560

gctcccgttg acggtcacag cttgtctgta agcggatgcc gggagcagac aagcccgtca   7620

gggcgcgtca gcgggtgttg gcgggtgtcg gggctggctt aactatgcgg catcagagca   7680
```

```
gattgtactg agagtgcacc ataaaattgt aaacgttaat attttgttaa aattcgcgtt   7740
aaatttttgt taaatcagct cattttttaa ccaataggcc gaaatcggca aaatccctta   7800
taaatcaaaa gaatagcccg agatagggtt gagtgttgtt ccagtttgga acaagagtcc   7860
actattaaag aacgtggact ccaacgtcaa agggcgaaaa accgtctatc agggcgatgg   7920
cccactacgt gaaccatcac ccaaatcaag ttttttgggg tcgaggtgcc gtaaagcact   7980
aaatcggaac cctaaaggga gcccccgatt tagagcttga cggggaaagc cggcgaacgt   8040
ggcgagaaag gaagggaaga aagcgaaagg agcgggcgct agggcgctgg caagtgtagc   8100
ggtcacgctg cgcgtaacca ccacacccgc cgcgcttaat gcgccgctac agggcgcgta   8160
ctatggttgc tttgacgtat gcggtgtgaa ataccgcaca gatgcgtaag gagaaaatac   8220
cgcatcaggc gccattcgcc attcaggctg cgcaactgtt gggaagggcg atcggtgcgg   8280
gcctcttcgc tattacgcca gctggcgaaa gggggatgtg ctgcaaggcg attaagttgg   8340
gtaacgccag ggttttccca gtcacgacgt tgtaaaacga cggccagtga attccatggt   8400
ctcaactttc                                                          8410
```

<210> SEQ ID NO 25
<211> LENGTH: 8431
<212> TYPE: DNA
<213> ORGANISM: Artificial Sequence
<220> FEATURE:
<223> OTHER INFORMATION: Synthetic polynucleotide

<400> SEQUENCE: 25

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgtt cccgttccag ccaatgtatc cgatgcagcc aatgccctat cgcaacccgt    960
tcgcggcccc gcgcaggccc tggttcccca gaaccgaccc ttttctggcg atgcaggtgc   1020
aggaattaac ccgctcgatg gctaacctga cgttcaagca acgccgggac gcgccacctg   1080
aggggccatc cgctaataaa ccgaagaagg aggcctcgca aaaacagaaa gggggaggcc   1140
aagggaagaa gaagaagaac caagggaaga agaaggctaa gacagggccg cctaatccga   1200
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
```

```
acgcttgtgt ggtcggaggg aagttattca ggccgatgca tgtggaaggc aagatcgaca   1380
acgacgttct ggccgcgctt aagacgaaga aagcatccaa atacgatctt gagtatgcag   1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc caagggagac agcggacgac ccattctgga taaccaggga cgggtggtcg   1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccggaaggaa aaggagatcc accgaggagc   1920
tgtttaatga gtataagcta acgcgccctt acatggccag atgcatcaga tgtgcagttg   1980
ggagctgcca tagtccaata gcaatcgagg cagtaaagag cgacgggcac gacggttatg   2040
ttagacttca gacttcctcg cagtatggcc tggattcctc cggcaactta aagggcagga   2100
ccatgcggta tgacatgcac gggaccatta aagagatacc actacatcaa gtgtcactct   2160
atacatctcg cccgtgtcac attgtggatg ggcacggtta tttcctgctt gccaggtgcc   2220
cggcagggga ctccatcacc atggaattta agaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggctccg   2460
gaggatccag ttcagtcacc gtgacacctc ctgatgggac tagcgccctg gtggaatgcg   2520
agtgtggcgg cacaaagatc tccgagacca tcaacaagac aaaacagttc agccagtgca   2580
caaagaagga gcagtgcaga gcatatcggc tgcagaacga taagtgggtg tataattctg   2640
acaaactgcc caaagcagcg ggagccacct taaaaggaaa actgcatgtc ccattcttgc   2700
tggcagacgg caaatgcacc gtgcctctag caccagaacc tatgataacc ttcggtttca   2760
gatcagtgtc actgaaactg caccctaaga atcccacata tctaatcacc cgccaacttg   2820
ctgatgagcc tcactacacg cacgagctca tatctgaacc agctgttagg aattttaccg   2880
tcaccgaaaa agggtgggag tttgtatggg gaaaccaccc gccgaaaagg ttttgggcac   2940
aggaaacagc acccggaaat ccacatgggc taccgcacga ggtgataact cattattacc   3000
acagataccc tatgtccacc atcctgggtt tgtcaatttg tgccgccatt gcaaccgttt   3060
ccgttgcagc gtctacctgg ctgttttgca gatcaagagt tgcgtgccta actccttacc   3120
ggctaacacc taacgctagg ataccatttt gtctggctgt gctttgctgc gcccgcactg   3180
cccgggccga gaccacctgg gagtccttgg atcacctatg gaacaataac caacagatgt   3240
tctggattca attgctgatc cctctggccg ccttgatcgt agtgactcgc ctgctcaggt   3300
gcgtgtgctg tgtcgtgcct tttttagtca tggccggcgc cgcaggcgcc ggcgcctacg   3360
agcacgcgac cacgatgccg agccaagcgg gaatctcgta taacactata gtcaacagag   3420
caggctacgc accactccct atcagcataa caccaacaaa gatcaagctg atacctacag   3480
tgaacttgga gtacgtcacc tgccactaca aaacaggaat ggattcacca gccatcaaat   3540
gctgcggatc tcaggaatgc actccaactt acaggcctga tgaacagtgc aaagtcttca   3600
caggggttta cccgttcatg tggggtggtg catattgctt ttgcgacact gagaacaccc   3660
```

```
aagtcagcaa ggcctacgta atgaaatctg acgactgcct tgcggatcat gctgaagcat   3720
ataaagcgca cacagcctca gtgcaggcgt tcctcaacat cacagtggga gaacactcta   3780
ttgtgactac cgtgtatgtg aatggagaaa ctcctgtgaa tttcaatggg gtcaaaataa   3840
ctgcaggtcc gctttccaca gcttggacac cctttgatcg caaaatcgtg cagtatgccg   3900
gggagatcta taattatgat tttcctgagt atggggcagg acaaccagga gcatttggag   3960
atatacaatc cagaacagtc tcaagctctg atctgtatgc caataccaac ctagtgctgc   4020
agagacccaa agcaggagcg atccacgtgc catacactca ggcaccttcg ggttttgagc   4080
aatggaagaa agataaagct ccatcattga aatttaccgc cccttttcgga tgcgaaatat   4140
atacaaaccc cattcgcgcc gaaaactgtg ctgtagggtc aattccatta gcctttgaca   4200
ttcccgacgc cttgttcacc agggtgtcag aaacaccgac actttcagcg gccgaatgca   4260
ctcttaacga gtgcgtgtat tcttccgact ttggtgggat cgccacggtc aagtactcgg   4320
ccagcaagtc aggcaagtgc gcagtccatg tgccatcagg gactgctacc ctaaaagaag   4380
cagcagtcga gctaaccgag caagggtcgg cgactatcca tttctcgacc gcaaatatcc   4440
acccggagtt caggctccaa atatgcacat catatgttac gtgcaaaggt gattgtcacc   4500
ccccgaaaga ccatattgtg acacaccctc agtatcacgc ccaaacattt acagccgcgg   4560
tgtcaaaaac cgcgtggacg tggttaacat ccctgctggg aggatcagcc gtaattatta   4620
taattggctt ggtgctggct actattgtgg ccatgtacgt gctgaccaac cagaaacata   4680
attaaggatc tagatctgct gtgccttcta gttgccagcc atctgttgtt tgcccctccc   4740
ccgtgccttc cttgaccctg gaaggtgcca ctcccactgt cctttcctaa taaaatgagg   4800
aaattgcatc gcattgtctg agtaggtgtc attctattct ggggggtggg gtggggcagg   4860
acagcaaggg ggaggattgg gaagacaata gcaggcatgc tggggatgcg gtgggctcta   4920
tgggtaccca ggtgctgaag aattgacccg gttcctcctg ggccagaaag aagcaggcac   4980
atccccttct ctgtgacaca ccctgtccac gcccctggtt cttagttcca gccccactca   5040
taggacactc atagctcagg agggctccgc cttcaatccc acccgctaaa gtacttggag   5100
cggtctctcc ctccctcatc agcccaccaa accaaaccta gcctccaaga gtgggaagaa   5160
attaaagcaa gataggctat taagtgcaga gggagagaaa atgcctccaa catgtgagga   5220
agtaatgaga gaaatcatag aattttaagg ccatgattta aggccatcat ggcctaagct   5280
tgaaaggaga taggatcaaa gcttggcgta atcatggtca tagctgtttc ctgtgtgaaa   5340
ttgttatccg ctcacaattc cacacaacat acgagccgga agcataaagt gtaaagcctg   5400
gggtgcctaa tgagtgagct aactcacatt aattgcgttg cgctcactgc ccgctttcca   5460
gtcgggaaac ctgtcgtgcc agctgcatta atgaatcggc caacgcgcgg ggagaggcgg   5520
tttgcgtatt gggcgctctt ccgcttcctc gctcactgac tcgctgcgct cggtcgttcg   5580
gctgcggcga gcggtatcag ctcactcaaa ggcggtaata cggttatcca cagaatcagg   5640
ggataacgca ggaaagaaca tgtgagcaaa aggccagcaa aaggccagga accgtaaaaa   5700
ggccgcgttg ctggcgtttt tccataggct ccgcccccct gacgagcatc acaaaaatcg   5760
acgctcaagt cagaggtggc gaaacccgac aggactataa agataccagg cgtttccccc   5820
tggaagctcc ctcgtgcgct ctcctgttcc gaccctgccg cttaccggat acctgtccgc   5880
ctttctccct tcgggaagcg tggcgctttc tcatagctca cgctgtaggt atctcagttc   5940
ggtgtaggtc gttcgctcca agctgggctg tgtgcacgaa ccccccgttc agcccgaccg   6000
ctgcgcctta tccggtaact atcgtcttga gtccaacccg gtaagacacg acttatcgcc   6060
```

```
actggcagca gccactggta acaggattag cagagcgagg tatgtaggcg gtgctacaga   6120
gttcttgaag tggtggccta actacggcta cactagaaga acagtatttg gtatctgcgc   6180
tctgctgaag ccagttacct tcggaaaaag agttggtagc tcttgatccg gcaaacaaac   6240
caccgctggt agcggtggtt tttttgtttg caagcagcag attacgcgca gaaaaaaagg   6300
atctcaagaa gatcctttga tcttttctac ggggtctgac gctcagtgga acgaaaactc   6360
acgttaaggg attttggtca tgagattatc aaaaaggatc ttcacctaga tccttttaaa   6420
ttaaaaatga agttttaaat caatctaaag tatatatgag taaacttggt ctgacagtta   6480
ccaatgctta atcagtgagg cacctatctc agcgatctgt ctatttcgtt catccatagt   6540
tgcctgactc cccgtcgtgt agataactac gatacgggag ggcttaccat ctggccccag   6600
tgctgcaatg ataccgcgag aaccacgctc accggctcca gatttatcag caataaacca   6660
gccagccgga agggccgagc gcagaagtgg tcctgcaact ttatccgcct ccatccagtc   6720
tattaattgt tgccgggaag ctagagtaag tagttcgcca gttaatagtt tgcgcaacgt   6780
tgttgccatt gctacaggca tcgtggtgtc acgctcgtcg tttggtatgg cttcattcag   6840
ctccggttcc caacgatcaa ggcgagttac atgatccccc atgttgtgca aaaaagcggt   6900
tagctccttc ggtcctccga tcgttgtcag aagtaagttg gccgcagtgt tatcactcat   6960
ggttatggca gcactgcata attctcttac tgtcatgcca tccgtaagat gcttttctgt   7020
gactggtgag tactcaacca agtcattctg agaatagtgt atgcggcgac cgagttgctc   7080
ttgcccggcg tcaatacggg ataataccgc gccacatagc agaactttaa aagtgctcat   7140
cattggaaaa cgttcttcgg ggcgaaaact ctcaaggatc ttaccgctgt tgagatccag   7200
ttcgatgtaa cccactcgtg cacccaactg atcttcagca tcttttactt tcaccagcgt   7260
ttctgggtga gcaaaaacag gaaggcaaaa tgccgcaaaa aagggaataa gggcgacacg   7320
gaaatgttga atactcatac tcttcctttt tcaatattat tgaagcattt atcagggtta   7380
ttgtctcatg agcggataca tatttgaatg tatttagaaa aataaacaaa taggggttcc   7440
gcgcacattt ccccgaaaag tgccacctga cgtctaagaa accattatta tcatgacatt   7500
aacctataaa aataggcgta tcacgaggcc ctttcgggtc gcgcgtttcg gtgatgacgg   7560
tgaaaacctc tgacacatgc agctcccgtt gacggtcaca gcttgtctgt aagcggatgc   7620
cgggagcaga caagcccgtc agggcgcgtc agcgggtgtt ggcgggtgtc ggggctggct   7680
taactatgcg gcatcagagc agattgtact gagagtgcac cataaaattg taaacgttaa   7740
tattttgtta aaattcgcgt taaatttttg ttaaatcagc tcatttttta accaataggc   7800
cgaaatcggc aaaatccctt ataaatcaaa agaatagccc gagatagggt tgagtgttgt   7860
tccagtttgg aacaagagtc cactattaaa gaacgtggac tccaacgtca aagggcgaaa   7920
aaccgtctat cagggcgatg gcccactacg tgaaccatca cccaaatcaa gttttttggg   7980
gtcgaggtgc cgtaaagcac taaatcggaa ccctaaaggg agcccccgat ttagagcttg   8040
acggggaaag ccggcgaacg tggcgagaaa ggaagggaag aaagcgaaag gagcgggcgc   8100
tagggcgctg gcaagtgtag cggtcacgct gcgcgtaacc accacacccg ccgcgcttaa   8160
tgcgccgcta cagggcgcgt actatggttg ctttgacgta tgcggtgtga aataccgcac   8220
agatgcgtaa ggagaaaata ccgcatcagg cgccattcgc cattcaggct gcgcaactgt   8280
tgggaagggc gatcggtgcg ggcctcttcg ctattacgcc agctggcgaa agggggatgt   8340
gctgcaaggc gattaagttg ggtaacgcca gggttttccc agtcacgacg ttgtaaaacg   8400
```

```
acggccagtg aattccatgg tctcaacttt c                                8431


<210> SEQ ID NO 26
<211> LENGTH: 8431
<212> TYPE: DNA
<213> ORGANISM: Artificial Sequence
<220> FEATURE:
<223> OTHER INFORMATION: Synthetic polynucleotide

<400> SEQUENCE: 26

gaattcccat tgcatacgtt gtatccatat cataatatgt acatttatat tggctcatgt    60

ccaacattac cgccatgttg acattgatta ttgactagtt attaatagta atcaattacg   120

gggtcattag ttcatagccc atatatggag ttccgcgtta cataacttac ggtaaatggc   180

ccgcctggct gaccgcccaa cgacccccgc ccattgacgt caataatgac gtatgttccc   240

atagtaacgc caatagggac tttccattga cgtcaatggg tggagtattt acggtaaact   300

gcccacttgg cagtacatca agtgtatcat atgccaagta cgccccctat tgacgtcaat   360

gacggtaaat ggcccgcctg gcattatgcc cagtacatga ccttatggga ctttcctact   420

tggcagtaca tctacgtatt agtcatcgct attaccatgg tgatgcggtt ttggcagtac   480

atcaatgggc gtggatagcg gtttgactca cggggatttc caagtctcca ccccattgac   540

gtcaatggga gtttgttttg gcaccaaaat caacgggact ttccaaaatg tcgtaacaac   600

tccgccccat tgacgcaaat gggcggtagg cgtgtacggt gggaggtcta tataagcaga   660

gctcgtttag tgaaccgtca gatcgcctgg agacgccatc cacgctgttt tgacctccat   720

agaagacacc gggaccgatc cagcctccgt taacggtgga gggcagtgta gtctgagcag   780

tactcgttgc tgccgcgcgc gccaccagac ataatagctg acagactaac agactgttcc   840

tttccatggg tcttttctgc agtcaccgtc gtcgacacgt gtgatcagat atcgcggccg   900

ccaccatgtt cccgttccag ccaatgtatc cgatgcagcc aatgccctat cgcaacccgt   960

tcgcggcccc gcgcaggccc tggttcccca gaaccgaccc ttttctggcg atgcaggtgc  1020

aggaattaac ccgctcgatg gctaacctga cgttcaagca acgccgggac gcgccacctg  1080

aggggccatc cgctaataaa ccgaagaagg aggcctcgca aaaacagaaa gggggaggcc  1140

aagggaagaa gaagaagaac caagggaaga agaaggctaa gacagggccg cctaatccga  1200

aggcacagaa tggaaacaag aagaagacca acaagaaacc aggcaagaga cagcgcatgg  1260

tcatgaaatt ggaatctgac aagacgttcc caatcatgtt ggaagggaag ataaacggct  1320

acgcttgtgt ggtcggaggg aagttattca ggccgatgca tgtggaaggc aagatcgaca  1380

acgacgttct ggccgcgctt aagacgaaga aagcatccaa atacgatctt gagtatgcag  1440

atgtgccaca gaacatgcgg gccgatacat tcaaatacac ccatgagaaa ccccaaggct  1500

attacagctg gcatcatgga gcagtccaat atgaaaatgg gcgtttcacg gtgccgaaag  1560

gagttggggc caagggagac agcggacgac ccattctgga taaccaggga cgggtggtcg  1620

ctattgtgct gggaggtgtg aatgaaggat ctaggacagc cctttcagtc gtcatgtgga  1680

acgagaaggg agttaccgtg aagtatactc cagagaactg cgagcaatgg tcactagtga  1740

ccaccatgtg tctgctcgcc aatgtgacgt tcccatgtgc tcaaccacca atttgctacg  1800

acagaaaacc agcagagact ttggccatgc tcagcgttaa cgttgacaac ccgggctacg  1860

atgagctgct ggaagcagct gttaagtgcc ccggaaggaa aaggagatcc accgaggagc  1920

tgtttaatga gtataagcta acgcgccctt acatggccag atgcatcaga tgtgcagttg  1980

ggagctgcca tagtccaata gcaatcgagg cagtaaagag cgacgggcac gacggttatg  2040
```

```
ttagacttca gacttcctcg cagtatggcc tggattcctc cggcaactta aagggcagga   2100
ccatgcggta tgacatgcac gggaccatta aagagatacc actacatcaa gtgtcactct   2160
atacatctcg cccgtgtcac attgtggatg ggcacggtta tttcctgctt gccaggtgcc   2220
cggcagggga ctccatcacc atggaattta agaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggcagtt   2460
ccggaggatc ctcagtcacc gtgacacctc ctgatgggac tagcgccctg gtggaatgcg   2520
agtgtggcgg cacaaagatc tccgagacca tcaacaagac aaaacagttc agccagtgca   2580
caaagaagga gcagtgcaga gcatatcggc tgcagaacga taagtgggtg tataattctg   2640
acaaactgcc caaagcagcg ggagccacct taaaaggaaa actgcatgtc ccattcttgc   2700
tggcagacgg caaatgcacc gtgcctctag caccagaacc tatgataacc ttcggtttca   2760
gatcagtgtc actgaaactg caccctaaga atcccacata tctaatcacc cgccaacttg   2820
ctgatgagcc tcactacacg cacgagctca tatctgaacc agctgttagg aattttaccg   2880
tcaccgaaaa agggtgggag tttgtatggg gaaaccaccc gccgaaaagg ttttgggcac   2940
aggaaacagc acccggaaat ccacatgggc taccgcacga ggtgataact cattattacc   3000
acagataccc tatgtccacc atcctgggtt tgtcaatttg tgccgccatt gcaaccgttt   3060
ccgttgcagc gtctacctgg ctgttttgca gatcaagagt tgcgtgccta actccttacc   3120
ggctaacacc taacgctagg ataccatttt gtctggctgt gctttgctgc gcccgcactg   3180
cccgggccga gaccacctgg gagtccttgg atcacctatg gaacaataac caacagatgt   3240
tctggattca attgctgatc cctctggccg ccttgatcgt agtgactcgc ctgctcaggt   3300
gcgtgtgctg tgtcgtgcct tttttagtca tggccggcgc cgcaggcgcc ggcgcctacg   3360
agcacgcgac cacgatgccg agccaagcgg gaatctcgta taacactata gtcaacagag   3420
caggctacgc accactccct atcagcataa caccaacaaa gatcaagctg atacctacag   3480
tgaacttgga gtacgtcacc tgccactaca aaacaggaat ggattcacca gccatcaaat   3540
gctgcggatc tcaggaatgc actccaactt acaggcctga tgaacagtgc aaagtcttca   3600
caggggttta cccgttcatg tggggtggtg catattgctt ttgcgacact gagaacaccc   3660
aagtcagcaa ggcctacgta atgaaatctg acgactgcct tgcggatcat gctgaagcat   3720
ataaagcgca cacagcctca gtgcaggcgt tcctcaacat cacagtggga gaacactcta   3780
ttgtgactac cgtgtatgtg aatggagaaa ctcctgtgaa tttcaatggg gtcaaaataa   3840
ctgcaggtcc gctttccaca gcttggacac cctttgatcg caaaatcgtg cagtatgccg   3900
gggagatcta taattatgat tttcctgagt atggggcagg acaaccagga gcatttggag   3960
atatacaatc cagaacagtc tcaagctctg atctgtatgc caataccaac ctagtgctgc   4020
agagacccaa agcaggagcg atccacgtgc catacactca ggcaccttcg ggttttgagc   4080
aatggaagaa agataaagct ccatcattga aatttaccgc ccctttcgga tgcgaaatat   4140
atacaaaccc cattcgcgcc gaaaactgtg ctgtagggtc aattccatta gcctttgaca   4200
ttcccgacgc cttgttcacc agggtgtcag aaacaccgac actttcagcg gccgaatgca   4260
ctcttaacga gtgcgtgtat tcttccgact ttggtgggat cgccacggtc aagtactcgg   4320
ccagcaagtc aggcaagtgc gcagtccatg tgccatcagg gactgctacc ctaaaagaag   4380
```

-continued

```
cagcagtcga gctaaccgag caagggtcgg cgactatcca tttctcgacc gcaaatatcc   4440
acccggagtt caggctccaa atatgcacat catatgttac gtgcaaaggt gattgtcacc   4500
ccccgaaaga ccatattgtg acacaccctc agtatcacgc ccaaacattt acagccgcgg   4560
tgtcaaaaac cgcgtggacg tggttaacat ccctgctggg aggatcagcc gtaattatta   4620
taattggctt ggtgctggct actattgtgg ccatgtacgt gctgaccaac cagaaacata   4680
attaaggatc tagatctgct gtgccttcta gttgccagcc atctgttgtt tgcccctccc   4740
ccgtgccttc cttgaccctg gaaggtgcca ctcccactgt cctttcctaa taaaatgagg   4800
aaattgcatc gcattgtctg agtaggtgtc attctattct ggggggtggg gtggggcagg   4860
acagcaaggg ggaggattgg gaagacaata gcaggcatgc tggggatgcg gtgggctcta   4920
tgggtaccca ggtgctgaag aattgacccg gttcctcctg ggccagaaag aagcaggcac   4980
atccccttct ctgtgacaca ccctgtccac gcccctggtt cttagttcca gccccactca   5040
taggacactc atagctcagg agggctccgc cttcaatccc acccgctaaa gtacttggag   5100
cggtctctcc ctccctcatc agcccaccaa accaaaccta gcctccaaga gtgggaagaa   5160
attaaagcaa gataggctat taagtgcaga gggagagaaa atgcctccaa catgtgagga   5220
agtaatgaga gaaatcatag aattttaagg ccatgattta aggccatcat ggcctaagct   5280
tgaaaggaga taggatcaaa gcttggcgta atcatggtca tagctgtttc ctgtgtgaaa   5340
ttgttatccg ctcacaattc cacacaacat acgagccgga agcataaagt gtaaagcctg   5400
gggtgcctaa tgagtgagct aactcacatt aattgcgttg cgctcactgc ccgctttcca   5460
gtcgggaaac ctgtcgtgcc agctgcatta atgaatcggc caacgcgcgg ggagaggcgg   5520
tttgcgtatt gggcgctctt ccgcttcctc gctcactgac tcgctgcgct cggtcgttcg   5580
gctgcggcga gcggtatcag ctcactcaaa ggcggtaata cggttatcca cagaatcagg   5640
ggataacgca ggaaagaaca tgtgagcaaa aggccagcaa aaggccagga accgtaaaaa   5700
ggccgcgttg ctggcgtttt tccataggct ccgcccccct gacgagcatc acaaaaatcg   5760
acgctcaagt cagaggtggc gaaacccgac aggactataa agataccagg cgtttccccc   5820
tggaagctcc ctcgtgcgct ctcctgttcc gaccctgccg cttaccggat acctgtccgc   5880
ctttctccct tcgggaagcg tggcgctttc tcatagctca cgctgtaggt atctcagttc   5940
ggtgtaggtc gttcgctcca agctgggctg tgtgcacgaa ccccccgttc agcccgaccg   6000
ctgcgcctta tccggtaact atcgtcttga gtccaacccg gtaagacacg acttatcgcc   6060
actggcagca gccactggta acaggattag cagagcgagg tatgtaggcg gtgctacaga   6120
gttcttgaag tggtggccta actacggcta cactagaaga acagtatttg gtatctgcgc   6180
tctgctgaag ccagttacct tcggaaaaag agttggtagc tcttgatccg gcaaacaaac   6240
caccgctggt agcggtggtt tttttgtttg caagcagcag attacgcgca gaaaaaaagg   6300
atctcaagaa gatcctttga tcttttctac ggggtctgac gctcagtgga acgaaaactc   6360
acgttaaggg attttggtca tgagattatc aaaaaggatc ttcacctaga tccttttaaa   6420
ttaaaaatga agttttaaat caatctaaag tatatatgag taaacttggt ctgacagtta   6480
ccaatgctta atcagtgagg cacctatctc agcgatctgt ctatttcgtt catccatagt   6540
tgcctgactc cccgtcgtgt agataactac gatacgggag ggcttaccat ctggccccag   6600
tgctgcaatg ataccgcgag aaccacgctc accggctcca gatttatcag caataaacca   6660
gccagccgga agggccgagc gcagaagtgg tcctgcaact ttatccgcct ccatccagtc   6720
tattaattgt tgccgggaag ctagagtaag tagttcgcca gttaatagtt tgcgcaacgt   6780
```

```
tgttgccatt gctacaggca tcgtggtgtc acgctcgtcg tttggtatgg cttcattcag   6840
ctccggttcc caacgatcaa ggcgagttac atgatccccc atgttgtgca aaaaagcggt   6900
tagctccttc ggtcctccga tcgttgtcag aagtaagttg gccgcagtgt tatcactcat   6960
ggttatggca gcactgcata attctcttac tgtcatgcca tccgtaagat gcttttctgt   7020
gactggtgag tactcaacca agtcattctg agaatagtgt atgcggcgac cgagttgctc   7080
ttgcccggcg tcaatacggg ataataccgc gccacatagc agaactttaa aagtgctcat   7140
cattggaaaa cgttcttcgg ggcgaaaact ctcaaggatc ttaccgctgt tgagatccag   7200
ttcgatgtaa cccactcgtg cacccaactg atcttcagca tcttttactt tcaccagcgt   7260
ttctgggtga gcaaaaacag gaaggcaaaa tgccgcaaaa aagggaataa gggcgacacg   7320
gaaatgttga atactcatac tcttcctttt tcaatattat tgaagcattt atcagggtta   7380
ttgtctcatg agcggataca tatttgaatg tatttagaaa aataaacaaa taggggttcc   7440
gcgcacattt ccccgaaaag tgccacctga cgtctaagaa accattatta tcatgacatt   7500
aacctataaa aataggcgta tcacgaggcc ctttcgggtc gcgcgtttcg gtgatgacgg   7560
tgaaaacctc tgacacatgc agctcccggt gacggtcaca gcttgtctgt aagcggatgc   7620
cgggagcaga caagcccgtc agggcgcgtc agcgggtgtt ggcgggtgtc ggggctggct   7680
taactatgcg gcatcagagc agattgtact gagagtgcac cataaaattg taaacgttaa   7740
tattttgtta aaattcgcgt taaatttttg ttaaatcagc tcattttta accaataggc   7800
cgaaatcggc aaaatccctt ataaatcaaa agaatagccc gagatagggt tgagtgttgt   7860
tccagtttgg aacaagagtc cactattaaa gaacgtggac tccaacgtca aagggcgaaa   7920
aaccgtctat cagggcgatg gcccactacg tgaaccatca cccaaatcaa gtttttggg    7980
gtcgaggtgc cgtaaagcac taaatcggaa ccctaaaggg agcccccgat ttagagcttg   8040
acggggaaag ccggcgaacg tggcgagaaa ggaagggaag aaagcgaaag gagcgggcgc   8100
tagggcgctg gcaagtgtag cggtcacgct gcgcgtaacc accacacccg ccgcgcttaa   8160
tgcgccgcta cagggcgcgt actatggttg ctttgacgta tgcggtgtga aataccgcac   8220
agatgcgtaa ggagaaaata ccgcatcagg cgccattcgc cattcaggct gcgcaactgt   8280
tgggaagggc gatcggtgcg ggcctcttcg ctattacgcc agctggcgaa agggggatgt   8340
gctgcaaggc gattaagttg ggtaacgcca gggttttccc agtcacgacg ttgtaaaacg   8400
acggccagtg aattccatgg tctcaacttt c                                  8431
```

<210> SEQ ID NO 27
<211> LENGTH: 8431
<212> TYPE: DNA
<213> ORGANISM: Artificial Sequence
<220> FEATURE:
<223> OTHER INFORMATION: Synthetic polynucleotide

<400> SEQUENCE: 27

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
```

```
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgtt cccgttccag ccaatgtatc cgatgcagcc aatgccctat cgcaacccgt    960
tcgcggcccc gcgcaggccc tggttcccca gaaccgaccc ttttctggcg atgcaggtgc   1020
aggaattaac ccgctcgatg gctaacctga cgttcaagca acgccgggac gcgccacctg   1080
aggggccatc cgctaataaa ccgaagaagg aggcctcgca aaaacagaaa gggggaggcc   1140
aagggaagaa gaagaagaac caagggaaga agaaggctaa gacagggccg cctaatccga   1200
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
acgcttgtgt ggtcggaggg aagttattca ggccgatgca tgtggaaggc aagatcgaca   1380
acgacgttct ggccgcgctt aagacgaaga aagcatccaa atacgatctt gagtatgcag   1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc caagggagac agcggacgac ccattctgga taaccaggga cgggtggtcg   1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccggaaggaa aaggagatcc accgaggagc   1920
tgtttaatga gtataagcta acgcgccctt acatggccag atgcatcaga tgtgcagttg   1980
ggagctgcca tagtccaata gcaatcgagg cagtaaagag cgacgggcac gacggttatg   2040
ttagacttca gacttcctcg cagtatggcc tggattcctc cggcaactta aagggcagga   2100
ccatgcggta tgacatgcac gggaccatta aagagatacc actacatcaa gtgtcactct   2160
atacatctcg cccgtgtcac attgtggatg ggcacggtta tttcctgctt gccaggtgcc   2220
cggcagggga ctccatcacc atggaattta agaaagattc cgtcagacac tcctgctcgg   2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggcagtt   2460
cagtcaccgt gacacctcct gatgggacta gcgccctggt ggaatgcgag tgtggctccg   2520
gaggatccgg cacaaagatc tccgagacca tcaacaagac aaaacagttc agccagtgca   2580
caaagaagga gcagtgcaga gcatatcggc tgcagaacga taagtgggtg tataattctg   2640
acaaactgcc caaagcagcg ggagccacct taaaaggaaa actgcatgtc ccattcttgc   2700
tggcagacgg caaatgcacc gtgcctctag caccagaacc tatgataacc ttcggtttca   2760
```

```
gatcagtgtc actgaaactg caccctaaga atcccacata tctaatcacc cgccaacttg   2820
ctgatgagcc tcactacacg cacgagctca tatctgaacc agctgttagg aattttaccg   2880
tcaccgaaaa agggtgggag tttgtatggg gaaaccaccc gccgaaaagg ttttgggcac   2940
aggaaacagc acccggaaat ccacatgggc taccgcacga ggtgataact cattattacc   3000
acagataccc tatgtccacc atcctgggtt tgtcaatttg tgccgccatt gcaaccgttt   3060
ccgttgcagc gtctacctgg ctgttttgca gatcaagagt tgcgtgccta actccttacc   3120
ggctaacacc taacgctagg ataccatttt gtctggctgt gctttgctgc gcccgcactg   3180
cccgggccga gaccacctgg gagtccttgg atcacctatg gaacaataac caacagatgt   3240
tctggattca attgctgatc cctctggccg ccttgatcgt agtgactcgc ctgctcaggt   3300
gcgtgtgctg tgtcgtgcct tttttagtca tggccggcgc cgcaggcgcc ggcgcctacg   3360
agcacgcgac cacgatgccg agccaagcgg gaatctcgta taacactata gtcaacagag   3420
caggctacgc accactccct atcagcataa caccaacaaa gatcaagctg atacctacag   3480
tgaacttgga gtacgtcacc tgccactaca aaacaggaat ggattcacca gccatcaaat   3540
gctgcggatc tcaggaatgc actccaactt acaggcctga tgaacagtgc aaagtcttca   3600
caggggttta cccgttcatg tggggtggtg catattgctt ttgcgacact gagaacaccc   3660
aagtcagcaa ggcctacgta atgaaatctg acgactgcct tgcggatcat gctgaagcat   3720
ataaagcgca cacagcctca gtgcaggcgt tcctcaacat cacagtggga gaacactcta   3780
ttgtgactac cgtgtatgtg aatggagaaa ctcctgtgaa tttcaatggg gtcaaaataa   3840
ctgcaggtcc gctttccaca gcttggacac cctttgatcg caaaatcgtg cagtatgccg   3900
gggagatcta taattatgat tttcctgagt atggggcagg acaaccagga gcatttggag   3960
atatacaatc cagaacagtc tcaagctctg atctgtatgc caataccaac ctagtgctgc   4020
agagacccaa agcaggagcg atccacgtgc catacactca ggcaccttcg ggttttgagc   4080
aatggaagaa agataaagct ccatcattga aatttaccgc ccctttcgga tgcgaaatat   4140
atacaaaccc cattcgcgcc gaaaactgtg ctgtagggtc aattccatta gcctttgaca   4200
ttcccgacgc cttgttcacc agggtgtcag aaacaccgac actttcagcg gccgaatgca   4260
ctcttaacga gtgcgtgtat tcttccgact ttggtgggat cgccacggtc aagtactcgg   4320
ccagcaagtc aggcaagtgc gcagtccatg tgccatcagg gactgctacc ctaaaagaag   4380
cagcagtcga gctaaccgag caagggtcgg cgactatcca tttctcgacc gcaaatatcc   4440
acccggagtt caggctccaa atatgcacat catatgttac gtgcaaaggt gattgtcacc   4500
ccccgaaaga ccatattgtg acacaccctc agtatcacgc ccaaacattt acagccgcgg   4560
tgtcaaaaac cgcgtggacg tggttaacat ccctgctggg aggatcagcc gtaattatta   4620
taattggctt ggtgctggct actattgtgg ccatgtacgt gctgaccaac cagaaacata   4680
attaaggatc tagatctgct gtgccttcta gttgccagcc atctgttgtt tgcccctccc   4740
ccgtgccttc cttgaccctg gaaggtgcca ctcccactgt cctttcctaa taaaatgagg   4800
aaattgcatc gcattgtctg agtaggtgtc attctattct ggggggtggg gtggggcagg   4860
acagcaaggg ggaggattgg gaagacaata gcaggcatgc tggggatgcg gtgggctcta   4920
tgggtaccca ggtgctgaag aattgacccg gttcctcctg ggccagaaag aagcaggcac   4980
atccccttct ctgtgacaca ccctgtccac gcccctggtt cttagttcca gccccactca   5040
taggacactc atagctcagg agggctccgc cttcaatccc acccgctaaa gtacttggag   5100
```

-continued

```
cggtctctcc ctccctcatc agcccaccaa accaaaccta gcctccaaga gtgggaagaa   5160
attaaagcaa gataggctat taagtgcaga gggagagaaa atgcctccaa catgtgagga   5220
agtaatgaga gaaatcatag aattttaagg ccatgattta aggccatcat ggcctaagct   5280
tgaaaggaga taggatcaaa gcttggcgta atcatggtca tagctgtttc ctgtgtgaaa   5340
ttgttatccg ctcacaattc cacacaacat acgagccgga agcataaagt gtaaagcctg   5400
gggtgcctaa tgagtgagct aactcacatt aattgcgttg cgctcactgc ccgctttcca   5460
gtcgggaaac ctgtcgtgcc agctgcatta atgaatcggc caacgcgcgg ggagaggcgg   5520
tttgcgtatt gggcgctctt ccgcttcctc gctcactgac tcgctgcgct cggtcgttcg   5580
gctgcggcga gcggtatcag ctcactcaaa ggcggtaata cggttatcca cagaatcagg   5640
ggataacgca ggaaagaaca tgtgagcaaa aggccagcaa aaggccagga accgtaaaaa   5700
ggccgcgttg ctggcgtttt tccataggct ccgcccccct gacgagcatc acaaaaatcg   5760
acgctcaagt cagaggtggc gaaacccgac aggactataa agataccagg cgtttccccc   5820
tggaagctcc ctcgtgcgct ctcctgttcc gaccctgccg cttaccggat acctgtccgc   5880
ctttctccct tcgggaagcg tggcgctttc tcatagctca cgctgtaggt atctcagttc   5940
ggtgtaggtc gttcgctcca agctgggctg tgtgcacgaa ccccccgttc agcccgaccg   6000
ctgcgcctta tccggtaact atcgtcttga gtccaacccg gtaagacacg acttatcgcc   6060
actggcagca gccactggta acaggattag cagagcgagg tatgtaggcg gtgctacaga   6120
gttcttgaag tggtggccta actacggcta cactagaaga acagtatttg gtatctgcgc   6180
tctgctgaag ccagttacct tcggaaaaag agttggtagc tcttgatccg gcaaacaaac   6240
caccgctggt agcggtggtt tttttgtttg caagcagcag attacgcgca gaaaaaaagg   6300
atctcaagaa gatcctttga tcttttctac ggggtctgac gctcagtgga acgaaaactc   6360
acgttaaggg attttggtca tgagattatc aaaaaggatc ttcacctaga tccttttaaa   6420
ttaaaaatga agttttaaat caatctaaag tatatatgag taaacttggt ctgacagtta   6480
ccaatgctta atcagtgagg cacctatctc agcgatctgt ctatttcgtt catccatagt   6540
tgcctgactc cccgtcgtgt agataactac gatacgggag ggcttaccat ctggccccag   6600
tgctgcaatg ataccgcgag aaccacgctc accggctcca gatttatcag caataaacca   6660
gccagccgga agggccgagc gcagaagtgg tcctgcaact ttatccgcct ccatccagtc   6720
tattaattgt tgccgggaag ctagagtaag tagttcgcca gttaatagtt tgcgcaacgt   6780
tgttgccatt gctacaggca tcgtggtgtc acgctcgtcg tttggtatgg cttcattcag   6840
ctccggttcc caacgatcaa ggcgagttac atgatccccc atgttgtgca aaaaagcggt   6900
tagctccttc ggtcctccga tcgttgtcag aagtaagttg gccgcagtgt tatcactcat   6960
ggttatggca gcactgcata attctcttac tgtcatgcca tccgtaagat gcttttctgt   7020
gactggtgag tactcaacca agtcattctg agaatagtgt atgcggcgac cgagttgctc   7080
ttgcccggcg tcaatacggg ataataccgc gccacatagc agaactttaa aagtgctcat   7140
cattggaaaa cgttcttcgg ggcgaaaact ctcaaggatc ttaccgctgt tgagatccag   7200
ttcgatgtaa cccactcgtg cacccaactg atcttcagca tcttttactt tcaccagcgt   7260
ttctgggtga gcaaaaacag gaaggcaaaa tgccgcaaaa aagggaataa gggcgacacg   7320
gaaatgttga atactcatac tcttcctttt tcaatattat tgaagcattt atcagggtta   7380
ttgtctcatg agcggataca tatttgaatg tatttagaaa aataaacaaa taggggttcc   7440
gcgcacattt ccccgaaaag tgccacctga cgtctaagaa accattatta tcatgacatt   7500
```

```
aacctataaa aataggcgta tcacgaggcc ctttcgggtc gcgcgtttcg gtgatgacgg   7560

tgaaaacctc tgacacatgc agctcccgtt gacggtcaca gcttgtctgt aagcggatgc   7620

cgggagcaga caagcccgtc agggcgcgtc agcgggtgtt ggcgggtgtc ggggctggct   7680

taactatgcg gcatcagagc agattgtact gagagtgcac cataaaattg taaacgttaa   7740

tattttgtta aaattcgcgt taaatttttg ttaaatcagc tcatttttta accaataggc   7800

cgaaatcggc aaaatccctt ataaatcaaa agaatagccc gagatagggt tgagtgttgt   7860

tccagtttgg aacaagagtc cactattaaa gaacgtggac tccaacgtca aagggcgaaa   7920

aaccgtctat cagggcgatg gcccactacg tgaaccatca cccaaatcaa gtttttttggg   7980

gtcgaggtgc cgtaaagcac taaatcggaa ccctaaaggg agcccccgat ttagagcttg   8040

acggggaaag ccggcgaacg tggcgagaaa ggaagggaag aaagcgaaag gagcgggcgc   8100

tagggcgctg gcaagtgtag cggtcacgct gcgcgtaacc accacacccg ccgcgcttaa   8160

tgcgccgcta cagggcgcgt actatggttg ctttgacgta tgcggtgtga aataccgcac   8220

agatgcgtaa ggagaaaata ccgcatcagg cgccattcgc cattcaggct gcgcaactgt   8280

tgggaagggc gatcggtgcg ggcctcttcg ctattacgcc agctggcgaa agggggatgt   8340

gctgcaaggc gattaagttg ggtaacgcca gggttttccc agtcacgacg ttgtaaaacg   8400

acggccagtg aattccatgg tctcaacttt c                                 8431
```

<210> SEQ ID NO 28
<211> LENGTH: 3750
<212> TYPE: DNA
<213> ORGANISM: Artificial Sequence
<220> FEATURE:
<223> OTHER INFORMATION: Synthetic polynucleotide

<400> SEQUENCE: 28

```
atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

caccgccaaa gacgcagtac taaggacaat tttaatgtct ataaagccac aagaccatat   1020

ctagctcatt gtcctgactg cggagaaggg cattcgtgcc acagccctat cgcattggag   1080
```

```
cgcatcagaa atgaagcaac ggacggaacg ctgaaaatcc aggtctcttt gcagatcggg   1140

ataaagacag atgacagcca cgattggacc aagctgcgct atatggatag ccatacgcca   1200

gcggacgcgg agcgagccgg attgcttgta aggacttcag caccgtgcac gatcaccggg   1260

accatgggac actttattct cgcccgatgc ccgaaaggag agacgctgac agtgggattt   1320

acggacagca gaaagatcag ccacacatgc acacacccgt tccatcatga accacctgtg   1380

ataggtaggg agaggttcca ctctcgacca caacatggta aagagttacc ttgcagcacg   1440

tacgtgcaga gcaccgctgc cactgctgag gagatagagg tgcatatgcc cccagatact   1500

cctgaccgca cgctgatgac gcagcagtcc ggaggatcca acgtgaagat cacagttaat   1560

gggcagacgg tgcggtacaa gtgcaactgc ggtggctcaa acgagggact gacaaccaca   1620

gacaaagtga tcaataactg caaaattgat cagtgccatg ctgcagtcac taatcacaag   1680

aattggcaat acaactcccc tttagtcccg cgcaacgctg aactcgggga ccgtaaagga   1740

aagatccaca tcccattccc attggcaaac gtgacttgca gagtgccaaa agcaagaaac   1800

cctacagtaa cttacggaaa aaaccaagtc accatgctgc tgtatcctga ccatccgaca   1860

ctcttgtctt accgtaacat gggacaggaa ccaaattacc acgaggagtg ggtgacacac   1920

aagaaggagg ttaccttgac cgtgcctact gagggtctgg aggtcacttg gggcaacaac   1980

gaaccataca agtactggcc gcagatgtct acgaacggta ctgctcatgg tcacccacat   2040

gagataatct tgtactatta tgagctgtac cccactatga ctgtagtcat tgtgtcggtg   2100

gcctcgttcg tgcttctgtc gatggtgggc acagcagtgg gaatgtgtgt gtgcgcacgg   2160

cgcagatgca ttacaccata tgaattaaca ccaggagcca ctgttccctt cctgctcagc   2220

ctgctatgct gcgtcagaac gaccaaggcg gccacatatt acgaggctgc ggcatatcta   2280

tggaacgaac agcagcccct gttctggttg caggctctta tcccgctggc cgccttgatc   2340

gtcctgtgca actgtctgaa actcttgcca tgctgctgta agaccctggc tttttttagcc   2400

gtaatgagca tcggtgccca cactgtgagc gcgtacgaac acgtaacagt gatcccgaac   2460

acggtgggag taccgtataa gactcttgtc aacagaccgg gttacagccc catggtgttg   2520

gagatggagc tacaatcagt caccttggaa ccaacactgt cacttgacta catcacgtgc   2580

gagtacaaaa ctgtcatccc ctccccgtac gtgaagtgct gtggtacagc agagtgcaag   2640

gacaagagcc taccagacta cagctgcaag gtctttactg gagtctaccc atttatgtgg   2700

ggcggcgcct actgcttttg cgacgccgaa aatacgcaat tgagcgaggc acatgtagag   2760

aaatctgaat cttgcaaaac agagtttgca tcggcctaca gagcccacac cgcatcggcg   2820

tcggcgaagc tccgcgtcct ttaccaagga aacaacatta ccgtagctgc ctacgctaac   2880

ggtgaccatg ccgtcacagt aaaggacgcc aagtttgtcg tgggcccaat gtcctccgcc   2940

tggacacctt ttgacaacaa aatcgtggtg tacaaaggcg acgtctacaa catggactac   3000

ccacctttttg gcgcaggaag accaggacaa tttggtgaca ttcaaagtcg tacaccggaa   3060

agtaaagacg tttatgccaa cactcagttg gtactacaga ggccagcagc aggcacggta   3120

catgtaccat actctcaggc accatctggc ttcaagtatt ggctgaagga acgaggagca   3180

tcgctacagc acacggcacc gttcggttgc cagattgcga caaacccggt aagagctgta   3240

aattgcgctg tggggaacat accaatttcc atcgacatac cggatgcggc ctttactagg   3300

gttgtcgatg caccctctgt aacggacatg tcatgcgaag taccagcctg cactcactcc   3360

tccgactttg ggggcgtcgc catcatcaaa tacacagcta gcaagaaagg taaatgtgca   3420

gtacattcga tgaccaacgc cgttaccatt cgagaagccg acgtagaagt agaggggaac   3480
```

```
tcccagctgc aaatatcctt ctcaacagcc ctggcaagcg ccgagtttcg cgtgcaagtg   3540

tgctccacac aagtacactg cgcagccgca tgccaccctc caaaggacca catagtcaat   3600

tacccagcat cacacaccac ccttggggtc caggatatat ccacaacggc aatgtcttgg   3660

gtgcagaaga ttacgggagg agtaggatta attgttgctg ttgctgcctt aattttaatt   3720

gtggtgctat gcgtgtcgtt tagcaggcac                                    3750


<210> SEQ ID NO 29
<211> LENGTH: 1250
<212> TYPE: PRT
<213> ORGANISM: Artificial Sequence
<220> FEATURE:
<223> OTHER INFORMATION: Synthetic peptide

<400> SEQUENCE: 29

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
```

```
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Gly
            500                 505                 510

Ser Asn Val Lys Ile Thr Val Asn Gly Gln Thr Val Arg Tyr Lys Cys
        515                 520                 525

Asn Cys Gly Gly Ser Asn Glu Gly Leu Thr Thr Thr Asp Lys Val Ile
    530                 535                 540

Asn Asn Cys Lys Ile Asp Gln Cys His Ala Ala Val Thr Asn His Lys
545                 550                 555                 560

Asn Trp Gln Tyr Asn Ser Pro Leu Val Pro Arg Asn Ala Glu Leu Gly
                565                 570                 575

Asp Arg Lys Gly Lys Ile His Ile Pro Phe Pro Leu Ala Asn Val Thr
            580                 585                 590

Cys Arg Val Pro Lys Ala Arg Asn Pro Thr Val Thr Tyr Gly Lys Asn
        595                 600                 605

Gln Val Thr Met Leu Leu Tyr Pro Asp His Pro Thr Leu Leu Ser Tyr
    610                 615                 620

Arg Asn Met Gly Gln Glu Pro Asn Tyr His Glu Glu Trp Val Thr His
625                 630                 635                 640

Lys Lys Glu Val Thr Leu Thr Val Pro Thr Glu Gly Leu Glu Val Thr
                645                 650                 655

Trp Gly Asn Asn Glu Pro Tyr Lys Tyr Trp Pro Gln Met Ser Thr Asn
            660                 665                 670

Gly Thr Ala His Gly His Pro His Glu Ile Ile Leu Tyr Tyr Tyr Glu
        675                 680                 685

Leu Tyr Pro Thr Met Thr Val Val Ile Val Ser Val Ala Ser Phe Val
    690                 695                 700

Leu Leu Ser Met Val Gly Thr Ala Val Gly Met Cys Val Cys Ala Arg
705                 710                 715                 720

Arg Arg Cys Ile Thr Pro Tyr Glu Leu Thr Pro Gly Ala Thr Val Pro
                725                 730                 735
```

```
Phe Leu Leu Ser Leu Leu Cys Cys Val Arg Thr Thr Lys Ala Ala Thr
            740                 745                 750

Tyr Tyr Glu Ala Ala Ala Tyr Leu Trp Asn Glu Gln Gln Pro Leu Phe
        755                 760                 765

Trp Leu Gln Ala Leu Ile Pro Leu Ala Ala Leu Ile Val Leu Cys Asn
    770                 775                 780

Cys Leu Lys Leu Leu Pro Cys Cys Cys Lys Thr Leu Ala Phe Leu Ala
785                 790                 795                 800

Val Met Ser Ile Gly Ala His Thr Val Ser Ala Tyr Glu His Val Thr
                805                 810                 815

Val Ile Pro Asn Thr Val Gly Val Pro Tyr Lys Thr Leu Val Asn Arg
            820                 825                 830

Pro Gly Tyr Ser Pro Met Val Leu Glu Met Glu Leu Gln Ser Val Thr
        835                 840                 845

Leu Glu Pro Thr Leu Ser Leu Asp Tyr Ile Thr Cys Glu Tyr Lys Thr
    850                 855                 860

Val Ile Pro Ser Pro Tyr Val Lys Cys Cys Gly Thr Ala Glu Cys Lys
865                 870                 875                 880

Asp Lys Ser Leu Pro Asp Tyr Ser Cys Lys Val Phe Thr Gly Val Tyr
                885                 890                 895

Pro Phe Met Trp Gly Gly Ala Tyr Cys Phe Cys Asp Ala Glu Asn Thr
            900                 905                 910

Gln Leu Ser Glu Ala His Val Glu Lys Ser Glu Ser Cys Lys Thr Glu
        915                 920                 925

Phe Ala Ser Ala Tyr Arg Ala His Thr Ala Ser Ala Ser Ala Lys Leu
    930                 935                 940

Arg Val Leu Tyr Gln Gly Asn Asn Ile Thr Val Ala Ala Tyr Ala Asn
945                 950                 955                 960

Gly Asp His Ala Val Thr Val Lys Asp Ala Lys Phe Val Val Gly Pro
                965                 970                 975

Met Ser Ser Ala Trp Thr Pro Phe Asp Asn Lys Ile Val Val Tyr Lys
            980                 985                 990

Gly Asp Val Tyr Asn Met Asp Tyr  Pro Pro Phe Gly Ala  Gly Arg Pro
        995                 1000                1005

Gly Gln  Phe Gly Asp Ile Gln  Ser Arg Thr Pro Glu  Ser Lys Asp
    1010                1015                1020

Val Tyr  Ala Asn Thr Gln Leu  Val Leu Gln Arg Pro  Ala Ala Gly
    1025                1030                1035

Thr Val  His Val Pro Tyr Ser  Gln Ala Pro Ser Gly  Phe Lys Tyr
    1040                1045                1050

Trp Leu  Lys Glu Arg Gly Ala  Ser Leu Gln His Thr  Ala Pro Phe
    1055                1060                1065

Gly Cys  Gln Ile Ala Thr Asn  Pro Val Arg Ala Val  Asn Cys Ala
    1070                1075                1080

Val Gly  Asn Ile Pro Ile Ser  Ile Asp Ile Pro Asp  Ala Ala Phe
    1085                1090                1095

Thr Arg  Val Val Asp Ala Pro  Ser Val Thr Asp Met  Ser Cys Glu
    1100                1105                1110

Val Pro  Ala Cys Thr His Ser  Ser Asp Phe Gly Gly  Val Ala Ile
    1115                1120                1125

Ile Lys  Tyr Thr Ala Ser Lys  Lys Gly Lys Cys Ala  Val His Ser
    1130                1135                1140
```

```
Met Thr  Asn Ala Val Thr Ile  Arg Glu Ala Asp Val  Glu Val Glu
    1145                 1150                 1155

Gly Asn  Ser Gln Leu Gln Ile  Ser Phe Ser Thr Ala  Leu Ala Ser
    1160                 1165                 1170

Ala Glu  Phe Arg Val Gln Val  Cys Ser Thr Gln Val  His Cys Ala
    1175                 1180                 1185

Ala Ala  Cys His Pro Pro Lys  Asp His Ile Val Asn  Tyr Pro Ala
    1190                 1195                 1200

Ser His  Thr Thr Leu Gly Val  Gln Asp Ile Ser Thr  Thr Ala Met
    1205                 1210                 1215

Ser Trp  Val Gln Lys Ile Thr  Gly Gly Val Gly Leu  Ile Val Ala
    1220                 1225                 1230

Val Ala  Ala Leu Ile Leu Ile  Val Val Leu Cys Val  Ser Phe Ser
    1235                 1240                 1245

Arg His
    1250
```

<210> SEQ ID NO 30
<211> LENGTH: 3756
<212> TYPE: DNA
<213> ORGANISM: Artificial Sequence
<220> FEATURE:
<223> OTHER INFORMATION: Synthetic polynucleotide

<400> SEQUENCE: 30

```
atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

caccgccaaa gacgcagtac taaggacaat tttaatgtct ataaagccac aagaccatat   1020

ctagctcatt gtcctgactg cggagaaggg cattcgtgcc acagccctat cgcattggag   1080

cgcatcagaa atgaagcaac ggacggaacg ctgaaaatcc aggtctcttt gcagatcggg   1140

ataaagacag atgacagcca cgattggacc aagctgcgct atatggatag ccatacgcca   1200

gcggacgcgg agcgagccgg attgcttgta aggacttcag caccgtgcac gatcaccggg   1260

accatgggac actttattct cgcccgatgc ccgaaaggag agacgctgac agtgggattt   1320

acggacagca gaaagatcag ccacacatgc acacacccgt tccatcatga accacctgtg   1380
```

```
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tccggaagtg gatccaacga gggactgaca   1620
accacagaca aagtgatcaa taactgcaaa attgatcagt gccatgctgc agtcactaat   1680
cacaagaatt ggcaatacaa ctccccttta gtcccgcgca acgctgaact cggggaccgt   1740
aaaggaaaga tccacatccc attcccattg gcaaacgtga cttgcagagt gccaaaagca   1800
agaaacccta cagtaactta cggaaaaaac caagtcacca tgctgctgta tcctgaccat   1860
ccgacactct tgtcttaccg taacatggga caggaaccaa attaccacga ggagtgggtg   1920
acacacaaga aggaggttac cttgaccgtg cctactgagg gtctggaggt cacttggggc   1980
aacaacgaac catacaagta ctggccgcag atgtctacga acggtactgc tcatggtcac   2040
ccacatgaga taatcttgta ctattatgag ctgtacccca ctatgactgt agtcattgtg   2100
tcggtggcct cgttcgtgct tctgtcgatg gtgggcacag cagtgggaat gtgtgtgtgc   2160
gcacggcgca gatgcattac accatatgaa ttaacaccag gagccactgt tcccttcctg   2220
ctcagcctgc tatgctgcgt cagaacgacc aaggcggcca catattacga ggctgcggca   2280
tatctatgga acgaacagca gcccctgttc tggttgcagg ctcttatccc gctggccgcc   2340
ttgatcgtcc tgtgcaactg tctgaaactc ttgccatgct gctgtaagac cctggctttt   2400
ttagccgtaa tgagcatcgg tgcccacact gtgagcgcgt acgaacacgt aacagtgatc   2460
ccgaacacgg tgggagtacc gtataagact cttgtcaaca gaccgggtta cagccccatg   2520
gtgttggaga tggagctaca atcagtcacc ttggaaccaa cactgtcact tgactacatc   2580
acgtgcgagt acaaaactgt catcccctcc ccgtacgtga agtgctgtgg tacagcagag   2640
tgcaaggaca agagcctacc agactacagc tgcaaggtct ttactggagt ctacccattt   2700
atgtggggcg gcgcctactg cttttgcgac gccgaaaata cgcaattgag cgaggcacat   2760
gtagagaaat ctgaatcttg caaaacagag tttgcatcgg cctacagagc ccacaccgca   2820
tcggcgtcgg cgaagctccg cgtcctttac caaggaaaca acattaccgt agctgcctac   2880
gctaacggtg accatgccgt cacagtaaag gacgccaagt ttgtcgtggg cccaatgtcc   2940
tccgcctgga caccttttga caacaaaatc gtggtgtaca aaggcgacgt ctacaacatg   3000
gactacccac cttttggcgc aggaagacca ggacaatttg gtgacattca aagtcgtaca   3060
ccggaaagta aagacgttta tgccaacact cagttggtac tacagaggcc agcagcaggc   3120
acggtacatg taccatactc tcaggcacca tctggcttca agtattggct gaaggaacga   3180
ggagcatcgc tacagcacac ggcaccgttc ggttgccaga ttgcgacaaa cccggtaaga   3240
gctgtaaatt gcgctgtggg gaacatacca atttccatcg acataccgga tgcggccttt   3300
actagggttg tcgatgcacc ctctgtaacg gacatgtcat gcgaagtacc agcctgcact   3360
cactcctccg actttggggg cgtcgccatc atcaaataca cagctagcaa gaaaggtaaa   3420
tgtgcagtac attcgatgac caacgccgtt accattcgag aagccgacgt agaagtagag   3480
gggaactccc agctgcaaat atccttctca acagccctgg caagcgccga gtttcgcgtg   3540
caagtgtgct ccacacaagt acactgcgca gccgcatgcc accctccaaa ggaccacata   3600
gtcaattacc cagcatcaca caccaccctt ggggtccagg atatatccac aacggcaatg   3660
tcttgggtgc agaagattac gggaggagta ggattaattg ttgctgttgc tgccttaatt   3720
```

ttaattgtgg tgctatgcgt gtcgtttagc aggcac 3756

<210> SEQ ID NO 31
<211> LENGTH: 1252
<212> TYPE: PRT
<213> ORGANISM: Artificial Sequence
<220> FEATURE:
<223> OTHER INFORMATION: Synthetic peptide

<400> SEQUENCE: 31

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
```

```
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Ser Gly Ser Asn Glu Gly Leu Thr Thr Thr Asp Lys
    530                 535                 540

Val Ile Asn Asn Cys Lys Ile Asp Gln Cys His Ala Ala Val Thr Asn
545                 550                 555                 560

His Lys Asn Trp Gln Tyr Asn Ser Pro Leu Val Pro Arg Asn Ala Glu
                565                 570                 575

Leu Gly Asp Arg Lys Gly Lys Ile His Ile Pro Phe Pro Leu Ala Asn
            580                 585                 590

Val Thr Cys Arg Val Pro Lys Ala Arg Asn Pro Thr Val Thr Tyr Gly
        595                 600                 605

Lys Asn Gln Val Thr Met Leu Leu Tyr Pro Asp His Pro Thr Leu Leu
    610                 615                 620

Ser Tyr Arg Asn Met Gly Gln Glu Pro Asn Tyr His Glu Glu Trp Val
625                 630                 635                 640

Thr His Lys Lys Glu Val Thr Leu Thr Val Pro Thr Glu Gly Leu Glu
                645                 650                 655

Val Thr Trp Gly Asn Asn Glu Pro Tyr Lys Tyr Trp Pro Gln Met Ser
            660                 665                 670

Thr Asn Gly Thr Ala His Gly His Pro His Glu Ile Ile Leu Tyr Tyr
        675                 680                 685

Tyr Glu Leu Tyr Pro Thr Met Thr Val Val Ile Val Ser Val Ala Ser
    690                 695                 700

Phe Val Leu Leu Ser Met Val Gly Thr Ala Val Gly Met Cys Val Cys
705                 710                 715                 720

Ala Arg Arg Arg Cys Ile Thr Pro Tyr Glu Leu Thr Pro Gly Ala Thr
                725                 730                 735

Val Pro Phe Leu Leu Ser Leu Leu Cys Cys Val Arg Thr Thr Lys Ala
            740                 745                 750

Ala Thr Tyr Tyr Glu Ala Ala Ala Tyr Leu Trp Asn Glu Gln Gln Pro
        755                 760                 765

Leu Phe Trp Leu Gln Ala Leu Ile Pro Leu Ala Ala Leu Ile Val Leu
    770                 775                 780
```

```
Cys Asn Cys Leu Lys Leu Leu Pro Cys Cys Cys Lys Thr Leu Ala Phe
785                 790                 795                 800

Leu Ala Val Met Ser Ile Gly Ala His Thr Val Ser Ala Tyr Glu His
                805                 810                 815

Val Thr Val Ile Pro Asn Thr Val Gly Val Pro Tyr Lys Thr Leu Val
            820                 825                 830

Asn Arg Pro Gly Tyr Ser Pro Met Val Leu Glu Met Glu Leu Gln Ser
        835                 840                 845

Val Thr Leu Glu Pro Thr Leu Ser Leu Asp Tyr Ile Thr Cys Glu Tyr
    850                 855                 860

Lys Thr Val Ile Pro Ser Pro Tyr Val Lys Cys Cys Gly Thr Ala Glu
865                 870                 875                 880

Cys Lys Asp Lys Ser Leu Pro Asp Tyr Ser Cys Lys Val Phe Thr Gly
                885                 890                 895

Val Tyr Pro Phe Met Trp Gly Gly Ala Tyr Cys Phe Cys Asp Ala Glu
            900                 905                 910

Asn Thr Gln Leu Ser Glu Ala His Val Glu Lys Ser Glu Ser Cys Lys
        915                 920                 925

Thr Glu Phe Ala Ser Ala Tyr Arg Ala His Thr Ala Ser Ala Ser Ala
    930                 935                 940

Lys Leu Arg Val Leu Tyr Gln Gly Asn Asn Ile Thr Val Ala Ala Tyr
945                 950                 955                 960

Ala Asn Gly Asp His Ala Val Thr Val Lys Asp Ala Lys Phe Val Val
                965                 970                 975

Gly Pro Met Ser Ser Ala Trp Thr Pro Phe Asp Asn Lys Ile Val Val
            980                 985                 990

Tyr Lys Gly Asp Val Tyr Asn Met  Asp Tyr Pro Pro Phe  Gly Ala Gly
        995                 1000                1005

Arg Pro  Gly Gln Phe Gly Asp  Ile Gln Ser Arg Thr  Pro Glu Ser
    1010                 1015                 1020

Lys Asp  Val Tyr Ala Asn Thr  Gln Leu Val Leu Gln  Arg Pro Ala
    1025                 1030                 1035

Ala Gly  Thr Val His Val Pro  Tyr Ser Gln Ala Pro  Ser Gly Phe
    1040                 1045                 1050

Lys Tyr  Trp Leu Lys Glu Arg  Gly Ala Ser Leu Gln  His Thr Ala
    1055                 1060                 1065

Pro Phe  Gly Cys Gln Ile Ala  Thr Asn Pro Val Arg  Ala Val Asn
    1070                 1075                 1080

Cys Ala  Val Gly Asn Ile Pro  Ile Ser Ile Asp Ile  Pro Asp Ala
    1085                 1090                 1095

Ala Phe  Thr Arg Val Val Asp  Ala Pro Ser Val Thr  Asp Met Ser
    1100                 1105                 1110

Cys Glu  Val Pro Ala Cys Thr  His Ser Ser Asp Phe  Gly Gly Val
    1115                 1120                 1125

Ala Ile  Ile Lys Tyr Thr Ala  Ser Lys Lys Gly Lys  Cys Ala Val
    1130                 1135                 1140

His Ser  Met Thr Asn Ala Val  Thr Ile Arg Glu Ala  Asp Val Glu
    1145                 1150                 1155

Val Glu  Gly Asn Ser Gln Leu  Gln Ile Ser Phe Ser  Thr Ala Leu
    1160                 1165                 1170

Ala Ser  Ala Glu Phe Arg Val  Gln Val Cys Ser Thr  Gln Val His
    1175                 1180                 1185
```

```
Cys Ala  Ala Ala Cys His Pro  Pro Lys Asp His Ile  Val Asn Tyr
    1190                 1195                 1200

Pro Ala  Ser His Thr Thr Leu  Gly Val Gln Asp Ile  Ser Thr Thr
    1205                 1210                 1215

Ala Met  Ser Trp Val Gln Lys  Ile Thr Gly Gly Val  Gly Leu Ile
    1220                 1225                 1230

Val Ala  Val Ala Ala Leu Ile  Leu Ile Val Val Leu  Cys Val Ser
    1235                 1240                 1245

Phe Ser  Arg His
    1250
```

<210> SEQ ID NO 32
<211> LENGTH: 3777
<212> TYPE: DNA
<213> ORGANISM: Artificial Sequence
<220> FEATURE:
<223> OTHER INFORMATION: Synthetic polynucleotide

<400> SEQUENCE: 32

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaaacccca aggctattac    600

agctggcatc atggagcagt ccaatatgaa aatgggcgtt tcacggtgcc gaaaggagtt    660

ggggccaagg gagacagcgg acgacccatt ctggataacc agggacgggt ggtcgctatt    720

gtgctgggag gtgtgaatga aggatctagg acagcccttt cagtcgtcat gtggaacgag    780

aagggagtta ccgtgaagta tactccagag aactgcgagc aatggtcact agtgaccacc    840

atgtgtctgc tcgccaatgt gacgttccca tgtgctcaac caccaatttg ctacgacaga    900

aaaccagcag agactttggc catgctcagc gttaacgttg acaacccggg ctacgatgag    960

ctgctggaag cagctgttaa gtgccccgga aggaaaagga gatccaccga ggagctgttt   1020

aatgagtata agctaacgcg cccttacatg gccagatgca tcagatgtgc agttgggagc   1080

tgccatagtc caatagcaat cgaggcagta aagagcgacg ggcacgacgg ttatgttaga   1140

cttcagactt cctcgcagta tggcctggat tcctccggca acttaaaggg caggaccatg   1200

cggtatgaca tgcacgggac cattaaagag ataccactac atcaagtgtc actctataca   1260

tctcgcccgt gtcacattgt ggatgggcac ggttatttcc tgcttgccag gtgcccggca   1320

ggggactcca tcaccatgga atttaagaaa gattccgtca gacactcctg ctcggtgccg   1380

tatgaagtga aatttaatcc tgtaggcaga gaactctata ctcatccccc agaacacgga   1440

gtagagcaag cgtgccaagt ctacgcacat gatgcacaga acagaggagc ttatgtcgag   1500

atgcacctcc cgggctcaga agtggacagc agtttggttt ccttgagcgg ctccggagga   1560

tccagttcag tcaccgtgac acctcctgat gggactagcg ccctggtgga atgcgagtgt   1620
```

```
ggcggcacaa agatctccga gaccatcaac aagacaaaac agttcagcca gtgcacaaag   1680
aaggagcagt gcagagcata tcggctgcag aacgataagt gggtgtataa ttctgacaaa   1740
ctgcccaaag cagcgggagc caccttaaaa ggaaaactgc atgtcccatt cttgctggca   1800
gacggcaaat gcaccgtgcc tctagcacca gaacctatga taaccttcgg tttcagatca   1860
gtgtcactga aactgcaccc taagaatccc acatatctaa tcacccgcca acttgctgat   1920
gagcctcact acacgcacga gctcatatct gaaccagctg ttaggaattt taccgtcacc   1980
gaaaaagggt gggagtttgt atggggaaac cacccgccga aaaggttttg ggcacaggaa   2040
acagcacccg gaaatccaca tgggctaccg cacgaggtga taactcatta ttaccacaga   2100
taccctatgt ccaccatcct gggtttgtca atttgtgccg ccattgcaac cgtttccgtt   2160
gcagcgtcta cctggctgtt ttgcagatca agagttgcgt gcctaactcc ttaccggcta   2220
acacctaacg ctaggatacc attttgtctg gctgtgcttt gctgcgcccg cactgcccgg   2280
gccgagacca cctgggagtc cttggatcac ctatggaaca ataaccaaca gatgttctgg   2340
attcaattgc tgatccctct ggccgccttg atcgtagtga ctcgcctgct caggtgcgtg   2400
tgctgtgtcg tgcctttttt agtcatggcc ggcgccgcag gcgccggcgc ctacgagcac   2460
gcgaccacga tgccgagcca agcgggaatc tcgtataaca ctatagtcaa cagagcaggc   2520
tacgcaccac tccctatcag cataacacca acaaagatca agctgatacc tacagtgaac   2580
ttggagtacg tcacctgcca ctacaaaaca ggaatggatt caccagccat caaatgctgc   2640
ggatctcagg aatgcactcc aacttacagg cctgatgaac agtgcaaagt cttcacaggg   2700
gtttacccgt tcatgtgggg tggtgcatat tgcttttgcg acactgagaa cacccaagtc   2760
agcaaggcct acgtaatgaa atctgacgac tgccttgcgg atcatgctga agcatataaa   2820
gcgcacacag cctcagtgca ggcgttcctc aacatcacag tgggagaaca ctctattgtg   2880
actaccgtgt atgtgaatgg agaaactcct gtgaatttca atggggtcaa aataactgca   2940
ggtccgcttt ccacagcttg gacacccttt gatcgcaaaa tcgtgcagta tgccggggag   3000
atctataatt atgattttcc tgagtatggg gcaggacaac caggagcatt tggagatata   3060
caatccagaa cagtctcaag ctctgatctg tatgccaata ccaacctagt gctgcagaga   3120
cccaaagcag gagcgatcca cgtgccatac actcaggcac cttcgggttt tgagcaatgg   3180
aagaaagata aagctccatc attgaaattt accgcccctt tcggatgcga aatatataca   3240
aaccccattc gcgccgaaaa ctgtgctgta gggtcaattc cattagcctt tgacattccc   3300
gacgccttgt tcaccagggt gtcagaaaca ccgacacttt cagcggccga atgcactctt   3360
aacgagtgcg tgtattcttc cgactttggt gggatcgcca cggtcaagta ctcggccagc   3420
aagtcaggca agtgcgcagt ccatgtgcca tcagggactg ctaccctaaa agaagcagca   3480
gtcgagctaa ccgagcaagg gtcggcgact atccatttct cgaccgcaaa tatccacccg   3540
gagttcaggc tccaaatatg cacatcatat gttacgtgca aaggtgattg tcaccccccg   3600
aaagaccata ttgtgacaca ccctcagtat cacgcccaaa catttacagc cgcggtgtca   3660
aaaaccgcgt ggacgtggtt aacatccctg ctgggaggat cagccgtaat tattataatt   3720
ggcttggtgc tggctactat tgtggccatg tacgtgctga ccaaccagaa acataat      3777
```

<210> SEQ ID NO 33
<211> LENGTH: 1259
<212> TYPE: PRT
<213> ORGANISM: Artificial Sequence
<220> FEATURE:
<223> OTHER INFORMATION: Synthetic peptide

<400> SEQUENCE: 33

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
```

```
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Gly Gly Ser Ser Ser Val Thr Val Thr Pro
        515                 520                 525

Pro Asp Gly Thr Ser Ala Leu Val Glu Cys Glu Cys Gly Gly Thr Lys
    530                 535                 540

Ile Ser Glu Thr Ile Asn Lys Thr Lys Gln Phe Ser Gln Cys Thr Lys
545                 550                 555                 560

Lys Glu Gln Cys Arg Ala Tyr Arg Leu Gln Asn Asp Lys Trp Val Tyr
                565                 570                 575

Asn Ser Asp Lys Leu Pro Lys Ala Ala Gly Ala Thr Leu Lys Gly Lys
            580                 585                 590

Leu His Val Pro Phe Leu Leu Ala Asp Gly Lys Cys Thr Val Pro Leu
        595                 600                 605

Ala Pro Glu Pro Met Ile Thr Phe Gly Phe Arg Ser Val Ser Leu Lys
    610                 615                 620

Leu His Pro Lys Asn Pro Thr Tyr Leu Ile Thr Arg Gln Leu Ala Asp
625                 630                 635                 640

Glu Pro His Tyr Thr His Glu Leu Ile Ser Glu Pro Ala Val Arg Asn
                645                 650                 655

Phe Thr Val Thr Glu Lys Gly Trp Glu Phe Val Trp Gly Asn His Pro
            660                 665                 670

Pro Lys Arg Phe Trp Ala Gln Glu Thr Ala Pro Gly Asn Pro His Gly
        675                 680                 685

Leu Pro His Glu Val Ile Thr His Tyr Tyr His Arg Tyr Pro Met Ser
    690                 695                 700

Thr Ile Leu Gly Leu Ser Ile Cys Ala Ala Ile Ala Thr Val Ser Val
705                 710                 715                 720

Ala Ala Ser Thr Trp Leu Phe Cys Arg Ser Arg Val Ala Cys Leu Thr
                725                 730                 735

Pro Tyr Arg Leu Thr Pro Asn Ala Arg Ile Pro Phe Cys Leu Ala Val
            740                 745                 750

Leu Cys Cys Ala Arg Thr Ala Arg Ala Glu Thr Thr Trp Glu Ser Leu
        755                 760                 765

Asp His Leu Trp Asn Asn Asn Gln Gln Met Phe Trp Ile Gln Leu Leu
    770                 775                 780

Ile Pro Leu Ala Ala Leu Ile Val Val Thr Arg Leu Leu Arg Cys Val
785                 790                 795                 800

Cys Cys Val Val Pro Phe Leu Val Met Ala Gly Ala Ala Gly Ala Gly
                805                 810                 815

Ala Tyr Glu His Ala Thr Thr Met Pro Ser Gln Ala Gly Ile Ser Tyr
            820                 825                 830
```

```
Asn Thr Ile Val Asn Arg Ala Gly Tyr Ala Pro Leu Pro Ile Ser Ile
        835                 840                 845

Thr Pro Thr Lys Ile Lys Leu Ile Pro Thr Val Asn Leu Glu Tyr Val
    850                 855                 860

Thr Cys His Tyr Lys Thr Gly Met Asp Ser Pro Ala Ile Lys Cys Cys
865                 870                 875                 880

Gly Ser Gln Glu Cys Thr Pro Thr Tyr Arg Pro Asp Glu Gln Cys Lys
                885                 890                 895

Val Phe Thr Gly Val Tyr Pro Phe Met Trp Gly Gly Ala Tyr Cys Phe
            900                 905                 910

Cys Asp Thr Glu Asn Thr Gln Val Ser Lys Ala Tyr Val Met Lys Ser
        915                 920                 925

Asp Asp Cys Leu Ala Asp His Ala Glu Ala Tyr Lys Ala His Thr Ala
    930                 935                 940

Ser Val Gln Ala Phe Leu Asn Ile Thr Val Gly Glu His Ser Ile Val
945                 950                 955                 960

Thr Thr Val Tyr Val Asn Gly Glu Thr Pro Val Asn Phe Asn Gly Val
                965                 970                 975

Lys Ile Thr Ala Gly Pro Leu Ser Thr Ala Trp Thr Pro Phe Asp Arg
            980                 985                 990

Lys Ile Val Gln Tyr Ala Gly Glu  Ile Tyr Asn Tyr Asp  Phe Pro Glu
        995                 1000                 1005

Tyr Gly  Ala Gly Gln Pro Gly  Ala Phe Gly Asp Ile  Gln Ser Arg
    1010                 1015                 1020

Thr Val  Ser Ser Ser Asp Leu  Tyr Ala Asn Thr Asn  Leu Val Leu
    1025                 1030                 1035

Gln Arg  Pro Lys Ala Gly Ala  Ile His Val Pro Tyr  Thr Gln Ala
    1040                 1045                 1050

Pro Ser  Gly Phe Glu Gln Trp  Lys Lys Asp Lys Ala  Pro Ser Leu
    1055                 1060                 1065

Lys Phe  Thr Ala Pro Phe Gly  Cys Glu Ile Tyr Thr  Asn Pro Ile
    1070                 1075                 1080

Arg Ala  Glu Asn Cys Ala Val  Gly Ser Ile Pro Leu  Ala Phe Asp
    1085                 1090                 1095

Ile Pro  Asp Ala Leu Phe Thr  Arg Val Ser Glu Thr  Pro Thr Leu
    1100                 1105                 1110

Ser Ala  Ala Glu Cys Thr Leu  Asn Glu Cys Val Tyr  Ser Ser Asp
    1115                 1120                 1125

Phe Gly  Gly Ile Ala Thr Val  Lys Tyr Ser Ala Ser  Lys Ser Gly
    1130                 1135                 1140

Lys Cys  Ala Val His Val Pro  Ser Gly Thr Ala Thr  Leu Lys Glu
    1145                 1150                 1155

Ala Ala  Val Glu Leu Thr Glu  Gln Gly Ser Ala Thr  Ile His Phe
    1160                 1165                 1170

Ser Thr  Ala Asn Ile His Pro  Glu Phe Arg Leu Gln  Ile Cys Thr
    1175                 1180                 1185

Ser Tyr  Val Thr Cys Lys Gly  Asp Cys His Pro Pro  Lys Asp His
    1190                 1195                 1200

Ile Val  Thr His Pro Gln Tyr  His Ala Gln Thr Phe  Thr Ala Ala
    1205                 1210                 1215

Val Ser  Lys Thr Ala Trp Thr  Trp Leu Thr Ser Leu  Leu Gly Gly
    1220                 1225                 1230
```

```
Ser Ala  Val Ile Ile Ile Ile  Gly Leu Val Leu Ala  Thr Ile Val
    1235                 1240                 1245

Ala Met  Tyr Val Leu Thr Asn  Gln Lys His Asn
    1250                 1255


<210> SEQ ID NO 34
<211> LENGTH: 3777
<212> TYPE: DNA
<213> ORGANISM: Artificial Sequence
<220> FEATURE:
<223> OTHER INFORMATION: Synthetic polynucleotide

<400> SEQUENCE: 34

atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaacccca aggctattac    600

agctggcatc atggagcagt ccaatatgaa aatgggcgtt tcacggtgcc gaaaggagtt    660

ggggccaagg gagacagcgg acgacccatt ctggataacc agggacgggt ggtcgctatt    720

gtgctgggag gtgtgaatga aggatctagg acagcccttt cagtcgtcat gtggaacgag    780

aagggagtta ccgtgaagta tactccagag aactgcgagc aatggtcact agtgaccacc    840

atgtgtctgc tcgccaatgt gacgttccca tgtgctcaac caccaatttg ctacgacaga    900

aaaccagcag agactttggc catgctcagc gttaacgttg acaacccggg ctacgatgag    960

ctgctggaag cagctgttaa gtgccccgga aggaaaagga gatccaccga ggagctgttt   1020

aatgagtata agctaacgcg cccttacatg gccagatgca tcagatgtgc agttgggagc   1080

tgccatagtc caatagcaat cgaggcagta aagagcgacg ggcacgacgg ttatgttaga   1140

cttcagactt cctcgcagta tggcctggat tcctccggca acttaaaggg caggaccatg   1200

cggtatgaca tgcacgggac cattaaagag ataccactac atcaagtgtc actctataca   1260

tctcgcccgt gtcacattgt ggatgggcac ggttatttcc tgcttgccag gtgcccggca   1320

ggggactcca tcaccatgga atttaagaaa gattccgtca gacactcctg ctcggtgccg   1380

tatgaagtga aatttaatcc tgtaggcaga gaactctata ctcatccccc agaacacgga   1440

gtagagcaag cgtgccaagt ctacgcacat gatgcacaga acagaggagc ttatgtcgag   1500

atgcacctcc cgggctcaga agtggacagc agtttggttt ccttgagcgg cagttccgga   1560

ggatcctcag tcaccgtgac acctcctgat gggactagcg ccctggtgga atgcgagtgt   1620

ggcggcacaa agatctccga gaccatcaac aagacaaaac agttcagcca gtgcacaaag   1680

aaggagcagt gcagagcata tcggctgcag aacgataagt gggtgtataa ttctgacaaa   1740

ctgcccaaag cagcgggagc caccttaaaa ggaaaactgc atgtcccatt cttgctggca   1800

gacggcaaat gcaccgtgcc tctagcacca gaacctatga taaccttcgg tttcagatca   1860

gtgtcactga aactgcaccc taagaatccc acatatctaa tcacccgcca acttgctgat   1920
```

```
gagcctcact acacgcacga gctcatatct gaaccagctg ttaggaattt taccgtcacc   1980
gaaaaagggt gggagtttgt atggggaaac cacccgccga aaaggttttg ggcacaggaa   2040
acagcacccg gaaatccaca tgggctaccg cacgaggtga taactcatta ttaccacaga   2100
taccctatgt ccaccatcct gggtttgtca atttgtgccg ccattgcaac cgtttccgtt   2160
gcagcgtcta cctggctgtt ttgcagatca agagttgcgt gcctaactcc ttaccggcta   2220
acacctaacg ctaggatacc attttgtctg gctgtgcttt gctgcgcccg cactgcccgg   2280
gccgagacca cctgggagtc cttggatcac ctatggaaca ataaccaaca gatgttctgg   2340
attcaattgc tgatccctct ggccgccttg atcgtagtga ctcgcctgct caggtgcgtg   2400
tgctgtgtcg tgcctttttt agtcatggcc ggcgccgcag gcgccggcgc ctacgagcac   2460
gcgaccacga tgccgagcca agcgggaatc tcgtataaca ctatagtcaa cagagcaggc   2520
tacgcaccac tccctatcag cataacacca acaaagatca agctgatacc tacagtgaac   2580
ttggagtacg tcacctgcca ctacaaaaca ggaatggatt caccagccat caaatgctgc   2640
ggatctcagg aatgcactcc aacttacagg cctgatgaac agtgcaaagt cttcacaggg   2700
gtttacccgt tcatgtgggg tggtgcatat tgcttttgcg acactgagaa cacccaagtc   2760
agcaaggcct acgtaatgaa atctgacgac tgccttgcgg atcatgctga agcatataaa   2820
gcgcacacag cctcagtgca ggcgttcctc aacatcacag tgggagaaca ctctattgtg   2880
actaccgtgt atgtgaatgg agaaactcct gtgaatttca atggggtcaa aataactgca   2940
ggtccgcttt ccacagcttg gacacccttt gatcgcaaaa tcgtgcagta tgccggggag   3000
atctataatt atgattttcc tgagtatggg gcaggacaac caggagcatt tggagatata   3060
caatccagaa cagtctcaag ctctgatctg tatgccaata ccaacctagt gctgcagaga   3120
cccaaagcag gagcgatcca cgtgccatac actcaggcac cttcgggttt tgagcaatgg   3180
aagaaagata aagctccatc attgaaattt accgcccctt tcggatgcga aatatataca   3240
aaccccattc gcgccgaaaa ctgtgctgta gggtcaattc cattagcctt tgacattccc   3300
gacgccttgt tcaccagggt gtcagaaaca ccgacacttt cagcggccga atgcactctt   3360
aacgagtgcg tgtattcttc cgactttggt gggatcgcca cggtcaagta ctcggccagc   3420
aagtcaggca agtgcgcagt ccatgtgcca tcagggactg ctaccctaaa agaagcagca   3480
gtcgagctaa ccgagcaagg gtcggcgact atccatttct cgaccgcaaa tatccacccg   3540
gagttcaggc tccaaatatg cacatcatat gttacgtgca aaggtgattg tcaccccccg   3600
aaagaccata ttgtgacaca ccctcagtat cacgcccaaa catttacagc cgcggtgtca   3660
aaaaccgcgt ggacgtggtt aacatccctg ctgggaggat cagccgtaat tattataatt   3720
ggcttggtgc tggctactat tgtggccatg tacgtgctga ccaaccagaa acataat      3777
```

<210> SEQ ID NO 35
<211> LENGTH: 1259
<212> TYPE: PRT
<213> ORGANISM: Artificial Sequence
<220> FEATURE:
<223> OTHER INFORMATION: Synthetic peptide

<400> SEQUENCE: 35

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30
```

```
Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
```

```
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Gly Gly Ser Ser Val Thr Val Thr Pro
        515                 520                 525

Pro Asp Gly Thr Ser Ala Leu Val Glu Cys Glu Cys Gly Gly Thr Lys
    530                 535                 540

Ile Ser Glu Thr Ile Asn Lys Thr Lys Gln Phe Ser Gln Cys Thr Lys
545                 550                 555                 560

Lys Glu Gln Cys Arg Ala Tyr Arg Leu Gln Asn Asp Lys Trp Val Tyr
                565                 570                 575

Asn Ser Asp Lys Leu Pro Lys Ala Ala Gly Ala Thr Leu Lys Gly Lys
            580                 585                 590

Leu His Val Pro Phe Leu Leu Ala Asp Gly Lys Cys Thr Val Pro Leu
        595                 600                 605

Ala Pro Glu Pro Met Ile Thr Phe Gly Phe Arg Ser Val Ser Leu Lys
    610                 615                 620

Leu His Pro Lys Asn Pro Thr Tyr Leu Ile Thr Arg Gln Leu Ala Asp
625                 630                 635                 640

Glu Pro His Tyr Thr His Glu Leu Ile Ser Glu Pro Ala Val Arg Asn
                645                 650                 655

Phe Thr Val Thr Glu Lys Gly Trp Glu Phe Val Trp Gly Asn His Pro
            660                 665                 670

Pro Lys Arg Phe Trp Ala Gln Glu Thr Ala Pro Gly Asn Pro His Gly
        675                 680                 685

Leu Pro His Glu Val Ile Thr His Tyr Tyr His Arg Tyr Pro Met Ser
    690                 695                 700

Thr Ile Leu Gly Leu Ser Ile Cys Ala Ala Ile Ala Thr Val Ser Val
705                 710                 715                 720

Ala Ala Ser Thr Trp Leu Phe Cys Arg Ser Arg Val Ala Cys Leu Thr
                725                 730                 735

Pro Tyr Arg Leu Thr Pro Asn Ala Arg Ile Pro Phe Cys Leu Ala Val
            740                 745                 750

Leu Cys Cys Ala Arg Thr Ala Arg Ala Glu Thr Thr Trp Glu Ser Leu
        755                 760                 765

Asp His Leu Trp Asn Asn Asn Gln Gln Met Phe Trp Ile Gln Leu Leu
    770                 775                 780

Ile Pro Leu Ala Ala Leu Ile Val Val Thr Arg Leu Leu Arg Cys Val
785                 790                 795                 800

Cys Cys Val Val Pro Phe Leu Val Met Ala Gly Ala Ala Gly Ala Gly
                805                 810                 815

Ala Tyr Glu His Ala Thr Thr Met Pro Ser Gln Ala Gly Ile Ser Tyr
            820                 825                 830

Asn Thr Ile Val Asn Arg Ala Gly Tyr Ala Pro Leu Pro Ile Ser Ile
        835                 840                 845

Thr Pro Thr Lys Ile Lys Leu Ile Pro Thr Val Asn Leu Glu Tyr Val
    850                 855                 860

Thr Cys His Tyr Lys Thr Gly Met Asp Ser Pro Ala Ile Lys Cys Cys
865                 870                 875                 880
```

```
Gly Ser Gln Glu Cys Thr Pro Thr Tyr Arg Pro Asp Glu Gln Cys Lys
                885                 890                 895

Val Phe Thr Gly Val Tyr Pro Phe Met Trp Gly Gly Ala Tyr Cys Phe
            900                 905                 910

Cys Asp Thr Glu Asn Thr Gln Val Ser Lys Ala Tyr Val Met Lys Ser
        915                 920                 925

Asp Asp Cys Leu Ala Asp His Ala Glu Ala Tyr Lys Ala His Thr Ala
    930                 935                 940

Ser Val Gln Ala Phe Leu Asn Ile Thr Val Gly Glu His Ser Ile Val
945                 950                 955                 960

Thr Thr Val Tyr Val Asn Gly Glu Thr Pro Val Asn Phe Asn Gly Val
                965                 970                 975

Lys Ile Thr Ala Gly Pro Leu Ser Thr Ala Trp Thr Pro Phe Asp Arg
            980                 985                 990

Lys Ile Val Gln Tyr Ala Gly Glu  Ile Tyr Asn Tyr Asp  Phe Pro Glu
        995                 1000                 1005

Tyr Gly  Ala Gly Gln Pro Gly  Ala Phe Gly Asp Ile  Gln Ser Arg
    1010                 1015                 1020

Thr Val  Ser Ser Ser Asp Leu  Tyr Ala Asn Thr Asn  Leu Val Leu
    1025                 1030                 1035

Gln Arg  Pro Lys Ala Gly Ala  Ile His Val Pro Tyr  Thr Gln Ala
    1040                 1045                 1050

Pro Ser  Gly Phe Glu Gln Trp  Lys Lys Asp Lys Ala  Pro Ser Leu
    1055                 1060                 1065

Lys Phe  Thr Ala Pro Phe Gly  Cys Glu Ile Tyr Thr  Asn Pro Ile
    1070                 1075                 1080

Arg Ala  Glu Asn Cys Ala Val  Gly Ser Ile Pro Leu  Ala Phe Asp
    1085                 1090                 1095

Ile Pro  Asp Ala Leu Phe Thr  Arg Val Ser Glu Thr  Pro Thr Leu
    1100                 1105                 1110

Ser Ala  Ala Glu Cys Thr Leu  Asn Glu Cys Val Tyr  Ser Ser Asp
    1115                 1120                 1125

Phe Gly  Gly Ile Ala Thr Val  Lys Tyr Ser Ala Ser  Lys Ser Gly
    1130                 1135                 1140

Lys Cys  Ala Val His Val Pro  Ser Gly Thr Ala Thr  Leu Lys Glu
    1145                 1150                 1155

Ala Ala  Val Glu Leu Thr Glu  Gln Gly Ser Ala Thr  Ile His Phe
    1160                 1165                 1170

Ser Thr  Ala Asn Ile His Pro  Glu Phe Arg Leu Gln  Ile Cys Thr
    1175                 1180                 1185

Ser Tyr  Val Thr Cys Lys Gly  Asp Cys His Pro Pro  Lys Asp His
    1190                 1195                 1200

Ile Val  Thr His Pro Gln Tyr  His Ala Gln Thr Phe  Thr Ala Ala
    1205                 1210                 1215

Val Ser  Lys Thr Ala Trp Thr  Trp Leu Thr Ser Leu  Leu Gly Gly
    1220                 1225                 1230

Ser Ala  Val Ile Ile Ile Ile  Gly Leu Val Leu Ala  Thr Ile Val
    1235                 1240                 1245

Ala Met  Tyr Val Leu Thr Asn  Gln Lys His Asn
    1250                 1255
```

<210> SEQ ID NO 36
<211> LENGTH: 3777

<212> TYPE: DNA
<213> ORGANISM: Artificial Sequence
<220> FEATURE:
<223> OTHER INFORMATION: Synthetic polynucleotide

<400> SEQUENCE: 36

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaacccca aggctattac    600

agctggcatc atggagcagt ccaatatgaa aatgggcgtt tcacggtgcc gaaaggagtt    660

ggggccaagg gagacagcgg acgacccatt ctggataacc agggacgggt ggtcgctatt    720

gtgctgggag gtgtgaatga aggatctagg acagcccttt cagtcgtcat gtggaacgag    780

aagggagtta ccgtgaagta tactccagag aactgcgagc aatggtcact agtgaccacc    840

atgtgtctgc tcgccaatgt gacgttccca tgtgctcaac caccaatttg ctacgacaga    900

aaaccagcag agactttggc catgctcagc gttaacgttg acaacccggg ctacgatgag    960

ctgctggaag cagctgttaa gtgccccgga aggaaaagga gatccaccga ggagctgttt   1020

aatgagtata agctaacgcg cccttacatg gccagatgca tcagatgtgc agttgggagc   1080

tgccatagtc caatagcaat cgaggcagta aagagcgacg ggcacgacgg ttatgttaga   1140

cttcagactt cctcgcagta tggcctggat tcctccggca acttaaaggg caggaccatg   1200

cggtatgaca tgcacgggac cattaaagag ataccactac atcaagtgtc actctataca   1260

tctcgcccgt gtcacattgt ggatgggcac ggttatttcc tgcttgccag gtgcccggca   1320

ggggactcca tcaccatgga atttaagaaa gattccgtca gacactcctg ctcggtgccg   1380

tatgaagtga aatttaatcc tgtaggcaga gaactctata ctcatccccc agaacacgga   1440

gtagagcaag cgtgccaagt ctacgcacat gatgcacaga acagaggagc ttatgtcgag   1500

atgcacctcc cgggctcaga agtggacagc agtttggttt ccttgagcgg cagttcagtc   1560

accgtgacac ctcctgatgg gactagcgcc ctggtggaat gcgagtgtgg ctccggagga   1620

tccggcacaa agatctccga gaccatcaac aagacaaaac agttcagcca gtgcacaaag   1680

aaggagcagt gcagagcata tcggctgcag aacgataagt gggtgtataa ttctgacaaa   1740

ctgcccaaag cagcgggagc caccttaaaa ggaaaactgc atgtcccatt cttgctggca   1800

gacggcaaat gcaccgtgcc tctagcacca gaacctatga taaccttcgg tttcagatca   1860

gtgtcactga aactgcaccc taagaatccc acatatctaa tcacccgcca acttgctgat   1920

gagcctcact acacgcacga gctcatatct gaaccagctg ttaggaattt taccgtcacc   1980

gaaaaagggt gggagtttgt atggggaaac cacccgccga aaaggttttg ggcacaggaa   2040

acagcacccg gaaatccaca tgggctaccg cacgaggtga taactcatta ttaccacaga   2100

taccctatgt ccaccatcct gggtttgtca atttgtgccg ccattgcaac cgtttccgtt   2160
```

```
gcagcgtcta cctggctgtt ttgcagatca agagttgcgt gcctaactcc ttaccggcta   2220

acacctaacg ctaggatacc attttgtctg gctgtgcttt gctgcgcccg cactgcccgg   2280

gccgagacca cctgggagtc cttggatcac ctatggaaca ataaccaaca gatgttctgg   2340

attcaattgc tgatccctct ggccgccttg atcgtagtga ctcgcctgct caggtgcgtg   2400

tgctgtgtcg tgcctttttt agtcatggcc ggcgccgcag gcgccggcgc ctacgagcac   2460

gcgaccacga tgccgagcca agcgggaatc tcgtataaca ctatagtcaa cagagcaggc   2520

tacgcaccac tccctatcag cataacacca acaaagatca agctgatacc tacagtgaac   2580

ttggagtacg tcacctgcca ctacaaaaca ggaatggatt caccagccat caaatgctgc   2640

ggatctcagg aatgcactcc aacttacagg cctgatgaac agtgcaaagt cttcacaggg   2700

gtttacccgt tcatgtgggg tggtgcatat tgcttttgcg acactgagaa cacccaagtc   2760

agcaaggcct acgtaatgaa atctgacgac tgccttgcgg atcatgctga agcatataaa   2820

gcgcacacag cctcagtgca ggcgttcctc aacatcacag tgggagaaca ctctattgtg   2880

actaccgtgt atgtgaatgg agaaactcct gtgaatttca atggggtcaa aataactgca   2940

ggtccgcttt ccacagcttg gacacccttt gatcgcaaaa tcgtgcagta tgccggggag   3000

atctataatt atgattttcc tgagtatggg gcaggacaac caggagcatt tggagatata   3060

caatccagaa cagtctcaag ctctgatctg tatgccaata ccaacctagt gctgcagaga   3120

cccaaagcag gagcgatcca cgtgccatac actcaggcac cttcgggttt tgagcaatgg   3180

aagaaagata aagctccatc attgaaattt accgcccctt tcggatgcga aatatataca   3240

aaccccattc gcgccgaaaa ctgtgctgta gggtcaattc cattagcctt tgacattccc   3300

gacgccttgt tcaccagggt gtcagaaaca ccgacacttt cagcggccga atgcactctt   3360

aacgagtgcg tgtattcttc cgactttggt gggatcgcca cggtcaagta ctcggccagc   3420

aagtcaggca agtgcgcagt ccatgtgcca tcagggactg ctaccctaaa agaagcagca   3480

gtcgagctaa ccgagcaagg gtcggcgact atccatttct cgaccgcaaa tatccacccg   3540

gagttcaggc tccaaatatg cacatcatat gttacgtgca aaggtgattg tcaccccccg   3600

aaagaccata ttgtgacaca ccctcagtat cacgcccaaa catttacagc cgcggtgtca   3660

aaaaccgcgt ggacgtggtt aacatccctg ctgggaggat cagccgtaat tattataatt   3720

ggcttggtgc tggctactat tgtggccatg tacgtgctga ccaaccagaa acataat      3777
```

```
<210> SEQ ID NO 37
<211> LENGTH: 1259
<212> TYPE: PRT
<213> ORGANISM: Artificial Sequence
<220> FEATURE:
<223> OTHER INFORMATION: Synthetic peptide

<400> SEQUENCE: 37

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80
```

-continued

```
Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
```

```
            500                 505                 510

Val Ser Leu Ser Gly Ser Ser Val Thr Val Thr Pro Pro Asp Gly Thr
        515                 520                 525

Ser Ala Leu Val Glu Cys Glu Cys Gly Ser Gly Gly Ser Gly Thr Lys
    530                 535                 540

Ile Ser Glu Thr Ile Asn Lys Thr Lys Gln Phe Ser Gln Cys Thr Lys
545                 550                 555                 560

Lys Glu Gln Cys Arg Ala Tyr Arg Leu Gln Asn Asp Lys Trp Val Tyr
                565                 570                 575

Asn Ser Asp Lys Leu Pro Lys Ala Ala Gly Ala Thr Leu Lys Gly Lys
            580                 585                 590

Leu His Val Pro Phe Leu Leu Ala Asp Gly Lys Cys Thr Val Pro Leu
        595                 600                 605

Ala Pro Glu Pro Met Ile Thr Phe Gly Phe Arg Ser Val Ser Leu Lys
    610                 615                 620

Leu His Pro Lys Asn Pro Thr Tyr Leu Ile Thr Arg Gln Leu Ala Asp
625                 630                 635                 640

Glu Pro His Tyr Thr His Glu Leu Ile Ser Glu Pro Ala Val Arg Asn
                645                 650                 655

Phe Thr Val Thr Glu Lys Gly Trp Glu Phe Val Trp Gly Asn His Pro
            660                 665                 670

Pro Lys Arg Phe Trp Ala Gln Glu Thr Ala Pro Gly Asn Pro His Gly
        675                 680                 685

Leu Pro His Glu Val Ile Thr His Tyr Tyr His Arg Tyr Pro Met Ser
    690                 695                 700

Thr Ile Leu Gly Leu Ser Ile Cys Ala Ala Ile Ala Thr Val Ser Val
705                 710                 715                 720

Ala Ala Ser Thr Trp Leu Phe Cys Arg Ser Arg Val Ala Cys Leu Thr
                725                 730                 735

Pro Tyr Arg Leu Thr Pro Asn Ala Arg Ile Pro Phe Cys Leu Ala Val
            740                 745                 750

Leu Cys Cys Ala Arg Thr Ala Arg Ala Glu Thr Thr Trp Glu Ser Leu
        755                 760                 765

Asp His Leu Trp Asn Asn Asn Gln Gln Met Phe Trp Ile Gln Leu Leu
    770                 775                 780

Ile Pro Leu Ala Ala Leu Ile Val Val Thr Arg Leu Leu Arg Cys Val
785                 790                 795                 800

Cys Cys Val Val Pro Phe Leu Val Met Ala Gly Ala Ala Gly Ala Gly
                805                 810                 815

Ala Tyr Glu His Ala Thr Thr Met Pro Ser Gln Ala Gly Ile Ser Tyr
            820                 825                 830

Asn Thr Ile Val Asn Arg Ala Gly Tyr Ala Pro Leu Pro Ile Ser Ile
        835                 840                 845

Thr Pro Thr Lys Ile Lys Leu Ile Pro Thr Val Asn Leu Glu Tyr Val
    850                 855                 860

Thr Cys His Tyr Lys Thr Gly Met Asp Ser Pro Ala Ile Lys Cys Cys
865                 870                 875                 880

Gly Ser Gln Glu Cys Thr Pro Thr Tyr Arg Pro Asp Glu Gln Cys Lys
                885                 890                 895

Val Phe Thr Gly Val Tyr Pro Phe Met Trp Gly Gly Ala Tyr Cys Phe
            900                 905                 910

Cys Asp Thr Glu Asn Thr Gln Val Ser Lys Ala Tyr Val Met Lys Ser
        915                 920                 925
```

```
Asp Asp Cys Leu Ala Asp His Ala Glu Ala Tyr Lys Ala His Thr Ala
    930                 935                 940

Ser Val Gln Ala Phe Leu Asn Ile Thr Val Gly Glu His Ser Ile Val
945                 950                 955                 960

Thr Thr Val Tyr Val Asn Gly Glu Thr Pro Val Asn Phe Asn Gly Val
                965                 970                 975

Lys Ile Thr Ala Gly Pro Leu Ser Thr Ala Trp Thr Pro Phe Asp Arg
            980                 985                 990

Lys Ile Val Gln Tyr Ala Gly Glu  Ile Tyr Asn Tyr Asp  Phe Pro Glu
        995                 1000                1005

Tyr Gly  Ala Gly Gln Pro Gly  Ala Phe Gly Asp Ile  Gln Ser Arg
    1010                1015                1020

Thr Val  Ser Ser Ser Asp Leu  Tyr Ala Asn Thr Asn  Leu Val Leu
    1025                1030                1035

Gln Arg  Pro Lys Ala Gly Ala  Ile His Val Pro Tyr  Thr Gln Ala
    1040                1045                1050

Pro Ser  Gly Phe Glu Gln Trp  Lys Lys Asp Lys Ala  Pro Ser Leu
    1055                1060                1065

Lys Phe  Thr Ala Pro Phe Gly  Cys Glu Ile Tyr Thr  Asn Pro Ile
    1070                1075                1080

Arg Ala  Glu Asn Cys Ala Val  Gly Ser Ile Pro Leu  Ala Phe Asp
    1085                1090                1095

Ile Pro  Asp Ala Leu Phe Thr  Arg Val Ser Glu Thr  Pro Thr Leu
    1100                1105                1110

Ser Ala  Ala Glu Cys Thr Leu  Asn Glu Cys Val Tyr  Ser Ser Asp
    1115                1120                1125

Phe Gly  Gly Ile Ala Thr Val  Lys Tyr Ser Ala Ser  Lys Ser Gly
    1130                1135                1140

Lys Cys  Ala Val His Val Pro  Ser Gly Thr Ala Thr  Leu Lys Glu
    1145                1150                1155

Ala Ala  Val Glu Leu Thr Glu  Gln Gly Ser Ala Thr  Ile His Phe
    1160                1165                1170

Ser Thr  Ala Asn Ile His Pro  Glu Phe Arg Leu Gln  Ile Cys Thr
    1175                1180                1185

Ser Tyr  Val Thr Cys Lys Gly  Asp Cys His Pro Pro  Lys Asp His
    1190                1195                1200

Ile Val  Thr His Pro Gln Tyr  His Ala Gln Thr Phe  Thr Ala Ala
    1205                1210                1215

Val Ser  Lys Thr Ala Trp Thr  Trp Leu Thr Ser Leu  Leu Gly Gly
    1220                1225                1230

Ser Ala  Val Ile Ile Ile Ile  Gly Leu Val Leu Ala  Thr Ile Val
    1235                1240                1245

Ala Met  Tyr Val Leu Thr Asn  Gln Lys His Asn
    1250                1255
```

<210> SEQ ID NO 38
<211> LENGTH: 8416
<212> TYPE: DNA
<213> ORGANISM: Artificial Sequence
<220> FEATURE:
<223> OTHER INFORMATION: Synthetic polynucleotide

<400> SEQUENCE: 38

```
gaattcccat tgcatacgtt gtatccatat cataatatgt acatttatat tggctcatgt      60
```

```
ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttccatggg tcttttctgc agtcaccgtc gtcgacacgt gtgatcagat atcgcggccg    900

ccaccatgga gttcatcccg acgcaaactt tctataacag aaggtaccaa ccccgaccct    960

gggccccacg ccctacaatt caagtaatta gacctagacc acgtccacag aggcaggctg   1020

ggcaactcgc ccagctgatc tccgcagtca acaaattgac catgcgcgcg gtacctcaac   1080

agaagcctcg cagaaatcgg aaaaacaaga agcaaaggca gaagaagcag gcgccgcaaa   1140

acgacccaaa gcaaaagaag caaccaccac aaaagaagcc ggctcaaaag aagaagaaac   1200

caggccgtag ggagagaatg tgcatgaaaa ttgaaaatga ttgcatcttc gaagtcaagc   1260

atgaaggcaa agtgatgggc tacgcatgcc tggtggggga taaagtaatg aaaccagcac   1320

atgtgaaggg aactatcgac aatgccgatc tggctaaact ggcctttaag cggtcgtcta   1380

aatacgatct tgaatgtgca cagataccgg tgcacatgaa gtctgatgcc tcgaagttta   1440

cccacgagaa acccgagggg tactataact ggcatcacgg agcagtgcag tattcaggag   1500

gccggttcac tatcccgacg ggtgcaggca agccgggaga cagcggcaga ccgatcttcg   1560

acaacaaagg acgggtggtg gccatcgtcc taggaggggc caacgaaggt gcccgcacgg   1620

ccctctccgt ggtgacgtgg aacaaagaca tcgtcacaaa aattacccct gagggagccg   1680

aagagtggag cctcgccctc ccggtcttgt gcctgttggc aaacactaca ttcccctgct   1740

ctcagccgcc ttgcacaccc tgctgctacg aaaaggaacc ggaaagcacc ttgcgcatgc   1800

ttgaggacaa cgtgatgaga cccggatact accagctact aaaagcatcg ctgacttgct   1860

ctccccaccg ccaaagacgc agtactaagg acaattttaa tgtctataaa gccacaagac   1920

catatctagc tcattgtcct gactgcggag aagggcattc gtgccacagc cctatcgcat   1980

tggagcgcat cagaaatgaa gcaacggacg gaacgctgaa aatccaggtc tctttgcaga   2040

tcgggataaa gacagatgac agccacgatt ggaccaagct gcgctatatg gatagccata   2100

cgccagcgga cgcggagcga gccggattgc ttgtaaggac ttcagcaccg tgcacgatca   2160

ccgggaccat gggacacttt attctcgccc gatgcccgaa aggagagacg ctgacagtgg   2220

gatttacgga cagcagaaag atcagccaca catgcacaca cccgttccat catgaaccac   2280

ctgtgatagg tagggagagg ttccactctc gaccacaaca tggtaaagag ttaccttgca   2340

gcacgtacgt gcagagcacc gctgccactg ctgaggagat agaggtgcat atgcccccag   2400

atactcctga ccgcacgctg atgacgcagc agtctggcaa cgtgaagatc acagttaatg   2460
```

```
gctccggagg atccggcggg cagacggtgc ggtacaagtg caactgcggt ggctcaaacg   2520
agggactgac aaccacagac aaagtgatca ataactgcaa aattgatcag tgccatgctg   2580
cagtcactaa tcacaagaat tggcaataca actccccttt agtcccgcgc aacgctgaac   2640
tcggggaccg taaaggaaag atccacatcc cattcccatt ggcaaacgtg acttgcagag   2700
tgccaaaagc aagaaaccct acagtaactt acggaaaaaa ccaagtcacc atgctgctgt   2760
atcctgacca tccgacactc ttgtcttacc gtaacatggg acaggaacca aattaccacg   2820
aggagtgggt gacacacaag aaggaggtta ccttgaccgt gcctactgag ggtctggagg   2880
tcacttgggg caacaacgaa ccatacaagt actggccgca gatgtctacg aacggtactg   2940
ctcatggtca cccacatgag ataatcttgt actattatga gctgtacccc actatgactg   3000
tagtcattgt gtcggtggcc tcgttcgtgc ttctgtcgat ggtgggcaca gcagtgggaa   3060
tgtgtgtgtg cgcacggcgc agatgcatta caccatatga attaacacca ggagccactg   3120
ttcccttcct gctcagcctg ctatgctgcg tcagaacgac caaggcggcc acatattacg   3180
aggctgcggc atatctatgg aacgaacagc agcccctgtt ctggttgcag gctcttatcc   3240
cgctggccgc cttgatcgtc ctgtgcaact gtctgaaact cttgccatgc tgctgtaaga   3300
ccctggcttt tttagccgta atgagcatcg gtgcccacac tgtgagcgcg tacgaacacg   3360
taacagtgat cccgaacacg gtgggagtac cgtataagac tcttgtcaac agaccgggtt   3420
acagccccat ggtgttggag atggagctac aatcagtcac cttggaacca acactgtcac   3480
ttgactacat cacgtgcgag tacaaaactg tcatcccctc cccgtacgtg aagtgctgtg   3540
gtacagcaga gtgcaaggac aagagcctac cagactacag ctgcaaggtc tttactggag   3600
tctacccatt tatgtggggc ggcgcctact gcttttgcga cgccgaaaat acgcaattga   3660
gcgaggcaca tgtagagaaa tctgaatctt gcaaaacaga gtttgcatcg gcctacagag   3720
cccacaccgc atcggcgtcg gcgaagctcc gcgtccttta ccaaggaaac aacattaccg   3780
tagctgccta cgctaacggt gaccatgccg tcacagtaaa ggacgccaag tttgtcgtgg   3840
gcccaatgtc ctccgcctgg acaccttttg acaacaaaat cgtggtgtac aaaggcgacg   3900
tctacaacat ggactaccca ccttttggcg caggaagacc aggacaattt ggtgacattc   3960
aaagtcgtac accggaaagt aaagacgttt atgccaacac tcagttggta ctacagaggc   4020
cagcagcagg cacggtacat gtaccatact ctcaggcacc atctggcttc aagtattggc   4080
tgaaggaacg aggagcatcg ctacagcaca cggcaccgtt cggttgccag attgcgacaa   4140
acccggtaag agctgtaaat tgcgctgtgg ggaacatacc aatttccatc gacataccgg   4200
atgcggcctt tactagggtt gtcgatgcac cctctgtaac ggacatgtca tgcgaagtac   4260
cagcctgcac tcactcctcc gactttgggg gcgtcgccat catcaaatac acagctagca   4320
agaaaggtaa atgtgcagta cattcgatga ccaacgccgt taccattcga gaagccgacg   4380
tagaagtaga ggggaactcc cagctgcaaa tatccttctc aacagccctg gcaagcgccg   4440
agtttcgcgt gcaagtgtgc tccacacaag tacactgcgc agccgcatgc caccctccaa   4500
aggaccacat agtcaattac ccagcatcac acaccaccct tggggtccag gatatatcca   4560
caacggcaat gtcttgggtg cagaagatta cgggaggagt aggattaatt gttgctgttg   4620
ctgccttaat tttaattgtg gtgctatgcg tgtcgtttag caggcactaa ggatctagat   4680
ctgctgtgcc ttctagttgc cagccatctg ttgtttgccc ctcccccgtg ccttccttga   4740
ccctggaagg tgccactccc actgtccttt cctaataaaa tgaggaaatt gcatcgcatt   4800
```

```
gtctgagtag gtgtcattct attctggggg gtggggtggg gcaggacagc aaggggggagg   4860
attgggaaga caatagcagg catgctgggg atgcggtggg ctctatgggt acccaggtgc    4920
tgaagaattg acccggttcc tcctgggcca gaaagaagca ggcacatccc cttctctgtg    4980
acacaccctg tccacgcccc tggttcttag ttccagcccc actcatagga cactcatagc    5040
tcaggagggc tccgccttca atcccacccg ctaaagtact tggagcggtc tctccctccc    5100
tcatcagccc accaaaccaa acctagcctc caagagtggg aagaaattaa agcaagatag    5160
gctattaagt gcagagggag agaaaatgcc tccaacatgt gaggaagtaa tgagagaaat    5220
catagaattt taaggccatg atttaaggcc atcatggcct aagcttgaaa ggagatagga    5280
tcaaagcttg gcgtaatcat ggtcatagct gtttcctgtg tgaaattgtt atccgctcac    5340
aattccacac aacatacgag ccggaagcat aaagtgtaaa gcctggggtg cctaatgagt    5400
gagctaactc acattaattg cgttgcgctc actgcccgct ttccagtcgg gaaacctgtc    5460
gtgccagctg cattaatgaa tcggccaacg cgcggggaga ggcggtttgc gtattgggcg    5520
ctcttccgct tcctcgctca ctgactcgct gcgctcggtc gttcggctgc ggcgagcggt    5580
atcagctcac tcaaaggcgg taatacggtt atccacagaa tcaggggata acgcaggaaa    5640
gaacatgtga gcaaaaggcc agcaaaaggc caggaaccgt aaaaaggccg cgttgctggc    5700
gtttttccat aggctccgcc cccctgacga gcatcacaaa aatcgacgct caagtcagag    5760
gtggcgaaac ccgacaggac tataaagata ccaggcgttt ccccctggaa gctccctcgt    5820
gcgctctcct gttccgaccc tgccgcttac cggatacctg tccgcctttc tcccttcggg    5880
aagcgtggcg ctttctcata gctcacgctg taggtatctc agttcggtgt aggtcgttcg    5940
ctccaagctg ggctgtgtgc acgaaccccc cgttcagccc gaccgctgcg ccttatccgg    6000
taactatcgt cttgagtcca acccggtaag acacgactta tcgccactgg cagcagccac    6060
tggtaacagg attagcagag cgaggtatgt aggcggtgct acagagttct tgaagtggtg    6120
gcctaactac ggctacacta gaagaacagt atttggtatc tgcgctctgc tgaagccagt    6180
taccttcgga aaaagagttg gtagctcttg atccggcaaa caaaccaccg ctggtagcgg    6240
tggttttttt gtttgcaagc agcagattac gcgcagaaaa aaaggatctc aagaagatcc    6300
tttgatcttt tctacggggt ctgacgctca gtggaacgaa aactcacgtt aagggatttt    6360
ggtcatgaga ttatcaaaaa ggatcttcac ctagatcctt ttaaattaaa aatgaagttt    6420
taaatcaatc taaagtatat atgagtaaac ttggtctgac agttaccaat gcttaatcag    6480
tgaggcacct atctcagcga tctgtctatt tcgttcatcc atagttgcct gactccccgt    6540
cgtgtagata actacgatac gggagggctt accatctggc cccagtgctg caatgatacc    6600
gcgagaacca cgctcaccgg ctccagattt atcagcaata aaccagccag ccggaagggc    6660
cgagcgcaga agtggtcctg caactttatc cgcctccatc cagtctatta attgttgccg    6720
ggaagctaga gtaagtagtt cgccagttaa tagtttgcgc aacgttgttg ccattgctac    6780
aggcatcgtg gtgtcacgct cgtcgtttgg tatggcttca ttcagctccg gttcccaacg    6840
atcaaggcga gttacatgat cccccatgtt gtgcaaaaaa gcggttagct ccttcggtcc    6900
tccgatcgtt gtcagaagta agttggccgc agtgttatca ctcatggtta tggcagcact    6960
gcataattct cttactgtca tgccatccgt aagatgcttt tctgtgactg gtgagtactc    7020
aaccaagtca ttctgagaat agtgtatgcg gcgaccgagt tgctcttgcc cggcgtcaat    7080
acgggataat accgcgccac atagcagaac tttaaaagtg ctcatcattg gaaaacgttc    7140
ttcggggcga aaactctcaa ggatcttacc gctgttgaga tccagttcga tgtaacccac    7200
```

```
tcgtgcaccc aactgatctt cagcatcttt tactttcacc agcgtttctg ggtgagcaaa   7260

aacaggaagg caaaatgccg caaaaaaggg aataagggcg acacggaaat gttgaatact   7320

catactcttc ctttttcaat attattgaag catttatcag ggttattgtc tcatgagcgg   7380

atacatattt gaatgtattt agaaaaataa acaaataggg gttccgcgca catttccccg   7440

aaaagtgcca cctgacgtct aagaaaccat tattatcatg acattaacct ataaaaatag   7500

gcgtatcacg aggccctttc gggtcgcgcg tttcggtgat gacggtgaaa acctctgaca   7560

catgcagctc ccgttgacgg tcacagcttg tctgtaagcg gatgccggga gcagacaagc   7620

ccgtcagggc gcgtcagcgg gtgttggcgg gtgtcggggc tggcttaact atgcggcatc   7680

agagcagatt gtactgagag tgcaccataa aattgtaaac gttaatattt tgttaaaatt   7740

cgcgttaaat ttttgttaaa tcagctcatt ttttaaccaa taggccgaaa tcggcaaaat   7800

cccttataaa tcaaaagaat agcccgagat agggttgagt gttgttccag tttggaacaa   7860

gagtccacta ttaaagaacg tggactccaa cgtcaaaggg cgaaaaaccg tctatcaggg   7920

cgatggccca ctacgtgaac catcacccaa atcaagtttt ttggggtcga ggtgccgtaa   7980

agcactaaat cggaacccta aagggagccc ccgatttaga gcttgacggg gaaagccggc   8040

gaacgtggcg agaaaggaag ggaagaaagc gaaaggagcg ggcgctaggg cgctggcaag   8100

tgtagcggtc acgctgcgcg taaccaccac acccgccgcg cttaatgcgc cgctacaggg   8160

cgcgtactat ggttgctttg acgtatgcgg tgtgaaatac cgcacagatg cgtaaggaga   8220

aaataccgca tcaggcgcca ttcgccattc aggctgcgca actgttggga agggcgatcg   8280

gtgcgggcct cttcgctatt acgccagctg gcgaaagggg gatgtgctgc aaggcgatta   8340

agttgggtaa cgccagggtt ttcccagtca cgacgttgta aaacgacggc cagtgaattc   8400

catggtctca actttc                                                   8416
```

```
<210> SEQ ID NO 39
<211> LENGTH: 3762
<212> TYPE: DNA
<213> ORGANISM: Artificial Sequence
<220> FEATURE:
<223> OTHER INFORMATION: Synthetic polynucleotide

<400> SEQUENCE: 39

atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780
```

```
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacacccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatggctcc   1560
ggaggatccg gcgggcagac ggtgcggtac aagtgcaact gcggtggctc aaacgaggga   1620
ctgacaacca cagacaaagt gatcaataac tgcaaaattg atcagtgcca tgctgcagtc   1680
actaatcaca agaattggca atacaactcc cctttagtcc cgcgcaacgc tgaactcggg   1740
gaccgtaaag gaaagatcca catcccattc ccattggcaa acgtgacttg cagagtgcca   1800
aaagcaagaa accctacagt aacttacgga aaaaaccaag tcaccatgct gctgtatcct   1860
gaccatccga cactcttgtc ttaccgtaac atgggacagg aaccaaatta ccacgaggag   1920
tgggtgacac acaagaagga ggttaccttg accgtgccta ctgagggtct ggaggtcact   1980
tggggcaaca acgaaccata caagtactgg ccgcagatgt ctacgaacgg tactgctcat   2040
ggtcacccac atgagataat cttgtactat tatgagctgt accccactat gactgtagtc   2100
attgtgtcgg tggcctcgtt cgtgcttctg tcgatggtgg gcacagcagt gggaatgtgt   2160
gtgtgcgcac ggcgcagatg cattacacca tatgaattaa caccaggagc cactgttccc   2220
ttcctgctca gcctgctatg ctgcgtcaga acgaccaagg cggccacata ttacgaggct   2280
gcggcatatc tatggaacga acagcagccc ctgttctggt tgcaggctct tatcccgctg   2340
gccgccttga tcgtcctgtg caactgtctg aaactcttgc catgctgctg taagaccctg   2400
gctttttttag ccgtaatgag catcggtgcc cacactgtga gcgcgtacga acacgtaaca   2460
gtgatcccga acacggtggg agtaccgtat aagactcttg tcaacagacc gggttacagc   2520
cccatggtgt tggagatgga gctacaatca gtcaccttgg aaccaacact gtcacttgac   2580
tacatcacgt gcgagtacaa aactgtcatc ccctccccgt acgtgaagtg ctgtggtaca   2640
gcagagtgca aggacaagag cctaccagac tacagctgca aggtctttac tggagtctac   2700
ccatttatgt ggggcggcgc ctactgcttt tgcgacgccg aaaatacgca attgagcgag   2760
gcacatgtag agaaatctga atcttgcaaa acagagtttg catcggccta cagagcccac   2820
accgcatcgg cgtcggcgaa gctccgcgtc ctttaccaag gaaacaacat taccgtagct   2880
gcctacgcta acggtgacca tgccgtcaca gtaaaggacg ccaagtttgt cgtgggccca   2940
atgtcctccg cctggacacc ttttgacaac aaaatcgtgg tgtacaaagg cgacgtctac   3000
aacatggact acccaccttt tggcgcagga agaccaggac aatttggtga cattcaaagt   3060
cgtacaccgg aaagtaaaga cgtttatgcc aacactcagt tggtactaca gaggccagca   3120
gcaggcacgg tacatgtacc atactctcag gcaccatctg gcttcaagta ttggctgaag   3180
```

```
gaacgaggag catcgctaca gcacacggca ccgttcggtt gccagattgc gacaaacccg   3240

gtaagagctg taaattgcgc tgtggggaac ataccaattt ccatcgacat accggatgcg   3300

gcctttacta gggttgtcga tgcaccctct gtaacggaca tgtcatgcga agtaccagcc   3360

tgcactcact cctccgactt tgggggcgtc gccatcatca aatacacagc tagcaagaaa   3420

ggtaaatgtg cagtacattc gatgaccaac gccgttacca ttcgagaagc cgacgtagaa   3480

gtagagggga actcccagct gcaaatatcc ttctcaacag ccctggcaag cgccgagttt   3540

cgcgtgcaag tgtgctccac acaagtacac tgcgcagccg catgccaccc tccaaaggac   3600

cacatagtca attacccagc atcacacacc acccttgggg tccaggatat atccacaacg   3660

gcaatgtctt gggtgcagaa gattacggga ggagtaggat taattgttgc tgttgctgcc   3720

ttaattttaa ttgtggtgct atgcgtgtcg tttagcaggc ac                      3762
```

<210> SEQ ID NO 40
<211> LENGTH: 1254
<212> TYPE: PRT
<213> ORGANISM: Artificial Sequence
<220> FEATURE:
<223> OTHER INFORMATION: Synthetic peptide

<400> SEQUENCE: 40

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255
```

```
Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Ser Gly Gly Ser Gly Gly Gln Thr Val
        515                 520                 525

Arg Tyr Lys Cys Asn Cys Gly Gly Ser Asn Glu Gly Leu Thr Thr Thr
    530                 535                 540

Asp Lys Val Ile Asn Asn Cys Lys Ile Asp Gln Cys His Ala Ala Val
545                 550                 555                 560

Thr Asn His Lys Asn Trp Gln Tyr Asn Ser Pro Leu Val Pro Arg Asn
                565                 570                 575

Ala Glu Leu Gly Asp Arg Lys Gly Lys Ile His Ile Pro Phe Pro Leu
            580                 585                 590

Ala Asn Val Thr Cys Arg Val Pro Lys Ala Arg Asn Pro Thr Val Thr
        595                 600                 605

Tyr Gly Lys Asn Gln Val Thr Met Leu Leu Tyr Pro Asp His Pro Thr
    610                 615                 620

Leu Leu Ser Tyr Arg Asn Met Gly Gln Glu Pro Asn Tyr His Glu Glu
625                 630                 635                 640

Trp Val Thr His Lys Lys Glu Val Thr Leu Thr Val Pro Thr Glu Gly
                645                 650                 655

Leu Glu Val Thr Trp Gly Asn Asn Glu Pro Tyr Lys Tyr Trp Pro Gln
            660                 665                 670

Met Ser Thr Asn Gly Thr Ala His Gly His Pro His Glu Ile Ile Leu
```

```
        675                 680                 685

Tyr Tyr Tyr Glu Leu Tyr Pro Thr Met Thr Val Val Ile Val Ser Val
    690                 695                 700

Ala Ser Phe Val Leu Leu Ser Met Val Gly Thr Ala Val Gly Met Cys
705                 710                 715                 720

Val Cys Ala Arg Arg Arg Cys Ile Thr Pro Tyr Glu Leu Thr Pro Gly
                725                 730                 735

Ala Thr Val Pro Phe Leu Leu Ser Leu Leu Cys Cys Val Arg Thr Thr
            740                 745                 750

Lys Ala Ala Thr Tyr Tyr Glu Ala Ala Ala Tyr Leu Trp Asn Glu Gln
        755                 760                 765

Gln Pro Leu Phe Trp Leu Gln Ala Leu Ile Pro Leu Ala Ala Leu Ile
    770                 775                 780

Val Leu Cys Asn Cys Leu Lys Leu Leu Pro Cys Cys Cys Lys Thr Leu
785                 790                 795                 800

Ala Phe Leu Ala Val Met Ser Ile Gly Ala His Thr Val Ser Ala Tyr
                805                 810                 815

Glu His Val Thr Val Ile Pro Asn Thr Val Gly Val Pro Tyr Lys Thr
            820                 825                 830

Leu Val Asn Arg Pro Gly Tyr Ser Pro Met Val Leu Glu Met Glu Leu
        835                 840                 845

Gln Ser Val Thr Leu Glu Pro Thr Leu Ser Leu Asp Tyr Ile Thr Cys
    850                 855                 860

Glu Tyr Lys Thr Val Ile Pro Ser Pro Tyr Val Lys Cys Cys Gly Thr
865                 870                 875                 880

Ala Glu Cys Lys Asp Lys Ser Leu Pro Asp Tyr Ser Cys Lys Val Phe
                885                 890                 895

Thr Gly Val Tyr Pro Phe Met Trp Gly Gly Ala Tyr Cys Phe Cys Asp
            900                 905                 910

Ala Glu Asn Thr Gln Leu Ser Glu Ala His Val Glu Lys Ser Glu Ser
        915                 920                 925

Cys Lys Thr Glu Phe Ala Ser Ala Tyr Arg Ala His Thr Ala Ser Ala
    930                 935                 940

Ser Ala Lys Leu Arg Val Leu Tyr Gln Gly Asn Asn Ile Thr Val Ala
945                 950                 955                 960

Ala Tyr Ala Asn Gly Asp His Ala Val Thr Val Lys Asp Ala Lys Phe
                965                 970                 975

Val Val Gly Pro Met Ser Ser Ala Trp Thr Pro Phe Asp Asn Lys Ile
            980                 985                 990

Val Val Tyr Lys Gly Asp Val Tyr  Asn Met Asp Tyr Pro  Pro Phe Gly
        995                 1000                1005

Ala Gly  Arg Pro Gly Gln Phe  Gly Asp Ile Gln Ser  Arg Thr Pro
    1010                1015                1020

Glu Ser  Lys Asp Val Tyr Ala  Asn Thr Gln Leu Val  Leu Gln Arg
    1025                1030                1035

Pro Ala  Ala Gly Thr Val His  Val Pro Tyr Ser Gln  Ala Pro Ser
    1040                1045                1050

Gly Phe  Lys Tyr Trp Leu Lys  Glu Arg Gly Ala Ser  Leu Gln His
    1055                1060                1065

Thr Ala  Pro Phe Gly Cys Gln  Ile Ala Thr Asn Pro  Val Arg Ala
    1070                1075                1080

Val Asn  Cys Ala Val Gly Asn  Ile Pro Ile Ser Ile  Asp Ile Pro
    1085                1090                1095
```

```
Asp Ala  Ala Phe Thr Arg Val  Val Asp Ala Pro Ser  Val Thr Asp
    1100                 1105                 1110

Met Ser  Cys Glu Val Pro Ala  Cys Thr His Ser Ser  Asp Phe Gly
    1115                 1120                 1125

Gly Val  Ala Ile Ile Lys Tyr  Thr Ala Ser Lys Lys  Gly Lys Cys
    1130                 1135                 1140

Ala Val  His Ser Met Thr Asn  Ala Val Thr Ile Arg  Glu Ala Asp
    1145                 1150                 1155

Val Glu  Val Glu Gly Asn Ser  Gln Leu Gln Ile Ser  Phe Ser Thr
    1160                 1165                 1170

Ala Leu  Ala Ser Ala Glu Phe  Arg Val Gln Val Cys  Ser Thr Gln
    1175                 1180                 1185

Val His  Cys Ala Ala Ala Cys  His Pro Pro Lys Asp  His Ile Val
    1190                 1195                 1200

Asn Tyr  Pro Ala Ser His Thr  Thr Leu Gly Val Gln  Asp Ile Ser
    1205                 1210                 1215

Thr Thr  Ala Met Ser Trp Val  Gln Lys Ile Thr Gly  Gly Val Gly
    1220                 1225                 1230

Leu Ile  Val Ala Val Ala Ala  Leu Ile Leu Ile Val  Val Leu Cys
    1235                 1240                 1245

Val Ser  Phe Ser Arg His
    1250


<210> SEQ ID NO 41
<211> LENGTH: 22
<212> TYPE: PRT
<213> ORGANISM: Artificial Sequence
<220> FEATURE:
<223> OTHER INFORMATION: Synthetic CD20 peptide

<400> SEQUENCE: 41

Tyr Asp Cys Glu Pro Ser Asn Ser Ser Glu Lys Asn Ser Pro Ser Thr
1               5                   10                  15

Gln Tyr Cys Asn Ser Ile
            20


<210> SEQ ID NO 42
<211> LENGTH: 29
<212> TYPE: PRT
<213> ORGANISM: Artificial Sequence
<220> FEATURE:
<223> OTHER INFORMATION: Synthetic CD20+linker peptide

<400> SEQUENCE: 42

Ser Gly Gly Ile Tyr Asn Cys Glu Pro Ala Asn Pro Ser Glu Lys Asn
1               5                   10                  15

Ser Pro Ser Thr Gln Tyr Cys Tyr Ser Ile Gln Gly Ser
            20                  25


<210> SEQ ID NO 43
<211> LENGTH: 27
<212> TYPE: PRT
<213> ORGANISM: Artificial Sequence
<220> FEATURE:
<223> OTHER INFORMATION: Synthetic CD20+linker peptide

<400> SEQUENCE: 43

Ser Gly Tyr Asp Cys Glu Pro Ser Asn Ser Ser Glu Lys Asn Ser Pro
1               5                   10                  15
```

Ser Thr Gln Tyr Cys Asn Ser Ile Gly Gly Ser
20 25

<210> SEQ ID NO 44
<211> LENGTH: 27
<212> TYPE: PRT
<213> ORGANISM: Artificial Sequence
<220> FEATURE:
<223> OTHER INFORMATION: Synthetic CD20+linker peptide

<400> SEQUENCE: 44

Ser Gly Gly Tyr Asp Cys Glu Pro Ser Asn Ser Ser Glu Lys Asn Ser
1 5 10 15

Pro Ser Thr Gln Tyr Cys Asn Ser Ile Gly Ser
20 25

<210> SEQ ID NO 45
<211> LENGTH: 3828
<212> TYPE: DNA
<213> ORGANISM: Artificial Sequence
<220> FEATURE:
<223> OTHER INFORMATION: Synthetic polynucleotide

<400> SEQUENCE: 45
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
caccgccaaa gacgcagtac taaggacaat tttaatgtct ataaagccac aagaccatat 1020
ctagctcatt gtcctgactg cggagaaggg cattcgtgcc acagccctat cgcattggag 1080
cgcatcagaa atgaagcaac ggacggaacg ctgaaaatcc aggtctcttt gcagatcggg 1140
ataaagacag atgacagcca cgattggacc aagctgcgct atatggatag ccatacgcca 1200
gcggacgcgg agcgagccgg attgcttgta aggacttcag caccgtgcac gatcaccggg 1260
accatgggac actttattct cgcccgatgc ccgaaaggag agacgctgac agtgggattt 1320
acggacagca gaaagatcag ccacacatgc acacacccgt tccatcatga accacctgtg 1380
ataggtaggg agaggttcca ctctcgacca caacatggta aagagttacc ttgcagcacg 1440
tacgtgcaga gcaccgctgc cactgctgag gagatagagg tgcatatgcc cccagatact 1500

```
cctgaccgca cgctgatgac gcagcagtct ggcaacgtga agatcacagt taatgggcag   1560
acggtgcggt acaagtgcaa ctgcggtggc tccggaggta tatacaactg tgaaccagct   1620
aatccctctg agaaaaactc cccatctacc caatactgtt acagcataca aggatccaac   1680
gagggactga caaccacaga caaagtgatc aataactgca aaattgatca gtgccatgct   1740
gcagtcacta atcacaagaa ttggcaatac aactcccctt tagtcccgcg caacgctgaa   1800
ctcggggacc gtaaaggaaa gatccacatc ccattcccat tggcaaacgt gacttgcaga   1860
gtgccaaaag caagaaaccc tacagtaact tacggaaaaa accaagtcac catgctgctg   1920
tatcctgacc atccgacact cttgtcttac cgtaacatgg gacaggaacc aaattaccac   1980
gaggagtggg tgacacacaa gaaggaggtt accttgaccg tgcctactga gggtctggag   2040
gtcacttggg gcaacaacga accatacaag tactggccgc agatgtctac gaacggtact   2100
gctcatggtc acccacatga gataatcttg tactattatg agctgtaccc cactatgact   2160
gtagtcattg tgtcggtggc ctcgttcgtg cttctgtcga tggtgggcac agcagtggga   2220
atgtgtgtgt gcgcacggcg cagatgcatt acaccatatg aattaacacc aggagccact   2280
gttcccttcc tgctcagcct gctatgctgc gtcagaacga ccaaggcggc cacatattac   2340
gaggctgcgg catatctatg gaacgaacag cagcccctgt tctggttgca ggctcttatc   2400
ccgctggccg ccttgatcgt cctgtgcaac tgtctgaaac tcttgccatg ctgctgtaag   2460
accctggctt ttttagccgt aatgagcatc ggtgcccaca ctgtgagcgc gtacgaacac   2520
gtaacagtga tcccgaacac ggtgggagta ccgtataaga ctcttgtcaa cagaccgggt   2580
tacagcccca tggtgttgga gatggagcta caatcagtca ccttggaacc aacactgtca   2640
cttgactaca tcacgtgcga gtacaaaact gtcatcccct ccccgtacgt gaagtgctgt   2700
ggtacagcag agtgcaagga caagagccta ccagactaca gctgcaaggt ctttactgga   2760
gtctacccat ttatgtgggg cggcgcctac tgcttttgcg acgccgaaaa tacgcaattg   2820
agcgaggcac atgtagagaa atctgaatct tgcaaaacag agtttgcatc ggcctacaga   2880
gcccacaccg catcggcgtc ggcgaagctc cgcgtccttt accaaggaaa caacattacc   2940
gtagctgcct acgctaacgg tgaccatgcc gtcacagtaa aggacgccaa gtttgtcgtg   3000
ggcccaatgt cctccgcctg gacacctttt gacaacaaaa tcgtggtgta caaaggcgac   3060
gtctacaaca tggactaccc accttttggc gcaggaagac caggacaatt tggtgacatt   3120
caaagtcgta caccggaaag taaagacgtt tatgccaaca ctcagttggt actacagagg   3180
ccagcagcag gcacggtaca tgtaccatac tctcaggcac catctggctt caagtattgg   3240
ctgaaggaac gaggagcatc gctacagcac acggcaccgt tcggttgcca gattgcgaca   3300
aacccggtaa gagctgtaaa ttgcgctgtg gggaacatac caatttccat cgacataccg   3360
gatgcggcct ttactagggt tgtcgatgca ccctctgtaa cggacatgtc atgcgaagta   3420
ccagcctgca ctcactcctc cgactttggg ggcgtcgcca tcatcaaata cacagctagc   3480
aagaaaggta aatgtgcagt acattcgatg accaacgccg ttaccattcg agaagccgac   3540
gtagaagtag aggggaactc ccagctgcaa atatccttct caacagccct ggcaagcgcc   3600
gagtttcgcg tgcaagtgtg ctccacacaa gtacactgcg cagccgcatg ccaccctcca   3660
aaggaccaca tagtcaatta cccagcatca cacaccaccc ttggggtcca ggatatatcc   3720
acaacggcaa tgtcttgggt gcagaagatt acgggaggag taggattaat tgttgctgtt   3780
gctgccttaa ttttaattgt ggtgctatgc gtgtcgttta gcaggcac                3828
```

<210> SEQ ID NO 46
<211> LENGTH: 1276
<212> TYPE: PRT
<213> ORGANISM: Artificial Sequence
<220> FEATURE:
<223> OTHER INFORMATION: Synthetic peptide

<400> SEQUENCE: 46

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
```

```
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Gly Ile Tyr Asn Cys Glu Pro Ala Asn Pro Ser Glu
    530                 535                 540

Lys Asn Ser Pro Ser Thr Gln Tyr Cys Tyr Ser Ile Gln Gly Ser Asn
545                 550                 555                 560

Glu Gly Leu Thr Thr Thr Asp Lys Val Ile Asn Asn Cys Lys Ile Asp
                565                 570                 575

Gln Cys His Ala Ala Val Thr Asn His Lys Asn Trp Gln Tyr Asn Ser
            580                 585                 590

Pro Leu Val Pro Arg Asn Ala Glu Leu Gly Asp Arg Lys Gly Lys Ile
        595                 600                 605

His Ile Pro Phe Pro Leu Ala Asn Val Thr Cys Arg Val Pro Lys Ala
    610                 615                 620

Arg Asn Pro Thr Val Thr Tyr Gly Lys Asn Gln Val Thr Met Leu Leu
625                 630                 635                 640

Tyr Pro Asp His Pro Thr Leu Leu Ser Tyr Arg Asn Met Gly Gln Glu
                645                 650                 655

Pro Asn Tyr His Glu Glu Trp Val Thr His Lys Lys Glu Val Thr Leu
            660                 665                 670

Thr Val Pro Thr Glu Gly Leu Glu Val Thr Trp Gly Asn Asn Glu Pro
        675                 680                 685

Tyr Lys Tyr Trp Pro Gln Met Ser Thr Asn Gly Thr Ala His Gly His
    690                 695                 700

Pro His Glu Ile Ile Leu Tyr Tyr Tyr Glu Leu Tyr Pro Thr Met Thr
705                 710                 715                 720

Val Val Ile Val Ser Val Ala Ser Phe Val Leu Leu Ser Met Val Gly
                725                 730                 735

Thr Ala Val Gly Met Cys Val Cys Ala Arg Arg Arg Cys Ile Thr Pro
            740                 745                 750

Tyr Glu Leu Thr Pro Gly Ala Thr Val Pro Phe Leu Leu Ser Leu Leu
        755                 760                 765

Cys Cys Val Arg Thr Thr Lys Ala Ala Thr Tyr Tyr Glu Ala Ala Ala
    770                 775                 780

Tyr Leu Trp Asn Glu Gln Gln Pro Leu Phe Trp Leu Gln Ala Leu Ile
785                 790                 795                 800
```

```
Pro Leu Ala Ala Leu Ile Val Leu Cys Asn Cys Leu Lys Leu Leu Pro
                805                 810                 815

Cys Cys Cys Lys Thr Leu Ala Phe Leu Ala Val Met Ser Ile Gly Ala
            820                 825                 830

His Thr Val Ser Ala Tyr Glu His Val Thr Val Ile Pro Asn Thr Val
        835                 840                 845

Gly Val Pro Tyr Lys Thr Leu Val Asn Arg Pro Gly Tyr Ser Pro Met
    850                 855                 860

Val Leu Glu Met Glu Leu Gln Ser Val Thr Leu Glu Pro Thr Leu Ser
865                 870                 875                 880

Leu Asp Tyr Ile Thr Cys Glu Tyr Lys Thr Val Ile Pro Ser Pro Tyr
                885                 890                 895

Val Lys Cys Cys Gly Thr Ala Glu Cys Lys Asp Lys Ser Leu Pro Asp
            900                 905                 910

Tyr Ser Cys Lys Val Phe Thr Gly Val Tyr Pro Phe Met Trp Gly Gly
        915                 920                 925

Ala Tyr Cys Phe Cys Asp Ala Glu Asn Thr Gln Leu Ser Glu Ala His
    930                 935                 940

Val Glu Lys Ser Glu Ser Cys Lys Thr Glu Phe Ala Ser Ala Tyr Arg
945                 950                 955                 960

Ala His Thr Ala Ser Ala Ser Ala Lys Leu Arg Val Leu Tyr Gln Gly
                965                 970                 975

Asn Asn Ile Thr Val Ala Ala Tyr Ala Asn Gly Asp His Ala Val Thr
            980                 985                 990

Val Lys Asp Ala Lys Phe Val Val  Gly Pro Met Ser Ser  Ala Trp Thr
        995                 1000                1005

Pro Phe  Asp Asn Lys Ile Val  Val Tyr Lys Gly Asp  Val Tyr Asn
    1010                1015                1020

Met Asp  Tyr Pro Pro Phe Gly  Ala Gly Arg Pro Gly  Gln Phe Gly
    1025                1030                1035

Asp Ile  Gln Ser Arg Thr Pro  Glu Ser Lys Asp Val  Tyr Ala Asn
    1040                1045                1050

Thr Gln  Leu Val Leu Gln Arg  Pro Ala Ala Gly Thr  Val His Val
    1055                1060                1065

Pro Tyr  Ser Gln Ala Pro Ser  Gly Phe Lys Tyr Trp  Leu Lys Glu
    1070                1075                1080

Arg Gly  Ala Ser Leu Gln His  Thr Ala Pro Phe Gly  Cys Gln Ile
    1085                1090                1095

Ala Thr  Asn Pro Val Arg Ala  Val Asn Cys Ala Val  Gly Asn Ile
    1100                1105                1110

Pro Ile  Ser Ile Asp Ile Pro  Asp Ala Ala Phe Thr  Arg Val Val
    1115                1120                1125

Asp Ala  Pro Ser Val Thr Asp  Met Ser Cys Glu Val  Pro Ala Cys
    1130                1135                1140

Thr His  Ser Ser Asp Phe Gly  Gly Val Ala Ile Ile  Lys Tyr Thr
    1145                1150                1155

Ala Ser  Lys Lys Gly Lys Cys  Ala Val His Ser Met  Thr Asn Ala
    1160                1165                1170

Val Thr  Ile Arg Glu Ala Asp  Val Glu Val Glu Gly  Asn Ser Gln
    1175                1180                1185

Leu Gln  Ile Ser Phe Ser Thr  Ala Leu Ala Ser Ala  Glu Phe Arg
    1190                1195                1200
```

```
Val Gln  Val Cys Ser Thr Gln  Val His Cys Ala Ala  Ala Cys His
    1205                 1210                 1215

Pro Pro  Lys Asp His Ile Val  Asn Tyr Pro Ala Ser  His Thr Thr
    1220                 1225                 1230

Leu Gly  Val Gln Asp Ile Ser  Thr Thr Ala Met Ser  Trp Val Gln
    1235                 1240                 1245

Lys Ile  Thr Gly Gly Val Gly  Leu Ile Val Ala Val  Ala Ala Leu
    1250                 1255                 1260

Ile Leu  Ile Val Val Leu Cys  Val Ser Phe Ser Arg  His
    1265                 1270                 1275


<210> SEQ ID NO 47
<211> LENGTH: 3822
<212> TYPE: DNA
<213> ORGANISM: Artificial Sequence
<220> FEATURE:
<223> OTHER INFORMATION: Synthetic polynucleotide

<400> SEQUENCE: 47

atggagttca tcccgacgca aactttctat aacagaaggt accaaccccg accctgggcc      60

ccacgcccta caattcaagt aattagacct agaccacgtc cacagaggca ggctgggcaa     120

ctcgcccagc tgatctccgc agtcaacaaa ttgaccatgc gcgcggtacc tcaacagaag     180

cctcgcagaa atcggaaaaa caagaagcaa aggcagaaga agcaggcgcc gcaaaacgac     240

ccaaagcaaa agaagcaacc accacaaaag aagccggctc aaaagaagaa gaaaccaggc     300

cgtagggaga gaatgtgcat gaaaattgaa aatgattgca tcttcgaagt caagcatgaa     360

ggcaaagtga tgggctacgc atgcctggtg ggggataaag taatgaaacc agcacatgtg     420

aagggaacta tcgacaatgc cgatctggct aaactggcct ttaagcggtc gtctaaatac     480

gatcttgaat gtgcacagat accggtgcac atgaagtctg atgcctcgaa gtttacccac     540

gagaaacccg aggggtacta taactggcat cacggagcag tgcagtattc aggaggccgg     600

ttcactatcc cgacgggtgc aggcaagccg ggagacagcg gcagaccgat cttcgacaac     660

aaaggacggg tggtggccat cgtcctagga ggggccaacg aaggtgcccg cacggccctc     720

tccgtggtga cgtggaacaa agacatcgtc acaaaaatta cccctgaggg agccgaagag     780

tggagcctcg ccctcccggt cttgtgcctg ttggcaaaca ctacattccc ctgctctcag     840

ccgccttgca caccctgctg ctacgaaaag gaaccggaaa gcaccttgcg catgcttgag     900

gacaacgtga tgagacccgg atactaccag ctactaaaag catcgctgac ttgctctccc     960

caccgccaaa gacgcagtac taaggacaat tttaatgtct ataaagccac aagaccatat    1020

ctagctcatt gtcctgactg cggagaaggg cattcgtgcc acagccctat cgcattggag    1080

cgcatcagaa atgaagcaac ggacggaacg ctgaaaatcc aggtctcttt gcagatcggg    1140

ataaagacag atgacagcca cgattggacc aagctgcgct atatggatag ccatacgcca    1200

gcggacgcgg agcgagccgg attgcttgta aggacttcag caccgtgcac gatcaccggg    1260

accatgggac actttattct cgcccgatgc ccgaaaggag agacgctgac agtgggattt    1320

acggacagca gaaagatcag ccacacatgc acacacccgt tccatcatga accacctgtg    1380

ataggtaggg agaggttcca ctctcgacca caacatggta aagagttacc ttgcagcacg    1440

tacgtgcaga gcaccgctgc cactgctgag gagatagagg tgcatatgcc cccagatact    1500

cctgaccgca cgctgatgac gcagcagtct ggcaacgtga agatcacagt taatgggcag    1560

acggtgcggt acaagtgcaa ctgcggtggc tccggatacg actgtgaacc atctaattcc    1620
```

```
tcagagaaaa actccccatc tacacagtac tgtaacagca ttggaggatc caacgaggga   1680
ctgacaacca cagacaaagt gatcaataac tgcaaaattg atcagtgcca tgctgcagtc   1740
actaatcaca agaattggca atacaactcc cctttagtcc cgcgcaacgc tgaactcggg   1800
gaccgtaaag gaaagatcca catcccattc ccattggcaa acgtgacttg cagagtgcca   1860
aaagcaagaa accctacagt aacttacgga aaaaaccaag tcaccatgct gctgtatcct   1920
gaccatccga cactcttgtc ttaccgtaac atgggacagg aaccaaatta ccacgaggag   1980
tgggtgacac acaagaagga ggttaccttg accgtgccta ctgagggtct ggaggtcact   2040
tggggcaaca acgaaccata caagtactgg ccgcagatgt ctacgaacgg tactgctcat   2100
ggtcacccac atgagataat cttgtactat tatgagctgt accccactat gactgtagtc   2160
attgtgtcgg tggcctcgtt cgtgcttctg tcgatggtgg gcacagcagt gggaatgtgt   2220
gtgtgcgcac ggcgcagatg cattacacca tatgaattaa caccaggagc cactgttccc   2280
ttcctgctca gcctgctatg ctgcgtcaga acgaccaagg cggccacata ttacgaggct   2340
gcggcatatc tatggaacga acagcagccc ctgttctggt tgcaggctct tatcccgctg   2400
gccgccttga tcgtcctgtg caactgtctg aaactcttgc catgctgctg taagaccctg   2460
gctttttag ccgtaatgag catcggtgcc cacactgtga gcgcgtacga acacgtaaca    2520
gtgatcccga acacggtggg agtaccgtat aagactcttg tcaacagacc gggttacagc   2580
cccatggtgt tggagatgga gctacaatca gtcaccttgg aaccaacact gtcacttgac   2640
tacatcacgt gcgagtacaa aactgtcatc ccctccccgt acgtgaagtg ctgtggtaca   2700
gcagagtgca aggacaagag cctaccagac tacagctgca aggtctttac tggagtctac   2760
ccatttatgt ggggcggcgc ctactgcttt tgcgacgccg aaaatacgca attgagcgag   2820
gcacatgtag agaaatctga atcttgcaaa acagagtttg catcggccta cagagcccac   2880
accgcatcgg cgtcggcgaa gctccgcgtc ctttaccaag gaaacaacat taccgtagct   2940
gcctacgcta acggtgacca tgccgtcaca gtaaaggacg ccaagtttgt cgtgggccca   3000
atgtcctccg cctggacacc ttttgacaac aaaatcgtgg tgtacaaagg cgacgtctac   3060
aacatggact acccaccttt tggcgcagga agaccaggac aatttggtga cattcaaagt   3120
cgtacaccgg aaagtaaaga cgtttatgcc aacactcagt tggtactaca gaggccagca   3180
gcaggcacgg tacatgtacc atactctcag gcaccatctg gcttcaagta ttggctgaag   3240
gaacgaggag catcgctaca gcacacggca ccgttcggtt gccagattgc gacaaacccg   3300
gtaagagctg taaattgcgc tgtggggaac ataccaattt ccatcgacat accggatgcg   3360
gcctttacta gggttgtcga tgcaccctct gtaacggaca tgtcatgcga agtaccagcc   3420
tgcactcact cctccgactt tgggggcgtc gccatcatca aatacacagc tagcaagaaa   3480
ggtaaatgtg cagtacattc gatgaccaac gccgttacca ttcgagaagc cgacgtagaa   3540
gtagagggga actcccagct gcaaatatcc ttctcaacag ccctggcaag cgccgagttt   3600
cgcgtgcaag tgtgctccac acaagtacac tgcgcagccg catgccaccc tccaaaggac   3660
cacatagtca attacccagc atcacacacc acccttgggg tccaggatat atccacaacg   3720
gcaatgtctt gggtgcagaa gattacggga ggagtaggat taattgttgc tgttgctgcc   3780
ttaattttaa ttgtggtgct atgcgtgtcg tttagcaggc ac                       3822
```

<210> SEQ ID NO 48
<211> LENGTH: 1274
<212> TYPE: PRT
<213> ORGANISM: Artificial Sequence
<220> FEATURE:
<223> OTHER INFORMATION: Synthetic peptide

<400> SEQUENCE: 48

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

```
Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Tyr Asp Cys Glu Pro Ser Asn Ser Ser Glu Lys Asn
    530                 535                 540

Ser Pro Ser Thr Gln Tyr Cys Asn Ser Ile Gly Gly Ser Asn Glu Gly
545                 550                 555                 560

Leu Thr Thr Thr Asp Lys Val Ile Asn Asn Cys Lys Ile Asp Gln Cys
                565                 570                 575

His Ala Ala Val Thr Asn His Lys Asn Trp Gln Tyr Asn Ser Pro Leu
            580                 585                 590

Val Pro Arg Asn Ala Glu Leu Gly Asp Arg Lys Gly Lys Ile His Ile
        595                 600                 605

Pro Phe Pro Leu Ala Asn Val Thr Cys Arg Val Pro Lys Ala Arg Asn
    610                 615                 620

Pro Thr Val Thr Tyr Gly Lys Asn Gln Val Thr Met Leu Leu Tyr Pro
625                 630                 635                 640

Asp His Pro Thr Leu Leu Ser Tyr Arg Asn Met Gly Gln Glu Pro Asn
                645                 650                 655

Tyr His Glu Glu Trp Val Thr His Lys Lys Glu Val Thr Leu Thr Val
            660                 665                 670

Pro Thr Glu Gly Leu Glu Val Thr Trp Gly Asn Asn Glu Pro Tyr Lys
        675                 680                 685

Tyr Trp Pro Gln Met Ser Thr Asn Gly Thr Ala His Gly His Pro His
    690                 695                 700

Glu Ile Ile Leu Tyr Tyr Tyr Glu Leu Tyr Pro Thr Met Thr Val Val
705                 710                 715                 720

Ile Val Ser Val Ala Ser Phe Val Leu Leu Ser Met Val Gly Thr Ala
                725                 730                 735

Val Gly Met Cys Val Cys Ala Arg Arg Arg Cys Ile Thr Pro Tyr Glu
            740                 745                 750

Leu Thr Pro Gly Ala Thr Val Pro Phe Leu Leu Ser Leu Leu Cys Cys
        755                 760                 765

Val Arg Thr Thr Lys Ala Ala Thr Tyr Tyr Glu Ala Ala Ala Tyr Leu
    770                 775                 780

Trp Asn Glu Gln Gln Pro Leu Phe Trp Leu Gln Ala Leu Ile Pro Leu
785                 790                 795                 800

Ala Ala Leu Ile Val Leu Cys Asn Cys Leu Lys Leu Leu Pro Cys Cys
                805                 810                 815
```

```
Cys Lys Thr Leu Ala Phe Leu Ala Val Met Ser Ile Gly Ala His Thr
            820                 825                 830

Val Ser Ala Tyr Glu His Val Thr Val Ile Pro Asn Thr Val Gly Val
        835                 840                 845

Pro Tyr Lys Thr Leu Val Asn Arg Pro Gly Tyr Ser Pro Met Val Leu
    850                 855                 860

Glu Met Glu Leu Gln Ser Val Thr Leu Glu Pro Thr Leu Ser Leu Asp
865                 870                 875                 880

Tyr Ile Thr Cys Glu Tyr Lys Thr Val Ile Pro Ser Pro Tyr Val Lys
                885                 890                 895

Cys Cys Gly Thr Ala Glu Cys Lys Asp Lys Ser Leu Pro Asp Tyr Ser
            900                 905                 910

Cys Lys Val Phe Thr Gly Val Tyr Pro Phe Met Trp Gly Gly Ala Tyr
        915                 920                 925

Cys Phe Cys Asp Ala Glu Asn Thr Gln Leu Ser Glu Ala His Val Glu
    930                 935                 940

Lys Ser Glu Ser Cys Lys Thr Glu Phe Ala Ser Ala Tyr Arg Ala His
945                 950                 955                 960

Thr Ala Ser Ala Ser Ala Lys Leu Arg Val Leu Tyr Gln Gly Asn Asn
                965                 970                 975

Ile Thr Val Ala Ala Tyr Ala Asn Gly Asp His Ala Val Thr Val Lys
            980                 985                 990

Asp Ala Lys Phe Val Val Gly Pro  Met Ser Ser Ala Trp  Thr Pro Phe
        995                 1000                 1005

Asp Asn  Lys Ile Val Val Tyr  Lys Gly Asp Val Tyr  Asn Met Asp
    1010                 1015                 1020

Tyr Pro  Pro Phe Gly Ala Gly  Arg Pro Gly Gln Phe  Gly Asp Ile
    1025                 1030                 1035

Gln Ser  Arg Thr Pro Glu Ser  Lys Asp Val Tyr Ala  Asn Thr Gln
    1040                 1045                 1050

Leu Val  Leu Gln Arg Pro Ala  Ala Gly Thr Val His  Val Pro Tyr
    1055                 1060                 1065

Ser Gln  Ala Pro Ser Gly Phe  Lys Tyr Trp Leu Lys  Glu Arg Gly
    1070                 1075                 1080

Ala Ser  Leu Gln His Thr Ala  Pro Phe Gly Cys Gln  Ile Ala Thr
    1085                 1090                 1095

Asn Pro  Val Arg Ala Val Asn  Cys Ala Val Gly Asn  Ile Pro Ile
    1100                 1105                 1110

Ser Ile  Asp Ile Pro Asp Ala  Ala Phe Thr Arg Val  Val Asp Ala
    1115                 1120                 1125

Pro Ser  Val Thr Asp Met Ser  Cys Glu Val Pro Ala  Cys Thr His
    1130                 1135                 1140

Ser Ser  Asp Phe Gly Gly Val  Ala Ile Ile Lys Tyr  Thr Ala Ser
    1145                 1150                 1155

Lys Lys  Gly Lys Cys Ala Val  His Ser Met Thr Asn  Ala Val Thr
    1160                 1165                 1170

Ile Arg  Glu Ala Asp Val Glu  Val Glu Gly Asn Ser  Gln Leu Gln
    1175                 1180                 1185

Ile Ser  Phe Ser Thr Ala Leu  Ala Ser Ala Glu Phe  Arg Val Gln
    1190                 1195                 1200

Val Cys  Ser Thr Gln Val His  Cys Ala Ala Ala Cys  His Pro Pro
    1205                 1210                 1215

Lys Asp  His Ile Val Asn Tyr  Pro Ala Ser His Thr  Thr Leu Gly
```

```
    1220                1225                1230

Val Gln  Asp Ile Ser Thr Thr  Ala Met Ser Trp Val  Gln Lys Ile
    1235                1240                1245

Thr Gly  Gly Val Gly Leu Ile  Val Ala Val Ala Ala  Leu Ile Leu
    1250                1255                1260

Ile Val  Val Leu Cys Val Ser  Phe Ser Arg His
    1265                1270


<210> SEQ ID NO 49
<211> LENGTH: 3822
<212> TYPE: DNA
<213> ORGANISM: Artificial Sequence
<220> FEATURE:
<223> OTHER INFORMATION: Synthetic polynucleotide

<400> SEQUENCE: 49

atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

caccgccaaa gacgcagtac taaggacaat tttaatgtct ataaagccac aagaccatat   1020

ctagctcatt gtcctgactg cggagaaggg cattcgtgcc acagccctat cgcattggag   1080

cgcatcagaa atgaagcaac ggacggaacg ctgaaaatcc aggtctcttt gcagatcggg   1140

ataaagacag atgacagcca cgattggacc aagctgcgct atatggatag ccatacgcca   1200

gcggacgcgg agcgagccgg attgcttgta aggacttcag caccgtgcac gatcaccggg   1260

accatgggac actttattct cgcccgatgc ccgaaaggag agacgctgac agtgggattt   1320

acggacagca gaaagatcag ccacacatgc acacacccgt tccatcatga accacctgtg   1380

ataggtaggg agaggttcca ctctcgacca caacatggta aagagttacc ttgcagcacg   1440

tacgtgcaga gcaccgctgc cactgctgag gagatagagg tgcatatgcc cccagatact   1500

cctgaccgca cgctgatgac gcagcagtct ggcaacgtga agatcacagt taatgggcag   1560

acggtgcggt acaagtgcaa ctgcggtggc tccggaggat acgactgtga accatctaat   1620

tcctcagaga aaaactcccc atctacacag tactgtaaca gcattggatc caacgaggga   1680

ctgacaacca cagacaaagt gatcaataac tgcaaaattg atcagtgcca tgctgcagtc   1740
```

```
actaatcaca agaattggca atacaactcc cctttagtcc cgcgcaacgc tgaactcggg   1800

gaccgtaaag gaaagatcca catcccattc ccattggcaa acgtgacttg cagagtgcca   1860

aaagcaagaa accctacagt aacttacgga aaaaaccaag tcaccatgct gctgtatcct   1920

gaccatccga cactcttgtc ttaccgtaac atgggacagg aaccaaatta ccacgaggag   1980

tgggtgacac acaagaagga ggttaccttg accgtgccta ctgagggtct ggaggtcact   2040

tggggcaaca acgaaccata caagtactgg ccgcagatgt ctacgaacgg tactgctcat   2100

ggtcacccac atgagataat cttgtactat tatgagctgt accccactat gactgtagtc   2160

attgtgtcgg tggcctcgtt cgtgcttctg tcgatggtgg gcacagcagt gggaatgtgt   2220

gtgtgcgcac ggcgcagatg cattacacca tatgaattaa caccaggagc cactgttccc   2280

ttcctgctca gcctgctatg ctgcgtcaga acgaccaagg cggccacata ttacgaggct   2340

gcggcatatc tatggaacga acagcagccc ctgttctggt tgcaggctct tatcccgctg   2400

gccgccttga tcgtcctgtg caactgtctg aaactcttgc catgctgctg taagaccctg   2460

gctttttag ccgtaatgag catcggtgcc cacactgtga gcgcgtacga acacgtaaca   2520

gtgatcccga acacggtggg agtaccgtat aagactcttg tcaacagacc gggttacagc   2580

cccatggtgt tggagatgga gctacaatca gtcaccttgg aaccaacact gtcacttgac   2640

tacatcacgt gcgagtacaa aactgtcatc cctccccgt acgtgaagtg ctgtggtaca   2700

gcagagtgca aggacaagag cctaccagac tacagctgca aggtctttac tggagtctac   2760

ccatttatgt ggggcggcgc ctactgcttt tgcgacgccg aaaatacgca attgagcgag   2820

gcacatgtag agaaatctga atcttgcaaa acagagtttg catcggccta cagagcccac   2880

accgcatcgg cgtcggcgaa gctccgcgtc ctttaccaag gaaacaacat taccgtagct   2940

gcctacgcta acggtgacca tgccgtcaca gtaaaggacg ccaagtttgt cgtgggccca   3000

atgtcctccg cctggacacc ttttgacaac aaaatcgtgg tgtacaaagg cgacgtctac   3060

aacatggact acccaccttt tggcgcagga agaccaggac aatttggtga cattcaaagt   3120

cgtacaccgg aaagtaaaga cgtttatgcc aacactcagt tggtactaca gaggccagca   3180

gcaggcacgg tacatgtacc atactctcag gcaccatctg gcttcaagta ttggctgaag   3240

gaacgaggag catcgctaca gcacacggca ccgttcggtt gccagattgc gacaaacccg   3300

gtaagagctg taaattgcgc tgtggggaac ataccaattt ccatcgacat accggatgcg   3360

gcctttacta gggttgtcga tgcaccctct gtaacggaca tgtcatgcga agtaccagcc   3420

tgcactcact cctccgactt tgggggcgtc gccatcatca aatacacagc tagcaagaaa   3480

ggtaaatgtg cagtacattc gatgaccaac gccgttacca ttcgagaagc cgacgtagaa   3540

gtagagggga actcccagct gcaaatatcc ttctcaacag ccctggcaag cgccgagttt   3600

cgcgtgcaag tgtgctccac acaagtacac tgcgcagccg catgccaccc tccaaaggac   3660

cacatagtca attacccagc atcacacacc acccttgggg tccaggatat atccacaacg   3720

gcaatgtctt gggtgcagaa gattacggga ggagtaggat taattgttgc tgttgctgcc   3780

ttaattttaa ttgtggtgct atgcgtgtcg tttagcaggc ac                      3822
```

```
<210> SEQ ID NO 50
<211> LENGTH: 1274
<212> TYPE: PRT
<213> ORGANISM: Artificial Sequence
<220> FEATURE:
<223> OTHER INFORMATION: Synthetic peptide

<400> SEQUENCE: 50
```

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415
```

```
Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Gly Gly Tyr Asp Cys Glu Pro Ser Asn Ser Ser Glu Lys
    530                 535                 540

Asn Ser Pro Ser Thr Gln Tyr Cys Asn Ser Ile Gly Ser Asn Glu Gly
545                 550                 555                 560

Leu Thr Thr Thr Asp Lys Val Ile Asn Asn Cys Lys Ile Asp Gln Cys
                565                 570                 575

His Ala Ala Val Thr Asn His Lys Asn Trp Gln Tyr Asn Ser Pro Leu
            580                 585                 590

Val Pro Arg Asn Ala Glu Leu Gly Asp Arg Lys Gly Lys Ile His Ile
        595                 600                 605

Pro Phe Pro Leu Ala Asn Val Thr Cys Arg Val Pro Lys Ala Arg Asn
    610                 615                 620

Pro Thr Val Thr Tyr Gly Lys Asn Gln Val Thr Met Leu Leu Tyr Pro
625                 630                 635                 640

Asp His Pro Thr Leu Leu Ser Tyr Arg Asn Met Gly Gln Glu Pro Asn
                645                 650                 655

Tyr His Glu Glu Trp Val Thr His Lys Lys Glu Val Thr Leu Thr Val
            660                 665                 670

Pro Thr Glu Gly Leu Glu Val Thr Trp Gly Asn Asn Glu Pro Tyr Lys
        675                 680                 685

Tyr Trp Pro Gln Met Ser Thr Asn Gly Thr Ala His Gly His Pro His
    690                 695                 700

Glu Ile Ile Leu Tyr Tyr Tyr Glu Leu Tyr Pro Thr Met Thr Val Val
705                 710                 715                 720

Ile Val Ser Val Ala Ser Phe Val Leu Leu Ser Met Val Gly Thr Ala
                725                 730                 735

Val Gly Met Cys Val Cys Ala Arg Arg Arg Cys Ile Thr Pro Tyr Glu
            740                 745                 750

Leu Thr Pro Gly Ala Thr Val Pro Phe Leu Leu Ser Leu Leu Cys Cys
        755                 760                 765

Val Arg Thr Thr Lys Ala Ala Thr Tyr Tyr Glu Ala Ala Ala Tyr Leu
    770                 775                 780

Trp Asn Glu Gln Gln Pro Leu Phe Trp Leu Gln Ala Leu Ile Pro Leu
785                 790                 795                 800

Ala Ala Leu Ile Val Leu Cys Asn Cys Leu Lys Leu Leu Pro Cys Cys
                805                 810                 815

Cys Lys Thr Leu Ala Phe Leu Ala Val Met Ser Ile Gly Ala His Thr
            820                 825                 830

Val Ser Ala Tyr Glu His Val Thr Val Ile Pro Asn Thr Val Gly Val
```

```
        835                 840                 845

Pro Tyr Lys Thr Leu Val Asn Arg Pro Gly Tyr Ser Pro Met Val Leu
    850                 855                 860

Glu Met Glu Leu Gln Ser Val Thr Leu Glu Pro Thr Leu Ser Leu Asp
865                 870                 875                 880

Tyr Ile Thr Cys Glu Tyr Lys Thr Val Ile Pro Ser Pro Tyr Val Lys
                885                 890                 895

Cys Cys Gly Thr Ala Glu Cys Lys Asp Lys Ser Leu Pro Asp Tyr Ser
            900                 905                 910

Cys Lys Val Phe Thr Gly Val Tyr Pro Phe Met Trp Gly Gly Ala Tyr
        915                 920                 925

Cys Phe Cys Asp Ala Glu Asn Thr Gln Leu Ser Glu Ala His Val Glu
    930                 935                 940

Lys Ser Glu Ser Cys Lys Thr Glu Phe Ala Ser Ala Tyr Arg Ala His
945                 950                 955                 960

Thr Ala Ser Ala Ser Ala Lys Leu Arg Val Leu Tyr Gln Gly Asn Asn
                965                 970                 975

Ile Thr Val Ala Ala Tyr Ala Asn Gly Asp His Ala Val Thr Val Lys
            980                 985                 990

Asp Ala Lys Phe Val Val Gly Pro  Met Ser Ser Ala Trp  Thr Pro Phe
        995                 1000                 1005

Asp Asn  Lys Ile Val Val Tyr  Lys Gly Asp Val Tyr  Asn Met Asp
    1010                 1015                 1020

Tyr Pro  Pro Phe Gly Ala Gly  Arg Pro Gly Gln Phe  Gly Asp Ile
    1025                 1030                 1035

Gln Ser  Arg Thr Pro Glu Ser  Lys Asp Val Tyr Ala  Asn Thr Gln
    1040                 1045                 1050

Leu Val  Leu Gln Arg Pro Ala  Ala Gly Thr Val His  Val Pro Tyr
    1055                 1060                 1065

Ser Gln  Ala Pro Ser Gly Phe  Lys Tyr Trp Leu Lys  Glu Arg Gly
    1070                 1075                 1080

Ala Ser  Leu Gln His Thr Ala  Pro Phe Gly Cys Gln  Ile Ala Thr
    1085                 1090                 1095

Asn Pro  Val Arg Ala Val Asn  Cys Ala Val Gly Asn  Ile Pro Ile
    1100                 1105                 1110

Ser Ile  Asp Ile Pro Asp Ala  Ala Phe Thr Arg Val  Val Asp Ala
    1115                 1120                 1125

Pro Ser  Val Thr Asp Met Ser  Cys Glu Val Pro Ala  Cys Thr His
    1130                 1135                 1140

Ser Ser  Asp Phe Gly Gly Val  Ala Ile Ile Lys Tyr  Thr Ala Ser
    1145                 1150                 1155

Lys Lys  Gly Lys Cys Ala Val  His Ser Met Thr Asn  Ala Val Thr
    1160                 1165                 1170

Ile Arg  Glu Ala Asp Val Glu  Val Glu Gly Asn Ser  Gln Leu Gln
    1175                 1180                 1185

Ile Ser  Phe Ser Thr Ala Leu  Ala Ser Ala Glu Phe  Arg Val Gln
    1190                 1195                 1200

Val Cys  Ser Thr Gln Val His  Cys Ala Ala Ala Cys  His Pro Pro
    1205                 1210                 1215

Lys Asp  His Ile Val Asn Tyr  Pro Ala Ser His Thr  Thr Leu Gly
    1220                 1225                 1230

Val Gln  Asp Ile Ser Thr Thr  Ala Met Ser Trp Val  Gln Lys Ile
    1235                 1240                 1245
```

-continued

```
Thr Gly  Gly Val Gly Leu Ile  Val Ala Val Ala Ala  Leu Ile Leu
    1250                 1255                 1260

Ile Val  Val Leu Cys Val Ser  Phe Ser Arg His
    1265                 1270


<210> SEQ ID NO 51
<211> LENGTH: 4
<212> TYPE: PRT
<213> ORGANISM: Artificial Sequence
<220> FEATURE:
<223> OTHER INFORMATION: Synthetic peptide

<400> SEQUENCE: 51

Ser Gly Ser Gly
1


<210> SEQ ID NO 52
<211> LENGTH: 5
<212> TYPE: PRT
<213> ORGANISM: Artificial Sequence
<220> FEATURE:
<223> OTHER INFORMATION: Synthetic peptide

<400> SEQUENCE: 52

Thr Arg Gly Gly Ser
1               5
```

VIRUS LIKE PARTICLE COMPOSITION

CROSS REFERENCE TO RELATED APPLICATIONS

This application claims the benefit of U.S. provisional Patent Application No. 61/599,746 filed on Feb. 16, 2012, the entire contents of which are incorporated by reference herein.

TECHNICAL FIELD

The present invention relates to a particle comprising a polypeptide and at least one antigen, and a composition comprising thereof.

BACKGROUND

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: GlaxoSmithKline's Engerix® (hepatitis B virus) and Cervarix® (human papillomavirus), and Merck and Co., Inc.'s Recombivax HB® (hepatitis B virus) and Gardasil® (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination (Expert Rev. Vaccines 9(10), 1149-1176, 2010).

Chikungunya virus (CHIKV) has infected millions of people in Africa, Europe and Asia since this alphavirus reemerged from Kenya in 2004. The severity of the disease and the spread of this epidemic virus present a serious public health threat in the absence of vaccines or antiviral therapies. It is reported that a VLP vaccine for epidemic Chikungunya virus protects non-human primates against infection (Nat Med. 2010 March; 16(3): 334-338). US patent publication No. 2012/0003266 discloses a virus-like particle (VLP) comprising one or more Chikungunya virus structural polypeptides which is useful for formulating a vaccine or antigenic composition for Chikungunya that induces immunity to an infection or at least one symptom thereof. WO2012/106356 discloses modified alphavirus or flavivirus virus-like particles (VLPs) and methods for enhancing production of modified VLPs for use in the prevention or treatment of alphavirus and flavivirus-mediated diseases. (these cited references are herein incorporated by reference).

SUMMARY OF THE INVENTION

In the first aspect, the present invention provides a particle which is capable of being self-assembled, comprising a polypeptide and at least one antigen, wherein said polypeptide comprises at least one first attachment site and said at least one antigen comprises at least one second attachment site, and wherein said polypeptide and said antigen are linked through said at least one first and said at least one second attachment site.

In the second aspect, the present invention provides a nucleic acid molecule comprising a nucleotide sequence that encodes a particle provided in the first aspect of the present invention.

In the third aspect, the present invention provides a composition comprising the particle provided in the first aspect of the present invention and/or the nucleic acid molecule provided in the second aspect of the present invention.

In the fourth aspect, the present invention provides a method of producing an antibody, comprising contacting the particle provided in the first aspect of the present invention and/or the nucleic acid molecule provided in the second aspect of the present invention to a mammal.

In the fifth aspect, the present invention provides a method of immunomodulation, a method of treating an autoimmune disease, a method of inducing and/or enhancing immune response against an antigen in a mammal, and a method of treating cancer comprising administering the composition provided in the third aspect of the present invention to a mammal.

In sixth aspect, the present invention provides a method of passive immunization, comprising administering the antibody provided in the fourth aspect of the present invention to a mammal.

In seventh aspect, the present invention provides a method of presenting an antigen on macrophage, comprising contacting the particle provided in the first aspect of the present invention and/or the nucleic acid molecule provided in the second aspect of the present invention to a mammal.

In eighth aspect, the present invention provides a method for producing the particle provided in the first aspect of the present invention, comprising preparing a gene comprising a nucleotide sequence encoding said particle; culturing a cell which is transfected with said gene to express said particle; and recovering said particle.

BRIEF DESCRIPTION OF THE DRAWINGS

FIG. 1 shows modification of TNF alpha sequence to be inserted into Venezuelan Equine Encephalitis virus (VEEV) structural polypeptide.

FIG. 2 shows results of Western Blot which indicates that TNF alpha conjugated VLP was expressed.

FIG. 6 shows VLP_VEEV VLP 518 vector.

FIG. 7 shows VLP_VEEV VLP 519 vector.

DETAILED DESCRIPTION OF THE INVENTION

Figure 3:
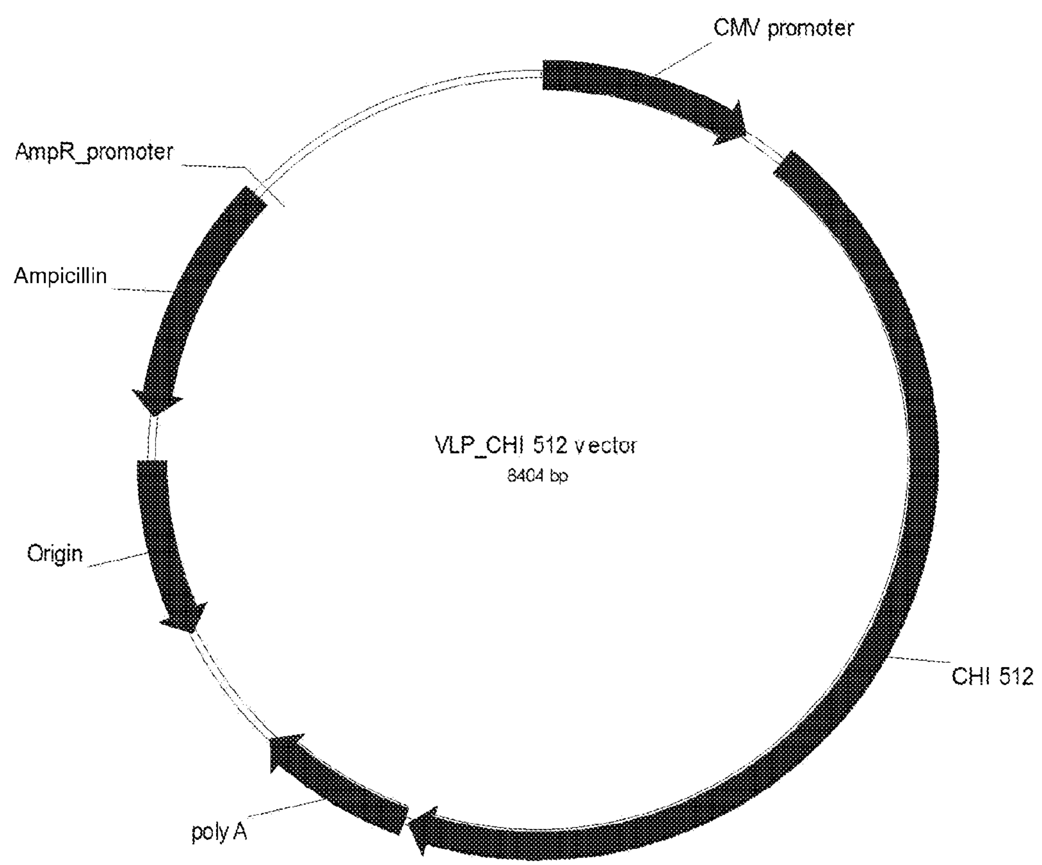
FIG. 3 shows VLP_CHI 512 vector.
Figure 4:
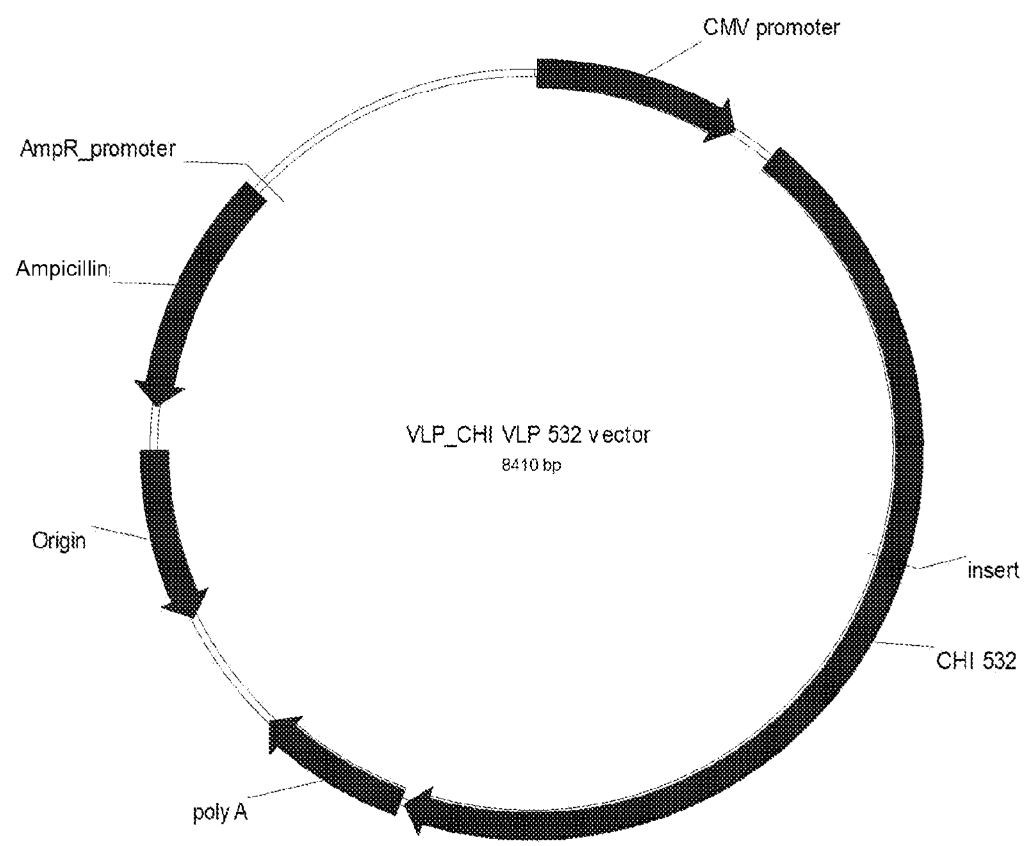
FIG. 4 shows VLP_CHI 532 vector.
Figure 5:
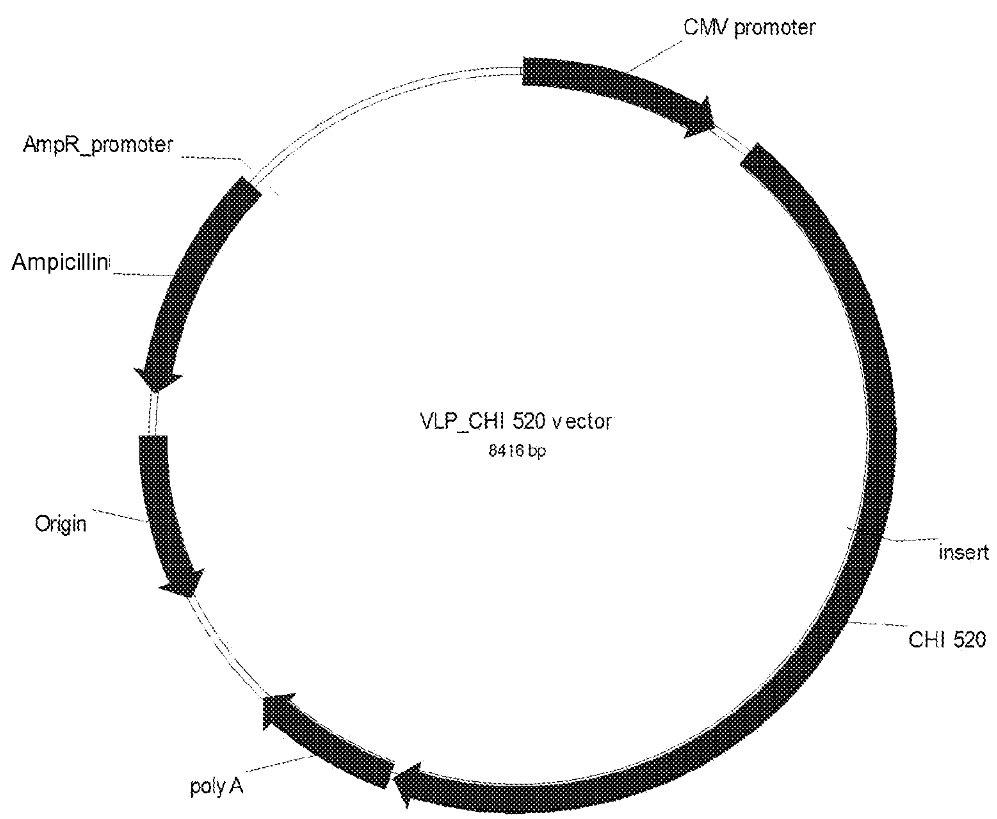
FIG. 5 shows VLP_CHI 520 vector.
Figure 8:
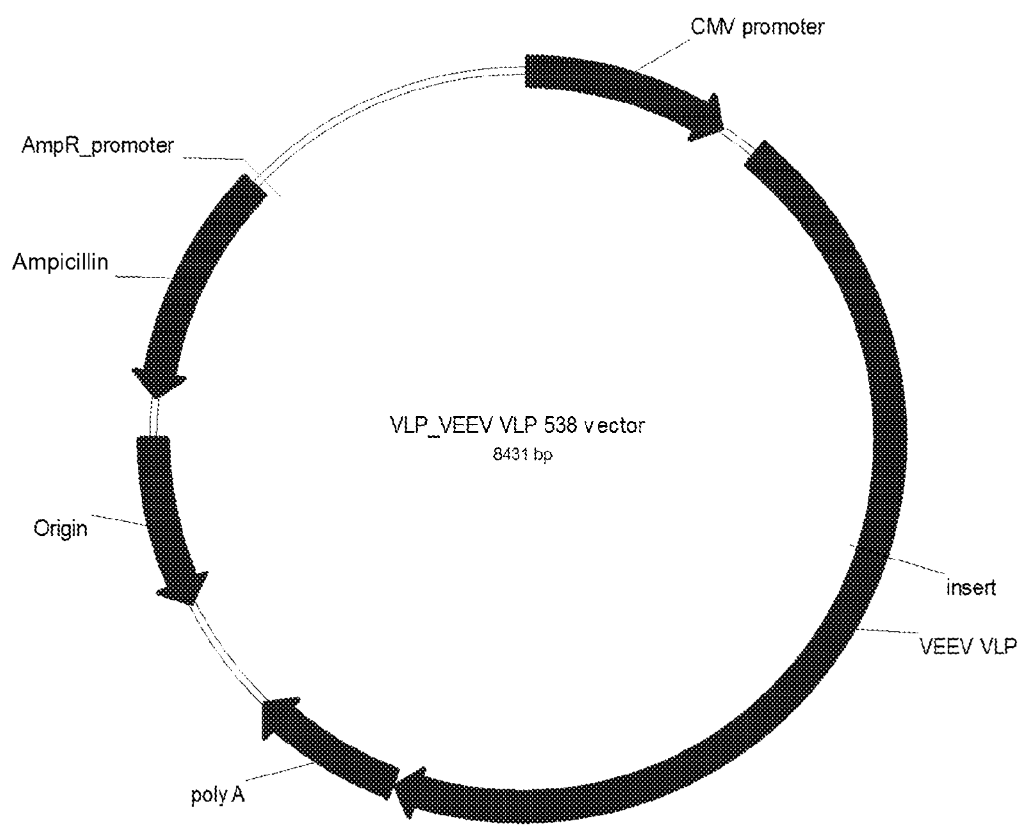
FIG. 8 shows VLP_VEEV VLP 538 vector.

(1) A Particle Comprising a Polypeptide and at Least One Antigen

In the first aspect, the present invention provides a particle which is capable of being self-assembled, comprising a polypeptide and at least one antigen, wherein said polypeptide comprises at least one first attachment site and said at least one antigen comprises at least one second attachment site, and wherein said polypeptide and said antigen are linked through said at least one first and said at least one second attachment site.

As used herein, "a particle which is capable of being self-assembled" refers to a particle formed by at least one constituent which is spontaneously assembled. The constituent may be a polypeptide or non-peptide chemical compound. In one embodiment, "a particle which is capable of being self-assembled" may be a particle comprising or consisting of at least one polypeptide. The at least one polypeptide consists of one or more kinds of peptide. In one embodiment, said particle has a diameter of at least 10 nm, for example, at least 20 nm, preferably at least 50 nm. In one embodiment, molecular weight of said particle is from 100 kDa to 100,000 kDa, preferably from 400 kDa to 30,000 kDa.

A polypeptide used for the present invention is not limited as long as it is spontaneously assembled. The polypeptide may be a virus structural polypeptide. Thus, the particle provided by the present invention may be a virus like particle.

A virus structural polypeptide may be a naturally occurring viral polypeptide or modified polypeptide thereof. In one embodiment, the modified polypeptide has at least 70%, 75%, 80%, 85%, 90%, 95% or 98% amino acid sequence identity to a naturally occurring viral structural polypeptide including capsid and envelope protein. In one embodiment, the modified polypeptide is a mutant where at most 10% of the amino acids are deleted, substituted, and/or added to a naturally occurring viral structural polypeptide including capsid and envelope protein.

In one embodiment, virus structural polypeptide used for the present invention consists of or comprises capsid and/or envelope protein or fragment thereof. For example, an envelope protein comprises at least one selected from the group consisting of E3, E2, 6K and E1. Virus structural polypeptide used for the present invention may be derived from Alphavirus or Flavivirus. Thus, the particle provided by the present invention may be a virus like particle derived from Alphavirus or Flavivirus. Examples of Alphavirus and Flavivirus include, but not limited to, Aura virus, Babanki virus, Barmah Forest virus (BFV), Bebaru virus, Cabassou virus, Chikungunya virus (CHIKV), Eastern equine encephalitis virus (EEEV), Eilat virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus (RRV), Salmon pancreas disease virus, Semliki Forest virus, Sindbis virus, Southern elephant seal virus, Tonate virus, Trocara virus, Una virus, Venezuelan equine encephalitis virus (VEEV), Western equine encephalitis virus (WEEV), Whataroa virus, West Nile virus, dengue virus, tick-borne encephalitis virus and yellow fever virus.

As used herein, the term "antigen" refers to a molecule capable of being bound by an antibody or a T cell receptor (TCR) if presented by MHC molecules. The term "antigen", as used herein, also encompasses T-cell epitopes. A T-cell epitope is recognized by a T-cell receptor in the context of a MHC class I, present on all cells of the body except erythrocytes, or class II, present on immune cells and in particular antigen presenting cells. This recognition event leads to activation of T-cells and subsequent effector mechanisms such as proliferation of the T-cells, cytokine secretion, perforin secretion etc. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a TH cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens. Antigens, as used herein, include but are not limited to allergens, self antigens, haptens, cancer antigens (i.e. tumor antigens) and infectious disease antigens as well as small organic molecules such as drugs of abuse (like nicotine) and fragments and derivatives thereof. Furthermore, antigens used for the present invention can be peptides, proteins, domains, carbohydrates, alkaloids, lipids or small molecules such as, for example, steroid hormones and fragments and derivatives thereof, autoantibody and cytokine itself.

Examples of cytokines include, but are not limited to, interleukin (IL) including over 30 type such as IL-1$\alpha$, IL-1$\beta$, IL-2, -3, -4, -5, -6, -7, -8, -9, -10, -11 to -37; interferon (IFN) such as IFN-$\alpha$, IFN-$\beta$ and IFN-$\gamma$; tumor necrosis factor (TNF) such as TNF-$\alpha$ and TNF-$\beta$; transforming growth factor (TGF) such as TGF-$\alpha$ and TGF-$\beta$; colony stimulating factor (CSF) such as granulocyte-colony-stimulating factor (G-CSF), granulocyte-macrophage-colony-stimulating factor (GM-CSF), macrophage-colony Stimulating factor (M-CSF), erythropoietin (EPO), stem cell factor (SCF) and monocyte chemotactic and activating factor (MCAF); growth factor (GF) such as epidermal growth factor (EGF), fibroblast growth factor (FGF), insulin like growth factor (IGF), nerve growth factor (NGF), Brain-derived neurotrophic factor (BDNF), platelet derived growth factor (PDGF), vascular endothelial growth factor (VEGF), hepatocyte growth factor (HGF), keratinocyte growth factor (KGF), thrombopoietin (TPO), and bone morphogenic protein (BMP); and other polypeptide factors including LIF, kit ligand (KL), MPO (Myeloperoxidase) and CRP (C-reactive protein); COX (Cyclooxygenase) such as COX-1, COX-2 and COX-3, NOS (Nitric oxide synthase) such as NOS-1, NOS-2 and NOS-3; and so on.

Cytokines also includes chemokines which are cytokines that induce chemotaxis. There are two major classes of chemokines, CXC and CC. The CXC chemokines, such as neutrophil-activating protein-2 (NAP-2) and melanoma growth stimulatory activity protein (MGSA) are chemotactic primarily for neutrophils and T lymphocytes, whereas the CC chemokines, such as RANTES, Macrophage inflammatory protein (MIP) including MIP-1$\alpha$ and MIP-1$\beta$, keratinocyte-derived chemokine (KC), the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, neutrophils, dendritic cells, and basophils. There also exist the chemokines lymphotactin-1, lymphotactin-2 (both C chemokines), and fractalkine (a CX3C chemokine) that do not fall into either of the major chemokine subfamilies.

As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant contains one or more epitopes.

As used herein, the term “antibody” refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, “human” antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

Antigen may be a substance (e.g. protein) which is not derived from virus (e.g. Chikungunya virus, Venezuelan equine encephalitis virus).

In one embodiment, antigen which is used for the present invention is at least one target or a polypeptide therefrom as listed in Table 1.

TABLE 1

| Target | Use |
|---|---|
| GD2 | neuroblastoma |
| CA-125 (imitation) | ovarian cancer |
| CD41 (integrin alpha-IIb) | platelet aggregation inhibitor |
| TNF-α | rheumatoid arthritis etc. |
| EpCAM | prostate and breast cancer |
| TNF-α | sepsis |
| CD20 | lymphoma |
| VEGFR2 | cancer |
| IL-6 | rheumatoid arthritis |
| CD52 | CLL, CTCL |
| CEA | colorectal cancer |
| TAG-72 | non-small cell lung carcinoma |
| HLA-DR | hematological cancers |
| CEA | gastrointestinal cancers |
| L-selectin (CD62L) | severely injured patients |
| IL-6 receptor | rheumatoid arthritis |
| Rhesus factor | hemolytic disease of the newborn |
| beta amyloid | Alzheimer’s disease |
| CD25 (α chain of IL-2 receptor) | prevention of organ transplant rejections |
| phosphatidylserine | cancer, viral infections |
| CD22 | non-Hodgkin’s lymphoma |
| BAFF | non-Hodgkin lymphoma etc. |
| CD125 | asthma |
| CCL11 (eotaxin-1) | severe allergic disorders |
| CEA-related antigen | inflammatory lesions and metastases |
| VEGF-A | metastatic cancer |
| fibrin II, beta chain | thromboembolism |
| CD44 v6 | squamous cell carcinoma |
| CD19 | cancer |
| CD30 (TNFRSF8) | hematologic cancers |
| IL-12, IL-23 | psoriasis, rheumatoid arthritis, inflammatory bowel diseases, multiple sclerosis |
| IL-1 | rheumatoid arthritis |
| mucin CanAg | colorectal cancer etc. |
| prostatic carcinoma cells | prostate cancer |
| EpCAM, CD3 | ovarian cancer, malignant ascites, gastric cancer |
| TAG-72 | tumor detection |
| CD4 | prevention of organ transplant rejections, treatment of autoimmune diseases |
| TNF-α | Crohn’s disease |
| EGFR | metastatic colorectal cancer and head and neck cancer |
| EpCAM | ovarian cancer and other solid tumors |
| IGF-1 receptor | solid tumors |
| CD4 | rheumatoid arthritis |
| MUC1 | pancreatic cancer |
| TRAIL-R2 | cancer |
| Influenza A hemagglutinin | infectious disease/influenza A |
| CD40 | hematologic cancers |
| CD25 (α chain of IL-2 receptor) | prevention of organ transplant rejections |
| RANKL | osteoporosis, bone metastases etc. |
| B-lymphoma cell | lymphoma |
| GD3 ganglioside | malignant melanoma |
| C5 | peroxysmal nocturnal hemoglobinuria |
| endotoxin | sepsis caused by Gram-negative bacteria |
| EpCAM | colorectal carcinoma |
| LFA-1 (CD11a) | psoriasis (blocks T-cell migration) |
| Hsp90 | invasive Candida infection |
| SLAMF7 | multiple meyloma |
| CD22 | cancer, SLE |
| ITGB2 (CD18) | heart attack, stroke, traumatic shock |
| HER2/neu. CD3 | breast cancer etc. |

TABLE 1-continued

| Target | Use |
|---|---|
| integrin αvβ3 | melanoma, prostate cancer, ovarian cancer etc. |
| hepatitis B surface antigen | hepatitis B |
| CD15 | appendicitis |
| folate receptor 1 | ovarian cancer |
| respiratory syncytial virus | respiratory syncytial virus infection |
| IL-22 | rheumatoid arthritis, psoriasis |
| IGF-1 receptor | adrenocortical carcinoma, non-small cell lung carcinoma etc. |
| IFN-γ | Crohn's disease etc. |
| rabies virus glycoprotein | rabies (prophylaxis) |
| TGF-β | idiopathic pulmonary fibrosis, focal segmental glomerulosclerosis, cancer |
| CD80 | B-cell lymphoma |
| beta amyloid | Alzheimer's disease |
| CD147 (benign) | graft versus host disease |
| CD33 | acute myelogenous leukemia |
| carbonic anhydrase 9 (CA-IX) | clear cell renal cell carcinoma |
| GPNMB | melanoma, breast cancer |
| TNF-α | rheumatoid arthritis, psoriatic arthritis, ankylosing spondylitis |
| CD23 (IgE receptor) | allergic asthma |
| CD4 | HIV infection |
| CD20 | non-Hodgkin's lymphoma |
| CA-125 | ovarian cancer |
| cardiac myosin | cardiac imaging |
| TNF-α | rheumatoid arthritis, ankylosing spondylitis, psoriatic arthritis, psoriasis, Crohn's disease, ulcerative colitis |
| CD51 | solid tumors (prostate cancer, melanoma) |
| CD25 (α chain of IL-2 receptor) | graft versus host disease |
| CD22 | cancer |
| CD152 | melanoma |
| CD30 (TNFRSF8) | Hodgkin's lymphoma |
| CD4 | chronic asthma |
| CEA | colorectal cancer |
| IL-13 | asthma |
| NCA-90 (granulocyte antigen) | diagnostic agent |
| TGF beta 2 | reduction of scarring after glaucoma surgery |
| TRAIL-R2 | cancer |
| hepatitis B surface antigen | hepatitis B |
| CD33 | cancer |
| CD56 | cancer |
| CD40 | multiple myeloma, non-Hodgkin's lymphoma, Hodgkin's lymphoma |
| CD23 (IgE receptor) | chronic lymphocytic leukemia |
| TRAIL-R1 | cancer |
| EGFR | colorectal, lung and stomach cancer |
| IL-5 | asthma and white blood cell diseases |
| TGF beta 1 | systemic scleroderma |
| CD74 | multiple myeloma and other hematological malignancies |
| CD3 ganglioside | small cell lung carcinoma |
| repiratory syncytial virus | respiratory syncytial virus (prevention) |
| CD3 | prevention of organ transplant rejections |
| C242 antigen | colorectal cancer |
| ST4 | non-small cell lung carcinoma, renal cell carcinoma |
| integrin α4 | multiple sclerosis, Crohn's disease |
| endotoxin | sepsis |
| EGFR | non-small cell lung carcinoma |
| EGFR | squamous cell carcinoma, head and neck cancer, nasopharyngeal cancer, glioma |
| CD20 | rheumatoiod arthritis, lupus arythematosus etc. |
| LFA-1 (CD11a) | prevention of organ transplant rejections, immunological diseases |
| CD20 | chronic lymphocytic leukemia etc. |
| PDGF-R α | cancer |
| IgE, Fc region | allergic asthma |
| EpCAM | cancer |
| CA-125 | ovarian cancer |
| CD3 | diabetes mellitus type I |
| lipotoichoic acid | sepsis (*Staphylococcus*) |
| respiratory syncytial virus | respiratory syncytial virus (prevention) |
| EGFR | colorectal cancer |
| respiratory syncytial virus | respiratory syncytial virus (prevention) |
| EGFR | colorectal cancer |
| *Pseudomonas aeruginosa* | *Pseudomonas aeruginosa* infection |
| IL-4 | asthma |
| MUC1 | cancer |
| HER2/neu | cancer |
| C5 | reduction of side effects of cardiac surgery |
| adenocarcinoma antigen | adenocarcinoma |
| CD4 | Crohn's disease, multiple sclerosis |
| vimentin | brain cancer |
| CCR5 | HIV infection |
| rabies virus glycoprotein | rabies (prophylaxis) |
| VEGFR2 | solid tumors |

TABLE 1-continued

| Target | Use |
| --- | --- |
| VEGF-A | macular degeneration (wet form) |
| anthrax toxin protective antigen | anthrax (prophylaxis and treatment) |
| cytomegalovirus glycoprotein B | cytomegalovirus infection |
| IL-5 | inflammations of the airways, skin and gastrointestinal tract |
| HGF | solid tumors |
| CD20 | lymphomas, leukemias, some autoimmune disorders |
| IGF-1 receptor | cancer |
| IFN-α | systemic lupus erythematosus |
| CD11, CD18 | haemorrhagic shock etc. |
| CD154 (CD40L) | rheumatic diseases |
| TAG-72 | cancer |
| cytomegalovirus | cytomegalovirus infection |
| FAP | cancer |
| IFN-α | SLE, dermatomyositis, polymyositis |
| CD2 | psoriasis, gragt-versus-host disease (prevention) |
| beta amyloid | Alzheimer's disease |
| sphingosine-1-phosphate | choroidal and retinal neovascularization |
| myostatin | muscular dystrophy |
| NCA-90 (granulocyte antigen) | osteomyelitis |
| alpha-fetoprotein | cancer |
| integrin αIIbβ3 | percutaneous coronary intervention |
| IgE | allergic reaction |
| NGF | pain |
| CD19 | cancer |
| clumping factor A | *Staphylococcus aureus* infection |
| tenascin C | cancer |
| CD3 | diabetes mellitus type 1 |
| CD28 | chronic lymphocytic leukemia, rheumatoid arthritis |
| CTLA-4 | cancer |
| TRAIL-R2 | cancer |
| IL-13 | Hodgkin's lymphoma |
| IL-6 receptor | rheumatoid arthritis |
| CD154 (CD40L) | rheumatoid arthritis, lupus nephritis etc |
| CD20 | follicular lymphoma |
| HER2/neu | breast cancer |
| CTLA-4 | cancer |
| EpCAM | cancer |
| hepatitis B virus | chronic hepatitis B |
| Escherichia coli | diarrhoea caused by *E. coli* |
| IL-12, IL-23 | multiple sclerosis, psoriasis, psoriatic arthritis |
| integrin α4β7 | Crohn's disease, ulcerative colitis |
| CD20 | non-Hodgkin's lymphoma |
| AOC3 (VAP-1) | inflammation |
| CD3 | Crohn's disease, ulcerative colitis |
| integrin α5β1 | solid tumors |
| tumor antigen CTAA1688 | colorectal tumors |
| EGFR | squamous cell carcinoma of the head and neck |
| CD4 | rheumatoid arthritis, psoriasis, T-cell lymphoma |
| CD5 | systemic lupus erythematosus, graft-versus-host disease |

In one embodiment, antigen which is used for the present invention is at least one protein or a polypeptide therefrom selected from the group consisting of CTLA-4, PD-1, TIM-3, BTLA, VISTA, LAG-3, CD28, OX40, GITR, CD137, CD27 and HVEM. CTLA-4, PD-1, TIM-3, BTLA, VISTA and LAG-3 are inhibitory receptors for T-cell stimulation, and CD28, OX40, GITR, CD137, CD27 and HVEM are activating receptors for T-cell stimulation (see Mellman et al., Nature 480, 480-489 (2011)).

The antigen used for the present invention can be modified polypeptide derived from a naturally occurring protein. The modified polypeptide may be a fragment of the naturally occurring protein. In one embodiment, the modified polypeptide has at least 70%, 75%, 80%, 85%, 90%, 95% or 98% amino acid sequence identity to a polypeptide derived from a naturally occurring protein. In one embodiment, the modified polypeptide derived is a mutant where at most 10% of the amino acids are deleted, substituted, and/or added based on a polypeptide derived from naturally occurring protein.

In the particle as provided by the present invention, a polypeptide and an antigen may be linked through at least one first attachment site which is present in the polypeptide and at least one second attachment site which is present in the antigen.

As used herein, each of "a first attachment site" and "a second attachment site" refers to a site where more than one substance is linked each other.

In one embodiment, the polypeptide and the antigen are directly fused. Alternatively, one or two linkers may intervene between N-terminal residue of the antigen and the polypeptide and/or between C-terminal residue of the antigen and the polypeptide.

The antigen or the polypeptide can be truncated and replaced by short linkers. In some embodiments, the antigen or the polypeptide include one or more peptide linkers. Typically, a linker consists of from 2 to 25 amino acids. Usually, it is from 2 to 15 amino acids in length, although in certain circumstances, it can be only one, such as a single glycine residue.

In one embodiment, a nucleic acid molecule, in which polynucleotide encoding the polypeptide is genetically fused with polynucleotide encoding the antigen, is expressed in a host cell so that the first attachment site and the second attachment site are linked through a peptide bond. In this case, the polypeptide and the antigen are linked through a peptide bond. Relating to this embodiment, the first attachment site and/or the second attachment site may be genetically modified from the original polypeptide or antigen. For example, the first attachment site is modified from the polypeptide so that through a linker peptide including SG, GS, SGG, GGS and SGSG, the polypeptide is conjugated with the antigen.

When the polypeptide are chemically conjugated with the antigen, the first attachment site and the second attachment site may be linked through a chemical cross-linker which is a chemical compound.

Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

In one embodiment, the particle provided by the present invention comprises a polypeptide linked to an antigen, wherein spatial distance between the N-terminal residue and C-terminal residue of the antigen is 30 Å or less when the distance is determined in a crystal of the antigen or a naturally occurring protein containing the antigen or modified protein therefrom.

The antigen used for the present invention can be designed by a person skilled in the art. For example, the antigen used for the present invention may be a naturally occurring protein or a fragment thereof. Alternatively, the antigen used for the present invention may be a protein modified from a naturally occurring protein or a fragment thereof. A person skilled in the art can design the antigen so that spatial distance between the N-terminal residue and C-terminal residue of the antigen is 30 Å or less when the distance is determined in a crystal of the antigen or a naturally occurring protein containing the antigen or modified protein therefrom. For example, the antigen used for the particle provided by the present invention can be designed using a free software including PyMOL (e.g. PyMOL v0.99: http:/www.pymol.org). In one embodiment, the spatial distance between the N-terminal residue and C-terminal residue of the antigen is (angstrom) or less, 20 Å or less, or 10 Å or less (e.g. from 5 Å to 15 Å, from 5 Å to 12 Å, from 5 Å to 11 Å, from 5 to 10 from 5 Å to 8 from 8 Å to 15 from 8 Å to 13 Å, from 8 Å to 12 Å, from 8 Å to 11 Å, from 9 Å to 12 Å, from 9 Å to 11 Å, from 9 Å to 10 Å or from 10 Å to 11 Å).

Chikungunya Virus Like Particle or a Venezuelan Equine Encephalitis Virus Like Particle In one embodiment, the present invention provides a Chikungunya virus like particle or a Venezuelan equine encephalitis virus like particle comprising a Chikungunya or Venezuelan equine encephalitis virus structural polypeptide and at least one antigen, wherein said Chikungunya virus structural polypeptide or said Venezuelan equine encephalitis virus structural polypeptide comprises at least one first attachment site and said at least one antigen comprises at least one second attachment site, and wherein said Chikungunya or Venezuelan equine encephalitis virus structural polypeptide and said at least one antigen are linked through said at least one first and said at least one second attachment site.

In one embodiment, a spatial distance between the N-terminal residue and C-terminal residue of the antigen may be 30 Å or less; 25 Å or less; 20 Å or less; 15 Å or less; 14 Å or less; 13 Å or less; 12 Å or less; 11 Å or less; 10 Å or less; 9 Å or less; or 8 Å or less (e.g. from 5 Å to 15 Å, from 5 Å to 12 Å, from 5 Å to 11 Å, from 5 Å to 10 Å, from 5 Å to 8 Å, from 8 Å to 15 Å, from 8 Å to 13 Å, from 8 Å to 12 Å, from 8 Å to 11 Å, from 9 Å to 12 Å, from 9 Å to 11 Å, from 9 Å to 11 Å or from 10 Å to 11 Å) when the distance is determined in a crystal of the antigen or a naturally occurring protein containing the antigen or modified protein therefrom.

In one embodiment, the antigen is linked to the Chikungunya or Venezuelan equine encephalitis virus structural polypeptide by way of chemical cross-linking or as a fusion protein produced by way of genetic engineering.

A Chikungunya or Venezuelan equine encephalitis virus structural polypeptide used in the present invention may comprise a Chikungunya or Venezuelan equine encephalitis virus envelope protein and/or a capsid.

Examples of Chikungunya virus include, but are not limited to, strains of 37997 and LR2006 OPY-1.

Examples of Venezuelan equine encephalitis virus include, but are not limited to, TC-83.

Chikungunya or Venezuelan equine encephalitis virus structural polypeptide used in the present invention may naturally occurring virus structural polypeptide or modified polypeptide thereof. The modified polypeptide may be a fragment of the naturally occurring virus structural polypeptide. In one embodiment, the modified polypeptide has at least 70%, 75%, 80%, 85%, 90%, 95% or 98% amino acid sequence identity to a naturally occurring viral capsid and/or envelope protein. In one embodiment, the modified polypeptide is a mutant where at most 10% of the amino acids are deleted, substituted, and/or added based on a naturally occurring viral capsid and/or envelope protein. For example, K64A or K64N mutation may be introduced into a capsid of Venezuelan equine encephalitis virus structural polypeptide used in the present invention.

Chikungunya or Venezuelan equine encephalitis virus envelope protein may comprise at least one selected from the group consisting of E3, E2, 6K and E1.

Examples of Chikungunya virus structural polypeptide include, but are not limited to, E3-E2-6K-E1 of Chikungunya virus Strain 37997, Capsid-E3-E2-6K-E1 of Chikungunya virus Strain 37997, E3-E2-6K-E1 of Chikungunya virus Strain LR2006 OPY-1 and Capsid-E3-E2-6K-E1 of Chikungunya virus LR2006 OPY-1.

Examples of Venezuelan equine encephalitis virus structural polypeptide include, but are not limited to, E3-E2-6K-E1 of Venezuelan equine encephalitis virus Strain TC-83 and Capsid-E3-E2-6K-E1 of Venezuelan equine encephalitis virus Strain TC-83.

An exemplary Chikungunya virus structural polypeptide sequence is provided at Genbank Accession No. ABX40006.1, which is described below (SEQ ID No.:1):

```
MEFIPTQTFYNRRYQPRPWTPRPTIQVIRPRPRPQRQAGGLAQLISAVNK

LTMRAVPQQKPRRNRKNKKQKQKQQAPQNNTNQKKQPPKKKPAQKKKKPG

RRERMCMKIENDCIFEVKHEGKVTGYACLVGDKVMKPAHVKGTIDNADLA

KLAFKRSSKYDLECAQIPVHMKSDASKFTHEKPEGYYNWHHGAVQYSGGR

FTIPTGAGKPGDSGRPIFDNKGRVVAIVLGGANEGARTALSVVTWNKDIV

TKITPEGAEEWSLAIPVMCLLANTTFPCSQPPCTPCCYEKEPEETLRMLE

DNVMRPGYYQLLQASLTCSPHRQRRSTKDNFNVYKATRPYLAHCPDCGEG

HSCHSPVALERIRNEATDGTLKIQVSLQIGIKTDDSHDWTKLRYMDNHMP

ADAERAGLFVRTSAPCTITGTMGHFILAREPKGETLTVGFTDSRKISHSC

THPFHHDPPVIGREKFHSRPQHGKELPCSTYVQSTAATTEEIEVHMPPDT

PDRTLMSQQSGNVKITVNGQTVRYKCNCGGSNEGLTTTDKVINNCKVDQC
```

-continued

```
HAAVTNHKKWQYNSPLVPRNAELGDRKGKIHIPFPLANVTCRVPKARNPT
VTYGKNQVIMLLYPDHPTLLSYRNMGEPNYQEEWVMHKKEVVLTYPTEGL
EVTWGNNEPYKYWPQLSTNGTAHGHPHEIILYYYELYPTMTVVVVSVATF
ILLSMVGMAAGMCMCARRRCITPYELTPGATVPFLLSLICCIRTAKAATY
GEAAIYLWNEQQPLFWLGALIPLAALIVLCNCLRLLPCCCKTIAFLAVMS
VGAHTVSAYEHYTVIPNTVGYPYKTLVNRPGYSPMVLEMELLSVTLEPTL
SLDYITCEYKTVIPSPYVKCCGTAECKDKNLPDYSCKVFTGVYPFMWGGA
YCFCDAENTQLSEAHVEKSESCKTEFASAYRAHTASASAKLRVLYQGNNI
TVTAYANGDHAVTVKDAKFIVGPMSSAWTPFDNKIVVYKGDVYNMDYPPF
GAGRPGQFGDIGSRTPESKDVYANTQLVLQRPAVGTVHVPYSQAPSGFKY
WLKERGASLGHTAPFGCQIATNPVRAVNCAVGNMPISIDIPEAAFTRVVD
APSLTDMSCEVPACTHSSDFGGVAIIKYAASKKGKCAVHSMTNAVTIREA
EIEVEGNSQLQISFSTALASAEFRVQVCSTQVHCAAECHPPKDHIVNYPA
SHTTLGVQDISATAMSWVQKITGGVGLVVAVAALILIVVLCVSFSRH
```

Another exemplary Chikungunya virus structural polypeptide sequence is provided at Genbank Accession No. ABX40011.1, which is described below (SEQ ID No.:2):

```
MEFIPTQTFYNRRYQPRPWAPRPTIQVIRPRPRPQRQAGQLAQLISAVNK
LTMRAVPQQKPRRNRKNKKQRQKKGAPQNDPKQKKQPPQKKPAQKKKKPQ
RRERMCMKIENDCIFEVKHEGKVMGYACLVGDKVMKPAHVKGTIDNADLA
KLAFKRSSKYDLECAQIPVHMKSDASKFTHEKPEGYYNWHHGAVQYSGGR
FTIPTGAGKPGDSGRPIFDNKGRVVAIVLGGANEGARTALSVVTWNKDIV
TKITPEGAEEWSLALPVLCLLANTTFPCSQPPCTPCCYEKEPESTLRMLE
DNVMRPGYYQLLKASLTCSPHRQRRSTKDNFNVYKATRPYLAHCPDCGEG
HSCHSPIALERIRNEATDGTLKIQVSLQIGIKTDDSHDWTKLRYMDSHTP
ADAERAGLLVRTSAPCTITGTMGHFILARCPKGETLTVGFTDSRKISHTC
THPFHHEPPVIGRERFHSRPQHGKELPCSTYVQSTAATAEEIEVHMPPDT
PDRTLMTQQSGNVKITVNGQTYRYKCNCGGSNEGLTTTDKVINNCKIDQC
HAAVTNHKNWQYNSPLVPRNAELGDRKGKIHIPFPLANVTCRVPKARNPT
VTYGKNQVTMLLYPDHPTLLSYRNMGQEPNYHEEWVTHKKEVTLTVPTEG
LEVTWGNNEPYKYWPQMSTNGTAHGHPHEIILYYYELYPTMTVVIVSVAS
FYLLSMVGTAVGMCVCARRRCITPYELTPGATVPFLLSLLCCVRTTKAAT
YYEAAAYLWNEQQPLFWLQALIPLAALIVLCNCLKLLPCCCKTLAFLAVM
SIGAHTVSAYEHYTVIPNTVGVPYKTLVNRPGYSPMVLEMELQSVTLEPT
LSLDYITCEYKTVIPSPYVKCCGTAECKDKSLPDYSCKVFTGVYPFTWGG
AYCFCDAENTQLSEAHVEKSESCKTEFASAYRAHTASASAKLRVLYQGNN
ITVAAYANGDHAVTVKDAKFVVGPMSSAWTPFDNKIVVYKGDVYNMDYPP
FGAGRPGQFGDIQSRTPESKDVYANTQLVLQRPAAGTVHVPYSQAPSGFK
YWLKERGASLGHTAPFGCQIATNPVRAVNCAVGNIPISIDIPDAAFTRVV
DAPSVTDMSCEVPACTHSSDFGGVAIIKYTASKKGKCAVHSMTNAVTIRE
ADVEVEGNSQLQISFSTALASAEFRVQVCSTQVHCAAACHPPKDHIVNYP
```

-continued

```
ASHTTLGVQDISTTAMSWVQKITGGVGLIVAVAALILIVVLCVSFSRH.
```

An exemplary Venezuelan equine encephalitis virus structural polypeptide is provided at Genbank Accession No. L01443.1 (www.ncbi.nlm.nih.gov/nuccore/L01443.1), which is described below (SEQ ID No.:3):

```
MFPFQPMYPMQPMPYRNPFAAPRRPWFPRTDPFLAMQVQELTRSMANLTF
KQRRDAPPEGPSAAKPKKEASQKQKGGGQGKKKKNQGKKKAKTGPPNPKA
QNGNKKKTNKKPGKRQRMVMKLESDKTFPIMLEGKINGYACVVGGKLFRP
MHVEGKIDNDVLAALKTKKASKYDLEYADVPQNMRADTFKYTHEKPQGYY
SWHHGAVQYENGRFTVPKGVGAKGDSGRPILDNQGRVVAIVLGGVNEGSR
TALSVVMWNEKGVTVKYTPENCEQWSLVTTMCLLANVTFPCAQPPICYDR
KPAETLAMLSVNVDNPGYDELLEAAVKCPGRKRRSTEELFNEYKLTRPYM
ARCIRCAVGSCHSPIAIEAVKSDGHDGYVRLQTSSQYGLDSSGNIKGRTM
RYDMHGTIKEIPLHQVSLYTSRPCHIVDGHGYFLLARCPAGDSITMEFKK
DSVRHSCSVPYEVKFNPVGRELYTHPPEHGVEQACQVYAHDAQNRGAYVE
MHLPGSEVDSSLVSLSGSSVTVTPPDGTSALVECECGGTKISETINKTKQ
FSQCTKKEQCRAYRLQNDKWVYNSDKLPKAAGATLKGKLHVPFLLADGKC
TVPLAPEPMITFGFTSVSLKLHPKNPTYLITRQLADEPHYTHELISEPAV
RNFTVTEKGWEFVWGNHPPKRFWAQETAPGNPHGLPHEVITHYYHRYPMS
TILGLSICAAIATVSVAASTWLFCRSRVACLTPYRLTPNARIPFCLAVLC
CARTARAETTWESLDHLWNNNQQMFWIQLLIPLAALIVVTRILRCVCCVV
PFLVMAGAAGAGAYEHATTMPSQAGISYNTIVNRAGYAPLPISITPTKIK
LIPTVNLEYVTCHYKTGMDSPAIKCCGSQECTPTYRPDEQCKVFTGVYPF
MWGGAYCFCDTENTQVSKAYVMKSDDCLADHAEAYKAHTASVQAFLNITV
GEHSIVTTVYVNGETPVNFNGVKITAGPLSTAWTPFDRKIVQYAGEIYNY
DFPEYGAGQPGAFGDIQSRTVSSSDLYANTNLVLQRPKAGAIHVIPYTQA
PSGFEQWKKDKAPSLKFTAPFGCEIYTNPIRAENCAVGSIPLAFDIPDAL
FTRVSETPTLSAAECTLNECVYSSDFGGIATVKYSASKSGKCAVHVPSGT
ATLKEAAVELTEQGSATIHFSTANIHPEFRLQICTSYVTCKGDCHPPKDH
IVTHPQYHAQTFTAAVSKTAWTWLTSLLGGSAVIIIIGLVLATIVAMYVL
TNQKHN.
```

In one embodiment, a first attachment site comprises an amino group, preferably an amino group of a lysine residue. In one embodiment, the second attachment site comprises sulfhydryl group, preferably, a sulfhydryl group of a cysteine.

In one embodiment, a conjugation of more than two substances (e.g. antigen and Chikungunya or Venezuelan equine encephalitis virus structural polypeptide) through a first attachment site or a second attachment site is achieved using chemical cross linker. Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

According to the present invention, a Chikungunya or Venezuelan equine encephalitis virus like particle comprising a Chikungunya or Venezuelan equine encephalitis virus structural polypeptide and an antigen, wherein said Chikungunya or Venezuelan equine encephalitis virus structural polypeptide and said antigen are expressed as a fusion protein can be provided.

In one embodiment, the antigen can be fused with any site of the Chikungunya or Venezuelan equine encephalitis virus structural polypeptide. For example, the antigen may be directly or indirectly linked to N- or C-terminal of the Chikungunya or Venezuelan equine encephalitis virus structural polypeptide (e.g. capsid, E3, E2, 6K or E1), or the antigen may be inserted into Chikungunya or Venezuelan equine encephalitis virus structural protein (e.g. capsid, E3, E2, 6K, or E1).

In one embodiment, at least one antigen is inserted into E2 of Chikungunya or Venezuelan equine encephalitis virus structural protein. For example, regarding Chikungunya virus structural protein, at least one antigen is inserted between residues 519 and 520 of SEQ ID Nos. 1 or 2 (i.e. between G at 519-position and Q at 520-position of SEQ ID Nos. 1 or 2); between residues 530 and 531 of SEQ ID Nos. 1 or 2 (i.e. between G at 530-position and S at 531-position of SEQ ID Nos. 1 or 2); between residues 531 and 532 of SEQ ID Nos. 1 or 2 (i.e. between S at 531-position and N at 532-position of SEQ ID Nos. 1 or 2); between residues 529 and 530 of SEQ ID Nos. 1 or 2 (i.e. between G at 529-position and G at 530-position of SEQ ID Nos. 1 or 2); or between residues 510 and 511 of SEQ ID Nos. 1 or 2 (i.e. between S at 510-position and G at 511-position of SEQ ID Nos. 1 or 2); or between residues 511 and 512 of SEQ ID Nos. 1 or 2 (i.e. between G at 511-position and N at 512-position of SEQ ID Nos. 1 or 2); or between residues 509 and 510 of SEQ ID Nos. 1 or 2 (i.e. between Q at 509-position and S at 510-position of SEQ ID Nos. 1 or 2).

For example, regarding Venezuelan equine encephalitis virus structural protein, at least one antigen is inserted between residues 517 and 518 of SEQ ID No. 3 (i.e. between G at 517-position and S at 518-position of SEQ ID No. 3); between residues 518 and 519 of SEQ ID No. 3 (i.e. between S at 518-position and S at 519-position of SEQ ID No. 3); between residues 519 and 520 of SEQ ID No. 3 (i.e. between S at 519-position and V at 520-position of SEQ ID No. 3); between residues 515 and 516 of SEQ ID No. 3 (i.e. between L at 515-position and S at 516-position of SEQ ID No. 3); between residues 516 and 517 of SEQ ID No. 3 (i.e. between S at 516-position and G at 517-position of SEQ ID No. 3); between residues 536 and 537 of SEQ ID No. 3 (i.e. between C at 536-position and G at 537-position of SEQ ID No. 3); between residues 537 and 538 of SEQ ID No. 3 (i.e. between G at 537-position and G at 538-position of SEQ ID No. 3); between residues 538 and 539 of SEQ ID No. 3 (i.e. between G at 538-position and T at 539-position of SEQ ID No. 3).

The fusion protein may be expressed using a conventional technique in the art. A variety of expression systems can be used for the expression of the fusion protein. For example, the fusion protein can be expressed in 293 cells, Sf9 cells or *E. coli*.

In one embodiment, antigen is a substance (e.g. protein) which is not derived from Chikungunya or Venezuelan equine encephalitis virus. Antigen may be at least one selected from the group consisting of self antigens and cancer antigens. For example, antigen is a polypeptide derived from TNF-α, CD20 or CTLA4. Thus, examples of combinations of the polypeptide and the antigen used for the present invention include, but are not limited to, i) a polypeptide derived from Chikungunya virus (CHIKV) and a polypeptide derived from TNF-α;

ii) a polypeptide derived from Chikungunya virus (CHIKV) and a polypeptide derived from CD20;

iii) a polypeptide derived from Venezuelan equine encephalitis virus (VEEV) and a polypeptide derived from TNF-α; or iv) a polypeptide derived from Venezuelan equine encephalitis virus (VEEV) and a polypeptide derived from CD20 v) a polypeptide derived from Venezuelan equine encephalitis virus (VEEV) and a polypeptide derived from CTLA4.

A polypeptide derived from Chikungunya virus (CHIKV) or Venezuelan equine encephalitis virus (VEEV) may be a naturally occurring viral polypeptide or modified polypeptide thereof. In addition, a polypeptide derived from TNF-α, CD20 or CTLA4 may be a naturally occurring polypeptide or modified polypeptide of the naturally occurring polypeptide or a fragment of the naturally occurring polypeptide or the modified peptide. The modified polypeptide may be a fragment of the naturally occurring virus structural polypeptide.

In one embodiment, the modified polypeptide derived from TNF-α, CD20 or CTLA4 has at least 70%, 75%, 80%, 85%, 90%, 95% or 98% amino acid sequence identity to a naturally occurring polypeptide. In one embodiment, the modified peptide derived from TNF-α, CD20 or CTLA4 is a mutant where at most 10% of the amino acids are deleted, substituted, and/or added based on a naturally occurring polypeptide derived from TNF-α, CD20 or CTLA4.

When a polypeptide derived from a virus is conjugated with a polypeptide derived from an antigen, a linker peptide including SG, GS, SGG, GGS SGSG (SEQ ID NO: 51) and TRGGS (SEQ ID NO: 52) may be used. Examples of conjugation of the polypeptide derived from a virus (referred to as "PFV" below) with the polypeptide derived from the antigen (referred to as "PFA" below) include, but not limited to: PFV-SG-PFA-GS-PFV; PFV-SG-PFA-GGS-PFV; PFV-SSG-PFA-GS-PFV; PFV-SGG-PFA-GGS-PFV; PFV-SGSG (SEQ ID NO: 51)-PFA-GS-PFV; and PFA-SGG-PFA-TRGGS(SEQ ID NO: 52)-PFV.

In one embodiment, the present invention provides a virus like particle comprising i) a fusion protein of a polypeptide derived from Chikungunya virus (CHIKV) and a polypeptide derived from TNF-α, which consists of an amino acid sequence represented by SEQ ID No. 4;

ii) a fusion protein of a polypeptide derived from Chikungunya virus (CHIKV) and a polypeptide derived from CD20, which consists of an amino acid sequence represented by SEQ ID No. 5;

iii) a fusion protein of a polypeptide derived from Venezuelan equine encephalitis virus (VEEV) and a polypeptide derived from TNF-α, which consists of an amino acid sequence represented by SEQ ID No. 6; or iv) a fusion protein of a polypeptide derived from Venezuelan equine encephalitis virus (VEEV) and a polypeptide derived from CD20, which consists of an amino acid sequence represented by SEQ ID No. 7;

v) a fusion protein of a polypeptide derived from Venezuelan equine encephalitis virus (VEEV) and a polypeptide derived from CTLA4, which consists of an amino acid sequence represented by SEQ ID No. 8.

In one embodiment, the present invention provides a virus like particle comprising a fusion protein which is modified from the fusion protein having an amino acid sequence represented by any one of SEQ ID Nos. 4-8. The modified fusion protein may have at least 70%, 75%, 80%, 85%, 90%, 95% or 98% amino acid sequence identity to the fusion protein having an amino acid sequence represented by any one of SEQ ID Nos. 4-8. Also, the modified fusion protein may be a mutant where at most 10% of the amino acids are deleted, substituted, and/or added based on the fusion protein having an amino acid sequence represented by any one of SEQ ID Nos. 4-8.

(2) Nucleotide, Vector, Host Cell

In the second aspect, the present invention provides a nucleic acid molecule comprising a nucleotide sequence that encodes a particle as provided in the first aspect of the present invention.

In one embodiment, the present invention provides a nucleic acid molecule comprising a nucleotide sequence that encodes the Chikungunya or Venezuelan equine encephalitis virus like particle as described above.

Examples of the nucleotide sequence that encodes the Chikungunya or Venezuelan equine encephalitis virus like particle include, but are not limited to, a nucleotide sequence encoding E3-E2-6K-E1 of Chikungunya virus Strain 37997, a nucleotide sequence encoding Capsid-E3-E2-6K-E1 of Chikungunya virus Strain 37997, a nucleotide sequence encoding E3-E2-6K-E1 of Chikungunya virus Strain LR2006 OPY-1, a nucleotide sequence encoding Capsid-E3-E2-6K-E1 of Chikungunya virus LR2006 OPY-1, a nucleotide sequence encoding E3-E2-6K-E1 of Venezuelan equine encephalitis virus Strain TC-83 and a nucleotide sequence encoding Capsid-E3-E2-6K-E1 of Venezuelan equine encephalitis virus TC-83.

Regarding Chikungunya virus, an exemplary nucleotide sequence that encodes E3-E2-6K-E1 is described below (SEQ ID No.:9):

```
Atgagcctcgccctcccggtcttgtgcctgttggcaaacactacattcccctgctctcagccgccttgcacacctgctgctacgaaaaggaaccgg
aaagcaccttgcgcatgcttgaggacaacgtgatgagacccggatactaccagctactaaaagcatcgctgacttgctctccccaccgccaaagac
gcagtactaaggacaattttaatgtctataaagccacaagaccatatctagctcattgtcctgactgcggagaagggcattcgtgccacagccctatc
gcattggagcgcatcagaaatgaagcaacggacggaacgctgaaaatccaggtctctttgcagatcgggataaagacagatgacagccacgnttg
gaccaagctgcgctatatggatagccatacgccagcggacgcggagcgagccggattgcttgtaaggacttcagcaccgtgcacgatcaccggg
accatgggacactttattctcgcccgatgcccgaaaggagagacgctgacagtgggatttacggacagcagaaagatcagccacacatgcacaca
cccgttccatgaaccacctgtgataggtagggagaggttccactctcgaccacaacatggtaaagagttaccttgcagcacgtacgtgcagag
caccgctgccactgctgaggagatagaggtgcatatgcccccagatactcctgaccgcacgctgatgacgcagcagtctggcaacgtgaagatca
cagttaatgggcagacggtgcggtacaagtgcaactgcggtggctcaaacgagggactgacaaccacagacaaagtgatcaataactgcaaaatt
gatcagtgccatgctgcagtcactaacacaagaattggcaatacaactcccctttagtcccgcgcaacgctgaactcggggaccgtaaaggaaag
atccacatcccattcccattggcaaacgtgacttgcagagtgccaaaagcaagaaaccctacagtaacttacggaaaaaccaagtcaccatgctg
ctgtatcctgaccatccgacactcttgtcttaccgtaacatgggacaggaaccaaattaccacgaggagtgggtgacacacaagaaggaggttacct
tgaccgtgcctactgagggtctggaggtcacttggggcaacaacgaaccatacaagtactggccgcagatgtctgacgaacggtactgctcatggtc
acccacatgagataatcttgtactattatgagctgtaccccactatgactgtagtcattgtgtcggtggcctcgttcgtgcttctgtcgatggtgggcaca
gcagtgggaatgtgtgtgcgcacggcgcagatgcattacaccatatgaattaacaccaggagccactgttcccttcctgctcagcctgctatgctg
cgtcagaacgaccaaggcggccacatattacgaggctgcggcatatctatggaacgaacagcagcccctgttctggttgcaggctcttatcccgct
ggccgccttgatcgtcctgtgcaactgtctgaaactcttgccatgctgctgtaagaccctggctttttttagccgtaatgagcatcggtgcccacactgtg
agcgcgtacgaacacgtaacagtgatcccgaacacggtgggagtaccgtataagactcttgtcaacagaccgggttacagccccatggtgttgga
gatggagctacaatcagtcaccttggaaccaacactgtcacttgactacatcacgtgcgagtacaaaactgtcatcccctccccgtacgtgaagtgct
gtggtacagcagagtgcaaggacaagagcctaccagactacagctgcaaggtctttactggagtctacccatttatgtggggcggcgcctactgctt
ttgcgacgccgaaaatacgcaattgagcgaggcacatgtagagaaactcgaatcttgcaaaacagagtttgcatcggcctacagagcccacaccg
catcggcgtcggcgaagctccgcgtcctttaccaaggaaacaacattaccgtagctgcctacgctaacggtgaccatgccgtcacagtaaaggac
gccaagtttgtcgtgggcccaatgtcctccgcctggacaccttttgacaacaaaatcgtggtgtacaaaggcgacgtctacaacatggactacccac
cttttggcgcaggngaccaggncaatttggtgacattcaaagtcgtacaccggaaagtaaagacgtttatgccaacactcagttggtactacagag
gccagcagcaggcacggtacatgtaccatactctcaggcaccatctggcttcaagtattggctgaaggaacgaggagcatcgctacagcacacgg
caccgttcggttgccagattgcgacaaacccggtaagagctgtaaattgcgctgtggggaacataccaatttccatcgacataccggatgcggcctt
tactagggttgtcgatgcaccctctgtaacggacatgtcatgcgaagtaccagcctgcactcactcctccgactttgggggcgtcgccatcatcaaat
acacagctagcaagaaaggtaaatgtgcagtacattcgatgaccaacgccgttaccattcgagaagccgacgtagaagtagaggggaactccca
gctgcaaatatccttctcaacagccctggcaagcgccgagtttcgcgtgcaagtgtgctccacacaagtacactgcgcagccgcatgccaccctcc
aaaggaccacatagtcaattacccagcatcacacaccacccttggggtccaggatatatccacaacggcaatgtcttgggtgcagaagattacggg
aggagtaggattaattgttgctgttgctgccttaattttaattgtggtgctatgcgtgtcgtttagcaggcac
```

Regarding Chikungunya virus, another exemplary nucleotide sequence that encodes E3-E2-6K-E1 is described below (SEQ ID No.:10):

```
Atgagtcttgccatcccagttatgtgcctgttggcaaacaccacgttcccctgctcccagccccccttgcacgccctgctgctacgaaaaggaaccgg
aggaaaccctacgcatgcttgaggacaacgtcatgagacctgggtactatcagctgctacaagcatccttaacatgttctccccaccgccagcgac
gcagcaccaaggacaacttcaatgtctataaagccacaagaccatacttagctcactgtcccgactgtggagaagggcactcgtgccatagtcccg
tagcactagaacgcatcagaaatgaagcgacagacgggacgctgaaaatccaggtctccttgcaaatcggaataaagacggatgacagccacga
ttggaccaagctgcgttatatggacaaccacatgccagcagacgcagagagggcggggctatttgtaagaacatcagcaccgtgtacgattactgg
aacaatgggacacttcatcctggcccgatgtccaaaaggggaaactctgacggtgggattcactgacagtaggaagattagtcactcatgtacgca
cccatttcaccacgaccctcctgtgataggtcgggaaaaattccattcccgaccgcagcacggtaaagagctaccttgcagcacgtacgtgcagag
caccgccgcaactaccgaggagatgaggtacactgcccccgacaccccgatcgcacattaatgtcacaacagtccggcaacgtaaagatc
acagtcaatggccagacggtgcggtacaagtgtaattgcggtggctcaaatgaaggactaacaactacagacaaagtgattaataactgcaaggtt
gatcaatgtcatgccgcggtcaccaatcacaaaaagtggcagtataactcccctctggtcccgcgtaatgctgaacttggggaccgaaaaggaaaa
attcacatcccgtttccgctggcaaatgtaacatgcagggtgcctaaagcaaggaaccccaccgtgacgtacgggaaaaaccaagtcatcatgcta
ctgtatcctgaccacccaacactcctgtcctaccggaatatgggagaagaaccaaactatcaagaagagtgggtgatgcataagaaggaagtcgtg
ctaaccgtgccgactgaagggctcgaggtcacgtggggcaacaacgagccgtataagtattggccgcagttatctacaaacggtacagcccatgg
ccacccgcatgagataattctgtattattatgagctgtaccccactatgactgtagtagttgtgtcagtggccacgttcatactcctgtcgatggtgggta
tggcagcggggatgtgcatgtgtgcacgacgcagatgcatcacaccgtatgaactgacaccaggagctaccgtccctttcctgcttagcctaatatg
ctgcatcagaacagctaaagaggccacataccaagaggctgcgatatcctgtggaacgagcagcaacctttgttttggctacaagcccttattccg
ctggcagccctgattgttctatgcaactgtctgagactcttaccatgctgctgtaaaacgttggctttttttagccgtaatgagcgtcggtgcccacactgt
gagcgcgtacgaacacgtaacagtgatcccgaacacggtgggagtaccgtataagactctagtcaatagacctggtctacagccccatggtattgg
agatggaactactgtcagtcactttggagccaacactatcgcttgattacatcacgtgcgagtacaaaaccgtcatcccgtctccgtacgtgaagtgct
gcggtacagcagagtgcaaggacaaaaacctacctgactacagctgtaaggtcttcaccggcgtctacccatttatgtggggcggcgcctactgctt
ctgcgacgctgaaaacacgcagttgagcgaagcacacgtggagaagtccgaacatgcaaaacagaatttgcatcagcatacaggctcataccg
catctgcatcagctaagctccgcgtcctttaccaaggaaataacatcactgtaactgcttatgcaaacggcgaccatgccgtcacagttaaggacgc
caaattcattgtggggccaatgtcttcagcctggacacctttcgacaacaaaattgtggtgtacaaaggtgacgtctataacatggactacccgccctt
tggcgcaggaagaccaggacaatttggcgatatccaaagtcgcacacctgagagtaaagacgtctatgctaatacacaactggtactgcagagac
cggctgtgggtacggtacagtgccatactctcaggcaccatctggctttaagtattggctaaaagaacgcggggcgtcgctgcagcacacagcac
catttggctgccaaatagcaacaaacccggtaagagcggtgaactgcgccgtagggaacatgcccatctccatcgacataccggagcggccttc
actagggtcgtcgacgccctctttaacggacatgtcgtgcgaggtaccagcctgcacccattcctagactttgggggcgtcgccattattaaata
tgcagccagcaagaaaggcaagtgtgcggtgcattcgatgactaacgccgtcactattcgggaagctgagatgaagttgaagggaattctcagct
gcaaatctctttctcgacggccttagccagcgccgaattccgcgtacaagtctgttctacacaagtacactgtgcagccgagtccacccccgaag
gaccacatagtcaactacccggcgtcacataccaccctcggggtccaggacatctccgctacggcgatgtcatgggtgcagaagatcacgggag
gtgtgggactggttgttgctgttgccgcactgattctaatcgtggtgctatgcgtgtcgttcagcaggcac
```

Regarding Chikungunya virus, an exemplary nucleotide sequence that encodes a Capsid-E3-E2-6K-E1 is described below (SEQ ID No.:11):

```
atggagttcatcccgacgcaaactttctataacagaaggtaccaaccccg
accctgggccccacgccctacaattcaagtaattagacctagaccacgtc
cacagaggcaggctgggcaactcgcccagctgatctccgcagtcaacaaa
ttgaccatgcgcgcggtacctcaacagaagcctcgcagaaatcggaaaaa
```

-continued

```
caagaagcaaaggcagaagaagcaggcgccgcaaaacgacccaaagcaaa
agaagcaaccaccacaaaagaagccggctcaaaagaagaagaaaccaggc
cgtagggagagaatgtgcatgaaaattgaaaatgattgcatcttcgaagt
caagcatgaaggcaaagtgatgggctacgcatgcctggtgggggataaag
taatgaaaccagcacatgtgaagggaactatcgacaatgccgatctggct
aaactggcctttaagcggtcgtctaaatacgatcttgaatgtgcacagat
```

-continued accggtgcacatgaagtctgatgcctcgaagtttacccacgagaaacccg aggggtactataactggcatcacggagcagtgcagtattcaggaggccgg ttcactatcccgacgggtgcaggcaagccgggagacagcggcagaccgat cttcgacaacaaaggacgggtggtggccatcgtcctaggaggggccaacg aaggtgcccgcacggccctctccgtggtgacgtggaacaaagacatcgtc acaaaaattacccctgagggagccgaagagtggagcctcgccctcccggt cttgtgcctgttggcaaacactacattcccctgctctcagccgccttgca caccctgctgctacgaaaaggaaccggaaagcaccttgcgcatgcttgag gacaacgtgatgagacccggatactaccagctactaaaagcatcgctgac ttgctctccccaccgccaaagacgcagtactaaggacaattttaatgtct ataaagccacaagaccatatctagctcattgtcctgactgcggagaaggg cattcgtgccacagccctatcgcattggagcgcatcagaaatgaagcaac ggacggaacgctgaaaatccaggtctctttgcagatcgggataaagacag atgacagccacgattggaccaagctgcgctatatggatagccatacgcca gcggacgcggagcgagccggattgcttgtaaggacttcagcaccgtgcac gatcaccgggaccatgggacactttattctcgcccgatgcccgaaaggag agacgctgacagtgggatttacggacagcagaaagatcagccacacatgc acacacccgttccatcatgaaccacctgtgataggtagggagaggttcca ctctcgaccacaacatggtaaagagttaccttgcagcacgtacgtgcaga gcaccgctgccactgctgaggagatagaggtgcatatgcccccagatact cctgaccgcacgctgatgacgcagcagtctggcaacgtgaagatcacagt taatgggcagacggtgcggtacaagtgcaactgcggtggctcaaacgagg gactgacaaccacagacaaagtgatcaataactgcaaaattgatcagtgc catgctgcagtcactaatcacaagaattggcaatacaactcccctttagt cccgcgcaacgctgaactcggggaccgtaaaggaaagatccacatcccat tcccattggcaaacgtgacttgcagagtgccaaaagcaagaaaccctaca gtaacttacggaaaaaaccaagtcaccatgctgctgtatcctgaccatcc gacactcttgtcttaccgtaacatgggacaggaaccaaattaccacgagg agtgggtgacacacaagaaggaggttaccttgaccgtgcctactgagggt ctggaggtcacttggggcaacaacgaaccatacaagtactggccgcagat gtctacgaacggtactgctcatggtcacccacatgagataatcttgtact attatgagctgtaccccactatgactgtagtcattgtgtcggtggcctcg ttcgtgcttctgtcgatggtgggcacagcagtgggaatgtgtgtgtgcgc acggcgcagatgcattacaccatatgaattaacaccaggagccactgttc ccttcctgctcagcctgctatgctgcgtcagaacgaccaaggcggccaca tattacgaggctgcggcatatctatggaacgaacagcagcccctgttctg gttgcaggctcttatcccgctggccgccttgatcgtcctgtgcaactgtc tgaaactcttgccatgctgctgtaagaccctggctttttagccgtaatg agcatcggtgcccacactgtgagcgcgtacgaacacgtaacagtgatccc gaacacggtgggagtaccgtataagactcttgtcaacagaccgggttaca -continued gccccatggtgttggagatggagctacaatcagtcaccttggaaccaaca ctgtcacttgactacatcacgtgcgagtacaaaactgtcatcccctcccc gtacgtgaagtgctgtggtacagcagagtgcaaggacaagagcctaccag actacagctgcaaggtctttactggagtctacccatttatgtggggcggc gcctactgcttttgcgacgccgaaaatacgcaattgagcgaggcacatgt agagaaatctgaatcttgcaaaacagagtttgcatcggcctacagagccc acaccgcatcggcgtcggcgaagctccgcgtcctttaccaaggaaacaac attaccgtagctgcctacgctaacggtgaccatgccgtcacagtaaagga cgccaagtttgtcgtgggcccaatgtcctccgcctggacaccttttgaca acaaaatcgtggtgtacaaaggcgacgtctacaacatggactacccacct tttggcgcaggaagaccaggacaatttggtgacattcaaagtcgtacacc ggaaagtaaagacgtttatgccaacactcagttggtactacagaggccag cagcaggcacggtacatgtaccatactctcaggcaccatctggcttcaag tattggctgaaggaacgaggagcatcgctacagcacacggcaccgttcgg ttgccagattgcgacaaacccggtaagagctgtaaattgcgctgtgggga acataccaatttccatcgacataccggatgcggcctttactagggttgtc gatgcaccctctgtaacggacatgtcatgcgaagtaccagcctgcactca ctcctccgactttgggggcgtcgccatcatcaaatacacagctagcaaga aaggtaaatgtgcagtacattcgatgaccaacgccgttaccattcgagaa gccgacgtagaagtagaggggaactcccagctgcaaatatccttctcaac agccctggcaagcgccgagtttcgcgtgcaagtgtgctccacacaagtac actgcgcagccgcatgccaccctccaaaggaccacatagtcaattaccca gcatcacacaccacccttggggtccaggatatatccacaacggcaatgtc ttgggtgcagaagattacgggaggagtaggattaattgttgctgttgctg ccttaattttaattgtggtgctatgcgtgtcgtttagcaggcactaa.

Regarding Chikungunya virus, another exemplary nucleotide sequence that encodes a Capsid-E3-E2-6K-E1 is described below (SEQ ID No.:12):

atggagttcatcccaacccaaactttttacaataggaggtaccagcctcg accctggactccgcgccctactatccaagtcatcaggcccagaccgcgcc ctcagaggcaagctgggcaacttgcccagctgatctcagcagttaataaa ctgacaatgcgcgcggtaccacaacagaagccacgcaggaatcggaagaa taagaagcaaaagcaaaaacaacaggcgccacaaaacaacacaaatcaaa agaagcagccacctaaaaagaaaccggctcaaaagaaaaagaagccgggc cgcagagagaggatgtgcatgaaaatcgaaaatgattgtattttcgaagt caagcacgaaggtaaggtaacaggttacgcgtgcctggtgggggacaaag taatgaaaccagcacacgtaaaggggaccatcgataacgcggacctggcc aaactggcctttaagcggtcatctaagtatgaccttgaatgcgcgcagat acccgtgcacatgaagtccgacgcttcgaagttcacccatgagaaaccgg aggggtactacaactggcaccacggagcagtacagtactcaggaggccgg ttcaccatccctacaggtgctggcaaaccaggggacagcggcagaccgat -continued

```
cttcgacaacaagggacgcgtggtggccatagtcttaggaggagctaatg
aaggagcccgtacagccctctcggtggtgacctggaataaagacattgtc
actaaaatcacccccgagggggccgaagagtggagtcttgccatcccagt
tatgtgcctgttggcaaacaccacgttcccctgctcccagccccttgca
cgccctgctgctacgaaaaggaaccggaggaaaccctacgcatgcttgag
gacaacgtcatgagacctgggtactatcagctgctacaagcatccttaac
atgttctccccaccgccagcgacgcagcaccaaggacaacttcaatgtct
ataaagccacaagaccatacttagctcactgtcccgactgtggagaaggg
cactcgtgccatagtcccgtagcactagaacgcatcagaaatgaagcgac
agacgggacgctgaaaatccaggtctccttgcaaatcggaataaagacgg
atgacagccacgattggaccaagctgcgttatatggacaaccacatgcca
gcagacgcagagagggcggggctatttgtaagaacatcagcaccgtgtac
gattactggaacaatgggacacttcatcctggcccgatgtccaaaagggg
aaactctgacggtgggattcactgacagtaggaagattagtcactcatgt
acgcacccatttcaccacgaccctcctgtgataggtcgggaaaaattcca
ttcccgaccgcagcacggtaaagagctaccttgcagcacgtacgtgcaga
gcaccgccgcaactaccgaggagatagaggtacacatgcccccagacacc
cctgatcgcacattaatgtcacaacagtccggcaacgtaaagatcacagt
caatggccagacggtgcggtacaagtgtaattgcggtggctcaaatgaag
gactaacaactacagacaaagtgattaataactgcaaggttgatcaatgt
catgccgcggtcaccaatcacaaaaagtggcagtataactcccctctggt
cccgcgtaatgctgaacttggggaccgaaaaggaaaaattcacatcccgt
ttccgctggcaaatgtaacatgcagggtgcctaaagcaaggaaccccacc
gtgacgtacgggaaaaaccaagtcatcatgctactgtatcctgaccaccc
aacactcctgtcctaccggaatatgggagaagaaccaaactatcaagaag
agtgggtgatgcataagaaggaagtcgtgctaaccgtgccgactgaaggg
ctcgaggtcacgtggggcaacaacgagccgtataagtattggccgcagtt
atctacaaacggtacagcccatggccacccgcatgagataattctgtatt
attatgagctgtaccccactatgactgtagtagttgtgtcagtggccacg
ttcatactcctgtcgatggtgggtatggcagcggggatgtgcatgtgtgc
acgacgcagatgcatcacaccgtatgaactgacaccaggagctaccgtcc
ctttcctgcttagcctaatatgctgcatcagaacagctaaagcggccaca
taccaagaggctgcgatatacctgtggaacgagcagcaacctttgttttg
gctacaagcccttattccgctggcagccctgattgttctatgcaactgtc
tgagactcttaccatgctgctgtaaaacgttggctttttagccgtaatg
agcgtcggtgcccacactgtgagcgcgtacgaacacgtaacagtgatccc
gaacacggtgggagtaccgtataagactctagtcaatagacctggctaca
gccccatggtattggagatggaactactgtcagtcactttggagccaaca
ctatcgcttgattacatcacgtgcgagtacaaaaccgtcatcccgtctcc
gtacgtgaagtgctgcggtacagcagagtgcaaggacaaaaacctacctg
```

-continued

```
actacagctgtaaggtcttcaccggcgtctacccatttatgtggggcggc
gcctactgcttctgcgacgctgaaaacacagcagttgagcgaagcacagt
ggagaagtccgaatcatgcaaaacagaatttgcatcagcatacagggctc
ataccgcatctgcatcagctaagctccgcgtcctttaccaaggaaataac
atcactgtaactgcctatgcaaacggcgaccatgccgtcacagttaagga
cgccaaattcattgtggggccaatgtcttcagcctggacacctttcgaca
acaaaattgtggtgtacaaaggtgacgtctataacatggactacccgccc
tttggcgcaggaagaccaggacaatttggcgatatccaaagtcgcacacc
tgagagtaaagacgtctatgctaatacacaactggtactgcagagaccgg
ctgtgggtacggtacacgtgccatactctcaggcaccatctggctttaag
tattggctaaaagaacgcggggcgtcgctgcagcacacagcaccatttgg
ctgccaaatagcaacaaacccggtaagagcggtgaactgcgccgtaggga
acatgcccatctccatcgacataccggaagcggccttcactagggtcgtc
gacgcgccctctttaacggacatgtcgtgcgaggtaccagcctgcaccca
ttcctcagactttgggggcgtcgccattattaaatatgcagccagcaaga
aaggcaagtgtgcggtgcattcgatgactaacgccgtcactattcgggaa
gctgagatagaagttgaagggaattctcagctgcaaatctctttctcgac
ggccttagccagcgccgaattccgcgtacaagtctgttctacacaagtac
actgtgcagccgagtgccacccccgaaggaccacatagtcaactacccg
gcgtcacataccaccctcggggtccaggacatctccgctacggcgatgtc
atgggtgcagaagatcacgggaggtgtgggactggttgttgctgttgccg
cactgattctaatcgtggtgctatgcgtgtcgttcagcaggcactaa.
```

In one embodiment, the present invention provides a vector comprising the nucleic acid molecule as described above, wherein the vector optionally comprises an expression control sequence operably linked to the nucleic acid molecule.

Examples of an expression control sequence include, but are not limited to, promoter such as CMV promoter, phage lambda PL promoter, the *E. coli* lac, phoA and tac promoters, the SV40 early and late promoters, and promoters of retroviral LTRs.

The expression vectors can be prepared by a person skilled in the art based on WO/2012/006180, the entire contents of which are incorporated by reference herein. Examples of vectors which can be used for expressing a fusion protein of a polypeptide derived from Chikungunya virus (CHIKV) and a polypeptide of antigen include a vector shown in VLP_CHI 512 vector (SEQ ID No.:23) containing CHIKV VLP polynucleotide (SEQ ID No. 28; corresponding amino acid sequence represented by SEQ ID No.:29); and VLP_CHI 532 vector (SEQ ID No.: 24) containing CHIKV VLP polynucleotide (SEQ ID No. 30; corresponding amino acid sequence represented by SEQ ID No.:31).

The expression vectors can be prepared by a person skilled in the art based on US2012/0003266, the entire contents of which are incorporated by reference herein. Examples of vectors which can be used for expressing a fusion protein of a polypeptide derived from Venezuelan equine encephalitis virus (VEEV) and a polypeptide of antigen include a vector shown in VLP_VEEV VLP 518 vector (SEQ ID No.:25) containing VEEV VLP polynucleotide (SEQ ID No. 32; corresponding amino acid sequence represented by SEQ ID No.:

33); VLP_VEEV VLP 519 vector (SEQ ID No. 26) containing VEEV VLP polynucleotide (SEQ ID No. 34; corresponding amino acid sequence represented by SEQ ID No.:35); and VLP_VEEV VLP 538 vector (SEQ ID No.: 27) containing VEEV VLP polynucleotide (SEQ ID No. 36; corresponding amino acid sequence represented by SEQ ID No.: 37).

In one embodiment, the present invention provides i) a nucleic acid molecule encoding a fusion protein of a polypeptide derived from Chikungunya virus (CHIKV) and a polypeptide derived from TNF-α, which consists of a nucleotide sequence represented by SEQ ID No. 13;

ii) a nucleic acid molecule encoding a fusion protein of a polypeptide derived from Chikungunya virus (CHIKV) and a polypeptide derived from CD20, which consists of a nucleotide sequence represented by SEQ ID No. 14;

iii) a nucleic acid molecule encoding a fusion protein of a polypeptide derived from Venezuelan equine encephalitis virus (VEEV) and a polypeptide derived from TNF-α, which consists of a nucleotide sequence represented by SEQ ID No. 15;

iv) a nucleic acid molecule encoding a fusion protein of a polypeptide derived from Venezuelan equine encephalitis virus (VEEV) and a polypeptide derived from CD20, which consists of a nucleotide sequence represented by SEQ ID No. 16; or v) a nucleic acid molecule encoding a fusion protein of a polypeptide derived from Venezuelan equine encephalitis virus (VEEV) and a polypeptide derived from CTLA4, which consists of a nucleotide sequence represented by SEQ ID No. 17.

In one embodiment, the present invention provides a nucleic acid molecule which is modified from the nucleic acid molecule having a nucleotide sequence represented by any one of SEQ ID Nos. 13-17. The modified nucleic acid molecule may have at least 70%, 75%, 80%, 85%, 90%, 95% or 98% nucleotide sequence identity to the nucleic acid molecule having a nucleotide sequence represented by any one of SEQ ID Nos. 13-17. Also, the modified nucleic acid molecule may be a mutant where at most 10% of the amino acids are deleted, substituted, and/or added based on the nucleic acid molecule having a nucleotide sequence represented by any one of SEQ ID Nos. 13-17.

(3) Composition

In the third aspect, the present invention provides a composition comprising the particle provided in the first aspect of the present invention and/or the nucleic acid molecule provided in the second aspect of the present invention.

In one embodiment, the present invention provides a composition comprising the Chikungunya or Venezuelan equine encephalitis virus like particle as described above or the nucleic acid molecule as described above.

The composition may further comprise a pharmaceutical acceptable carrier and/or adjuvant. Examples of adjuvant include, but are not limited to Ribi solution (Sigma Adjuvant system, Sigma-Aldrich).

The pharmaceutical composition of the present invention may contain a single active ingredient or a combination of two or more active ingredients, as far as they are not contrary to the objects of the present invention. For example, cytokines including chemokines, anti-body of cytokines such as anti TNF antibody (e.g. infliximab, adalimumab), anti-VEGF antibody (e.g. bevacizumab and ranibizumab), cytokine receptor antagonist such as anti HER2 antibody (e.g. Trastuzumab), anti EGF receptor antibody (e.g. Cetuximab), anti VEGF aptamer (e.g. Pegaptanib) and immunomodulator such as cyclosporine, tacrolimus, ubenimex may be used for the combination therapy.

In a combination of plural active ingredients, their respective contents may be suitably increased or decreased in consideration of their therapeutic effects and safety.

The term "combination" used herein means two or more active ingredient are administered to a patient simultaneously in the form of a single entity or dosage, or are both administered to a patient as separate entities either simultaneously or sequentially with no specific time limits, wherein such administration provides therapeutically effective levels of the two components in the body, preferably at the same time.

In one embodiment, the composition is a vaccine composition including a DNA vaccine. In one embodiment, the DNA vaccine provided by the present invention comprises CpG containing oligonucleotide.

(4) Method of Producing an Antibody, Method of Immunomodulation, Method of Treating an Autoimmune Disease, Method of Inducing and/or Enhancing Immune Response Against an Antigen in a Mammal, Method of Treating Cancer, Method of Passive Immunization, Method of Presenting an Antigen on Macrophage, and Method for Producing a Particle In the fourth aspect, the present invention provides a method of producing an antibody, comprising contacting the particle provided in the first aspect of the present invention and/or the nucleic acid molecule provided in the second aspect of the present invention to a mammal.

The antibody produced in the fourth aspect of the present invention may be humanized using a conventional technique. Thus, in one embodiment, the method provided in the fourth aspect of the invention further comprises a step of humanizing non-human mammal produced antibody.

The particle provided in the first aspect of the present invention and/or the nucleic acid molecule provided in the second aspect of the present invention may be administered directly into the patient, into the affected organ or systemically, or applied ex vivo to cells derived from the patient or a human cell line which are subsequently administered to the patient, or used in vitro to select a subpopulation from immune cells such as B-cell and T-cell derived from the patient, which are then re-administered to the patient.

According to the present invention, the virus like particle can be applied for the immune therapy.

In the fifth aspect, the present invention provides a method of immunomodulation, a method of treating an autoimmune disease, a method of inducing and/or enhancing immune response against an antigen in a mammal, and a method of treating cancer comprising administering the composition provided in the third aspect of the present invention to a mammal.

In sixth aspect, the present invention provides a method of passive immunization, comprising administering the antibody provided in the fourth aspect of the present invention to a mammal.

In seventh aspect, the present invention provides a method of presenting an antigen on macrophage, comprising contacting the particle provided in the first aspect of the present invention and/or the nucleic acid molecule provided in the second aspect of the present invention to a mammal.

In eighth aspect, the present invention provides a method for producing the particle provided in the first aspect of the present invention, comprising preparing a gene comprising a nucleotide sequence encoding said particle; culturing a cell which is transfected with said gene to express said particle; and recovering said particle.

In one embodiment, the present invention provides a method of producing an antibody, comprising contacting the Chikungunya or Venezuelan equine encephalitis virus like particle as described above and/or the nucleic acid molecule as described above to a mammal. The produced antibody may be an antibody which can specifically bind to the antigen comprised in the Chikungunya or Venezuelan equine encephalitis virus like particle or the antigen encoded by the nucleic acid molecule. The method of producing an antibody provided by the present invention may be a useful method for producing a monoclonal or polyclonal antibody against an antigen (e.g. TNF a, CD20 and CLTA4).

In one embodiment, the antibody obtained by the method of producing an antibody according to the present invention is used for passive immunization. The method of passive immunization may comprise administering the obtained antibody to a mammal.

According to the present invention, the composition of the present invention is useful for immunomodulation. Especially said immunomodulation is for the treatment of autoimmune disease, neural disease, inflammatory disease such as inflammatory lung disease, including the acute respiratory distress syndrome, chronic obstructive pulmonary disease and asthma, angiogenesis associated diseases including neoplasm.

In one preferred embodiment, the immunomodulation provided by the present invention is inducing and/or enhancing immune response against an antigen in a mammal. Thus, in one embodiment, the present invention provides a method of inducing and/or enhancing immune response against an antigen in a mammal, comprising administering an effective amount of the composition as described above to the mammal. Examples of mammal include, but are not limited to, a human.

Since many antibodies are useful for the treatment of disease, the method and the composition which are provided by the present invention can be useful for the treatment of diseases. For example, an antibody which specifically binds the target as listed in Table 1 or an antibody which binds an epitope on the target as listed in Table 1 is useful for the treatment of the disease as listed in Table 1.

In one embodiment, at least one antigen which is used for the present invention is at least one target as listed in Table 1. When at least one antigen which is used for the present invention is at least one target as listed in Table 1, the particle, the isolated nucleic acid, the vector, the composition and the method provided by the present invention can be useful for the treatment of the disease or the condition as listed in Table 1 (see "Use" of Table 1).

For example, when at least one antigen used for the present invention is one or more cancer antigen, the particle, the isolated nucleic acid, the vector, the composition and the method provided by the present invention can be useful for the treatment of cancer.

Examples of cancer antigen include, but are not limited to, VEGF, epidermal growth factor receptor, CD33, CD20 and ErbB2. When the composition of the present invention comprising two or more cancer antigens is administered to a mammal, antibodies directed to the two or more cancer antigens can attack the cancer.

For example, when at least one antigen used for the present invention is amyloid β, the isolated nucleic acid, the vector, the composition and the method provided by the present invention can be useful for the treatment of Alzheimer's disease.

For example, when at least one antigen used for the present invention is TNF alpha, the isolated nucleic acid, the vector, the composition and the method provided by the present invention can be useful for the treatment of inflammation; auto immune disease including rheumatoid arthritis; psoriasis, Crohn's disease; ulcerative colitis etc.

For example, when at least one antigen used for the present invention is CD20, the isolated nucleic acid, the vector, the composition and the method provided by the present invention can be useful for the treatment of auto immune disease including rheumatoid arthritis and SLE; cancer including Non-Hodgkin lymphoma etc.

For example, when at least one antigen used for the present invention is CTLA4, the isolated nucleic acid, the vector, the composition and the method provided by the present invention can be useful for the treatment of cancer including melanoma; and useful for activating T cells etc.

Given the symptom of patients infected with Chikungunya or Venezuelan equine encephalitis together with unusual big molecule of Chikungunya or Venezuelan equine encephalitis, this VLP can act effectively and efficiently to target macrophage and its composition such as cytokines and immunomodulative compounds.

In one aspect, the present invention provides a method of presenting an antigen on macrophage, comprising administering the Chikungunya or Venezuelan equine encephalitis virus like particle as described above and/or the nucleic acid molecule as described above to a mammal. The Chikungunya or Venezuelan equine encephalitis virus like particle provided by the present invention is good to target macrophage. In one embodiment, the Chikungunya or Venezuelan equine encephalitis virus like particle provided by the present invention is a kind of delivery system of the at least one antigen, which is comprised in the Chikungunya or Venezuelan equine encephalitis virus like particle, to macrophage.

In one embodiment, the present invention provides a method for producing Chikungunya or Venezuelan equine encephalitis virus like particle provided in the first aspect of the present invention, comprising preparing a gene comprising a nucleotide sequence encoding said particle; culturing a cell which is transfected with said gene to express said particle; and recovering said particle. In this embodiment, transfection can be conducted using a conventional method. Cells using for the transfection may be 293 cells. Recovering VLP may include collecting a conditioned medium after cells are transfected with a plasmid comprising a gene, and may further include purify VLP from the conditioned medium using ultracentrifugation. In one embodiment, further step may be included in the method for producing Chikungunya or Venezuelan equine encephalitis virus like particle provided in the eighth aspect of the present invention, where a polynucleotide encoding an antigen is designed so that spatial distance between the N-terminal residue and C-terminal residue of the antigen is 30 Å or less (e.g. from 5 Å to 15 Å, from 5 to 12 Å, from 5 Å to 11 Å, from 5 Å to 10 Å, from 5 Å to 8 from 8 Å to 15 Å, from 8 Å to 13 Å, from 8 Å to 12 from 8 Å to 11 Å, from 9 Å to 12 Å, from 9 Å to 11 Å, from 9 Å to 10 Å, or from 10 Å to 11 when the distance is determined in a crystal of the antigen or a naturally occurring protein containing the antigen or modified protein therefrom.

Immune system evolves to recognize foreign antigens for killing pathogens such as viruses or bacteria. It also evolves not to recognize self proteins to protect self proteins. It is called immune tolerance system. Therefore it is difficult to induce antibodies against self-antigen by traditional immunization methods. To overcome the immune tolerance, we developed a novel vaccine method using a self-assembly subunit containing an self-antigen. The self-assembly subunit spontaneously assembles and forms a stable organized unit that presents highly repetitive antigens on the surface. Highly repetitive antigens immunogen strengthen signal pathways in B cells and result in stimulation of antibody responses than single antigen immunogen such as traditional immunization methods. Applying this mechanism to vaccine development not only increases antibody responses against target immunogens but also overcome self-antigen tolerance.

The present invention will be described in detail with reference to the following example, which, however, is not intended to limit the scope of the present invention.

EXAMPLES

(1) Preparation of Chikungunya Virus Like Particle Comprising a Virus Structural Polypeptide and a Fragment of Human TNF Alpha It was expected that a monomer of TNF alpha polypeptide fused with Chikungunya virus structural polypeptide is difficult to be stably expressed because TNF alpha is found as a trimer under natural conditions. However, use of a fusion protein, in which TNF alpha monomer peptide (a fragment of TNF alpha monomer peptide) is fused with the Chikungunya virus structural polypeptide through linkers at N- and C-terminal of TNF alpha-derived peptide for attaching TNF alpha-derived peptide to the Chikungunya virus structural polypeptide, resulted in stable expression of a Chikungunya virus like particle comprising a virus structural polypeptide and TNF alpha monomer-derived peptide.

In detail, polynucleotide encoding the original human TNF alpha was modified to prepare a polynucleotide encoding modified TNF alpha-derived peptide where RTPSD which is N-terminal sequence of the original TNF alpha-derived peptide is replaced with SGG and TRGGS (SEQ ID NO: 52) is attached to C-terminal of the TNF alpha (see SEQ ID Nos. 18-20 as shown in FIG. 1). The resulting polynucleotide was inserted between the codons encoding G at 519-position and Q at 520-position of SEQ ID No. 2 to construct a plasmid (hereinafter referred to as CHIKV-TNFa4) for expressing Chikungunya virus like particle where the modified TNF alpha-derived peptide is inserted into E2 of Chikungunya virus structural polypeptide (C-E3-E2-6K-E1). Subsequently, 293F cells ($1.5\times10^6$ cells/ml) was transfected with 250 μg of CHIKV-TNFa4. After culturing for 4 days, the supernatant was collected. The obtained supernatant was overlaid onto Opti Prep (Sigma D1556) followed by being ultracentrifuged (20000 rpm, 120 min) using SW28 rotor to concentrate VLP (i.e. virus like particle). The concentrated VLP was mixed with Opti Prep to form density gradient followed by ultracentrifuged (75000 rpm, 4 hours) using NVT100 rotor. After the ultracentrifugation, purified VLP was collected. The expression of VLP comprising TNF alpha conjugated with Chikungunya virus structural polypeptide was confirmed by Western Blot using an antibody specific for CHIVK (ATCC: VR-1241AF) and an antibody specific for TNF alpha (Cell Signal: #6945).

The spatial distance between the N-terminal residue and C-terminal residue of the TNF alpha-derived peptide is 8.27 Å when the distance is determined in a crystal of TNF alpha.

(2) Preparation of Venezuelan Equine Encephalitis Virus Like Particle Comprising a Virus Structural Polypeptide and Human TNF Alpha-Derived Peptide (Referred to as "VEEV-TNFa VLPS")

According to the above-described (1), polynucleotide encoding modified TNF alpha-derived peptide fused with polynucleotide encoding Venezuelan equine encephalitis virus structural polypeptide was prepared (see SEQ ID No. 15) to construct an expression vector followed by transfection in 293F cells.

VEEV-TNFa VLPs were purified by density gradient centrifuge. As seen in Lane 4, TNF alpha-derived peptide and VEEV expression was confirmed by Western blot using TNFa monoclonal antibody (top panel) and VEEV polyclonal antibodies (bottom panel), respectively (see FIG. 2).

The spatial distance between the N-terminal residue and C-terminal residue of the TNF alpha-derived peptide is 8.27 Å when the distance is determined in a crystal of TNF alpha.

(3) Detection of Anti-Human TNF Alpha Antibody in Immunized Mouse

Mice were divided into three groups (n=5 for each group). The Chikungunya virus like particle comprising a virus structural polypeptide and human TNF alpha-derived polypeptide prepared according to the above-described (1) (referred to as "CHIKV-TNF alpha" below), Chikungunya virus like particle without comprising human TNF alpha-derived polypeptide (referred to as "CHIKV-VLP" below), Venezuelan equine encephalitis virus like particle comprising a virus structural polypeptide and human TNF alpha-derived polypeptide prepared according to the above-described (2) (referred to as "VEEV-TNF alpha" below), Venezuelan equine encephalitis virus like particle without comprising human TNF alpha-derived polypeptide (referred to as "VEEV-VLP" below) or vehicle (i.e. PBS) were intramuscularly administered to each group of mice. The mice were administered at the beginning of the experiment (referred to as "0 week" below) and three weeks after the first administration (referred to as "3 week" below) as described below: Group 1: VEEV-TNF alpha (0 week), CHIKV-TNF alpha (3 week); Group 2: VEEV-VLP (0 week), CHIKV-VLP (3 week); and Group 3: PBS (0 week), PBS (3 week).

Figure 9:
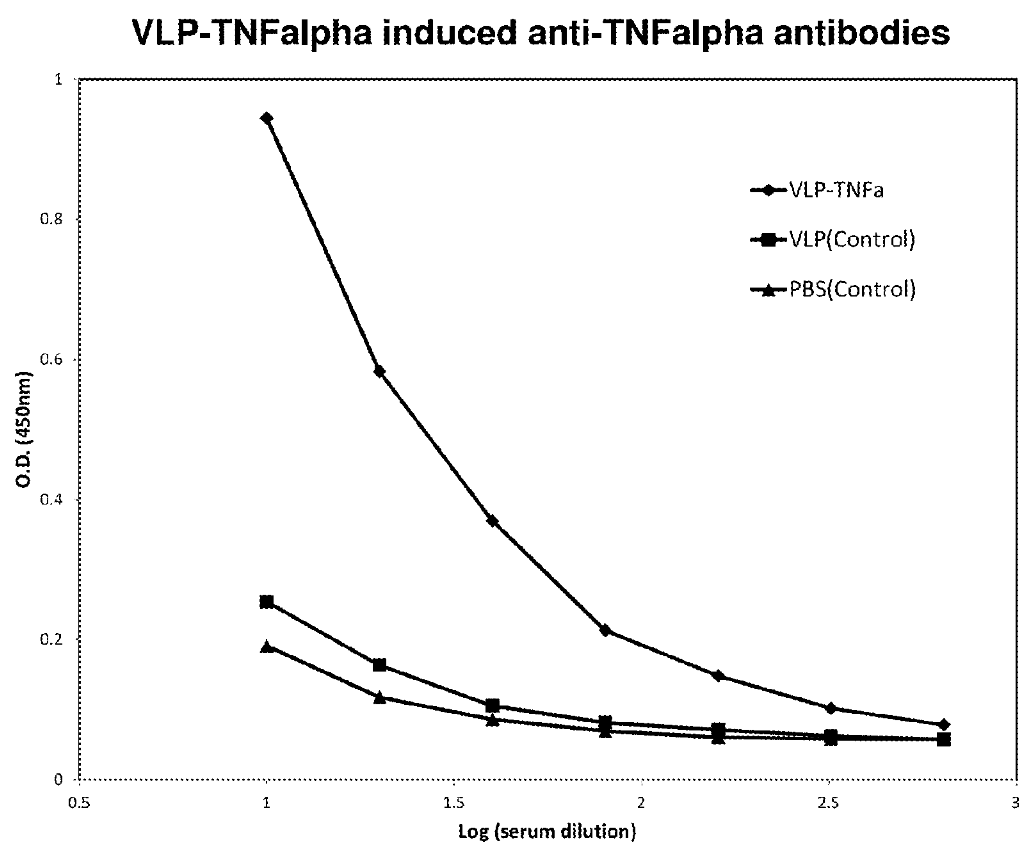
FIG. 9 shows detection of anti-TNF alpha antibodies induced by TNF alpha derived peptide-conjugated virus like particle.

6 weeks after the beginning of the experiment, blood sample was obtained from each mouse and serum was prepared. Produced anti-human TNF alpha antibody was detected using ELISA where TNF alpha protein was coated on ELISA plate. The results show that the virus like particle comprising a virus structural polypeptide and human TNF alpha-derived polypeptide induced anti-human TNF alpha antibodies in mouse (see FIG. 9).

(4) Preparation of Venezuelan Equine Encephalitis Virus Like Particle Comprising a Virus Structural Polypeptide and a Fragment of Human CD20

According to the above-described (1) and (2), VEEV-CD20 VLPs were purified by density gradient centrifuge, and a fragment of CD20 and VEEV expression was confirmed by Western blot. IYNCEPANPSEKNSPSTQYCYSIQ (SEQ ID No.: 21), which is a fragment of CD20, was used as an antigen fused with Venezuelan equine encephalitis virus structural polypeptide.

The spatial distance between the N-terminal residue and C-terminal residue of the CD20 fragment is 10.07 Å when the distance is determined in a crystal of CD20.

(5) Preparation of Venezuelan Equine Encephalitis Virus Like Particle Comprising a Virus Structural Polypeptide and a Fragment of Human CTLA4

A fragment of CTLA4: CKVELMYPPPYYLGIG (SEQ ID No.: 22) was selected based on the full-length CTLA4 amino acid sequence so that spatial distance between the N-terminal residue and the C-terminal residue of the fragment, which is fused into Venezuelan equine encephalitis virus structural polypeptide E2, is about 5.6 Å when the distance is determined in a crystal of CLTA4.

A polynucleotide encoding the fragment of CTLA4 was introduced into VLP_VEEV VLP 518 vector to construct a plasmid for the expression of the fragment of CTLA4 fused with Venezuelan equine encephalitis virus structural polypeptide consisting of the amino acid sequence by SEQ ID No.:8.

(6) Preparation of Venezuelan Equine Encephalitis Virus Like Particle Comprising a Virus Structural Polypeptide and Full Length Human CTLA4

A polynucleotide encoding full length human CTLA4 was introduced into VLP_VEEV VLP 518 vector to construct a plasmid for the expression of CTLA4 fused with Venezuelan equine encephalitis virus structural polypeptide.

The spatial distance between the N-terminal residue and the C-terminal residue of full length human CTLA4 is about 39.6 Å when the distance is determined in a crystal of CLTA4.

Expression of CTLA4 fused with Venezuelan equine encephalitis virus structural polypeptide was not be able to be detected by ELISA after transfecting 293 cells with the prepared plasmid.

(7) Preparation of Chikungunya Virus Like Particle Comprising a Virus Structural Polypeptide and a Fragment of Human or Mouse CD20 and Detection of Anti-Human or Mouse CD20 Antibody Chikungunya virus like particles comprising a virus structural polypeptide and a fragment of human or mouse CD20 were prepared using VLP_CHI 532 vector and a fragment of human or mouse TNF alpha antibody. The fragment of human and mouse TNF alpha antibody are described below: CD20 Human IYNCEPANPSEKNSPSTQYCYSIQ (SEQ ID No.: 21); CD20 Mouse YDCEPSNSSEKNSPSTQYCNSI (SEQ ID No.:41).

Linkers (e.g. SGG, SG, GS or GGS) were used to insert the fragment of CD20 as described below between G at 519-position and Q at 520-position of SEQ ID No. 2:

```
CD20 Human:
                                        (SEQ ID No.: 42)
SGGIYNCEPANPSEKNSPSTQYCYSICIGS

CD20 Mouse version2:
                                        (SEQ ID No.: 43)
SGYDCEPSNSSEKNSPSTQYCNSIGGS

CD20 Mouse version3:
                                        (SEQ ID No.: 44)
SGGYDCEPSNSSEKNSPSTQYCNSIGS.
```

Plasmids: VLP_CHI VLP 532 CD20H, VLP_CHI VLP 532 CD20-2 mouse and VLP_CHI VLP 532 CD20-3 mouse were used for the expression of Chikungunya virus like particles comprising a virus structural polypeptide and a fragment of human or mouse CD20 (SEQ ID No.: 45 (the amino acid sequence of the expressed polypeptide is represented by SEQ ID No.: 46), SEQ ID No.: 47 (the amino acid sequence of the expressed polypeptide is represented by SEQ ID No.: 48) and SEQ ID No.: 49 (the amino acid sequence of the expressed polypeptide is represented by SEQ ID No.: 50).

Figure 10:
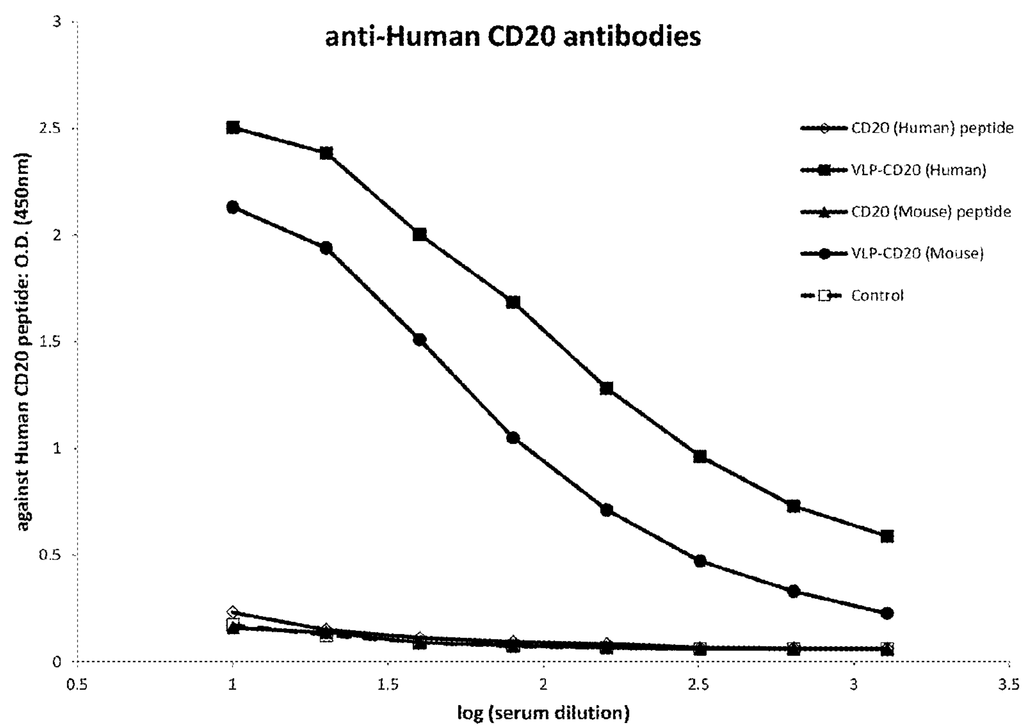
FIG. 10 shows detection of anti-human CD20 antibodies induced by CD20 derived peptide-conjugated virus like particle.
Figure 11:
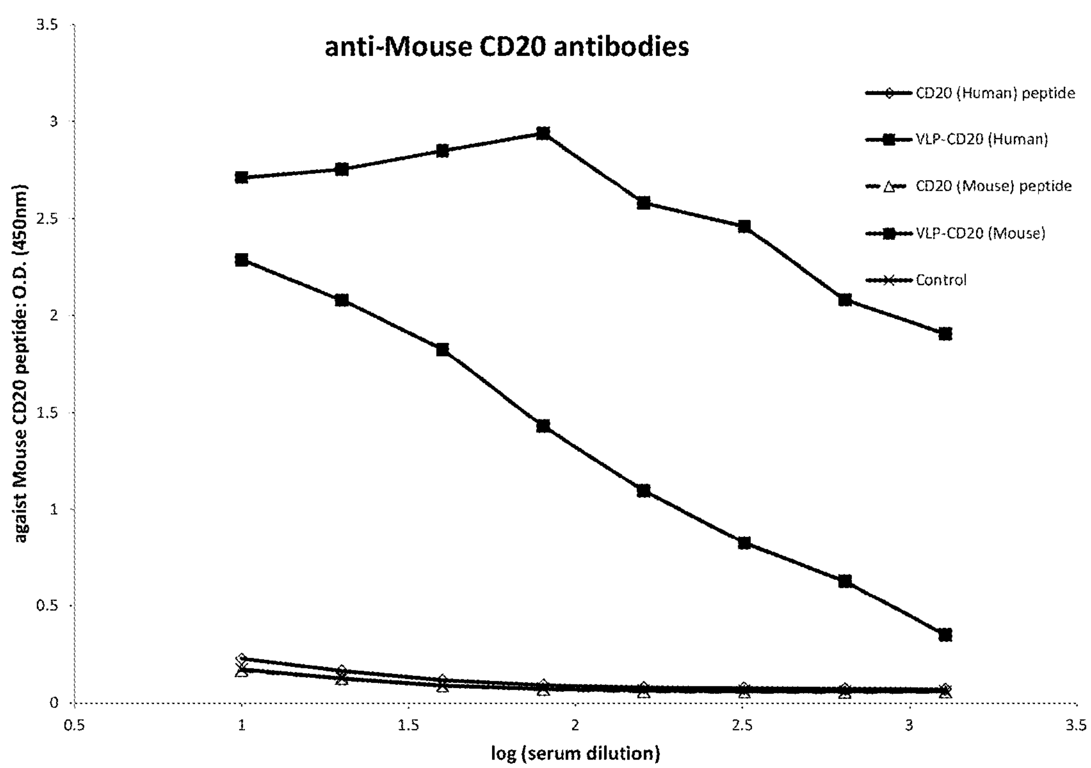
FIG. 11 shows detection of anti-mouse CD20 antibodies induced by CD20 derived peptide-conjugated virus like particle.

Virus like particles were purified according to the method as described in (1). Mice were immunized once with 100 μg of the purified VLPs; 100 μg of the fragment of human or mouse CD20; or PBS (control). Ten days after the immunization, blood sample were obtained from the mice and serum was prepared. Anti-human CD20 antibody induced by the immunization was detected by ELISA coated with the fragment of human CD20, and anti-mouse CD20 antibody induced by the immunization was detected by ELISA coated with the fragment of mouse CD20. The results showed that anti-human CD20 antibodies and anti-mouse CD20 antibodies were adequately induced by administration of the Chikungunya virus like particle comprising the fragment of human or mouse CD20 fused with virus structural polypeptide. Also, the results showed that antibody specific for a self antigen can be adequately induced by administering Chikungunya virus like particle comprising a fragment of the self antigen fused with virus structural polypeptide (see FIG. 10 and FIG. 11).

The invention claimed is:

1. A Chikungunya virus (CHIKV) or Venezuelan equine encephalitis virus (VEEV) virus-like particle, wherein said virus-like particle contains at least one antigen inserted into an E2 envelope protein to form a fusion protein, wherein the at least one antigen is inserted within a CHIKV E2 envelope protein within a region that corresponds in position to residues 509-512, residues 519-520, or residues 529-533 of SEQ ID NO: 1 or 2; or wherein the at least one antigen is inserted within a VEEV E2 envelope protein within a region that corresponds in position to residues 515-520, or residues 536-539 of SEQ ID NO: 3.

2. The virus-like particle according to claim 1, wherein the at least one antigen is a self-antigen or a cancer antigen.

3. The virus-like particle according to claim 1, wherein the at least one antigen is a polypeptide derived from TNF-$\alpha$, CD20 or CTLA4.

4. The virus-like particle according to claim 1, wherein said virus-like particle is selected from the group consisting of:

i) a Chikungunya virus (CHIKV) virus-like particle, wherein the at least one antigen is TNF-$\alpha$;

ii) a Chikungunya virus (CHIKV) virus-like particle, wherein the at least one antigen is CD20;

iii) a Venezuelan equine encephalitis virus (VEEV) virus-like particle, wherein the at least one antigen is TNF-$\alpha$;

iv) a Venezuelan equine encephalitis virus (VEEV) virus-like particle, wherein the at least one antigen is CD20; and v) a Venezuelan equine encephalitis virus (VEEV) virus-like particle, wherein the at least one antigen is CTLA4.

5. The virus-like particle according to claim 1, wherein the at least one antigen is directly fused to the envelope protein.

6. The virus-like particle according to claim 1, wherein one or two linkers intervene between the N-terminal residue of the at least one antigen and the envelope protein, and/or between the C-terminal residue of the at least one antigen and the envelope protein.

7. The virus-like particle according to claim 1, wherein the at least one antigen is inserted into a CHIKV E2 envelope protein that comprises the amino acid sequence of SEQ ID NO: 1 or 2, and wherein the at least one antigen is inserted between residues 519 and 520 of SEQ ID NO: 1 or 2, between residues 530 and 531 of SEQ ID NO: 1 or 2, between residues 531 and 532 of SEQ ID NO: 1 or 2, or between residues 532 and 533 of SEQ ID NO: 1 or 2.

8. The virus-like particle according to claim 1, wherein said fusion protein comprises an amino acid sequence selected from the group consisting of SEQ ID NOs: 4, 5, 6, 7 and 8.

9. The virus-like particle according to claim 1, wherein said fusion protein comprises an amino acid sequence having 90% or more sequence identity to an amino acid sequence selected from the group consisting of SEQ ID NOs: 4, 5, 6, 7 and 8.

10. A composition comprising the virus-like particle according to claim 1.

11. A pharmaceutical composition comprising:

(a) the virus-like particle according to claim 1; and (b) a pharmaceutically acceptable carrier.

12. A vaccine composition comprising the virus-like particle according to claim 1.

13. The virus-like particle according to claim 1, wherein the at least one antigen is inserted into a VEEV E2 envelope protein that comprises the amino acid sequence of SEQ ID NO: 3, and wherein the at least one antigen is inserted between residues 515 and 516 of SEQ ID NO: 3, between residues 516 and 517 of SEQ ID NO: 3, between residues 517 and 518 of SEQ ID NO: 3, between residues 518 and 519 of SEQ ID NO: 3, between residues 519 and 520 of SEQ ID NO: 3, between residues 536 and 537 of SEQ ID NO: 3, between residues 537 and 538 of SEQ ID NO: 3, or between residues 538 and 539 of SEQ ID NO: 3.

14. The virus-like particle according to claim 1, wherein the at least one antigen is inserted into a CHIKV E2 envelope protein that comprises the amino acid sequence of SEQ ID NO: 1 or 2, and wherein the at least one antigen is inserted between residues 519 and 520 of SEQ ID NO: 1 or 2, between residues 529 and 530 of SEQ ID NO: 1 or 2, between residues 530 and 531 of SEQ ID NO: 1 or 2, between residues 531 and 532 of SEQ ID NO: 1 or 2, between residues 532 and 533 of SEQ ID NO: 1 or 2, between residues 509 and 510 of SEQ ID NO: 1 or 2, between residues 510 and 511 of SEQ ID NO: 1 or 2, or between residues 511 and 512 of SEQ ID NO: 1 or 2.

* * * * *